(12) United States Patent
Ruezinsky et al.

(10) Patent No.: US 7,268,276 B2
(45) Date of Patent: Sep. 11, 2007

(54) PRODUCTION OF INCREASED OIL AND PROTEIN IN PLANTS BY THE DISRUPTION OF THE PHENYLPROPANOID PATHWAY

(75) Inventors: Diane M. Ruezinsky, Woodland, CA (US); Kristen A. Bennett, Davis, CA (US); Georg Jander, Ithaca, NY (US)

(73) Assignee: Monsanto Technology LLC, St. Louis, MO (US)

( * ) Notice: Subject to any disclaimer, the term of this patent is extended or adjusted under 35 U.S.C. 154(b) by 529 days.

(21) Appl. No.: 10/715,872

(22) Filed: Nov. 17, 2003

(65) Prior Publication Data

US 2005/0005333 A1    Jan. 6, 2005

Related U.S. Application Data

(60) Provisional application No. 60/427,313, filed on Nov. 18, 2002.

(51) Int. Cl.
- C12N 15/09 (2006.01)
- C12N 15/29 (2006.01)
- C12N 15/82 (2006.01)
- A01H 5/00 (2006.01)
- A01H 5/10 (2006.01)

(52) U.S. Cl. .............. 800/306; 800/281; 800/286; 800/298; 800/312; 800/320.1; 536/23.1; 536/23.6; 435/320.1; 426/630

(58) Field of Classification Search .......... 536/23.1, 536/23.2, 23.6; 800/278, 281, 282, 286, 800/287, 306, 312, 320.1, 298; 426/630
See application file for complete search history.

(56) References Cited

FOREIGN PATENT DOCUMENTS

| WO | WO99/00501 | * | 6/1998 |
|----|------------|---|--------|
| WO | WO99/00501 |   | 1/1999 |

OTHER PUBLICATIONS

Walker A. et al. The Plant Cell; vol. 11, pp. 1337-1349.*

Dong et al., "Functional Conservation of Plant Secondary Metabolic Enzymes Revealed by Complementation of *Arabidopsis* Flavonoid Mutants With Maize Genes," *Plant Physiol.*, 127:46-57 (2001).
Jander et al., "*Arabidopsis* Map-Based Cloning in the Post-Genome era", *Plant Physiol.*, 129:440-450 (2002).
Lee et al., "WEREWOLF, a MYB-Related Protein in *Arabidopsis*, is a Position-Dependent Regulator of Epidermal Cell Patterning," *Cell*, 99:473-483 (Nov. 24, 1999).
Napoli et al., "Introduction of a Chimeric Chalcone Synthase Gene into Petunia Results in Reversible Co-Suppression of Homologous Genes *in trans,*" *Plant Cell*, 2:279-289 (1990).
Nesi et al., "The TRANSPARENT TESTA16 Locus Encodes the *Arabidopsis* BSISTER MADS Domain Protein and is Required for Proper Development and Pigmentation of the Seed Coat," *Plant Cell*, 14:2463-2479 (2002).
Smith et al., "Gene Expression: Total Silencing by Intron-spliced Hairpin RNAs," *Nature*, vol. 407, 319-320 (2000).
Walker et al., "The *TRANSPARENT TESTA GLADRA1* Locus, Which Regulates Trichome Differentiation and Anthocyanin Biosynthesis in *Arabidopsis*, Encodes a WD40 Repeat Protein," *Plant Cell*, 11:1337-1349 (1999).
NCBI General Identifier No. 166669, Accession No. M20308.
NCBI General Identifier No. 5123715, Accession No. AJ133743.
Blount et al., "Altering Expression of Cinnamic Acid 4-Hydrosylase in Transgenic Plants Provides Evidence for a Feedback Loop at the Entry Point into the Phenylpropanoid Pathway", Plant Physiology, 122:107-116, 2000.
Sewalt et al., "Reduced Lignin Content and Altered Lignin Composition in Transgenic Tobacco Down-Regulated in Expression of L-Phenylalanine Ammonia-Lyase or Cinnamate 4-Hydroxylase", Plant Physiol., 115:41-50, 1997.
Carey et al., NCBI General Identifier No. 37544702, Accession No. AY115485.

* cited by examiner

Primary Examiner—Russell P. Kallis
(74) Attorney, Agent, or Firm—Fulbright & Jaworski L.L.P.

(57) ABSTRACT

The present invention provides methods and compositions relating to generating plants having increased levels of oil and protein. This invention further provides recombinant expression cassettes, host cells, transgenic plants and genetically altered plants. The invention further provides isolated polynucleotides and their encoded proteins that are involved in phenylpropanoid biosynthesis.

22 Claims, 6 Drawing Sheets

```
        1                                                           50
Col   MVAVERVESL AKSGIISIPK EYIRPKEELE SINDVFLEEK KEDGPQVPTI
Ler   MVAVERVESL AKSGIISIPK EYIRPKEELE SINDVFLEEK KEDGPQVPTI
oil4  MVAVERVESL AKSGIISIPK EYIRPKEELE SINDVFLEEK KEDGPQVPTI 51                                                          100
Col   DLKNIESDDE KIRENCIEEL KKASLDWGVM HLINHGIPAD LMERVKKAGE
Ler   DLKNIESDDE KIRENCIEEL KKASLDWGVM HLINHGIPAD LMERVKKAGE
oil4  DLKNIESDDE KIRENCIEEL KKASLDWGVM HLINHGIPAD LMERVKKAGE 101                                                         150
Col   EFFSLSVEEK EKYANDQATG KIQGYGSKLA NNASGQLEWE DYFFHLAYPE
Ler   EFFSLSVEEK EKYANDQATG KIQGYGSKLA NNASGQLEWE DYFFHLAYPE
oil4  EFFSLSVEEK EKYANDQATG KIQGYGSKLA NNASGQLEWE DYFFHLAYSE 151                                                         200
Col   EKRDLSIWPK TPSDYIEATS EYAKCLRLLA TKVFKALSVG LGLEPDRLEK
Ler   EKRDLSIWPK TPSDYIEATS EYAKCLRLLA TKVFKALSVG LGLEPDRLEK
oil4  EKRDLSIWPK TPSDYIEATS EYAKCLRLLA TKVFKALSVG LGLEPDRLEK 201                                                         250
Col   EVGGLEELLL QMKINYYPKC PQPELALGVE AHTDVSALTF ILHNMVPGLQ
Ler   EVGGLEELLL QMKINYYPKC PQPELALGVE AHTDVSALTF ILHNMVPGLQ
oil4  EVGGLEELLL QMKINYYPKC PQPELALGVE AHTDVSALTF ILHNMVPGLQ 251                                                         300
Col   LFYEGKWVTA KCVPDSIVMH IGDTLEILSN GKYKSILHRG LVNKEKVRIS
Ler   LFYEGKWVTA KCVPDSIVMH IGDTLEILSN GKYKSILHRG LVNKEKVRIS
oil4  LFYEGKWVTA KCVPDSIVMH IGDTLEILSN GKYKSILHRG LVNKEKVRIS 301                                                         350
Col   WAVFCEPPKD KIVLKPLPEM VSVESPAKFP PRTFAQHIEH KLFGKEQEEL
Ler   WAVFCEPPKD KIVLKPLPEM VSVESPAKFP PRTFAQHIEH KLFGKEQEEL
oil4  WAVFCEPPKD KIVLKPLPEM VSVESPAKFP PRTFAQHIEH KLFGKEQEEL 351
Col   VSEKND     [SEQ ID NO: 124]
Ler   VSEKND     [SEQ ID NO: 125]
oil4  VSEKND     [SEQ ID NO: 126]
```

Figure 3

```
                           SEQUENCE LISTING

<160> NUMBER OF SEQ ID NOS: 176

<210> SEQ ID NO 1
<211> LENGTH: 341
<212> TYPE: PRT
<213> ORGANISM: Arabidopsis thaliana

<400> SEQUENCE: 1

Met Asp Asn Ser Ala Pro Asp Ser Leu Ser Arg Ser Glu Thr Ala Val
1               5                   10                  15

Thr Tyr Asp Ser Pro Tyr Pro Leu Tyr Ala Met Ala Phe Ser Ser Leu
            20                  25                  30

Arg Ser Ser Gly His Arg Ile Ala Val Gly Ser Phe Leu Glu Asp
        35                  40                  45

Tyr Asn Asn Arg Ile Asp Ile Leu Ser Phe Asp Ser Asp Ser Met Thr
    50                  55                  60

Val Lys Pro Leu Pro Asn Leu Ser Phe Glu His Pro Tyr Pro Pro Thr
65                  70                  75                  80

Lys Leu Met Phe Ser Pro Pro Ser Leu Arg Arg Pro Ser Ser Gly Asp
                85                  90                  95

Leu Leu Ala Ser Ser Gly Asp Phe Leu Arg Leu Trp Glu Ile Asn Glu
            100                 105                 110

Asp Ser Ser Thr Val Glu Pro Ile Ser Val Leu Asn Asn Ser Lys Thr
        115                 120                 125

Ser Glu Phe Cys Ala Pro Leu Thr Ser Phe Asp Trp Asn Asp Val Glu
    130                 135                 140

Pro Lys Arg Leu Gly Thr Cys Ser Ile Asp Thr Thr Cys Thr Ile Trp
145                 150                 155                 160

Asp Ile Glu Lys Ser Val Val Glu Thr Gln Leu Ile Ala His Asp Lys
                165                 170                 175

Glu Val His Asp Ile Ala Trp Gly Glu Ala Arg Val Phe Ala Ser Val
            180                 185                 190

Ser Ala Asp Gly Ser Val Arg Ile Phe Asp Leu Arg Asp Lys Glu His
        195                 200                 205

Ser Thr Ile Ile Tyr Glu Ser Pro Gln Pro Asp Thr Pro Leu Leu Arg
    210                 215                 220

Leu Ala Trp Asn Lys Gln Asp Leu Arg Tyr Met Ala Thr Ile Leu Met
225                 230                 235                 240

Asp Ser Asn Lys Val Val Ile Leu Asp Ile Arg Ser Pro Thr Met Pro
                245                 250                 255
```

```
Val Ala Glu Leu Glu Arg His Gln Ala Ser Val Asn Ala Ile Ala Trp
            260                 265                 270

Ala Pro Gln Ser Cys Lys His Ile Cys Ser Gly Gly Asp Asp Thr Gln
        275                 280                 285

Ala Leu Ile Trp Glu Leu Pro Thr Val Ala Gly Pro Asn Gly Ile Asp
    290                 295                 300

Pro Met Ser Val Tyr Ser Ala Gly Ser Glu Ile Asn Gln Leu Gln Trp
305                 310                 315                 320

Ser Ser Ser Gln Pro Asp Trp Ile Gly Ile Ala Phe Ala Asn Lys Met
                325                 330                 335

Gln Leu Leu Arg Val
            340

<210> SEQ ID NO 2
<211> LENGTH: 1405
<212> TYPE: DNA
<213> ORGANISM: Glycine max

<400> SEQUENCE: 2
acatttttga tcttccttcc tctgaaacaa gaaccaaaat ggagaattcg accgaagaat      60
cccatctccg atcggaaaac tccgtcactt acgagtcccc ttaccctatc tacggcatgt     120
cattctcccc ctcccacccc caccgcctcg ccctcggcag cttcatcgaa gaatacaaca     180
accgcgtcga catcctctct ttccaccctg acacccttc ggtaactccc cacccttctc     240
tctccttcga ccaccttac cctcccacca aactcatgtt ccaccccgc aaaccctccc     300
cttcctcttc ctccgacctc ctcgccacct ccggcgacta cctccgcctc tgggagatcc     360
gtgataactc cgtggatgcc gtctccctct caacaacag caagaccagc gagttctgcg     420
cccccttaac ctctttcgac tggaacgaca tcgaccccaa ccgcatcgcc acctccagca     480
tcgacaccac ctgcaccatc tgggacatcg aacgcaccct cgtcgaaacc caactcatcg     540
ctcacgacaa ggaggtttac gacatcgcct ggggagaggc cagagtcttc gcctccgtct     600
ccgccgacgg ctccgttaga atcttcgacc ttcgcgacaa ggagcactcc accatcatct     660
acgagagccc ccaccctgac accccttgc tccgcttggc ttggaacaaa caggacctga     720
ggtacatggc caccatttta atggacagta ataaagttgt gattttggat attaggtctc     780
ccactacccc tgttgcggag ttagagaggc accgtgggag tgtgaacgcc attgcttggg     840
ctcctcatag ctccacgcat atttgttctg ctggtgatga tactcaggct cttatttggg     900
aattgcccac gcttgcttct cccactggga ttgatcccgt ctgcatgtac tctgctggct     960
gtgaaattaa ccagctgcag tggtccgccg cccagcccga ttggattgcc attgcttttg    1020
ccaacaagat gcagcttttg aaggtttgag gtcagaacaa acaattacac attctagcca    1080
cttcattgtg gcatagacat agcaacttct gatcacttga gtgactgagt tatatatatt    1140
attgtagttg tgcaaactag tttgccctcc tcatgtttta cttgtggcga aattaacgat    1200
gttcaatttg tctgttaaag atggattttt aacctgttgt gaagtaagat ttcttgtctg    1260
tgatgtggaa gccatagcta ttagtttctt agttaacatg agaaatcaca tgtagtatgt    1320
ggaatcaatt accacacatc cagattatag gtcgtaaaat cttcagtgtt tgtattccca    1380
tttgatttta aacaccctac ctctg                                            1405

<210> SEQ ID NO 3
<211> LENGTH: 1184
<212> TYPE: DNA
<213> ORGANISM: Zea mays
```

<400> SEQUENCE: 3

| | | | | | |
|---|---|---|---|---|---|
| ccggccggga | acggcacaac | ctcagtcctc | agcccggcga | gccgccgccc | gcatcgttca | 60 |
| accccccgtgc | ccggccgccg | tttacctacc | gctcgcacgc | gcgcgtcgct | ccttttatca | 120 |
| cctctcaagt | cccagcagga | tcggcccccg | cgcagcttcg | ccccacatc | tatcgacccg | 180 |
| aattctccac | tcaatggacc | cacccaagcc | gccgtcctcg | gtcgcctcgt | cgtcggggcc | 240 |
| ggagacgccg | aacccgcacg | ccttcacctg | cgagctcccg | cactcgatct | acgcgctcgc | 300 |
| cttctccccc | gtcgcgcccg | tcctcgcctc | cggcagcttc | ctcgaggacc | tccacaaccg | 360 |
| cgtctccctg | ctctccttcg | accccgtccg | cccctccgcc | gcctccttcc | gcgccctccc | 420 |
| ggcgctctcc | ttcgaccacc | cttacccacc | caccaagctc | cagttcaacc | ccgcgccgc | 480 |
| cgcgccgtcc | ctcctcgcct | cctccgccga | cacgctccgc | atctggcaca | ccccgctcga | 540 |
| cgacctctcc | gacaccgccc | ccgcgcccga | gctccgctcc | gttctcgaca | accgcaaggc | 600 |
| ctcctccgag | ttctgcgcac | ccctcacctc | cttcgattgg | aacgaggtcg | agcccgccg | 660 |
| tatcgggacc | gcctccatcg | acaccacctg | caccgtctgg | gacatcgatc | gcggggtcgt | 720 |
| ggagacgcag | ctcatcgcgc | acgacaaggc | cgtgcacgac | atcgcctggg | gggaggccgg | 780 |
| ggtcttcgcc | tccgtatcgg | ccgacggctc | cgtccgcgtc | ttcgaccttc | gggacaagga | 840 |
| gcactccacc | atcgtctacg | agagccccg | ccccgacacg | ccgctactaa | ggctggcgtg | 900 |
| gaaccgctct | gacctccgct | atatggccgc | gctgctcatg | gacagcagcg | ccgtcgtcgt | 960 |
| gctcgacata | cgtgcgcccg | gggtgccggt | ggccgagctg | caccggcacc | gggcgtgcgc | 1020 |
| caacgcagtc | gcgtgggcgc | cgcaagccac | taggcacctc | tgttcggctg | gggacgacgg | 1080 |
| gcaagcattg | atctgggaac | tgcctgagac | ggcggcggct | gtacccgccg | aggggattga | 1140 |
| tcctgtgcta | gtgtacgatg | caggcgccga | aataaaccaa | cttc | | 1184 |

<210> SEQ ID NO 4
<211> LENGTH: 2330
<212> TYPE: DNA
<213> ORGANISM: Zea mays

<400> SEQUENCE: 4

| | | | | | |
|---|---|---|---|---|---|
| gccggccggg | gtcgggatta | agactagcta | actagcgtga | attagctcct | ccgacgacta | 60 |
| ctagctctcg | cttgctccga | cgacgacccc | tgccggtaaa | aaaaaaaaa | aaaaaaaaa | 120 |
| aaaaaaaaa | aaaaaaaaa | aaaaccccc | atacttggat | tgggggcccc | ccggcggggc | 180 |
| ggggacacca | cagctcccac | acacagcagg | cagcagctcg | atcgctagct | cctccgaacc | 240 |
| ggaaagccaa | gccgctttg | gcgatcgtgc | ttgcttgctt | ggttccttca | attcctgccg | 300 |
| gagccagcga | gagctagctg | ctgctgtcgc | gtggtagacg | tcgtcttgcc | agcgagagcc | 360 |
| tagctcgatc | ggtctctctg | gtacaacgta | gggagaaaga | tcgaggggga | gaggacgacg | 420 |
| acgatggccg | gcgcgaccgt | gaccgtggag | gaggtgagga | aggcccagcg | cgccaccggc | 480 |
| cccgccaccg | tgctggcgat | cggcaccgcc | acgcccgcca | actgcgtgta | ccaggccgac | 540 |
| tacccggact | actacttccg | gatcaccaag | agcgagcacc | tcaccgacct | caaggagaaa | 600 |
| ttcaaggaga | tgtgcgacaa | gtcgatgatc | cggaagcgtt | acatgcacct | gacggaggag | 660 |
| ttcctggcgg | agaacccgag | catgtgcgcg | tacatggcgc | cgtcgctgga | cgcgcggcag | 720 |
| gacgtggtgg | tggtggaggt | gccgaagctg | ggaaggcgg | cggcgcagaa | ggcgatcaag | 780 |
| gagtgggggc | agccaaagtc | gcggatcacg | cacctggtgt | tctgcaccac | gtccggggtg | 840 |

```
gacatgccgg gcgccgacta ccagctgacc aaggcgctgg gcctgcgccc ctccgtgaac      900
cgcctcatga tgtaccagca ggggtgcttc gcgggcggca cggtgctgcg cgtggccaag      960
gacctcgcgg agaacaaccg cggcgcgcgg gtgctggtgg tgtgctccga gatcacggcc     1020
gtcacgttcc gcggcccctc cgagtcgcac ctcgactcgc tcgtgggcca ggcgctgttc     1080
ggcgacggcg cggcggccgt ggtcgtgggc gccgacccgg acgaccgcgt cgagcgcccg     1140
ctcttccagc tagtctccgc cgcccagacc atcctgcccg actcggaggg cgccatcgac     1200
ggccacctcc gcgaggtggg gctcaccttc cacctgctca aggacgtgcc tgggctcatc     1260
tccaagaaca tcggccgcgc gctggacgac gcgttcaagc cgctcggcat ctccgactgg     1320
aactccatct tctgggtggc cacccccggc gggcccgcca tcctcgacca ggtggaggcc     1380
aaggtcgggc tggacaaggc caggatgcgc gccacccgcc acgtcctctc cgagtacggc     1440
aacatgtcca gcgcctgcgt cctcttcatc ctcgacgaga tgcgcaagcg ctccgccgag     1500
gacggacagg ccaccacggg cgagggcctc gactggggcg tcctcttcgg cttcggcccg     1560
ggactcaccg tcgagaccgt cgtgctccac agcgtcccca tcaccaccgg agcggccacc     1620
gcctgattca tcgattcatc aacgatcaaa ttcctcccct ctccgatcca attcgtcgtc     1680
gtctcgttcg tcattatttt acgtcgtccg tccgcaaata ataatgtgct ctctgctata     1740
attgtcgtgt gtagtagtaa gtagctgtta ctatttttcc atgtactgtc agtcgcacaa     1800
tcatcatata taattaatat ctctatatat gcatttcatg caagaccagg gtagagagct     1860
agcttgagga gaagacccctt atcgttgtca ctttagcatg catggggtgg tgaggtattg     1920
ggtatacctg tgtaagacaa gcttggctgg tttaattata tattttttt aaaaaaaaa       1980 aaaaaaaaa aaaaaaaaaa aaaaaaaaaa aaaaaaaaa aaaaaaaaa aaccctaaaa        2040 aaaaaaaaa aaggggcggc cgttttaaag acccaagtt aacttccccg ggctggcaag       2100
gtaatagctt tttttgggg cccccaaatt caatttcagg gcccgcggtt taacaccgtg      2160
gggacgggaa accccgggg gtacccaact taattggctt ggaagaactt cccctttggg     2220
caagttgggt tattaccaaa aaggcccgca ccgttcgcct ttcccaacat tggcccaacc     2280
ctaatgggca atgggaacgc ccccctgtag gggcgcttaa accccgcgga               2330
```

<210> SEQ ID NO 5
<211> LENGTH: 1932
<212> TYPE: DNA
<213> ORGANISM: Zea mays
<220> FEATURE:
<221> NAME/KEY: misc_feature
<222> LOCATION: (10)..(10)
<223> OTHER INFORMATION: n = unknown

<400> SEQUENCE: 5

```
aggtaccccn ccgggaaaaa aaccgggcaa aaaaaaaaaa aaaacccggg cgggcgccca       60
caccacagct cccacacaca cagcaggcag cagcacagcc cacagctcga tcgctcctcc      120
gaaccggaaa gccaagccgc tttggcgatc gtgcgtcttg cttggttcct gccggccgga      180
gccagcgaga gctagctagc tgctgctgtc gtggtagacg tcttgccgca cgcacgccta      240
gctcggtctc tctggtacaa cgtagggagg acgccgacga cgacgatggc cggcgcgacc      300
gtgaccgtgg aggaggtgag gaaggcccag cgcgccaccg ccccgccac cgtgctggcg      360 atcggcaccg ccacgccgc caactgcgtg taccaggccg actacccgga ctactacttc      420
cggatcacca agagcgagca cctcaccgac ctcaaggaga aattcaagag gatgtgcgac      480
aagtcgatga tccggaagcg ttacatgcac ctgacggagg agttcctggc ggagaacccg      540
```

```
agcatgtgcg cgtacatggc gccgtcgctg gacgcgcggc aggacgtggt ggtggtggag    600
gtgccgaagc tggggaaggc ggcggcgcag aaggcgatca aggagtgggg gcagcccaag    660
tcgcggatca cgcacctggt gttctgcacc acgtccgggg tggacatgcc gggcgccgac    720
taccagctga ccaaggcgct gggcctgcgc ccctccgtga accgcctcat gatgtaccag    780 cagggggtgct cgcgggcgg gacggtgctg cgcgtggcca aggacctggc ggagaacaac    840
cgcggcgcgc gggtgctggt ggtgtgctcc gagatcacgg ccgtcacgtt ccgcggcccc    900
tccgagtcgc acctcgactc gctcgtgggc caggcgctgt tcggcgacgg cgcggcggcc    960
gtggtcgtgg gcgccgaccc ggacgaccgc gtcgagcgcc cgctcttcca gctcgtctcc   1020
gccgcccaga ccatcctgcc cgactcggag ggcgccatcg acggccacct ccgcgaggtg   1080
gggctcacct tccgcctgct caaggacgtg cccgggctca tctccaagaa catcggccgc   1140
gcgctggacg acgcgttcaa gccgctcggc atctccgact ggaactccat cttctgggtg   1200
gcgcaccccg gcgggcccgc cattctggac caggtggagg ccaaggtcgg gctggacaag   1260
gccaggatgc gcgccacccg ccacgtcctc tccgagtacg gcaacatgtc cagcgcctgc   1320
gtcctcttca tcctcgacga gatgcgcaag cgctccgccg aggacggaca ggccaccacg   1380
ggcgagggcc tcgactgggg cgtcctcttc ggcttcggcc cgggactcac cgtcgagacc   1440
gtcgtgctcc acagcgtccc catcaccacc ggagcggcca ccgcctgatt catcatcaac   1500
gatccaattc gtcgtcgtct cgttcgtcat tattttacgt cgtccgtccg caaataataa   1560
tgtgctctct gctataattg tcgtgtgtag taagtagctg atactatttt tccatgtact   1620
gtcagtcgca caatcatcat atataatatc tctatatatg catttcatgc aagaccaggg   1680
tagagctagc ttgaggagaa daccottatc gttgtcactt tagcatgcat ggggtggtga   1740
ggtattgggt atacctgtgt aagacaagct tggctggttt aattatatat ttttttaaaa   1800
aaatctgttt gctacaaaaa aaaaacctgt aatgtgcatg gtgatggcaa attggccgcc   1860
attttcagtg cacctaaagc tgtattggat aaatgcttct actcgattat tgattgtaag   1920
aggtccactg tt                                                       1932

<210> SEQ ID NO 6
<211> LENGTH: 1734
<212> TYPE: DNA
<213> ORGANISM: Zea mays

<400> SEQUENCE: 6
cccacgcgtc cgcgactact ggctctcgct tgctccggcg acccagaaag agctaggcta     60
tagccaccga cgacccctgc cggccgcctc tggtacaacg tacgtagaga gagagagaaa    120
gagagacgat cgtcgatggc cggcgccacc gtgaccgtgg acgaggtgag aagggccag    180 cgcgccagcg gccccgccac cgtgctggcc atcgggacgg ccacgcccgc caactgcgtg    240
taccaggccg actacccgga ctactacttc cggatcacca agagcgacca cctcaccgac    300
ctcaaggaga agttcaagag gatgtgcgac aagtcgatga tccggaagcg gtacatgcac    360
ctgacggagg agttcctgtc ggagaacccg agcatgtgcg cgtacatggc gccgtcgctg    420
gacgcgcggc aggacgtggt ggtgacggag gtgccgaagc tggggaaggc ggcggcgcag    480
aaggcgatca aggagtgggg gcagcccaag tcgcggatca cgcacctggt gttctgcacc    540
acgtcggggg tggacatgcc gggcgccgac taccagctga ccaaggcgct ggggctgcgc    600
ccgtccgtga accgcctgat gatgtaccag cagggggtgct cgcgggcgg cacggtgctg    660
```

| | |
|---|---:|
| cgcgtggcca aggacctggc ggagaacaac cgcggggcga gggtcctggt ggtgtgctcg | 720 |
| gagatcacgg ccgtgacgtt ccggggcccc tccgagtcgc acctggactc gctcgtgggg | 780 |
| caggcgctgt tcggcgacgg cgcggcggcc gtcgtggtgg gcgccgaccc ggacgggcgg | 840 |
| gtcgagcgcc cgctgttcca gctcgtgtcg gcggcgcaga ccatcctgcc cgactcggag | 900 |
| ggcgccatcg acggccacct ccgcgaggtg gggctgacgt tccacctgct caaggacgtg | 960 |
| cccgggctca tctccaagaa catcgagcgc gcgctggagg acgcgttcaa gccgctcggc | 1020 |
| atctccgact ggaactccat cttctggggtg gcgcacccccg gcgggcccgc catcctggac | 1080 |
| caggtggagg ccagggtcgg gctggacaag gccaggatgc gcgccacccg ccacgtcctc | 1140 |
| tccgagtacg gcaacatgtc cagcgcctgc gtgctcttca tcctcgacga gatgcgcaag | 1200 |
| cgctccgccg aggacggcca ggccaccacc ggcgaggggc tcgactgggg cgtcctcttc | 1260 |
| ggcttcggcc cgggcctcac cgtcgagacc gtcgtgctcc acagcgtccc catcaccacc | 1320 |
| ggagcgccca ccgccgcctg agtcgtccat ctatcctcgc gatcgctcca gagacatgaa | 1380 |
| cgacccgacc tacgaataat gtatctgcgt aattaatttc tatctgtgtt gtgtcctagt | 1440 |
| agctgttaag taccgttttta aaacccctta attaatttta ttatgggtga gctagctcaa | 1500 |
| gagtggagtc ataaaaccgc atggatggtg aggtattgta tagtacctgt gtaagacaag | 1560 |
| cttggctggt tttttatttt atatttaat ctgtttgctc aagacaaaac aaaaaatgaa | 1620 |
| ttgttgagct gtcattaatt tgcagtgcac cagctcaagt tggttgtact cctatcctat | 1680 |
| gtatgaatga aatcccttct agtagtatct aaaaaaaaaa aaaaaaaaaa aaaa | 1734 |

<210> SEQ ID NO 7
<211> LENGTH: 1825
<212> TYPE: DNA
<213> ORGANISM: Zea mays

<400> SEQUENCE: 7

| | |
|---|---:|
| ccggccggga tcagacggat tcacagctcg caggacctga accacttgag aacctgccag | 60 |
| ctagctaacc aaccggcgga gtcaagaaca aggaagagac acttgccccg tccaggtaac | 120 |
| tatgtgcaac tccagacgtc atagtccgct gggcgcgtga aagagctcct ccgacgacta | 180 |
| ctggctctcg cttgctccgg cgacccagaa agagctaggc tatagccacc gacgaccccct | 240 |
| gccggccgcc tctggtacaa cgtacgtaga gagagagaga aagagagacg atcgtcgatg | 300 |
| gccggcgcca ccgtgaccgt ggacgaggtg aggaagggcc agcgcgccag cggccccgcc | 360 |
| accgtgctgg ccatcgggac ggccacgccc gccaactgcg tgtaccaggc cgactacccg | 420 |
| gactactact tccggatcac caagagcgac cacctcaccg acctcaagga gaagttcaag | 480 |
| aggatgtgcg acaagtcgat gatccggaag cggtacatgc acctgacgga ggagttcctg | 540 |
| tcggagaacc cgagcatgtg cgcgtacatg gcgccgtcgc tggacgcgcg caggacgtg | 600 |
| gtggtgacgg aggtgccgaa gctggggaag gcggcggcgc agaaggcgat caaggagtgg | 660 |
| gggcagccca gtcgcggat cacgcacctg gtgttctgca ccacgtcggg ggtggacatg | 720 |
| ccgggcgccg actaccagct gaccaaggcg ctggggctgc gccgtccgt gaaccgcctg | 780 |
| atgatgtacc agcaggggtg cttcgcgggc ggcacggtgc tgcgcgtggc caaggacctg | 840 |
| gcggagaaca accgcgggc gagggtcctg gtggtgtgct cggagatcac ggccgtgacg | 900 |
| ttccggggcc cctccgagtc gcacctggac tcgctcgtgg ggcaggcgct gttcggcgac | 960 |
| ggcgcggcgg ccgtcgtggt gggcgccgac cggacgggcg ggtcgagcg cccgctgttc | 1020 |
| cagctcgtgt cggcggcgca gaccatcctg cccgactcgg agggcgccat cgacggccac | 1080 |

```
ctccgcgagg tgggctgac gttccacctg ctcaaggacg tgcccgggct catctccaag    1140
aacatcgagc gcgcgctgga ggacgcgttc aagccgctcg gcatctccga ctggaactcc    1200
atcttctggg tggcgcaccc cggcgggccc gccatcctgg accaggtgga ggccagggtc    1260
gggctggaca aggccaggat gcgcgccacc cgccacgtcc tctccgagta cggcaacatg    1320
tccagcgcct gcgtgctctt catcctcgac gagatgcgca agcgctccgc cgaggacggc    1380
caggccacca ccggcgaggg gctcgactgg ggcgtcctct tcggcttcgg cccgggcctc    1440
accgtcgaga ccgtcgtgct ccacagcgtc cccatcacca ccggagcgcc caccgccgcc    1500
tgagtcgtcc atctatcctc gcgatcgctc cagagacatg aacgacccga cctacgaata    1560
atgtatctgc gtaattaatt tctatctgtg ttgtgtccta gtagctgtta agtaccgttt    1620
taaaaaccct taattaattt tattatgggt gagctagctc aagagtggag tcataaaacc    1680
gcatggatgg tgaggtattg tatagtacct gtgtaagaca agcttggctg gttttttatt    1740
ttatatttta atctgtttgc tcaagacaaa aaaaaaaaaa aaaaaaaaaa aaaaaaaaa     1800 aaaaaaaaaa aaaaaaaaaa aaaaa                                         1825

<210> SEQ ID NO 8
<211> LENGTH: 1617
<212> TYPE: DNA
<213> ORGANISM: Zea mays

<400> SEQUENCE: 8
gggtacctcg aggccgggtc gccggccggg ggttaagact agctaactag cgtgaaagag     60
ctcctccgac gactactagc tctcgcttgc tccgacgacc cctgccggcc gcctctggta    120
caacgtacga gaggaagaga gacgatcgat ggccggcgcc accgtgaccg tggacgaggt    180
gaggaagggc cagcgcgcga ccggccccgc caccgtgctg ccatcgggga cggcgacgcc    240
cgccaactgc gtgtaccagg ccgactaccc ggactactac ttccggatca ccaagagcga    300
ccacctcacc gacctcaagg agaagttcaa gaggatgtgc gacaagtcga tgatccggaa    360
gcggtacatg cacctgacgg aggagttcct gtcggagaac ccgagcatgt gcgcgtacat    420
ggcgccgtcg ctggacgcgc ggcaggacgt ggtggtgacg gaggtgccga agctggggaa    480
ggcggcggcg cagaaggcga tcaaggagtg ggggcagccc aagtcgcgga tcacgcacct    540
ggtgttctgc accacgtcgg gggtggacat gccgggcgcc gactaccagc tgaccaaggc    600
gctggggctc cgcccgtccg tgaaccgcct gatgatgtac cagcagggt gcttcgcggg    660 cggcacggtg ctgcgcgtgg ccaaggacct ggcggagaac aaccgcgggg cgagggtcct    720
ggtggtgtgc tcggagatca cggccgtgac gttccggggc ccctccgagt cgcacctgga    780
ctcgctcgtg gggcaggcgc tgttcggcga cggcgcggcg gccgtcgtgg tgggcgccga    840
cccggacgac cgcgtcgagc gccgctgtt ccagctcgtg tcggcggcgc agaccatcct    900
gcccgactcg gagggcgcca tcgacggcca cctccgcgag gtgggctga cgttccacct    960 gctcaaggac gtgcccgggc tcatctccaa gaacatcgag cgcgcgctgg aggacgcgtt   1020
cgagccgctc ggcatctccg actggaactc catcttctgg gtggcgcacc ccggcgggcc   1080
cgccatcctg gaccaggtgg aggccagggt cgggctggac aaggccagga tgcgcgccac   1140
ccgccacgtc ctctccgagt acggcaacat gtccagcgcc tgcgtgctct tcatcctcga   1200
cgagatgcgc aagcgctccg ccgaggacgg ccaggccacc accggcgagg ggctcgactg   1260
gggcgtcctc ttcggcttcg gcccgggcct caccgtcgag accgtcgtgc tccacagcgt   1320
```

```
cccatcacc accggagcgc ccaccgccgc ctgagtcgtc catcctcgat cgctccagtc    1380
cagacatgaa cgacccggcc tacgaataat gtatctgcgt aattaatttc tatctgtctt    1440
gtgtcctagt agctgttaag taccgtttta aaacccttaa ttaattttat tatgggcgag    1500
ctagctcaag agtggagtca taaaaccgca tggatggtga ggtattgtat agtacatgtg    1560
taagacaagc ttggctggtt ttttatttta atctgtttgc tcaagacaaa acaaaaa       1617
```

<210> SEQ ID NO 9
<211> LENGTH: 1622
<212> TYPE: DNA
<213> ORGANISM: Glycine max

<400> SEQUENCE: 9

```
ccgggccccc ccatgacgcg tacgtattcg gctcgagccc aattcttccc cctccaccca     60
cccagcatat ctctctattc ctatttatta gcacccctca cattaccttg tgtcaccaac    120
tactttgact cctttaccat accattacaa taattatcaa acctaaccag taaaaatggt    180
gaccgtggag gaaatccgca acgctcagcg ttcccatgga cccgccacca tcttggcctt    240
cggcaccgcc acgccgtcca actgcgtctc ccaagccgat taccctgact actacttccg    300
cattaccaac agcgaacaca tgactgatct caaagaaaag ttcaagcgca tgtgtgaaaa    360
gtccatgata aagaagcgat acatgcacct gacggaggag tttctgaaag agaacccgaa    420
catgtgcgag tacatggcgc atcgctgga cgtgagacaa gacgtagtgg tgatggaggt    480
gccgaagctg ggaaaacaag ccgcaacgaa agcgattaag gagtggggtc aaccaaagtc    540
aaagatcaca caccttgtgt tctgcaccac ttcaggcgtg gacatgcccg gagcagatta    600
ccagctcacg aagcttctcg gcctgaggcc tccgtgaag cgcctcatga tgtatcagca    660
gggctgcttc gccggcggca ccgtactccg cctcgcgaag gacctcgccg agaacaacaa    720
gggtgcgagg gtgctcgttg tctgctccga gataaccgcc gtgacgttcc gcggcccctc    780
ggacacgcac ctcgactcgc tcgtgggaca ggcactgttc ggagatggcg ccgcagcgtt    840
gatcatcgga tcagaccccg acccagcagt ggagcggccg atattcgaga tgatatcggc    900
cgcccagaca atcctgcccg actctgacgg tgctatagat gggcaccttc gggaggtggg    960
actcacgttc cacctcttga agatgtgcc cgggatcatc tcgaagaaca ttgagaagag   1020
tcttgttgaa gcttttgagc catcgggat cagcgactgg aactctatct tctggatcgc   1080
acatcccggt ggtccgcgca tcctcgatca agtcgaggag aagctccggc tcaagccgga   1140
gaaactccag tccacccggc atgtgctgag tgagtacgga acatgtcaa gcgcgtgtgt   1200 tttgttcatt ctggatgaaa tgaggaagaa gtctaaggag gaagggaaga gtaccactgg   1260
agaagggtta gagtggggg tgctattcgg attcgggccg ggtctaaccg ttgagaccgt   1320
tgttcttcac agtgttccct tggagggata aatcatgctg atgcggtgac tagtgattta   1380
agagtgatca ataaggaacc ctcggaaata ccagggaaaa tttgttatta ttactagttt   1440
cacttgtgga tttatcgtag cataatgttg tacaagaata atttaatatg aacaagatcg   1500
tgtgtttgtt attgatttt tcaaagttat atagtccgta cttattcggc attgcatttt   1560
aaaaaaaaag gacagagcgg ctctagatct acagagtctc acgcatgcgt gcatgtgaag   1620
tc                                                                   1622
```

<210> SEQ ID NO 10
<211> LENGTH: 1629
<212> TYPE: DNA
<213> ORGANISM: Glycine max

<400> SEQUENCE: 10

```
cgctggtaca ctttagtata ctaatcaact aggatttttt tttttttttt ctaaaacaaa      60
tgcctgttat tgataattag ctaaaaagc caccaaacac gtattattat tttaatataa      120
acgtacacaa acaaactcta acgagtttt ttttttttg gtggttgttg ttgttacaaa      180
ccccaagcaa gtttgaaaag tggtacacaa taatgaaata atatatgagg catctcagat      240
ggccacacta tgcaaaacaa cagtttcaat ggtaagtcca ggtccaaaac cgaacaacac      300
accccattca gtccttcac ctgtggtttt atgtccattt tcagcagatt tcctcctcat       360
ctcatccaag atgaaaagaa cacaagcact tgacatgttc ccatattcac taagcacatc      420
tctagtggcc ttcatcttct caggtttgag acccaacttt tgctcaactt ggtctaaaat      480
cgcaggccca ccagggtgtg caatccaaaa gatggagttg taatcagaga tgttcaatgg      540
gttgaaagcc tcaaaaagtg ccttatcaat gttctttgag acaatcccgg gaacatcctt      600
gaggaggtga atgtgagtc caacttcacg aaggtgtcca tcaatagcac cttcactgtc      660
tggagcaatt gtttgtgcag tccaaacaag ctcatacaaa gcttctcaa cttgtggaat      720
tgggtcagaa ccaacaatga ctgcagcagc tccatctcca aacaatgctt ggcccacaag      780
actatcaagg tgagtgtcac ttggcccacg aatgtgact gcagtgatct cagagcagac       840
aacaagcaca cgtgcaccct tgttgttctc agccaaatcc ttggccaaac gaagaaccgt      900
gccacctgca agcaaccttt gttggtacat catgtacctc ttcacataag ggcgaaggcc      960
caattgtttg gtgagttggt aatcagcacc aggcatgtcc acaccgctag tggtgcagaa     1020
gatcaagtgg gtaatctttg actttggctg gccccactcc tttatggcct ttactgcagc     1080
ctctttccct agctttggta cctctaccac caccatgtct tgcctagcat ccaaagaagg     1140
tgccatgtaa gcacacatgt ttggattctc tttcaagatc tcttcgttta ggtacatata     1200
tctcgtcttg atcatagact tgtcacacat gcgctgaaat ttctctttga gctcggtcat     1260
gtggtcactg ttggtgattc tgaagtagta atcaggatag gtgctctgat caacacggtt     1320
tggtgggttt gcagttccaa tggcaaggat ggttgctggg ccttctgccc tttgtgcctg     1380
cctgatctca gctacgctaa ccatctttcc tgatttcaga taccaatgcg atttgattga     1440
actcaaaaca agtcacagct agcagtagta gagagaatta agctgtggtt ctagtttttg     1500
acctacaatt aggtgtttgt ttttgcgata atttcttact atacaccaac atatacatt      1560
ttccaccgtc tactacgact gtttgttagt ttgtgaccta tgtatgagtt tggcctcgtg     1620
ccgaattcc                                                              1629
```

<210> SEQ ID NO 11
<211> LENGTH: 1397
<212> TYPE: DNA
<213> ORGANISM: Glycine max

<400> SEQUENCE: 11

```
ctttttttc taaaacaaat gcctgttatt gataattagg ctaaaaggcc accaaacacg       60
tattattatt ttaatataaa cgtacacaaa caaactctaa acgagtttt tttttttgg       120
tggttgttgt tgttacaaac cccaagcaag tttgaaaagt gtaagtccag gtccaaaacc     180
gaacaacaca ccccattcaa gtccttcacc tgtggtttta tgtccatttt cagcagattt     240
cctcctcatc tcatccaaga tgaaaagaac acaagcactt gacatgttcc catattcact     300
aagcacatct ctagtggcct tcatcttctc aggtttgaga cccaacttt gctcaacttg     360
```

```
gtctaaaatc gcaggcccac cagggtgtgc aatccaaaag atggagttgt aatcagagat    420
gttcaatggg ttgaaagcct caaaaagtgc cttatcaatg ttctttgaga caatcccggg    480
aacatccttg aggaggtgaa atgtgagtcc aacttcacga aggtgtccat caatagcacc    540
ttcactgtct ggagcaattg tttgtgcagt ccaaacaagc tcatacaaag gcttctcaac    600
ttgtggaatt gggtcagaac caacaatgac agcagcagct ccatctccaa acaatgcttg    660
gcccacaaga ctatcaaggt gagtgtcact tggtccacgg aatgtgactg cagtgatctc    720
agaacagaca acaagcacac gtgcacccct gttgttctca gccaaatcct tggccaaacg    780
aagaaccgtg ccacctgcaa agcaaccttg ttggtacatc atatacctct tcacataggg    840
gcgaaggccc aattgtttgg tcagttggta atcagcacca gcatgtcaa caccactggt     900 ggtgcagaag atcaagtggg taatctttga ctttggctgg ccccactcct ttatggcctt    960
tactgcagcc tctttcccta gctttggtac ctctaccacc accatgtctt gcctagcatc   1020
caaagaaggt gccatgtaag cacacatgtt tggattctct ttcaagatct cttcgtttag   1080
gtacatatat ctcctcttga tcatagactt gtcacacatg cgctggaatt tctctttgag   1140
ctcggtcatg tgctcactgt tggtgattct gaagtagtag tcaggatagg tgctctgatc   1200
aacacagttt ggtgggtttg cagttccaat ggcaaggatg gttgctgggc cttctgccct   1260
ttgtgcctgg cggatctcag ctacgctcac catctttcct tcaaattaag tgatgatatt   1320
cagaaatcaa ttaaagtact gggagctatt tgatcgaact caattacaaa atcagagagg   1380
ttgaaacgaa ggcctcg                                                   1397

<210> SEQ ID NO 12
<211> LENGTH: 1184
<212> TYPE: DNA
<213> ORGANISM: Zea mays

<400> SEQUENCE: 12
ccggccggga acggcacaac ctcagtcctc agcccggcga gccgccgccc gcatcgttca     60 accccgtgc ccggccgccg tttacctacc gctcgcacgc gcgcgtcgct ccttttatca    120
cctctcaagt cccagcagga tcggcccccg cgcagcttcg cccccacatc tatcgacccg    180
aattctccac tcaatggacc cacccaagcc gccgtcctcg gtcgcctcgt cgtcggggcc    240
ggagacgccg aacccgcacg ccttcacctg cgagctcccg cactcgatct acgcgctcgc    300 cttctcccccc gtcgcgcccg tcctcgcctc cggcagcttc ctcgaggacc tccacaaccg    360
cgtctccctg ctctccttcg accccgtccg ccccctccgcc gcctccttcc gcgccctccc    420
ggcgctctcc ttcgaccacc cttacccacc caccaagctc cagttcaacc ccgcgccgc     480 cgcgccgtcc ctcctcgcct cctccgccga cacgctccgc atctggcaca cccgctcga    540 cgacctctcc gacaccgccc ccgcgcccga gctccgctcc gttctcgaca accgcaaggc    600
ctcctccgag ttctgcgcac ccctcacctc cttcgattgg aacgaggtcg agcccgccg    660 tatcgggacc gcctccatcg acaccacctg caccgtctgg gacatcgatc gcgggggtcgt   720 ggagacgcag ctcatcgcgc acgacaaggc cgtgcacgac atcgcctggg ggaggccgg    780 ggtcttcgcc tccgtatcgg ccgacggctc cgtccgcgtc ttcgaccttc gggacaagga    840
gcactccacc atcgtctacg agagccccg ccccgacacg ccgctactaa ggctggcgtg     900
gaaccgctct gacctccgct atatggccgc gctgctcatg gacagcagcg ccgtcgtcgt    960
gctcgacata cgtgcgcccg gggtgccggt ggccgagctg caccggcacc gggcgtgcgc   1020
caacgcagtc gcgtgggcgc cgcaagccac taggcacctc tgttcggctg gggacgacgg   1080
```

```
gcaagcattg atctgggaac tgcctgagac ggcggcggct gtacccgccg agggggattga    1140 tcctgtgcta gtgtacgatg caggcgccga aataaaccaa cttc                       1184
```

<210> SEQ ID NO 13
<211> LENGTH: 1665
<212> TYPE: DNA
<213> ORGANISM: Zea mays

<400> SEQUENCE: 13

```
tgacggcctt cactgcacac tacaatcaat cagccggctt ttcctctctt cccctcgaca      60
gaagccccca aatccgatac cttcccctat ccacctcgag tcccttcctt ccttagcggc     120
ggcgcgaagg cggcggagcc atgggcgag tcggcgaagg tgacgcgtgg gcggatcagg      180
agcagggcaa cggcggggc agccgtggtg ttggcggtgg cggcggcgag gcgaagcggt      240
cggagatcta cacgtacgag gccgcctggc acatctacgc gatgaactgg agcgtgcggc    300
gcgataagaa ataccgcctt gccatcgcca gccttctcga gcaggtcacc aaccgcgtcg    360
aggtcgtcca gctcgatgag gcctcggtg acatcgcccc cgtcctcacc ttcgaccatc      420
agtacccgcc caccaagacc atgttcatgc cggacccgca cgcgctccgc cccgacctgc     480
tcgccacctc cgccgaccac ctgcgcatct ggcgcatccc gtcctccgac gacgccgagg     540
acggcgccgc ctccgccaac aacaacaacg gctccgtccg ctgcaacggc acccagcagc     600
cgggcatcga gctacgctcc gagctcaacg gcaaccgcaa cagcgactac tgcgggccgc     660
tcacctcctt cgactggaac gacgccgatc cgcgccgcat cggtacctcc tccatcgaca     720
ccacctgcac aatctgggac gtcgagcgcg aggccgttga cacccagctc atcgcccacg     780
acaaggaggt ctacgacatc gcctggggcg gcgcgggggc ttttgcctcc gtctccgccg     840
acggctctgt tcgcgtcttt gatttacggg acaaggagca ctccacaatc atttatgagt     900
ctggttcagg tggcagcagc ggcggcggtt ccaactctgg cgccggagat ggtgggactg     960
cgtcccccgac accactcgtg aggttgggct ggaacaagca ggacccaagg tacatggcca    1020
ccatcatcat ggacagcccc aagtggttg tgcttgatat ccgctaccca acactgccag     1080
tggtagagct acaccgtcac catgcccctg tcaatgccat tgcgtgggca cctcactctt    1140
cttgccacat ctgcacagct ggggatgaca tgcaggcact gatatgggat ttgtcgtcta    1200
tgggaactgg tagcaatggc agtggcaatg gaatggtaa cacagccgct ggagcagcag    1260
cagagggcgg tcttgatccc attttggcat atacagcagg ggcagagatt gagcagttgc    1320
agtggtcggc gacccagcct gactgggttg caatcgcatt cgccaataag cttcagattc    1380
tcagggtctg atttcctagt tccaccctgt ttcagtgagg agtaaaaat gctaaacttg     1440
gataatgagc tgatgcccgg aggataatct tgcaattgct ttactgttgc ttatttatgt    1500
tgtggacaac tgatattcat ggcgggttag ttctagaaat agaacagaag actttctagt    1560
tagaagctga attgtcaatg aatttggttt gtagagtaag gaactgctct ggtgttagcg    1620
atggtgataa tgggaactga atttagtttg taataaaaa aaaaa                    1665
```

<210> SEQ ID NO 14
<211> LENGTH: 1479
<212> TYPE: DNA
<213> ORGANISM: Glycine max

<400> SEQUENCE: 14

```
tcagctacta ggcccccccc ccccacaact ctacattttt gatcttcctt cctctgaaac      60
```

-continued

```
aagaaccaaa atggagaatt cgaccgaaga atcccatctc cgatcggaaa actccgtcac      120
ttacgagtcc ccttacccta tctacggcat gtcattctcc ccctcccacc cccaccgcct      180
cgccctcggc agcttcatcg aagaatacaa caaccgcgtc gacatcctct ctttccaccc      240
tgacacccct tcggtaactc cccacccttc tctctccttc gaccacccct accctcccac      300
caaactcatg ttccaccccc gcaaaccctc ccttcctct tcctccgacc tcctcgccac       360
ctccggcgac tacctccgcc tctgggagat ccgtgataac tccgtggatg ccgtctccct      420
cttcaacaac agcaagacca gcgagttctg cgccccctta acctctttcg actggaacga      480
catcgacccc aaccgcatcg ccacctccag catcgacacc acctgcacca tctgggacat      540
cgaacgcacc ctcgtcgaaa cccaactcat cgctcacgac aaggaggtct acgacatcgc      600
atggggagag gccagagtct tcgcctccgt ctccgccgac ggctccgtta gaatcttcga      660
ccttcgcgac aaggagcact ccaccatcat ctacgagagc ccccacccctg acaccccttt     720 gctccgcttg gcttggaaca acaggacct gaggtacatg gccaccattt taatggacag       780
taataaagtt gtgattttgg atattaggtc tcccactacc cctgttgcgg agttagagag      840
gcaccgtggg agtgtgaacg ccattgcttg ggctcctcat agctccacgc atatttgttc      900
tgctggtgat gatactcagg ctcttatttg ggaattgccc acgcttgctt ctcccactgg      960
gattgatccc gtctgcatgt actctgctgg ctgtgaaatt aaccagctgc agtggtccgc     1020
cgcccagccc gattggattg ccattgcttt tgccaacaag atgcagcttt tgaaggtttg     1080
aggtcagaac aaacaattac acattctagc cacttcattg tggcatagac atagcaactt     1140
ctgatcactt gagtgactga gttatatata ttattgtagt tgtgcaaact agtttgccct     1200
cctcatgttt tacttgtggc gaaattaacg atgttcaatt tgtctgttaa agatggattt     1260
ttaacctgtt gtgaagtaag atttcttgtc tgtgatgtgg aagccatagc tattagtttc     1320
ttagttaaca tgagaaatca catgtagtat gtggaatcaa ttaccacaca tccagattat     1380
aggtcgtaaa atcttcagtg tttgtattcc catttgattt taaacaccct acctctgata     1440
tgtatggact atggatctgt attcttgagc ttttgccat                            1479
```

<210> SEQ ID NO 15
<211> LENGTH: 1437
<212> TYPE: DNA
<213> ORGANISM: Glycine max

<400> SEQUENCE: 15

```
acaacacttc cagtgatcat cttctccatc cagaacgaac aaaaatggag aattcgaccc       60
aagaatccca cctccgatcc gaaaactccg tgagctacga atcccctac ccaatctacg      120 gcatgtcgtt ctcccttcc cacccccacc gcctggccct cggcagcttc attgaagaat       180
acaccaaccg cgttgacatc ctctccttcc accccgacac cctctccctc accccaacc      240 cttctctctc ctttgaccac ccttaccctc ccaccaaact catgttccac cccgcaaac      300 cccctcctc ctcctccgac ctcctcgcca ctccggcga ctacctccgc tctgggagg       360 tccgcgacaa ctccgtggag gccgtctccc ttttcaacaa cagcaagacc agcgagttct     420 gcgcccctt aacctccttc gactggaacg atatcgaccc caaccgcatc gccacctcca     480
gcatcgacac cacctgcacc atctgggaca tcgaacgcac cctcgtcgaa acccaactca     540
tcgcgcacga caaagaggt tacgacatcg catggggaga ggccagagtc ttcgcctccg      600
tctccgccga cggctccgtt agaatcttcg acctacgcga caaggagcac tccaccatca     660
tctacgagag cccccacccct gacacccctc tgctccgttt ggcttggaac aaacaggacc    720
```

```
tgaggtacat ggctactatt ttaatggaca gtaataaagt tgtgattttg gatattaggt      780
ctcccactac ccctgttgcg gagttagaga ggcaccgtgg gagtgtgaac gctattgctt      840
gggctcctca tagttccacg catatttgtt ctgctggga tgatactcag gctcttattt       900
gggatttgcc cactctggct ctccccactg ggattgatcc cgtgtgtatg tattctgctg      960
gctgtgaaat taaccagctg cagtggtctg ccgtgcagcc cgaatggatt gccattgctt     1020
ttgccaacaa gatgcagctt tgaaggttt gaggtgagtc gagggagaat aaacacaatt      1080
ctagttactc aaacttgatt gtgggataga taggactcct ttcgcggatg ctgcaacttc     1140
ttagttctcg tggcttgtgt ataagagtga gcgagttagt actatatata atactattgt     1200
agttgttgac tgtaaaatag tttgccctcc tcatgtttta cttgtagcga aattgatgat     1260
caatttgtct gttgaggata gctttagat acatgtatgt cctgttcagg atttaagatt      1320
ccatgtctgt tgatgtggaa gccataacta ttagtttctt agtaaacatg aaaaatcaca     1380
tgtccagatg atagttgtaa aatgttcagt gtatgtatta gcatttgatt gttatta       1437
```

<210> SEQ ID NO 16
<211> LENGTH: 512
<212> TYPE: DNA
<213> ORGANISM: Glycine max

<400> SEQUENCE: 16

```
aaaaaaatcc agacccttag cccatacata taaggggggg ggggttaaaa ataaaagggg       60
aatacaaacc ctgaaaattt taccccctat aatcgggatg ggggaaatg gatcccacat       120 actacagggg atttctaatg taaacaaaaa aactaaaagc tttggtttcc acatcacaaa      180
caaaattttt tatttcaaaa cgggtaaaaa atccttttt aacaaacaaa ttgaacattg       240
ttatttcccc cacaagaaaa acatgggggg ggcaaactat tttgcccacc tccaatattt      300
tttttacctc agcccctcaa gggaccaaaa gttgttttt ttttcccaca atgaaggggc       360
taaaatggga aattgtttgt tttgacctaa aaccttaaaa agctgttttt tgtgggaaaa      420
agcaagggca atccaatggg gctggggggg ggaccactgc agttggttaa tttcacagcc      480
agcaaagtac atgcagacgg gatcaatccc ag                                    512
```

<210> SEQ ID NO 17
<211> LENGTH: 2191
<212> TYPE: DNA
<213> ORGANISM: Glycine max

<400> SEQUENCE: 17

```
ttcccgcccc acgcgttcct gtaccggctt gcgccgacag accgaacaga ttttttttc        60 tttgaaccca ttcccatacc gcaaactcat tgagccagct gcgtttgttc cttcttcagt      120
tgggtttgat tgcgagtgag tgacgatggg cgcgagcagc gaccctaccc aagacggttc      180
cgacgagcag cagaagcgtt cggagatcta cacctacgag gcccctggc acatctacgc       240 catgaactgg agcgtccgcc gcgacaagaa gtaccgcctg gccatcgctt ccctcctgga      300
gcagtatccg aaccgcgtgg agatcgtcca gctcgacgac tccaacggcg agatccgatc      360
cgatccctcc ctctccttcg agcatcccta ccctcccacc aaatccatct tcatccccga      420
caaggactgc caccgcccccg acctcctcgc cacctcctcc gacttcctcc gcgtctggca      480
catctccgaa tcctccgttg aactcaagtc cctcctcaac ggcaacaaga acagcgagta      540
ctgcggcccc ctcacctcct tcgactggaa cgaagccgag cccagaagaa tcggcacctc      600
```

```
cagcatcgac accacctgca ccatctggga cattgagaag gaaaccgtag acacgcaact    660
cattgcgcac gataaagagg tctacgacat cgcctggggc ggcgtcggag tcttcgcctc    720
cgtctccgcc gacggctccg ttagggtttt cgatctccgc gacaaggagc actccactat    780
aatctacgag agctcggagc ctgacacgcc tctggtgcgt ctcgggtgga acaagcagga    840
cccgcggtac atggcgacga taatcatgga cagtgcaaag gtggtggtgt tggacattcg    900
ttttcccacg ctccctgtgg tggagctgca gcggcaccag gcgagtgtga acgcgattgc    960
gtgggccccg catagctcgt gccatatatg cacggccggg gatgattcgc aggcgctgat   1020
ttgggacctt tcttccatgg gtcaacccgt ggagggtggg cttgacccta ttcttgcgta   1080
cactgccgga gcggagattg agcagcttca gtggtcgtct tcgcagcctg attgggtcgc   1140
tattgctttc tccaccaagc ttcagattct tagggtttga aatttgattt cactgaaact   1200
tctgtttccc tgtatgtgca aacgaaaatt ggggatactt tagatttgaa acaaaacac    1260
agttgtattg ttgtttcttt ttattgttga aactaatgct aaccccttgg taatttctgg   1320
ctttgggacg aaagtagttt tgattagggt ttagggcgta aaactagcct tagtttgttt   1380
ctgctaagtt agtctgcaag tattttaaag aaattttccg tcacatcaat attggcttca   1440
atgtcgaggt ttttggatta tctgtggctg cattgtgaag gattgaggcg aaactgcgac   1500
tgatattttg cagtttcgcc gcaattgcgg gaaattgtgg acaaatatgg ctttagagag   1560
tctaaaacct tgatattgtt gtttgtcgca ttcttgttta ctaggaaatg gaatgacctt   1620
gtatgtaaat gtttttgctt cggttttgtc catgtttcct atgtgactct ttaactcaaa   1680
gaaattcact tatgatgcac cacaactgtc cacaagattc gtgttgtgtt tgatgctgtc   1740
taaaaccttg atgttgtttg gcgcattctt gtttgtcgca tttgttgcat tcttgtttaa   1800
taggaaatag cctttgtatg taaatgttgt gacttttgtc catgtttcca ctgtgcctca   1860
ttaactcaaa gaaattcact tatgatgtgc cacaagggtt gtgttgtgtg tttgacattg   1920
actatttgtg gtttggattt tgatggtttt tgcctgagct gtccggtgat tgaatgttat   1980
ggtgcagatc cattgtggct gactccacct agtgggaaaa ggtttggttc ttgttggtgt   2040
ttgttgctta agctgttttg tgttggtttg tctggatgat ggatgcactt gtgtgtgtgt   2100
gtggatgctc tgtatatctta attgtttaat cttttggggg gggggggctg attacgagaa   2160
agctgatcca agagtggtgt cattggagta c                                   2191
```

<210> SEQ ID NO 18
<211> LENGTH: 553
<212> TYPE: DNA
<213> ORGANISM: Glycine max

<400> SEQUENCE: 18

```
caccctgaca ccccttttgct ccgcttggct tggaacaaac aggacctgag gtacatggcc     60
accattttaa tggacagtaa taagttgtg attttggata ttaggtctcc cactacccct    120
gttgcggagt tagagaggca ccgtgggagt gtgaacgcca ttgcttgggc tcctcatagc    180
tccacgcata tttgttctgc tggtgatgat actcaggctc ttatttggga attgcccacg    240
cttgcttctc ccactgggat tgatcccgtc tgcatgtact ctgctggctg tgaaattaac    300
cagctgcagt ggtccgccgc ccagcccgat tggattgcca ttgcttttgc caacaagatg    360
cagcttttga aggtttgagg tcagaacaaa caattacaca ttctagccac ttcattgtgg    420
catagacata gcaacttctg atcacttgag tgactgagtt atatatatta ttgtagttgt    480
gcaaactagt ttgccctcct catgttttac ttgtggcgaa attaacgatg ttcaatttgt    540
```

-continued

```
ctgttaaaga tgg                                                        553

<210> SEQ ID NO 19
<211> LENGTH: 550
<212> TYPE: DNA
<213> ORGANISM: Glycine max
<220> FEATURE:
<221> NAME/KEY: misc_feature
<222> LOCATION: (541)..(541)
<223> OTHER INFORMATION: n = unknown

<400> SEQUENCE: 19
catctgggac atcgaacgca ccctcgtcga acccaactc atcgctcacg acaaggaggt        60
ttacgacatc gcctggggag aggccagagt cttcgcctcc gtctccgccg acggctccgt      120
tagaatcttc gaccttcgcg acaaggagca ctccaccatc atctacgaga gcccccaccc      180
tgacacccct ttgctccgct tggcttggaa caaacaggac ctgaggtaca tggccaccat      240
tttaatggac agtaataaag ttgtgatttt ggatattagg tctcccacta cccctgttgc      300
ggagttagag aggcaccgtg ggagtgtgaa cgccattgct tgggctcctc atagctccac      360
gcatatttgt tctgctggtg atgatactca ggctcttatt tgggaattgc ccacgcttgc      420
ttctcccact gggattgatc ccgtctgcat gtacctctgc tgctgtgaaa ttaaccagct      480
gcagtggtcc gccgcccagc ccgattggat tgccattgct tttgccaaca agatgcagct      540 ntttgaggtt                                                            550

<210> SEQ ID NO 20
<211> LENGTH: 519
<212> TYPE: DNA
<213> ORGANISM: Glycine max

<400> SEQUENCE: 20
tggggagagg ccagagtctt cgcctccgtc tccgccgacg gctccgttag aatcttcgac       60
cttcgcgaca aggagcactc caccatcatc tacgagagcc ccacccctga cacccctttg      120
ctccgcttgg cttggaacaa acaggacctg aggtacatgg ccaccatttt aatggacagt      180
aataaagttg tgattttgga tattaggtct cccactaccc ctgttgcgga gttagagagg      240
caccgtggga gtgtgaacgc cattgcttgg gctcctcata gctccacgca tatttgttct      300
gctggtgatg atactcaggc tcttatttgg gaattgccca cgcttgcttc tcccactggg      360
attgatcccg tctgcatgta ctctgctggc tgtgaaatta accagctgca gtggtccgcc      420
gcccagcccg attggattgc cattgctttt gccaacaaga tgcagctttt gaaggtttga      480
ggtcagaaca acaattaca cattctagcc acttcattg                             519

<210> SEQ ID NO 21
<211> LENGTH: 498
<212> TYPE: DNA
<213> ORGANISM: Glycine max

<400> SEQUENCE: 21
cttccttcct ctgaaacaag aaccaaaatg gagaattcga ccgaagaatc ccatctccga       60
tcggaaaact ccgtcactta cgagtcccct taccctatct acggcatgtc attctccccc      120
tcccaccccc accgcctcgc cctcggcagc ttcatcgaag aatacaacaa ccgcgtcgac      180
atcctctctt tccaccctga cacccttttcg gtaactcccc acccttctct tccttcgac      240 caccctttacc ctcccaggaa actcatgttc caccccgca aaccctcccc ttcctcttcc      300
```

```
tccgacctcc tcgccacctc cggcgactac ctccgcctct gggagatccg tgataactcc    360
gtggatgccg tctccctctt caacaacagc aagaccagcg agttctgcgc cccccttaacc   420 tctttcgact gggacgacat cgaccccaac cgcatcgcca cctccaggat cgacaccacc    480
tgcaccatct gggacatc                                                  498

<210> SEQ ID NO 22
<211> LENGTH: 492
<212> TYPE: DNA
<213> ORGANISM: Glycine max

<400> SEQUENCE: 22
gacacccttt cggtaactcc ccacccttct ctctccttcg accaccctta ccctcccacc    60
aaactcatgt tccaccccg caaacccctcc ccttcctctt cctccgacct cctgccacc    120 tccggcgact acctccgcct ctgggagatc cgtgataact ccgtggatgc cgtctccctc    180
ttcaacaaca gcaagaccag cgagttctgc gccccctaa cctctttcga ctggaacgac    240
atcgacccca accgcatcgc cacctccagc atcgacacca cctgcaccat ctgggacatc    300
gaacgcaccc tcgtcgaaac ccaactcatc gctcacgaca aggaggttta cgacatcgcc    360
tggggagagg ccagagtctt cgcctccgtc tccgccgacg gctccgttag aatcttcgac    420
cttcgcgaca aggaacactc caccatcatc tacgagagcc cccaccctga ccccccttg    480 ctccggcttg gt                                                        492

<210> SEQ ID NO 23
<211> LENGTH: 553
<212> TYPE: DNA
<213> ORGANISM: Glycine max

<400> SEQUENCE: 23
tccagaacga acaaaaatgg agaattcgac ccaagaatcc cacctccgat ccgaaaactc    60
cgtgagctac gaatccccct acccaatcta cggcatgtcg ttctccccctt cccacccca    120 ccgcctggcc ctcggcagct tcattgaaga atacaccaac cgcgttgaca tcctctcctt    180
ccaccccgac ccctctcccc tcacccccaa cccttctctc cctttgacc acccttaccc    240 tcccaccaaa ctcatgttcc accccgcaa accccctcc tcctcctccg acctcctcgc    300
cacctccggc gactacctcc gcctctggga ggtccgcgac aactccgtgg aggccgtctc    360
ccttttcaac aacagcaaga ccagcgagtt ctgcgccccc ttaacctcct tcgactggaa    420
cgatatcgac cccaaccgca tcgccacctc cagcatcgac accacctgca ccatctggga    480
catcgaacgc accctcgtcg aaacccaact catcgcgcac gacaaagagg tctacgacat    540
cgcatgggga gag                                                       553

<210> SEQ ID NO 24
<211> LENGTH: 582
<212> TYPE: DNA
<213> ORGANISM: Glycine max

<400> SEQUENCE: 24 gcctttcaa caacagcaag accagcgagt ctgcgcccc cttaacctcc ttcgactgga     60
acgatatcga cccaaccgc atcgccacct ccagcatcga caccacctgc accatctggg    120
acatcgaacg caccctcgtc gaaacccaac tcatcgcgca cgacaaagag gtctacgaca    180
tcgcatgggg agaggccaga gtcttcgcct ccgtctccgc cgacggctcc gttagaatct    240
tcgacctacg cgacaaggag cactccacca tcatctacga gagcccccac cctgacaccc    300
```

```
ctctgctccg tttggcttgg aacaaacagg acctgaggta catggctact attttaatgg      360
acagtaataa agttgtgatt ttggatatta ggtctcccac taccctgtt gcggagttag       420 agaggcacca aactcatgtt ccaccctcgc atacccgcct actactgctc cgacctgctc      480
gccacctccg gcgactacct ccgcctctgg gatgtccgcg caactccgt ggaggccgtc       540 ttccttttca acaacagcag accagctagt cttgcgcccc tt                        582

<210> SEQ ID NO 25
<211> LENGTH: 378
<212> TYPE: DNA
<213> ORGANISM: Glycine max

<400> SEQUENCE: 25
ggtctcccac taccctgtt gcggagttag agaggcaccg tgggagtgtg aacgccattg       60
cttgggctcc tcatagctcc acgcatattt gttctgctgg tgatgatact caggctctta     120
tttgggaatt gcccacgctt gcttctccca ctgggattga tcccgtctgc atgtactctg     180
ctggctgtga aattaaccag ctgcagtggt ccgccgccca gccgattgg attgccattg      240 cttttgccaa caagatgcag cttttgaagg tttgaggtca gaacaaacaa ttacacattc     300
tagccacttc attgtggcat agacatagca acttctgatc acttgagtga ctgagttata    360
tatattattg tagttgtg                                                   378

<210> SEQ ID NO 26
<211> LENGTH: 360
<212> TYPE: DNA
<213> ORGANISM: Glycine max

<400> SEQUENCE: 26
acgaggtttg cacaactaca ataatatata taactcagtc actcaagtga tcagaagttg     60
ctatgtctat gccacaatga agtggctaga atgtgtaatt gtttgttctg acctcaaacc    120
ttcaaaagct gcatcttgtt ggcaaaagca atggcaatcc aatcgggctg gcggcggac     180 cactgcagct ggttaatttc acagccagca gagtacatgc agacgggatc aatcccagtg    240
ggagaagcaa gcgtgggcaa ttcccaaata agagcctgag tatcatcacc agcagaacaa    300
aatatgcgtg gagctatgag gagccccagc aaatgcgttc acacttccac ggtgcctctc    360

<210> SEQ ID NO 27
<211> LENGTH: 476
<212> TYPE: DNA
<213> ORGANISM: Glycine max

<400> SEQUENCE: 27
cttctccatc cagaacgaac aaaaatggag aattcgaccc aagaatccca cctccgatcc      60
gaaaactccg tgagctacga atccccctac ccaatctacg gcatgtcgtt ctccccttcc    120 caccccacc gcctggccct cggcagcttc attgaagaat acaccaaccg cgttgacatc     180
ctctccttcc accccgacac cctctccctc accccaaccc cttctctctc ctttgaccac    240
ccttaccctc ccaccaaact catgttccac cccgcaaac ccccctcctc ctcctccgac     300
ctcctcgcca cctccggcga ctacctccgc ctctgggagg tccgcgacaa ctccgtggag    360
gccgtctccc ttttcaacaa cagcaagacc agcgagttct gcgccccctt aacctccttc    420
gactggaacg atatcgaccc caaccgcatc gccacctcca gcatcgacac cacctg        476

<210> SEQ ID NO 28
```

<211> LENGTH: 440
<212> TYPE: DNA
<213> ORGANISM: Glycine max

<400> SEQUENCE: 28

```
ggaacgaaca aaaatggaga attcgaccca agaatcccac ctccgatccg aaaactccgt      60
gagctacgaa tcccctacc caatctacgg catgtcgttc tcccttccc accccaccg        120
cctggccctc ggcagcttca ttgaagaata caccaaccgc gttgacatcc tctccttcca    180
ccccgacacc ctctccctca ccccaaccc ttctctctcc tttgaccacc cttaccctcc     240
caccaaactc atgttccacc cccgcaaacc ccctcctcc tcctccgacc tcctcgccac     300
ctccggcgac tacctccgcc tctgggaggt ccgcgacaac tccgtggagg ccgtctccct    360
tttcaacaac agcaagacca gcgagttctg cgccccctta acctccttcg actggaacga    420
tatcgacccc aaccgcatcg                                                 440
```

<210> SEQ ID NO 29
<211> LENGTH: 467
<212> TYPE: DNA
<213> ORGANISM: Brassica napus

<400> SEQUENCE: 29

```
gacaactcag ctccggactt tttacctaaa tcggtaaccg ccgccaccta cgactctccg      60
ggcgggttct acgcgatgtc cggctgctcc tccaccaacc gaatcgccgt cgggagcttc    120
ctcgaggact acaacaaccg catcgacatc ctctccttcg actccggctc catgtccctc    180
aagccccttc catccctctc cttcgagcac ccttaccctc ccaccaagct catgttcagt    240
ccccctccc tccgccgcag cggcgggggc gaccttctct tctcctccgg cgacttcctc    300
cgcctctggg aggtcaacga agactcctcc tccgcggagc cagtatcggt cctcaacaac   360
agcaagacga gcgagttctg cgcgccgctg acctccttcg actggaacga cgtggagccc   420
aagcggttag gcacgtgcag catcgacacc acgtgcacga tcttgga                 467
```

<210> SEQ ID NO 30
<211> LENGTH: 469
<212> TYPE: DNA
<213> ORGANISM: Brassica napus
<220> FEATURE:
<221> NAME/KEY: misc_features
<222> LOCATION: (208)..(302)
<223> OTHER INFORMATION: n = unknown
<220> FEATURE:
<221> NAME/KEY: misc_feature
<222> LOCATION: (208)..(302)
<223> OTHER INFORMATION: n = unknown

<400> SEQUENCE: 30

```
gacaactcag ctccggactt tttacctaaa tcggtaaccg ccgccaccta cgactctccg      60
ggcgggttct acgcgatgtc cggctgctcc tccaccaacc gaatcgccgt cgggagcttc    120
ctcgaggact acaacaaccg catcgacatc ctctgcttcg actccgactc catgtccctc    180
agccccttcc atcctctcct tcgagcancc cttaccnctg ccaccaaag ctcatgttca    240
gtccccctc cctccgcccg aacgggcggg gcgacctnct cgccttctnc ggcgacttcc    300
tncgccttct ggaggtcaac gaagactcct cctccgcgga gccagtatcg gtcctcaaca   360
acagcaagac gagcgagttc tgcgcgccgc tgacctcctt cgactggaac gacgtggagc   420
ccaagcggtt aggcacgtgc agcatcgaca ccacgtgcac gatcttgga                469
```

<210> SEQ ID NO 31
<211> LENGTH: 1531
<212> TYPE: DNA
<213> ORGANISM: Arabidopsis thaliana

<400> SEQUENCE: 31

| | | | | | |
|---|---|---|---|---|---|
| gaaatacacc | taacttgttt | agtacacaac | agcaacatca | aactctaata | aacccaagtt | 60 |
| ggtgtatact | ataatggtga | tggctggtgc | ttcttctttg | gatgagatca | gacaggctca | 120 |
| gagagctgat | ggacctgcag | gcatcttggc | tattggcact | gctaaccctg | agaaccatgt | 180 |
| gcttcaggcg | gagtatcctg | actactactt | ccgcatcacc | aacagtgaac | acatgaccga | 240 |
| cctcaaggag | aagttcaagc | gcatgtgcga | caagtcgaca | attcggaaac | gtcacatgca | 300 |
| tctgacggag | gaattcctca | aggaaaaccc | acacatgtgt | gcttacatgg | ctccttctct | 360 |
| ggacaccaga | caggacatcg | tggtggtcga | agtccctaag | ctaggcaaag | aagcggcagt | 420 |
| gaaggccatc | aaggagtggg | gccagcccaa | gtcaaagatc | actcatgtcg | tcttctgcac | 480 |
| tacctccggc | gtcgacatgc | ctggtgctga | ctaccagctc | accaagcttc | ttggtctccg | 540 |
| tccttccgtc | aagcgtctca | tgatgtacca | gcaaggttgc | ttcgccggcg | gtactgtcct | 600 |
| ccgtatcgct | aaggatctcg | ccgagaacaa | tcgtggagca | cgtgtcctcg | ttgtctgctc | 660 |
| tgagatcaca | gccgttacct | tccgtggtcc | ctctgacacc | cacccttgact | ccctcgtcgg | 720 |
| tcaggctctt | ttcagtgatg | gcgccgccgc | actcattgtg | gggtcggacc | ctgacacatc | 780 |
| tgtcggagag | aaacccatct | ttgagatggt | gtctgccgct | cagaccatcc | ttccagactc | 840 |
| tgatggtgcc | atagacggac | atttgaggga | agttggtctc | accttccatc | tcctcaagga | 900 |
| tgttcccggc | ctcatctcca | agaacattgt | gaagagtcta | gacgaagcgt | ttaaacettt | 960 |
| ggggataagt | gactggaact | ccctcttctg | gatagcccac | cctggaggtc | cagcgatcct | 1020 |
| agaccaggtg | gagataaagc | taggactaaa | ggaagagaag | atgagggcga | cacgtcacgt | 1080 |
| gttgagcgag | tatggaaaca | tgtcgagcgc | gtgcgttctc | ttcatactag | acgagatgag | 1140 |
| gaggaagtca | gctaaggatg | gtgtggccac | gacaggagaa | gggttggagt | ggggtgtctt | 1200 |
| gtttggtttc | ggaccaggtc | tcactgttga | gacagtcgtc | ttgcacagcg | ttcctctcta | 1260 |
| aacagaacgc | ttgccttcta | tctgcctacc | tacctacgca | aaactttaat | cctgtcttat | 1320 |
| gttttatata | atataatcat | tatatgttta | cgcaataatt | aaggaagaat | tcatttgatg | 1380 |
| tgatatgtga | tatgtgctgg | acaggtctat | tcgactgttt | ttgtactctc | ttttttgtgt | 1440 |
| cttttttacaa | tattaaatct | atgggtcttg | aatgacatca | aatctttgtt | aaaaaatata | 1500 |
| tatatatatt | cgttttttttt | tttttttttt | t | | | 1531 |

<210> SEQ ID NO 32
<211> LENGTH: 1493
<212> TYPE: DNA
<213> ORGANISM: Hordeum vulgare

<400> SEQUENCE: 32

| | | | | | |
|---|---|---|---|---|---|
| cgttgctgtc | gggaagtcgc | tagtgctgct | aatggctgcg | gtgaggttga | aggaagtgag | 60 |
| aatggcacag | cgggctgagg | gcctggcgac | agtgctggcc | attggcaccg | ccgtgccggc | 120 |
| caactgcgtg | taccaggcga | cctacccaga | ctattacttc | agagtcacga | agagcgagca | 180 |
| cctcgcggac | ctcaaggaga | agttccagag | gatgtgcgac | aagtccatga | tcagaaagag | 240 |
| gcacatgcac | ctaaccgagg | agatactaat | taagaaccccc | aagatctgcg | cgcacatgga | 300 |
| gacctcgctt | gacgcgcgcc | atgccattgc | gctcgtcgag | gtcccgaagc | tggggcaagg | 360 |

```
agctgcggag aaggcaatca aggagtgggg ccagccattg tccaagatca cccacctcgt      420
gttctgcaca acctctggcg tcgacatgcc aggcgccgac taccagctga ccaagttgct      480
cggcctctcc ccgacggtga aacgcctgat gatgtaccag cagggtgct tcggcggcgc       540 cacggttctt cgccttgcca aggacatcgc tgagaacaac cgcggcgctc gtgtgctggt      600
tgtctgctcg gagataaccg ccatggcctt ccgtggtcct tgcaagtccc atctcgactc      660
gctggtcggc catgcactct ttggcgatgg cgcagctgct gccatcatcg gcgctgaccc      720
tgaccagctg gacgagcagc cagtgttcca gctggtgtca gcgagccaga ccatcctgcc      780
ggagtcggag ggagccatcg acggccacct tacgaggcg ggcctgacca tccaccttct       840
caaggacgtg ccgggactca tctctgagaa tatcgagcaa gcattagagg acgcgtttga      900
gcctctgggc atccacaact ggaactccat cttctggatt gctcaccctg ggggcctgc       960 catccttgac agggtcgagg acagagttgg ccttgacaag aagcgcatgc gcgcaagccg      1020
ggaggttctg tcgagtacg gaaacatgtc cagcgcaagt gtactcttcg tccttgacgt       1080
tatgcgtaag agctccgcca aggatggcct cgccacaact ggagaaggca aggactgggg      1140
tgtcctcttc ggcttcggcc ctggcctcac cgtcgagaca ctcgtcctcc acagcgtccc      1200
cgtccccgtc cccaccgccg ctagtgcatg atcgacgcat gccatattta gcttatttgg      1260
gtcaagacaa taaataagc ggcccacaaa tatgaaccac gtccgacaat acgagcacct       1320 ggctggggc gctcctgcct gttaaaccat agatgtacgt acctcgtgat tgtgtctac       1380 agtatattgt aaacgttcac ccatcaaagt tgtattttca tccttaaaaa aaaaaaaaa      1440 aaaaaaaaa aaaaaaaaa aaaaaaaaa aaaaaaaaa aaaaaaaaa aaa                 1493
```

<210> SEQ ID NO 33
<211> LENGTH: 1456
<212> TYPE: DNA
<213> ORGANISM: Brassica napus

<400> SEQUENCE: 33

```
gacccacgcg tcagcccacg cgtccgtcga cccgagacat acataacttg cttactacgc       60
aaagtaacac atcgatcaaa ctttagttaa aacctagttg gtttaatatg gtgatggggc      120
cttcttcgtt ggatgagatc agaaaggcac agagagcaga cggtcctgca ggcatcttgg      180
cgataggtac ggccaaccct gcgaaccatg tgctccaagc tgagtatcca gactactact      240
tccgcatcac caacagtgaa cacatgaccg accttaagga gaagttcaag cgcatgtgcg      300
ataagtcgac cataagaaaa cgccacatgc acttgaccga ggagttcttg aaagagaacc      360
ctaacatgtg cgcctacatg gctccttctc tcgacgctag acaagacctc gtggtggttg      420
aagtccctaa gctaggcaaa gatgcagcag tgaaggccat caaggagtgg ggtcagccta      480
agtcaaagat cacacacgtt gtcttctgca ccacctctgg agttgacatg cctggtgctg      540
actaccagct caccaagctc cttggccttc gcccttccgt gaagcgtctc atgatgtacc      600
agcaaggttg cttcgccggc ggcactgtcc tccgtctcgc caaggacctc gctgagaaca      660
accgtggcgc acgtgtcctc gtggtctgct ccgagatcac agccgtcacc ttccgtggcc      720
cctctgacac ccaccttgac tcactcgtgg acaagctct cttcagtgac ggtgcagccg      780
cgctcattgt cggttcggac cctgatgtct ctgctggaga aagcccatc ttcgagatgg       840 tgtctgcggc gcagaccatc ctcccagact cggacggtgc catagatgga cacttgaggg      900
aagtgggact caccttccat ctcctcaagg acgtccctgg actcatctcc aagaacattg      960
agaagagtct agacgaagcg tttaaaccct tagggataag tgactggaac tccctcttct      1020
```

-continued

```
ggatagctca ccctggtggt ccagcgatcc ttgacgacgt tgagaagaag ctaggactca    1080
aggcagagaa gatgagagcc acgcgtcacg tgttgagcga gtatggaaac atgtctagcg    1140
cctgtgtcct ctttatattg gatgagatga ggaggaagtc taaggaagat ggtgtggcca    1200
cgacaggtga agggttagaa tggggtgtct tgtttgggtt cggaccaggt ctcaccgtgg    1260
agacagttgt cttgcacagc gttcctctct aaacagaaag ctctcttcct ataaatgcct    1320
acctaccttt cacatactta ccatcatatc atgtctttat gttttttttt ttcaatttaa    1380
gataatattt gtaatgcaat aattaaaaaa aaaaaattca ttagtgtgac aaaaaaaaaa    1440
aaaaaagggc ggccgc                                                    1456
```

<210> SEQ ID NO 34
<211> LENGTH: 1357
<212> TYPE: DNA
<213> ORGANISM: Brassica napus

<400> SEQUENCE: 34

```
acacaagatc acacatctat caaactcttg taaaacatgg tcatgagtag gccgtcatca     60
tcgttggatg agatcagaaa ggcacaaaga gctgatggtc ccgcaggtat cttggctata    120
ggcacggcca accctgcgaa ccatgtgatc aagcggagt atcctgacta ctacttccgc    180
atcaccaaca gtgaacacat gactgacctc aaggaaaagt tcaagcgcat gtgtgacaag    240
tcgatgataa ggaaacgaca catgcaccta accgaggagt tcttgaagga gaatccgaac    300
atgtgcgcct acatggctcc ttctctcgac gtcagacaag acatcgtggt ggttgaagtc    360
cctaagctag gtaaagaagc tgcagtgaag gccatcaagg agtggggcca gcccaagtcc    420
aagatcacac acgttgtctt ctgtacaacc tcaggagtcg acatgcctgg tgctgactac    480
cagctcacca agctccttgg tcttcgtccc tccgtaaagc gtctcatgat gtaccagcaa    540
ggctgcttcg ccggcggcac tgtcctccgt ctcgccaagg acctgctga aacaaccgt    600 ggcgcacgtg tcctcgttgt ctgctccgag atcacagccg tcacgttccg tggcccctct    660
gacactcatc ttgactccct cgttggacag gctctcttca gtgacggcgc cgcggcgctt    720
attgttgggt cggatcctga tgcatccgta ggggagaagc caatctttga gatggtgtct    780
gcggcgcaga ccattcttcc cgactcggat ggagccatag atggacactt gagggaagtg    840
ggactcacct tccatctcct caaggacgtc cctgggctca tctccaagaa catagagaag    900
agtcttgaag aagcgtttaa accgctaggg ataagtgact ggaactccct cttttggatc    960
gctcaccctg gtggtccagc gatccttgac gaggttgaga agaagcttgg actcaaggca   1020
gagaagatga gagccacgcg tcaggtcttg agcgagtacg gaaacatgtc tagcgcttgc   1080 gttctctta tattggacga gatgaggagg aagtctgcga agatggtgt ggctacgacg   1140 ggagaaggtc tggagtgggg tgtcttgttt ggtttcggac ctggtctcac cgtagagact   1200
gttgtcttgc acagcgttcc tgtttgaaca gatctctttc tatctatatg ccttaccaac   1260
ctactacaca tacttcccag catcgtgtct tttaatgtat ttcaatttga tatggaatat   1320
gtaatgccaa taactaatga agagttcatt tagtgtg                             1357
```

<210> SEQ ID NO 35
<211> LENGTH: 695
<212> TYPE: DNA
<213> ORGANISM: Brassica napus

<400> SEQUENCE: 35

```
cggacgcgtg ggcggacgcg tgggcggacg cgtgggcgga cgcgtgggt gcagccgcgc      60 tcattgtcgg ctcggaccct gatgtctctg ctggagagaa gcccatcttc gagatggtgt    120
ctgctgctca gaccatcctc ccagactcgg acggtgccat agatggacac ttaagggaag    180
tgggactcac cttccatctc ctcaaggacg tccccggact catctccaag aacattgaga    240
agagtctaga cgaagcgttt aaaccttag ggataagtga ctggaactcc ctcttctgga    300
tagctcaccc tggtggtcca gcgatccttg acgacgttga agaagcta ggactcaagg      360 cggagaagat gagagccacg cgccacgtgt tgagcgagta cggtaacatg tctagcgcgt    420
gtgttctctt catattggac gagatgagga ggaagtctgc ggaagatggt gtggccacga    480
caggagaagg gttggagtgg ggtgtcttgt tcggtttcgg accaggtctt accgtagaga    540
cagtggtctt gcacagcgtt cctgtttgaa cagaaacgct tccttcctat atgcctacct    600
acctacatat accaccatca tcttgtcttc tgtttcttca aatctatata ttaatatatg    660
taatgcaata attaaggaag aattcattaa gtttg                               695

<210> SEQ ID NO 36
<211> LENGTH: 422
<212> TYPE: DNA
<213> ORGANISM: Brassica napus

<400> SEQUENCE: 36
aaccagggtt gtttcgccgg cggaactgtc ttctttttgg ccaaggacct ggttgagaac     60
aaccgggggg cacgtgtcct cggggtcggt tccaaaataa cagccggaac tttccggggc    120
ccttttgaca ttaacttgga ctaattcggg ggacaggttt ttttaatgga cggtgcagcc    180
gcactaattg ccggttcaaa ccctgatgtt tttgttgggg ggaagcccat cttcgggatg    240
gggtttgccg tgaaacacaa tcttccaaga ctcggacggg gccatcattg gaaacttaag    300
ggaggtgggc ctaaccttcc atttcttaag ggacgtcctt ggattaattt ccagaaactt    360 tgaaagggc ctagacgaac cgtttaaacc gttggggtta agtgattgga actcctttt     420 tt                                                                   422

<210> SEQ ID NO 37
<211> LENGTH: 1892
<212> TYPE: DNA
<213> ORGANISM: Zea mays
<220> FEATURE:
<221> NAME/KEY: misc_feature
<222> LOCATION: (1)..(926)
<223> OTHER INFORMATION: n = unknown

<400> SEQUENCE: 37
nttgctccca cacacagcag gcagcagctc gatcgctagc tcctccgaac cggaaagcca     60
agcccgcttt ggcgatcgtg cttgcttgct tggttccttc aattcctgcc ggagccagcg    120
agagctagct gctgctgtcg cgtggtagac gtcgtcttgc cagcgagagc ctagctcgat    180
cggtctctct ggtacaacgt agggagaaag atcgaggggg agaggacgac gacgatggcc    240
ggcgcgaccg tgaccgtgga ggaggtgagg aaggcccagc gcgccaccgg ccccgccacc    300
gtgctggcga tcggcaccgc cacgcccgcc aactgcgtgt accaggccga ctacccggac    360
tactacttcc ggatcaccaa gagcgagcac ctcaccgacc tcaaggagaa attcaagagg    420
atgtgcgaca agtcgatgat ccggaagcgt tacatgcacc tgacggagga gttcctggcg    480
gagaacccga gcatgtgcgc gtacatggcg ccgtcgctgg acgcgcggca ggacgtggtg    540
gtggtgggag gtgccgaagc tgggaaggc ggcggcgcag aaggcgatca aggagtgggg    600
```

-continued

```
gcagccaaag nnnnnnnnnn nnnnnnnnnn nnnnnncacc acgtccgggg tggacatgcc    660
gggcgccgac taccagctga ccaaggcgct gggcctgcgc ccctccnnnn nnnnnnnnnn    720
nnnnnnnnnn nnnnnnggct cgcgggcgg cacggtgctg cgcgtggcca aggacctcgc     780
ggagaacaac cgcggcgcgc gggtgctggg ggggtgctcc gagatcacgg ccgtcacgtt    840
ccgcggcccc tccgagtcgc acctcgactc gctcgtgggc caggcgctgt tcggcgacgg    900
cgnnnnnnnn nnnnnnnnnn nnnnnnaccc ggacgaccgc gtcgagcgcc cgctcttcca    960
gctcgtctcc gccgcccaga ccatcctgcc cgactcggag ggcgccatcg acggccacct   1020
ccgcgaggtg gggctcacct cccacctgct caaggacgtg cctggcctca tctccaagaa   1080
catcggccgc cgcgctggac g acgcgttcaa gccgctcggc aactccgact ggaactccat  1140
cttcggggtg gcgcacccg cgggcccgc catcctcgac caggtggagg ccaaggtcgg     1200
gctggacaag gccaggatgc gcgccacccg ccacgtcctc tccgagtacg caacatgtc    1260 cagcgcctgc gtcctcttca tcctcgacga gatgcgcaag cgctccgccg aggacggaca   1320
ggccaccacg ggcgagggcc tcgactgggg cgtcctcttc ggcttcggcc cgggactcac   1380
cgtcgagacc gtcgtgctcc acagcgtccc catcaccacc ggagcggcca ccgcctgatt   1440
catcatcaac gatccaattc gtcgtcgtct cgttcgtcat tattttacgt cgtccgtccg   1500
caaataataa tgtgctctct gctataattg tcgtgtgtag taagtagctg atactatttt   1560
tccatgtact gtcagtcgca caatcatcat atataatatc tctatatatg catttcatgc   1620
aagaccaggg tagagctagc ttgaggagaa gaccctatc gttgtcactt tagcatgcat    1680
ggggtggtga gtattgggt atacctgtgt aagacaagct tggctggttt aattatatat    1740 tttttttcaaa aaaatctgtt tgctacaaaa acaaacctg taatgtgcat ggtgacggca    1800
aattggccgc cattttcagt gcacctaaag ctgtattgga taaatgcttc tactcgatta   1860
ttgattgtaa gaggtccact gttagcttgt gt                                 1892
```

<210> SEQ ID NO 38
<211> LENGTH: 2285
<212> TYPE: DNA
<213> ORGANISM: Zea mays

<400> SEQUENCE: 38

```
gccggccggg gtcgggatta agactagcta actagcgtga aagagctcct ccgacgacta     60
ctggctctcg cttgctccgg cgacccagaa agagctaggc tatagccacc gacgaccct    120 gccggccgcg cttttggggc ccccggcgg ggcggggaca ccacagctcc cacacacagc    180
aggcagcagc tcgatcgcta gctcctccga accggaaagc caagcccgct ttggcgatcg   240
tgcttgcttg cttggttcct tcaattcctg ccggagccag cgagagctag ctgctgctgt   300
cgcgtggtag acgtcgtctt gccagcgaga gcctagctcg atcggtctct ctggtacaac   360
gtagggagaa agatcgaggg ggagaggacg acgacgatgc ccggcgcgac cgtgaccgtg   420
gaggaggtga ggaaggccca gcgcgccacc ggccccgcca ccgtgctggc gatcggcacc   480
gccacgcccg ccaactgcgt gtaccaggcc gactacccgg actactactt ccggatcacc   540
aagagcgagc acctcaccga cctcaaggag aaattcaaga ggatgtgcga caagtcgatg   600
atccggaagc gttacatgca cctgacggag gagttcctgg cggagaaccc gagcatgtgc   660
gcgtacatgg cgccgtcgct ggacgcgcgcg caggacgtgg tggtggtgga ggtgccgaag   720
ctggggaagg cggcggcgca gaaggcgatc aaggagtggg gcagccaaa gtcgcggatc    780
```

| | |
|---|---|
| acgcacctgg tgttctgcac cacgtccggg gtggacatgc cgggcgccga ctaccagctg | 840 |
| accaaggcgc tgggcctgcg cccctccgtg aaccgcctca tgatgtacca gcagggtgc | 900 |
| ttcgcgggcg gcacggtgct gcgcgtggcc aaggacctcg cggagaacaa ccgcggcgcg | 960 |
| cgggtgctgg tggtgtgctc cgagatcacg gccgtcacgt tccggggccc ctccgagtcg | 1020 |
| cacctggact cgctcgtggg ccaggcgctg ttcggcgacg gcgcggcggc cgtcgtggtg | 1080 |
| ggcgccgacc cggacggccg ggtcgagcgc ccgctgttcc agctcgtctc ggcggggcag | 1140 |
| accatcctgc ccgactcgga gggcgccatc gacggccacc tccgcgaggt ggggctgacg | 1200 |
| tgccacctgc tcaaggacgt gcccgggctc atctccgagc gcgcgctcga ctggaactcc | 1260 |
| atcttctggg tggcgcaccc cggcgggccc gccatcctga ccagtggagg ccaggtcggg | 1320 |
| ctggacaagg ccaggatgcg cgccaccgc cacctccgag tacggcaaca tgtccagcgc | 1380 |
| ctgcgtgctc ttcatcctcg acgagatgcg caagcgctcc gccgaggacg gccaggccac | 1440 |
| caccggcgag gggctcgact ggggcgtcct cttcggcttc ggcccgggcc tcaccgtcga | 1500 |
| gaccgtcgtg ctccacagcg tccccatcac caccggagcg cccaccgccg cctgagtcgt | 1560 |
| ccatctatcc tcgcgatcgc tccagagaca tgaacgaccc gacctacgaa taatgtatct | 1620 |
| gcgtaattaa tttctatctg tgttgtgtcc tagtagctgt taagtaccgt tttaaaaacc | 1680 |
| cttaattaat tttattatgg gtgagctagc tcaagagtgg agtcataaaa ccgcatggat | 1740 |
| ggtgaggtat tgtatagtac ctgtgtaaga caagcttggc tggttttta ttttatattt | 1800 |
| taatctgttt gctcaagaca aaacaaaaaa tgaattgttg agctgtcatt aatttgcagt | 1860 |
| gcaccagctc aagttggttg tactcctatc ctatgtatga atgaaatccc ttctagtagt | 1920 |
| atcttccaag accagggtag agctaggagg aaaagaccct tatcgttgtc tttagcatgc | 1980 |
| atgggtggt gaggtattgg gtctgtgtaa gacaagcttg gctggtttaa ttatatattt | 2040 |
| ttttaaaaaa atctgtttgc tacaaaaaca aaacctgtaa tgtgcatggt gatggcaaat | 2100 |
| tggccgccat tttcagtgca cctaaagctg tattggataa atgcttctac tcgattattg | 2160 |
| attgtttgag gagggcgctt accaggacct agggcacaag acgacatgga gatcaattac | 2220 |
| tgacatacat tattagcatg ctggcccgct catgtgtgga gctccacagc cacatgatgg | 2280 |
| aggag | 2285 |

<210> SEQ ID NO 39
<211> LENGTH: 1852
<212> TYPE: DNA
<213> ORGANISM: Zea mays

<400> SEQUENCE: 39

| | |
|---|---|
| atggccggct cgagccggcc ggaaaaaaaa aaaaaaaaa aaaagaaaa aaaaaaaaa | 60 |
| aaaaaaaaaa acaccacagc tcccacacac agcaggcagc agctcgatcg ctagctcctc | 120 |
| cgaaccggaa agccaagccc gctttggcga tcgtgcttgc ttgcttggtt ccttcaattc | 180 |
| ctgccggagc cagcgagagc tagctgctgc tgtcgcgtgg tagacgtcgt cttgccagcg | 240 |
| agagcctagc tcgatcggtc tctctggtac aacgtaggga gaaagatcga gggggagagg | 300 |
| acgacgacga tggccggcgc gaccgtgacc gtggaggagg tgaggaaggc ccagcgcgcc | 360 |
| accggccccg ccaccgtgct ggcgatcggc accgccacgc ccgccaactg cgtgtaccag | 420 |
| gccgactacc cggactacta cttccggatc accaagagcg agcacctcac cgacctcaag | 480 |
| gagaaattca gaggatgtg cgacaagtcg atgatccgga agcgttacat gcacctgacg | 540 |
| gaggagttcc tggcggagaa cccgagcatg tgcgcgtaca tggcgccgtc gctggacgcg | 600 |

```
cggcaggacg tggtggtggt ggaggtgccg aagctgggga aggcggcggc gcagaaggcg      660
atcaaggagt gggggcagcc caagtcgcgg atcacgcacc tggtgttctg caccacgtcc      720
ggggtggaca tgccgggcgc cgactaccag ctgaccaagg cgctgggcct gcgcccctcc      780
gtgaaccgcc tcatgatgta ccagcagggg tgcttcgcgg gcggcacggt gctgcgcgtg      840
gccaaggacc tcgcggagaa caaccgcggc gcgcgggtgc tggtggtgtg ctccgagatc      900
acggccgtca cgttccgcgg ccccctccgag tcgcacctcg actcgctcgt gggccaggcg      960
ctgttcggcg acgcgcggc ggccgtggtc gtgggcgccg acccggacga ccgcgtcgag     1020
cgcccgctct ccagctagt ctccgccgcc cagaccatcc tgcccgactc ggagggcgcc     1080
atcgacggcc acctccgcga ggtggggctc accttccacc tgctcaagga cgtgcccggg     1140
ctcatctcca agaacatcgg ccgcgcgctg gacgacgcgt tcaagccgct cggcatctcc     1200
gactggaact ccatcttctg ggtggcgcac cccggcgggc cgccatcct ggaccaggtg      1260
gaggccaagg tcgggctgga caaggccagg atgcgcgcca cccgccacgt cctctccgag     1320
tacggcaaca tgtccagcgc ctgcgtcctc ttcatcctcg acgagatgcg caagcgctcc     1380
gccgaggacg gacaggccac cacgggcgag ggcctcgact ggggcgtcct cttcggcttc     1440
ggcccgggac tcaccgtcga ccgtcgtg ctccacagcg tccccatcac caccggagcg      1500
gccaccgcct gattcatcga ttcatcaacg atcaaattcc tccctctcc gatccgccag      1560
tcgtcgtctc gttcgtcatt attttacgtc gtccgtccgc aaataataat gtgctctctg     1620
ctataattgt cgtgtgtagt aagtagctga tactatttt ccatgtactg tcagtcgcac      1680
aatcatcata tataatatct ctctatatat atgcatttca tgcaagacca gggtagacga     1740
gctagcttga ggagaagacc cttatcgttg tcactttagc atgcatgggg tggtgaggta     1800
ttgggtatac ctgtgtaaga caagcttggc tggtttaatt atatatttt tt               1852

<210> SEQ ID NO 40
<211> LENGTH: 803
<212> TYPE: DNA
<213> ORGANISM: Zea mays
<220> FEATURE:
<221> NAME/KEY: misc_feature
<222> LOCATION: (698)..(700)
<223> OTHER INFORMATION: n = unknown

<400> SEQUENCE: 40
gggtacctcg aggccggccg ggatagccgg gcctaatagt actccatcag cacggcattc       60
ccacaccact tggatttttgt cgacctgacc ggcgacaagt cgatgatccg gaagcgttac      120
atgcacctga cggaggagtt cctggcggag aacccgagca tgtgcgcgta catgcgccg       180
tcgctggacg cgcggcagga cgtggtggtg gtggaggcgc cgaagctggg gaaggcggcg      240
gcgcagaagg cgatcaagga gtgggggcag cccaagtcgc ggatcacgca cctggtgttc      300
tgcaccacgt ccggggtgga catgccgggc gccgactacc agctgaccaa ggcgctgggc      360
ctgcgcccct ccgtgaaccg cctcatgatg taccagcagg ggtgcttcgc gggcgggacg      420
gtgctgcgcg tggccaagga cctggcggag aacaaccgcg gcgcgcgggt gctggtggtg      480
tgctccgaga tcacggccgt cacgttccgc ggccccctcc gagtcgcacct cgactcgctc      540
gtgggccagg cgctgttcgg cgacgcgcg gcggtcgtgg tcgtgggcgc cgacccggac      600
gaccgcgtcg agcgcccgct cttccagctc gtctccgccg cccagaccat cctgcccgac      660
tcggagggcg ccatcgacgg ccacctcccg cgaggtgnnn gctcaccttc cacctgctca     720
```

| aggacgtgcc cgggctcatc tccaagaaca tcggccgcgc gctggacgac gcgttcaagc | 780 |
| cgctcggcat ctccgactgg act | 803 |

<210> SEQ ID NO 41
<211> LENGTH: 1895
<212> TYPE: DNA
<213> ORGANISM: Zea mays

<400> SEQUENCE: 41

| gggtactccg cggccggcca ttaagactag ctaactagcg tgaaagagct cctccgacga | 60 |
| ctactagctc tcgcttgctc cgacgacccc tgccggccgc ctctggtaca acgtacgaga | 120 |
| ggaagagaga cgatcgatgg ccggcgccac cgtgaccgtg gacgaggtga ggaagggcca | 180 |
| gcgcgcgacc ggccccgcca ccgtgctggc catcgggacg gcgacgcccg ccaactgcgt | 240 |
| gtaccaggcc gactacccgg actactactt ccggatcacc aagagcgacc acctcaccga | 300 |
| cctcaaggag aagttcaaga ggatgtgcga caagtcgatg atccggaagc ggtacatgca | 360 |
| cctgacggag gagttcctgt cggagaaccc gagcatgtgc gcgtacatgg cgccgtcgct | 420 |
| ggacgcgcgg caggacgtgg tggtgacgga ggtgccgaag ctggggaagg cggcggcgca | 480 |
| gaaggcgatc aaggagtggg ggcagcccaa gtcgcggatc acgcacctgg tgttctgcac | 540 |
| cacgtcgggg gtggacatgc cgggcgccga ctaccagctg accaaggcgc tggggctgcg | 600 |
| cccgtccgtg aaccgcctga tgatgtacca gcaggggtgc ttcgcgggcg gcacggtgct | 660 |
| gcgcgtggcc aaggacctgg cggagaacaa ccgcggggcg agggtcctgg tggtgtgctc | 720 |
| ggagatcacg gccgtgacgt tccgcgggcc gtccgagtcg cacctggact cgctcgtggg | 780 |
| gcaggcgctg ttcggcgacg gcgcggcggc cgtcgtggtg ggcgccgacc cggacggccg | 840 |
| cgtcgagcgc ccgctgttcc agctcgtgtc ggcggcgcag accatcctgc ccgactcgga | 900 |
| gggcgccatc gacggccacc tccgcgaggt ggggctgacg ttccacctgc tcaaggacgt | 960 |
| gcccgggctc atctccaaga acatcgagcg cgcgctggag gacgcgttcg agccgctcgg | 1020 |
| catctccgac tggaactcca tcttctgggt ggcgcacccc ggcgggcccg ccatcctgga | 1080 |
| ccaggtggag gccagggtcg ggctggacaa ggccaggatg cgcgccaccc gccacgtcct | 1140 |
| ctccgagtac ggcaacatgt ccagcgcctg cgtgctcttc atcctcgacg agatgcgcaa | 1200 |
| gcgctccgcc gaggacggcc aggccaccac cggcgagggg ctcgactggg gcgtcctctt | 1260 |
| cggcttcggc ccgggcctca ccgtcgagac cgtcgtgctc cacagcgtcc ccatcaccac | 1320 |
| cggagcgccc accgccgcct gagtcgtcca tctatcctcg cgatcgctcc agtccagaca | 1380 |
| tgaacgaccc ggcctacgaa taatgtatct gcgtaattaa tttctatctg tcttgtgtcc | 1440 |
| tagtagctgt taagtaccgt tttaaaaccc ttaattaatt ttattatggg cgagctagct | 1500 |
| caagagtgga gtcataaaac cgcatggatg gtgaggtatt gtatagtaca tgtgtaagac | 1560 |
| aagcttggct ggttttttat tttaatctgt ttgctcaaga caaaacctgc aataattgtc | 1620 |
| gtgtgtagta agaaactgat actatttttc catgtgctgt cagtggccca atcatcaaaa | 1680 |
| aaaaaatctc tctataaaaa ggcatttcat gcaagaccag ggtatacgag ctagcttgag | 1740 |
| gagaagaccc ttatcgttgt ccctttagca tgcatgggt ggtaaggtat tgggtatacc | 1800 |
| tgtgtaaacc aagcttggct ggtttaatta tatattcctt tttaaaaaaa aaaaaaacca | 1860 |
| caaaaaaaaa aaaaaaaaa aaaaaaaat aaaag | 1895 |

<210> SEQ ID NO 42
<211> LENGTH: 581

<212> TYPE: DNA
<213> ORGANISM: Zea mays

<400> SEQUENCE: 42

```
aaaagctgga gctccccgcg gtggcggccg ctctagaact agtggatccc ccgggctgca    60
ggaattcggc accagctcac tagtccccccc cccccccaca cctaacttgt ttagtacaca   120
acagcaacat caaactctaa taaacccaag ttggtgtata ctataatggt gatggctggt   180
gcttcttctt tggatgagat cagacaggct cagagagctg atggacctgc aggcatcttg   240
gctattggca ctgctaaccc tgagaaccat gtgcttcagg cggagtatcc tgactactac   300
ttccgcatca ccaacagtga acacatgacc gacctcaagg agaagttca agccgcatgt    360
gcgacaagtc aacaattcgg aaacgtcaca tgcatctgac gggaggaatt cctcaaggaa   420
aacccacaca tgtgtgctta catggctcct tctctggaca ccagacagga catcgtggtg   480
gtcgaagtcc ctaagctagg caaagaagcg gcagtgaagg ccatcaagga gtggggccag   540
cccaagtcaa agatcacctc atgtcgtctt ctgcactacc t                         581
```

<210> SEQ ID NO 43
<211> LENGTH: 999
<212> TYPE: DNA
<213> ORGANISM: Zea mays
<220> FEATURE:
<221> NAME/KEY: misc_feature
<222> LOCATION: (8)..(26)
<223> OTHER INFORMATION: n = unknown

<400> SEQUENCE: 43

```
gtaccctncg ngggctctgg ccgggnaaaa aaaaaaaaaa aaaaaaaaaa aactcccaca    60
ccattggtcc tcgaggccgg ccgggagtga gcacacttgt gaggacgaca cgaaaaaaaa   120
ttattattcg ccacccggcc gggggggccac accacagctc ccacacacac agcaggcagc   180
agcacagccc acagctcgat cgctcctccg aaccggaaag ccaagccgct ttggcgatcg   240
tgcgtcttgc ttggttcctg ccggccggag ccagcgagag ctagctagct gctgctgtcg   300
tggtagacgt cttgccgcac gcacgcctag ctcggtctct ctggtacaac gtagggagga   360
cgccgacgac gacgatggcc ggcgcgaccg tgaccgtgga ggaggtgagg aaggcccagc   420
gcgccaccgg ccccgccacc gtgctggcga tcggcaccgc cacgcccgcc aactgcgtgt   480
accaggccga ctaccggac tactacttcc ggatcaccaa gagcgagcac ctcaccgacc   540
tcaaggagaa attcaagagg atgtgcgaca agtcgatgat ccggaagcgt acatgcacc    600
tgacggagga gttcctggcg gagaacccga gcatgtgcgc gtacatggcg ccgtcgctgg   660
acgcgcggca ggacgtggtg gtggtggagg tgccgaagct ggggaaggcg gcggcgcaga   720
aggcgatcaa ggagtggggg cagcccaagt cgcggatcac gcacctggtg ttctgcacca   780
cgtccggggt ggacatgccg ggcgccgact accagctgac caaggcgctg gcctgcgcc    840
cctccgtgaa ccgcctcatg atgtaccagc agggtgctt cgcgggcggg acggtgctgc   900
gcgtggccaa ggacctggcg gagaacaccg cggcgcgcgg gtgctggtgg tgtgctagat   960
ccacaagtcg atgatccgga aagcgttaca tgcacctga                           999
```

<210> SEQ ID NO 44
<211> LENGTH: 2109
<212> TYPE: DNA
<213> ORGANISM: Zea mays

<400> SEQUENCE: 44

-continued

```
accaggtgga ggccaaggtc gggctggaca aggccaggat gcgcgccacc cgccacgtcc      60
tctccgagta cggcaacatg tccagcgcct gcgtcctctt catcctcgac gagatgcgca     120
agcgctccgc cgaggacgga caggccacca cgggcgaggg cctcgactgg ggcgtcctct     180
tcggcggtac ccggaaaaaa aaaaaaaaaa aaaaaaaaa caccacagct cccacacaca     240
gcaggcagca gctcgatcgc tagctcctcc gaaccggaaa gccaagcccg ctttggcgat     300
cgtgcttgct tgcttggttc cttcaattcc tgccggagcc agcgagagct agctgctgct     360
gtcgcgtggt agacgtcgtc ttgccagcga gagcctagct cgatcggtct ctctggtaca     420
acgtagggag aaagatcgag ggggagagga cgacgacgat ggccgcgcg accgtgaccg     480
tggaggaggt gaggaaggcc cagcgcgcca ccggccccgc caccgtgctg gcgatcggca     540
ccgccacgcc cgccaactgc gtgtaccagg ccgactaccc ggactactac ttccggatca     600
ccaagagcga gcacctcacc gacctcaagg agaaattcaa gaggatgtgc gacaagtcga     660
tgatccggaa gcgttacatg cacctgacgg aggagttcct gcggagaaac ccgagcatgt     720
gcgcgtacat ggcgccgtcg ctggacgcgc ggcaggacgt ggtggtggtg gaggtgccga     780
agctggggaa ggcggcggcg cagaaggcga tcaaggagtg ggggcagcca agtcgcggat     840
tcacgcacct ggtgttctgc accacgtccg gggtggacat gccgggcgcc gactaccagc     900
tgaccaaggc gctgggcctg cgcccctccg tgaaccgcct catgatgtac cagcaggcgt     960
acatcgcgcc ccggacgagg ctgccggtgg gggaggacct ctcggagctc gacgaggtgg    1020
cccgccgagg acgacaggc caccacgggc gagggcctcg actggggcgt cctcttcggc    1080
ttcggcccgg gactcaccgt cgagaccgtc gtgctccaca gcgtccccat caccaccgga    1140
gcggccaccg cctgattcat cgattcatca acgatcaaat tcctcccctc tccgatccaa    1200
ttcgtcgtcg tctcgttcgt cattatttta cgtcgtccgt ccgcaaataa tgtgctctct    1260
gctataattg tcgtgtgtag tagtaagtag ctgttactat ttttccatgt actgtcagtc    1320
gcacaatcat catatataat taatatctct atatatgcat ttcatgcaag accagggtag    1380
agctagcttg aggagaagac ccttatcgtt gtcactttag catgcatggg gtggtgaggt    1440
attgggtata cctgtgtaag acaagcttgg ctggtttaat tatatatttt ttttaaaaaa    1500
aaaatctgtt tgatacaaaa ataacacctg taatgtgcat ggtgacggca aattgaccgc    1560
cattttcagg cacctaaagc tgtattggat atcggcccgg gactcaccgt cgagaccgtc    1620
gtgctccaca gcgtccccat caccaccgga gcggccaccg cctgattcat catcaacgat    1680
ccaattcgtc gtcgtctcgt tcgtcattat tttacgtcgt ccgtccgcaa ataataatgt    1740
gctctctgct ataattgtcg tgtgtagtaa gtagctgata ctatttttcc atgtactgtc    1800
agtcgcacaa tcatcatata taatatctct atatatgcat ttcatgcaag accagggtag    1860
agctagcttg aggagaagac ccttatcgtt gtcactttag catgcatggg gtggtgaggt    1920
attgggtata cctgtgtaag acaagcttgg ctggtttaat tatatatttt ttttaaaaaa    1980
tctgtttgct acaaaaacaa aacctgtaat gtgcatggtg atggcaaatt ggccgccatt    2040
ttcagtgcac ctaaagctgt attggataaa tgcttctact cgattattga ttgtaagagg    2100
tccactgtt                                                            2109
```

<210> SEQ ID NO 45
<211> LENGTH: 1427
<212> TYPE: DNA
<213> ORGANISM: Zea mays

<400> SEQUENCE: 45

```
attggtacct cgagccggcg ggaccccagc tcccacacac agcaggcagc agctcgatcg      60
ctagctcctc cgaaccggaa agccaagccc gctttggcga tcgtgcttgc ttgcttggtt     120
ccttcaattc ctgccggagc cagcgagagc tagctgctgc tgtcgcgtgg tagacgtcgt     180
cttgccagcg agagcctggc tcgatcggtc tctctggtac aacgtaggga gaaagatcga     240
gggggagagg acgacgacga tggccggcgc gaccgtgacc gtggaggagg tgaggaaggc     300
ccagcgcgcc accggccccg ccaccgtgct ggcgatcggc acggtgctgc gcgtggccaa     360
ggacctcgcg gagaacaacc gcggcgcgcg ggtgctggtg gtgtgctccg agatcacggc     420
cgtcacgttc cgcggcccct ccgagtcgca cctcgactcg ctcgtgggcc aggcgctgtt     480
cggcgacggc gcggcggccg tggtcgtggg cgccgaccg gacgaccgcg tcgagcgccc     540
gctcttccag ctcgtctccg ccgcccagac catcctgccc gactcggagg gcgccatcga     600
cggccacctc cgcgaggtgg ggctcacctt ccacctgctc aaggacgtgc ctggcctcat     660
ctccaagaac atcggccgcg cgctggacga cgcgttcaag ccgctcggca tctccgactg     720
gaactccatc ttctgggtgg cgcacccccg cgggcccgcc atcctcgacc aggtggaggc     780
caaggtcggg ctggacaagg ccaggatgcg cgccacccgc cacgtcctct ccgagtacgg     840
caacatgtcc agcgcctgcg tcctcttcat cctcgacgag atgcgcaagc gctccgccga     900
ggacggacag gccaccacgg gcgagggcct cgactggggc gtcctcttcg gcttcggccc     960
gggactcacc gtcgagaccg tcgtgctcca cagcgtcccc atcaccaccg gagcggccac    1020
cgcctgattc atcgattcat caacgatcaa attcctcccc tctccgatcc aattcgtcgt    1080
cgtctcgttc gtcattattt tacgtcgtcc gtccgcaaat aatgtgctct ctgctataat    1140
tgtcgtgtgt agtagtaagt agctgttact attttttccat gtactgtcag tcgcacaatc    1200
atcatatata attaatatct ctatataaaa aaaaaaaaa aagcaaaaaa aaaaaaaaa    1260 agctaatata ccaaagaaaa atactaaaag atgaaaccaa ttaagaaagc aacaagaaat    1320
taatgagaac aaataccggg gggggcgct ttttaaggat ccaaattttt cgaccggggc    1380
tttgaccgat tatattttt tttggtgggg ccaaaattaa attacct                  1427
```

<210> SEQ ID NO 46
<211> LENGTH: 1204
<212> TYPE: DNA
<213> ORGANISM: Zea mays
<220> FEATURE:
<221> NAME/KEY: misc_feature
<222> LOCATION: (385)..(385)
<223> OTHER INFORMATION: n = unknown

<400> SEQUENCE: 46

```
cgaggccggc cggaacaccc tttctcccca cacagcaggc agcagctcga tcgctagctc      60
ctccgaaccg gaaagccaag cccgctttgg cgatcgtgct tgcttgcttg gttccttcaa     120
ttcctgccgg agccagcgag agctagctgc tgctgtcgcg tggtagacgt cgtcttgcca     180
gcgagagcct agctcgatcg gtctctctgg tacaacgtag ggagaaagat cgaggggagag     240 aggacgacga cgatggccgg cgcgaccgtg accgtggagg aggtggtgtg ctccgagatc     300
acggccgtca cgttccgcgg ccctccgag tcgcacctcg actcgctcgt gggcaggcg     360 ctgttcggcg acgcgcggc gccgntgggt cgtgggcgcc gacccggacg accgcgtcga     420
gcgcccgctc ttccagctcg tctccgccgc ccagaccatc ctgccgact cggagggcgc     480 catcgacggc cacctccgcg aggtggggct caccttccac ctgctcaagg acgtgcctgg     540
```

```
cctcatctcc aagaacatcg gccgcgcgct ggacgacgcg ttcaagccgc tcggcatctc      600
cgactggaac tccatctttc tgggtggcgc gctctggcgg gcccgccatc ctcgaccagg      660
tggaggccaa ggtcgggctg acaaggcca ggatgcgcgc cacccgcca cgcctctccg        720 agtacggcaa catgtccagc gcctgcgtcc tcttcatcct cgacgagatg cgcaagcgct      780
ccgccgagga cggacaggcc accacggcg agggcctcga ctgggcgtc ctcttcggct        840 tcggcccggg actcaccgtc gagaccgtcg tgctccacag cgtccccatc accaccggag      900
cggccaccgc ctgattcatc atcaacgatc caattcgtcg tcgtctcgtt cgtcattatt      960
ttacgtcgtc cgtccgcaaa taataatgtc gtgtgtagta agtagctgat actatttttc     1020
catgtactgt cagtcgcaca gtcatcatat ataatatctc tatatatgca tttcatgcaa     1080
gaccagggta gagctagctt gaggagaaga cccttatcgt tgtcacttta gcatgcatgg     1140
ggtggtgagg tattgggtat acctgtgtaa gacaagcttg gctggtttaa ttatatattt     1200
ttcg                                                                  1204

<210> SEQ ID NO 47
<211> LENGTH: 788
<212> TYPE: DNA
<213> ORGANISM: Zea mays

<400> SEQUENCE: 47
gcgaggtggg gctcacctcc cacctgctca aggacgtgcc tggcctcatc tccaagaaca       60
tcggccgcgc gctggacgac gcgttcaagc cgctcggcat ctccgactgg aactccatct      120 tctggtggc gcaccccggc gggcccgcca tcctcgacca ggtggaggcc aaggtcgggc       180
tggacaaggc caggatgcgc gccacccgcc acgtcctctc cgagtacggc aacatgtcca      240
gcgcctgcgt cctcttcatc ctcgacgaga tgcgcaagcg ctccgccgag acggacagg       300 ccaccacggg cgagggcctc gactgggcg tcctcttcgg cttcggcccg ggactcaccg       360
tcgagaccgt cgtgctccac agcgtcccca tcaccaccgg agcggccacc gcctgattca      420
tcatcaacga tccaattcgt cgtcgtctcg ttcgtcatta ttttacgtcg tccgtccgca      480
aataataatg tgctctctgc tataattgtc gtgtgtagta agtagctgat actatttttc     540
catgtactgt cagtcgcaca atcatcatat ataatatctc tatatatgca tttcatgcaa     600
gaccagggta gagctagctt gaggagaaga cccttatcgt tgtcacttta gcatgcatgg     660
ggtggtgagg tattgggtat acctgtgtaa gacaagcttg gctggtttaa ttatatattt     720
ttttaaaaaa aaaaaatgtt tgctacaaaa aaaaaaaaaa aaacgttaag gatccaagtt     780
agtaggtg                                                              788

<210> SEQ ID NO 48
<211> LENGTH: 401
<212> TYPE: DNA
<213> ORGANISM: Zea mays
<220> FEATURE:
<221> NAME/KEY: misc_feature
<222> LOCATION: (377)..(377)
<223> OTHER INFORMATION: n = unknown

<400> SEQUENCE: 48
aagaatatgt tgggctcagg gctcacaggg cagacagcaa cggcatgccg gccgatccgc       60
catcgtccgg tcccatcggc gtccgtgcta gctacggtgc tataggtcct agctaataat      120
tccatcgcat ggcatccgtg caggcgacaa gtcgatgatc cggaagcggt acatgcacct      180
gacggaggag ttcctgtcgg agaaccccgag catgtgcgcg tacatggcgc cgtcgctgga      240
```

```
cgcgcggcag gacgtggtgg tgacggaggt gcccgaagct ggggaaggcg gcggcgcaga    300
aggcgatcaa ggagtggggg cakcccaagt cgcggatcac gcacctggtg ttctgcacca    360 cgtcggggt ggacatnccg ggcgccgact accagctgac c                        401
```

<210> SEQ ID NO 49
<211> LENGTH: 1401
<212> TYPE: DNA
<213> ORGANISM: Zea mays

<400> SEQUENCE: 49

```
ggtagctttg tagcaaccat gggaagcgct tgggccaacg tccgcgagat ctgccgcgca     60
cagcgtgccg acggcccgc agccgtgctc gccatcggca cggccaaccc ggcgaactgc    120
gtgccccagg acgagttccc cgacttctac ttccgcgcca ccaagagcga ccacctcact    180
ggcctcaagg aaaagttcaa agagtttgc cagaagctgg gcgtgcagaa gcgctacctg    240
caccacaccg aggagctgct gagcgcgcac ccggagttcc tggaccgctc ctcgccgtcc    300
ctcgacgcgc ggctggacat cgtcaagacc gccgtcccgg agctcgccgc gcaggcctgc    360
aggaaggcca tcgccgagtg gggccgcccg gccgccgacg tcacgcacct cgtcgtcgcc    420
accaactccg gcgcgcacat cccgggcgtc gacttccagc tggtctcgct cctgggcctc    480
cgcccgaccg tgcgccgcac catgctctac ctcaacggct gctccgcggg cgccgccgcg    540
ctgcgcctcg ccagggacct ggccgagaac aaccgcggcg cgcgcgtgct cgtcgcctgc    600
gccgagatca ccgtcctgct ctttgacggg cccgaggagg gctgtttcca gacgctcgtc    660
aaccagggcc tgttcggcga cggcgcggga gccgtcgtcg tcggcgccga cccggcggcc    720
ccggccgagc gcccgctgtt cgagatcgtg tccgccgcgc agaccgtcat accggactcc    780
gagggcgtca tcaccatgca cctcaccaag ggtggctacg gcggcaacat ctccaccagg    840
caggtccccg tactcatcgg cgaccacatc gagcgctgtc tcacggacgc ttttgcgccg    900
ctcggcgtcg gcgccggatg gaacgacctg ttctgggacg tgcacccggg ctcgtcggcg    960
atcctggacc aggtcgacgc cgtgctcaag ctcaagcctg agaagctggc ggcgagcaga   1020
cgtgtcctca gcgagtacgg gaacatgttc ggcgtcacgg tgatcttcgt gctcgacgag   1080
ctgccgccgc ggatgacgaa tggggaagag gaggggcgc ctgcagagtg gggggtcatg   1140
gtggcgtttg acccgggct caccgtcgag acgatggtgc tccaccgatc aggcaccca    1200 gccgagacga aactaggtga ggcatgaaaa ggtggacgtg accaatttgt gttggaactt   1260
ggatcaggat tgcatcattg catgcatgtt acttggtcaa catattccga ctatgtcact   1320
attcttgact tcagcctata ataaattcaa ctacataaac aactgttaaa aacttaaaaa   1380 aaaaaaaaa aaagggcggg c                                              1401
```

<210> SEQ ID NO 50
<211> LENGTH: 1670
<212> TYPE: DNA
<213> ORGANISM: Gossypium hirsutum

<400> SEQUENCE: 50

```
ttttactcgt gggccggccg ccggggccgg cgcccgggct ttttaccatt catagcatag     60
cagcttagtc caactccaca cccaccacca ttggctgttt gtgatcatcc gaaaaagaat    120
ggtgaccgtg gaagaagttc gtaaggctca acgtgcccaa ggccctgcca ccgtgttggc    180
catcggcaca tcaaccccgc ctaattgtgt tgatcagagc acatacccctg actactattt    240
```

-continued

```
ccgtatcaca aatagtgagc acaagaccga gttgaaagag aagttcaagc gcatgtgtga      300
aaaatcgatg atcaagaagc gatacatgta ccttacagaa gagattttga aagagaatcc      360
caatgtatgt gaatacatgg ctccttcact ggacgctagg caagatatgg tggtagttga      420
ggtgccaaag ctaggcaaag aagcagccac caaggccatt aaggagtggg gccagcccaa      480
gtccaagatc acccaccttg tcttttgcac cactagcggt gtggacatgc ctggggctga      540
ctaccagctc accaagcttt taggcctccg ccctccgtt aagcgcctca tgatgtacca       600
acaaggttgc ttcgcagggg ggacggtgct ccgagtggct aaggacttag ctgagaacaa      660
caaaggtgct cgtgtacttg ttgtgtgctc ggagattact gctgttacct ttcgtggacc      720
tagtgacact cacctagaca gtcttgtggg ccaagcattg tttggtgatg gtgccgcagc      780
tgttataatc ggggcagacc ccgtgcccga aatcgagaag cccatgtttg aactagtctc      840
agcagcccaa acgatcttgc cagatagtga tggtgcgatt gatggtcacc ttcgtgaagt      900
tggtcttaca tttcacccttc ttaaggatgt tccggggctt atttcgaaga atatagaaaa     960
gagcctggta gaagcatttc aaccattggg catatccgat tggaactccc ttttttggat     1020
tgctcatcct ggtggtccag caatattaga tcaagtagaa gccaaattag cactgaagcc     1080
agagaagcta cgagccacaa ggcacgttct ttcagagtat ggtaacatgt caagtgcttg     1140 tgttctatttt attttggatg agatgaggaa gaaatcaagg gaagatgggc ttcagaccac     1200
aggagaagga ttggagtggg gagtgctctt tgggtttgga cctggcctca ctgttgagac     1260
tgttgtgctc catagtgttg ctgcttaaag ttaaacaaac atgccttta agtaattggt       1320 cgtgctccac ttggcttgca gttttatctt cttctttttt ccttttttag aatcctatga     1380
atttgtgtgt ttattgttaa agactagaag ccttttgatgg tgtgggcggg aagcttaacg    1440
cctattcagt tcatgtatca acttatatta aatttatggc aataataagt tactttgcaa     1500
actattctac caaaaaaaaa aaaaaaaaaa ttatatttag ctaacaataa agaaaacaat     1560
aaataaggga tggaagttcg acctttgaaa ttttaaaaat taaaaacctt tttttgttcc    1620
tccaaaaatt tttaataaag agaaattttt gggggtcct ttttgaaggg                1670
```

<210> SEQ ID NO 51
<211> LENGTH: 636
<212> TYPE: DNA
<213> ORGANISM: Gossypium hirsutum

<400> SEQUENCE: 51

```
ccccgcgtcc gacccgcgtc cgccccccgc gcggccggcg tccgcgatga tcaagaagcg       60
atacatgtac cttacagaag agattttgaa agagaatccc aatgtatgcg aatacatggc      120
tccttcactg gatgctaggc aagatatggt ggtagttgag gtgccaaagc tgggcggaga     180
gagcagccac caaggccatt aaggagtggg gccagcccaa gtccaagatc acccaccttg     240
tcttttgcac cactagtggt gtggacatgc ctggggctga ctaccagctc accaagcttt     300
tgggcctccg ccctccgtt aagcgcctca tgatgtacca acaaggttgc ttcgcagggg      360
ggacggtgct ccgagtggct aaggacttag ctgagaacaa caaaggtgct cgtgtacttg     420
ttgtgtgctc cgagattact gctgttacct tccgtggacc tagtgacact cacctagaca     480
gtctagtggg ccaagcattg tttggtgatg gtgccgcagc tgttataatc ggggcagacc     540
ccatgcccga aatcgagaag cccatgtttg aaatagtctc agtagcccaa acgatcttgc     600
cagatagtga tggtgcaatt gatggtcacc ttcgtg                                636
```

<210> SEQ ID NO 52
<211> LENGTH: 671
<212> TYPE: DNA
<213> ORGANISM: Gossypium hirsutum

<400> SEQUENCE: 52

```
cccgggtcga cccacgccgt tcgccccgcg cccgtccaat cccacgggag cgggggggcct      60
gtttgtagat catcccggaa aaagaatgg tgaccgtggg aagaagttcg taagggctca      120
aacgtgccca aggccccttg ccaccgtgtt ggccatcggc accatcaacc cccccccttt      180
aattgtgttg atcagagcac ataccctgga cctgctgtgt ctccgtatca caaataggtg      240
agcacgaaaa caccgagttg aaaggagaag ttcaagcgca tgtgtgaaaa atcgatgatc      300
aagaagcgat acatgtacct tacagaagag attttgaaag agaatcccaa tgtatgtgaa      360
tacatggctc cttcactgga cgctaggcaa gatatggtgg tagttgaggt gccaaagcta      420
ggcaaagaag cagccaccaa ggccattaag gagtggggcc agcccaagtc caagatcacc      480
caccttgtct tttgcaccac tagcggtgtg gacatgcctg ggctgactac ccagctcacc      540
aagcttttgg gcctccgccc ctccgttaag cgcctcatga tgtaccaaca aggttgcttc      600
gcaggggga cggtgctccg agtggctaag gacttagctg agaacaacaa agtgctcgtg      660
tacttgttgt g                                                           671
```

<210> SEQ ID NO 53
<211> LENGTH: 759
<212> TYPE: DNA
<213> ORGANISM: Gossypium hirsutum

<400> SEQUENCE: 53

```
cccccccgcgt gcccttatca cccttagcca ccaccacaac tcttgggttg tttttctttt      60
tccttttgtt gaagctttaa aaaaaatgct gacagtggag gaagttcgta aggcacaacg      120
agccgaaggg ccggccaccg tgttggcgat cggtacgtcg actccaccca attgtgtgga      180
tcagagcacg taccctgatt actatttccg tatcacaaat agtgagcaca agactgagct      240
gaaagagaaa ttcaagcgca tgtgcgaaaa atcaatgatc aaaaagcgtt acatgtatct      300
aacggaagag attttgaaag agaaccccaa tgtatgtgaa tacatggcac catcactaga      360
tgcaagacaa gatatggtgg tagttgaggt accaaagcta ggtaaagaag ccgccacaaa      420
ggctattaag gaatggggtc agcccaaatc caagatcacc cacctcgtgt tttgcaccac      480
cagtggtgtc gacatgcccg gtgccgatta ccagctcact aagcttttgg gccttcgccc      540
gtcggttaag cgtctcatga tgtatcaaca aggttgtttc gctggggta ctgtgctccg      600
tgtggccaag gacttggctg agaacaacaa gggcgctcgc gtgcttgttg tttgctcgga      660
aatcaccgcg gttactttcc gtgggccgag tgatactact tgatagttag ttgccaagcg      720
ttgtcgtgat gtgctgtgtg tatagagtgc gatcatgct                              759
```

<210> SEQ ID NO 54
<211> LENGTH: 415
<212> TYPE: DNA
<213> ORGANISM: Gossypium hirsutum

<400> SEQUENCE: 54

```
cccacgcgtc cgcaaatagt gagcacaaga ctgagctgaa agagaaattc aagcgcatgt      60
gcgaaaaatc aatgatcaaa aagcgttaca tgtatctaac agaagagatt ttgaaagaga      120
accccaatgt atgtgaatac atggcaccat cactagatgc aagacaagat atggtggtag      180
```

| | |
|---|---|
| ttgaggcacc aaggctatta aggaatgggg tcagcccaaa tccaagatca cccacctcgt | 240 |
| gttttgcacc accagtggtg tcgacatgcc cggtgccgat taccagctca ctaagctttt | 300 |
| gggccttcgc ccgtcggtta agcgcctcat gatgtatcaa caaggttgtt tcgctggtgg | 360 |
| tactgtgctc cgtgtggcca aggacttggc cgagaacaac aagggcgctc gcgtg | 415 |

<210> SEQ ID NO 55
<211> LENGTH: 1508
<212> TYPE: DNA
<213> ORGANISM: Gossypium hirsutum

<400> SEQUENCE: 55

| | |
|---|---|
| cttatcaccc ttagccacca ccacaactgc tgtcagttcc tctgttgctg tgtgctaact | 60 |
| cttgggttgt tttttctttt tccttttgtt gaagctttaa aaaaaatggt gacagtggag | 120 |
| gaagttcgta aggcacaacg cgccgaaggg ccggccaccg tgttggcgat cggtacgtcg | 180 |
| actccaccga attgtgtgga tcagagcacg taccctgatt actatttccg tatcacaaat | 240 |
| agtgagcaca agactgagct gaaagagaaa ttcaagcgca tgtgcgaaaa atcaatgatc | 300 |
| aaaaagcgtt acatgtatct aacagaagag attttgaaag agaaccccaa tgtatgtgaa | 360 |
| tacatggcac catcactaga tgcaagacaa gatatggtgg tagttgaggt accaaggcta | 420 |
| ggcaaagaag ccgccaccaa ggctattaag gaatggggtc agcccaaatc caagatcacc | 480 |
| cacctcgtgt tttgcaccac cagtggtgtc gacatgcccg gtgccgatta ccagctcact | 540 |
| aagcttttgg gccttcgccc gtcggttaag cgcctcatga tgtatcaaca aggttgtttc | 600 |
| gctggtggta ctgtgctccg tgtggccaag gacttggccg agaacaacaa gggcgctcgc | 660 |
| gtgcttgttg tttgctcgga aatcaccgcg gttactttcc gtgggccgag tgatactcac | 720 |
| ttggatagtt tagttggcca agcgttgttc ggtgatggtg ctgctgctgt tatagtaggt | 780 |
| gcggatccat tggctgaaat cgagaagcct atgtttgaac tcgtctcggc ggcccaaacg | 840 |
| atcttgccag acagcgatgg tgccattgac ggtcaccttc gtgaagttgg acttacattt | 900 |
| caccttctca aggatgttcc cggcctaatt tcaaagaaca ttgaaaagag cctagctgag | 960 |
| gcatttcaac ctttgggcat ttcggattgg aactcgctct tttggatcgc tcaccccggt | 1020 |
| ggtccagcca tattggatca ggttgaggcg aagctagccc ttaaacccga aaaactccga | 1080 |
| gccacgaggc acgtgctttc agaatatggg aacatgtcaa gtgcttgtgt gctgttcata | 1140 |
| ttggatgaga tgaggaagaa atcaaaggaa gatggacttg gaaccacggg tgaagggctc | 1200 |
| gagtgggggtg tcctgtttgg tttcggacca gggctcactg ttgagaccgt ggtgcttcat | 1260 |
| agtatctctg cttaaacaag gttctaatgt tcatgttggc tagcccaggc tgcactacca | 1320 |
| tttgctttgc attttatttt atttttatttt ccttttttatt actgaaatttt gtgatttgta | 1380 |
| tggttatttg aaagagagta aagctctcac atatggtgtt taacgcctgt agaatttatg | 1440 |
| taccaccta tattttatgg taataataaa ttgccttttt tttaggtgaa aaaatgaag | 1500 |
| ggcaactg | 1508 |

<210> SEQ ID NO 56
<211> LENGTH: 609
<212> TYPE: DNA
<213> ORGANISM: Gossypium hirsutum

<400> SEQUENCE: 56

| | |
|---|---|
| aacattgaaa agagcctagc tgaggcattt caacctttgg gcatttcgga ttggaactcg | 60 |
| ctcttttgga tcgctcaccc cggtggtcca gccatattgg atcaggttga ggcgaagcta | 120 |

```
gcccttaaat ccgaaaaact ccgagccacg aggcacgtgc tttcagaata tgggaacatg        180
tcaagtgctt gtgtgctgtt catattggat gagatgagga agaaatcaaa ggaagatgga        240
cttggaacca cggtgaagg gctcgagtgg ggtgtcctgt ttgggttcgg accagggctc         300
actgttgaga ccgtggtgct tcatagtatc tctgcttaaa caaggtttta atgttcatgt        360
tggctagccc tggctgcact acaatttgct ttgcattttt atttatttta ttttcctttt        420
tattaatgaa atttgggatt tgtatggtta tttgaaagag agtaaagctc tcacatatgg        480
tgtttaacgc ctgtagaatt tatgtgccac cttatatttt atgatatggt gtttaacgcc        540
tgtagaattt atgtgccacc ttatatttta tggaaataat aaattgcctt ttttttaggt       600
gaaaaaagg                                                               609

<210> SEQ ID NO 57
<211> LENGTH: 960
<212> TYPE: DNA
<213> ORGANISM: Gossypium hirsutum

<400> SEQUENCE: 57
cgaaagaagc gcacaaagcc aggagaggat gggggcaccc taaatctaag atcacccacc        60
ttgttttctg cactacttct ggtgtagaca tgccgggtgc ggactaccaa cttaccaagc       120
tcctaggact gagaccttcc gtgaagagga tcatgatgat cagcaaggct gctttgctgg       180 tgaaccgtg cttcgtctcg ccaaagattt ggctgaaaat aacaaggacg ctcgggttct        240
ggtggtggct ccgagatcac ggctgcactt ttcgtgaccc ctcgatactc acttggattc       300
tctggtgggc aagcactttt gctgatggcg ctggagctgt catcataggc gctgaccctg       360
attccaaatc tgaacgccca ctattccagt ttgtatcagt tgcttatcaa tctgttctga       420 ttttttatttt gcaattgacg gacacttgcg tgatgtcggc ctcaatttcc atttgttgaa       480
agacgtgacc gggattgatc tcaaagaaca ttgaaaaaag cttggttgaa gcattcccac       540
caattggcat ctgggactgg aactccatct tctggatcgc tcaccctggt ggccctgcaa       600
tacttgacca aatcgaagcc aaactatgtc tcaaagaaga caaactcagg gctacccgtc       660
atgtgctgag cgagtttggc aacatgtcaa gtgcatgtgt gttatttatc atggacgaga       720
tgagaaagaa atcccttgac caaggtatgc ccaccaccgg tgaagggtat gagtgggtg        780 tccttttcgg attcggtcca ggtctcactg tggaaactgt tgtgctacac agtatacta       840 cacgggcaaa ctgacccaga caaaaagtga gacgatcgtg tggcttggag aggatgatac       900
aatataattt ttctatttat atgtgatatt ttttttccaaa taaatatgc tattttgtgt       960

<210> SEQ ID NO 58
<211> LENGTH: 382
<212> TYPE: DNA
<213> ORGANISM: Gossypium hirsutum

<400> SEQUENCE: 58
ccgattggaa ctcccttttt tggattgctc atcctggtgg tccagcaata ttagatcagg        60
tagaagccaa gttagcactg aagccagaga agctacgagc cacaaggcac gttctttcag       120
agtatggtaa catgtcaagt gcttgggttc tatttatttt ggatgagatg aggaagaaat       180
caagggaaga tggcttcaa accacaagag aagggttgga gtggggagtg ctctttgggt       240
ttggacctgg cctcactgtt gagactgttg tgctccatag tgttgctgct taaagttaaa       300
caaacatgct ttttaaagta ttggtcgtgc tccacttggc ttgcagtttt taaaaaaaaa       360
```

-continued

| aaattatatt aatttatata tt | 382 |

<210> SEQ ID NO 59
<211> LENGTH: 1432
<212> TYPE: DNA
<213> ORGANISM: Solanum tuberosum

<400> SEQUENCE: 59

| ggtattttca tatacataaa gcttagtaac acatcaacac aagccattt ttcttcttcg | 60 |
| cttgctaata tttgtataat attttggta ttttcatata cataaagctt agtaaaaaaa | 120 |
| aaacacgaaa atggtcaccg tagaggaggt tcgaaaggcg caacgtgcaa aggggccggc | 180 |
| tactatcatg gccataggca cggcgactcc ttcgaactgt gttgatcaaa gcacttatcc | 240 |
| tgattattat tttcgaatta ctaatagcga gcatatgact gagcttaaag agaaatttaa | 300 |
| gcgcatgtgt gataaatcaa tgattaataa gagatatatg cacttaacag aggaaattct | 360 |
| gaaagagaac ccaaatattt gtgaatacat ggctccttcg cttgatgcta ggcaagatat | 420 |
| agtggtggtt gaagtgccaa acttggcaa agaagcagcc caaaaggcca ttaaagaatg | 480 |
| gggccagccc aagtccaaga ttacccatgt ggtcttttgc accactagtg gggtggacat | 540 |
| gcctggggct gactaccaac tcactaagct tcttggtctt cgaccttcgg tcaagcgact | 600 |
| catgatgtac caacaaggtt gctttgctgg tgggactgtt atccgactgg caaggacttt | 660 |
| agctgaaaac aacaagggtg ctcgagtcct tgttgtttgc tcagagatca ctgcagttac | 720 |
| ttttagtggc ccaagtgata ctcacttgga tagtatggtt ggacaagccc tttttggtga | 780 |
| tggggcagct gcgatgatta taggttcaga tccattacca gaagttgaaa ggcctttgtt | 840 |
| tgaactcgtc tctgcagccc aaactctcct ccctgatagc gaaggtgcta ttgatggtca | 900 |
| ccttcgcgaa gttgggctaa catttcattt actcaaagat gttcctggat tgatctcaaa | 960 |
| aaacatcgaa aagagtttga ttgaagcatt ccaaccgtta ggcatttctg attggaactc | 1020 |
| tatcttttgg atcgctcacc ctggtgggcc ggcaattctt gaccaagttg aactaaaatt | 1080 |
| gggcctaaag cccgaaaaac ttcaggctac taggcaagtt ttaagtgact atggaaatat | 1140 |
| gtctagtgct tgtgttctat ttattttaga tgaaatgaga aaggcctcat ccaaagaagg | 1200 |
| gcttagtacc actggtgaag gccttgattg gggtgtactt tttggatttg ggcctgggct | 1260 |
| tacagttgag actgttgtgc tccatagtgt gtctacttag ttattaatta aattgattat | 1320 |
| ctatgtaata atcttaaatc tcttatattt ggtgtatcat gtatttgttt tgttttcaat | 1380 |
| tgaactttaa tttgtaatgc atattgtgtg taaaaaaagt tcatttccc tt | 1432 |

<210> SEQ ID NO 60
<211> LENGTH: 1419
<212> TYPE: DNA
<213> ORGANISM: Solanum tuberosum

<400> SEQUENCE: 60

| cataacataa agacatttat cactcttcgt tcacgtagta ctaaacacct aaaaaaaacc | 60 |
| tagcataacc acagtttttt ccggcgaaaa tggtcaccgt ggaggagtat cgtaaggcac | 120 |
| aacgtgccga gggtccagct acgatcctgg ccattggaac atctacgcct ccaactgtg | 180 |
| ttgatcagta tacttatcct gattattatt ttcgtatcac taatagtgag cacaagactg | 240 |
| agctcaagga aaaatttaag cgcatgtgtg ataaatcaat gattaagaag agatatatgc | 300 |
| acttaaccga ggaaatcttg aaagagaacc ctaacatgtg tgcatacatg gcgccttccc | 360 |
| tcgatgcaag gcaagacata gttgttgttg aagtgcctaa acttggcaaa gaggcggccc | 420 |

-continued

| | |
|---|---|
| aaaaggccat aaaagaatgg ggccagccca atccaagat tactcatttg gtcttttgta | 480 |
| caactagtgg tgtggacatg cccgggtgcg actaccaact cgctaagctc ctcgggcttc | 540 |
| gcccatcagt caagcgactc atgatgtacc aacaaggttg cttttgccggg ggaacagttc | 600 |
| tccggctagc caaggacttg gctgagaaca acaagggcgc tagagtcctt gttgtttgct | 660 |
| ctgagatcac tgcagtcacg ttccgtggac ccagtgaatc tcacttagat agcctggtag | 720 |
| gccaagccct ttttggtgat ggggcggccg ctatcattat gggttcggac ccaattatag | 780 |
| gggttgaaag gcctttattc gaactcgtct cagcagctca aactcttgtc cccgatagcg | 840 |
| aaggtgctat cgatggacat ctccgtgagg ttgggcttac gttccactta ctcaaggatg | 900 |
| ttcctgggct aatctcaaaa acatcgaaa agagccttct agaagcattt caacctctag | 960 |
| gtatatctga ctggaactct ctattttgga tcgctcaccc aggcgggcct gcgattttgg | 1020 |
| accaagttga attaaagttg ggcctaaagc aagagaaact tagggctaca agagaagtac | 1080 |
| tgagtaacta tggcaatatg tcaagtgctt gtgtgttgtt tattttggat gaaatgagaa | 1140 |
| aggcctctac aaacgaaggc ctaggaacta caggtgaagg gcttgaatgg ggtgtccttt | 1200 |
| ttggatttgg gcctgggctt acagttgaga ctgttgttct tcacagtgtt gctacttagt | 1260 |
| gggttgggct tatattgtgg gcctctaaaa tttgtttgct attaatgtat ttgctatatt | 1320 |
| ttgttatttta atatttatgt tatccttgcg aataaagata tttgtaatga gaactatgta | 1380 |
| atcaaatacc taataaattt ctgtctaatt ttaattttt | 1419 |

<210> SEQ ID NO 61
<211> LENGTH: 1836
<212> TYPE: DNA
<213> ORGANISM: Oryza sativa

<400> SEQUENCE: 61

| | |
|---|---|
| gccaacccag cagcagcaag cagcgcacaa gccccagcac cagcaagctg ctactcatca | 60 |
| tcagcgagag ctagctagct gtgtgtgcca cttacactgc tgctgctgct ggttctagct | 120 |
| aagctcaccg atcgtcgtct tcgtcatcgc cggtgacctg gtgaattagt cgagagagat | 180 |
| ggcggcggcg gtgacggtgg aggaggtgag gagggcgcag agggcggagg ggccggcgac | 240 |
| ggtgctggcg atcgggacgg cgacgccggc gaactgcgtg taccaggccg actacccgga | 300 |
| ctactacttc aggatcacca agagcgagca catggtcgag ctcaaggaga gttcaagag | 360 |
| gatgtgtgac aagtcgcaga tcaggaagag gtacatgcac ctgacggagg agatcctgca | 420 |
| ggagaacccc aacatgtgcg cgtacatggc gccgtcgctg gacgcgcggc aggacatcgt | 480 |
| cgtcgtcgag gtccccaagc tggggaaggc ggcggcgcag aaggcgatca aggagtgggg | 540 |
| gcagccgcgc tcccgcatca cccacctcgt cttctgcacc acctccggcg tcgacatgcc | 600 |
| cggcgccgac taccagctcg ccaagatgct cggcctgagg cccaacgtga accgcctcat | 660 |
| gatgtaccag caggggtgct cgccggcgg cacggtgctc cgcgtcgcca aggacctcgc | 720 |
| cgagaacaac cgcggcgcgc gcgtcctcgc cgtgtgctcc gagatcacgg cggtgacgtt | 780 |
| ccgggggccc tccgagtccc acctcgactc catggtcggg caggcgctgt tcggcgacgg | 840 |
| cgcggcggcg gtgatcgtcg gctccgaccc gacgagggcc gtcgagcggc cgctgttcca | 900 |
| gatggtgtcg gcgagccaga ccatcctccc ggacagcgag ggcgccatcg acggccacct | 960 |
| gagggaggtc gggctgacgt tccacctgct caaggacgtg ccggggctca tctcgaagaa | 1020 |
| catcgagcgc gcgctgggcg acgcgttcac accgctgggg atctcggact ggaactccat | 1080 |

-continued

```
cttctgggtg gcgcaccccg gaggtccggc gatcctggac caggtggagg cgaaggttgg    1140
gctggacaag gagaggatga gggcgacgcg ccacgtgctg tccgagtacg caacatgtc    1200 gagcgcctgc gtgctcttca tcctcgacga gatgcgcaag cgctccgccg aggacggcca    1260
cgccaccacc ggcgagggca tggactgggg cgtcctcttc ggcttcggcc ccggcctcac    1320
cgtcgagacc gtcgtcctcc acagcgtccc catcaccgcc ggcgccgccg cctgagcgct    1380
ccgccctggt cgccgccggc cggcctacgt acgccacacg tcatctttta tcatcgatca    1440
taaaaaaaaa ttatatatat atcgatatcg atatatatat atttcctaat aataactact    1500
actacaataa caacgttatc gaattaaaaa gttattccct tttgccgtgt gttggtaggg    1560
ataaaaagtg aaaaaaaaaa ttattacttt gttttgcatg tgtcatgtat gggtggtttg    1620
gttggtagta gcatatatat gtatactgaa agagaaagg gaggtcaatt aagtgtcatg    1680
gatggtgagg tttattgtaa acctgtgtaa gagatgcttg gctgttacta ttcaatttga    1740
aaacttaatt aattttgtgt acctaaaaaa aaaaaaaaa aaaaaaaaat gatcttttt    1800 tttaaaaaaa aaaaaaaaaa aaaaaaaaa aaaaaa                                1836
```

<210> SEQ ID NO 62
<211> LENGTH: 464
<212> TYPE: DNA
<213> ORGANISM: Oryza sativa

<400> SEQUENCE: 62

```
gcagagggat ttttcaggcg tatcggcgtc gggcagtgag aagcgtttct tccaccacac     60
ggaggagatg atcaacgcgc accctgaatt cctcgaccgc gcgacgccgt cgctggacgc    120
gcgcctggag atcgccgccg cggccgtccc tgagctcgcc gcgacggccg cggcgagggc    180
catcgcccag tggggccgcc ccgccaccga ggtcacccac ctcgtcgtca ccaccaacgc    240
gggcgcccac gccccgggcg ccgacgtccg cctcgccgcg ctcctcggcc tccgccccac    300
cgtgcgccgc accatgatcc acctcaacgg ctgctccgcg ggcgccgccg cgctgcgcct    360
cgccaaggac ctcgccgaga acagccgcgg cgcgcgcgtc ctcgtcgcct gcgtcgagct    420
caccgtcctc accttccgcg ggccggacag gccccacacc gtca                      464
```

<210> SEQ ID NO 63
<211> LENGTH: 1561
<212> TYPE: DNA
<213> ORGANISM: Sorghum bicolor
<220> FEATURE:
<221> NAME/KEY: misc_feature
<222> LOCATION: (1547)..(1547)
<223> OTHER INFORMATION: n = unknown

<400> SEQUENCE: 63

```
gcacgcacga gggtactacg ataagctttg ccactagtta gcttcggtct tgtattcttg     60
ttgctgttag ttctctgtgt gccagcagca tccggccggt aggaaaaatg acgactggga    120
aggtaacatt ggaggcggtg agaaaggcgc agcgcgccga gggacctgct acggtgttgg    180
ccattgggac ggcgacaccg gcaaactgcg tgtatcaggc tgactacccg gactactact    240
tccgggtcac caagagcgaa caccttaccg acctcaagga aaaattcaag aggatatgcc    300
acaagtcgat gattaggaag cgttacatgc atttgactga ggcatcccta gaggagaacc    360
ccaacatgag ctcgtactgg gcaccatccc tagacgcacg ccaggatatc ctgatacagg    420
agatacccaa gctgggcgcg gaagctgcag agaaggcgct caaagagtgg ggccagccac    480
gttcccggat cacgcacctc gtcttctgca ccacctccgg cgtggacatg cctggcgccg    540
```

```
actaccagct catcaagcta ctcggtctct gccctctgt gaaccgagcg atgatgtacc      600
accagggttg cttcgccggc ggaatggtgc tccgtcttgc caaggacctt gccgagaaca      660
accgtggtgc ccgggtgctc atcgtgtgct ccgagatcac cgtggtcacg ttccggggc      720
cctcggagtc tcaccttgac tcgcttgtcg gccaagctct cttcggtgac ggcgcagctg      780
cggtgatcgt cggcgcagac cccagcgagc ctgctgagcg gccattgttc catctagtat      840
cagcgagcca gaccattctc ccagactcag agggtgccat cgagggccac ctccgtgagg      900
tggggctcac cttccatctc caggacaggg ttccacagct catctccatg aacattgagc      960
gcttgctgga agacgctttc gcaccgcttg gcatctccga ttggaactcc atcttttggg     1020
tggcgcaccc tggcggtcca gccatactga acatggtgga ggctaaggtt ggccttgaca     1080
aggccagaat gtgtgccacc cgccacatcc tggcagagta tggcaacatg tcaagcgttt     1140
gtgtcctctt catccttgat gagatgcgaa acaggtctgc caaggacgga cacaccacaa     1200
ctggggaggg tatggagtgg ggtgtcctct tcggcttcgg ccccggcctc accgtcgaga     1260
ccatcgttct tcacagcgtt cccatcacca cagtggctgc atgaccgctg tgtgcatgtt     1320
gctccgggtg acgcgtgtgc atggctattc acctttacac tttacagttt attttggttt     1380
ctcacacaaa taatgtactg cggcttctat gtgccgtgct gtgtgggtgc ttgctgtttg     1440
tctttacacg aatacctgag atatctgtgc tagtgttaaa tgaataaaac agtacaagtc     1500
aacacagtgc agtggttata ataatttatt aataccatgt gcccctnaat attatactcg     1560
t                                                                     1561
```

<210> SEQ ID NO 64
<211> LENGTH: 1785
<212> TYPE: DNA
<213> ORGANISM: Sorghum bicolor

<400> SEQUENCE: 64

```
gcacgagggc ccggtccaac cgcccaggcc cagccccgcc ctcctccccc agcctctcca       60
cgcagccaca gctgccgctc tcgcaggtcg agctcatcct gccagcagcc cgatcgtcga      120
tgggcgtgag cgcggtgtcc ctggaagaat gtgcttggcg gaacgcaggg acagggtaga      180
gagaaagagc cgatggggc ggcggccgga gccgccgtga gcgtggagga ggtgcagcgg      240
gcgccgggcc cggcgggccc ggccgccgtg ctggcggtct cgagggcgac gccgggccac      300
cacgtgcaca agcccgacta ccggtaccag aacctacgga gcacaaagag cgagcacatg      360
accgaactct aggagaagtt gaacaacatg tgcgacaagt ggcagagccg caagcggtgc      420
acgcaccaga ctgagggga catggccgac atccccgaca actgggcgta catgcgccg       480
tcgctggatg cccgccagga gatcgtggtg ccgaggtgc gcaagctagg caagccggcg      540
gcgcagaagg cgatcacgga gtggaagcag ccgaaatcca agatcactca cctcgtcttc      600
tgcaccacct ccggcgtcga catgccctgc gccgactacc agctcccca agatgctcgg      660
tctgcgcccc tcgtgctacc gcctgatgat gtaccagcag gggtggttcg cgggcggcac      720
gttgctgcgc gtggcgaagg aactcgccga gaacaaccgc ccgcgtgcg atctggtggt      780
atgctccgag atcaccgccg gcacgttccg tggaccctcc gagtcccacc tctcactcca      840
tggttggcca agcgctgttc ggcgacggtg ctgcggcggt tattgtggga gctgacccctg     900
acgagcgcgt ggagcgcccg ctgttccagc tcgtgtcggc gtcgcagaca atcctgccgg      960
actccgaggg cgccatcgac ggccacctcc gtgaggtcgg gctcacgttc cacctgctca     1020
```

-continued

| | | |
|---|---|---|
| aggacgtgcc cgggctcatc tccaaaaaca tagagcgctc gctggaggag gcgttcaagc | 1080 |
| cgctggggat caccgactac aactccatct tctgggtggc gcaccctggc gggccagcaa | 1140 |
| tcctggacca ggtggaggcc aaggtcgggc tagagaagga gcggatgcgt gccacgcgcc | 1200 |
| atgtcctgtc cgagtacggc aacatgtcta gtgcgtgcgt gctcttcatc ctcgacgaga | 1260 |
| tgcgcaaacg ctccgccgag gacggccagg caaccaccgg cgaaggcttc gactggggcg | 1320 |
| tgctcttcgg cttcggtcct gggctcaccg tcgagaccgt cgtgctccac agcgtcccca | 1380 |
| tcaccaccgg agcggccatc accgcgtgag atgaagtacc acgccgcgcg caccgcacct | 1440 |
| cgctcggtct ccatgaatcc ctcctctcca caaccaccag tcgtcgatcg ttcgtgatta | 1500 |
| tttgcctcgt aacgcaaata atgtgctctg tattgtctgc ataattgccg tgtatcgtag | 1560 |
| tagctgctat tattttccat gtactgttgc cagtcgcaca atgtgaacat gcatgtaagc | 1620 |
| cctggtagta gaaccttaat tttaagggcg agctagctca cggataaaag accgttgtta | 1680 |
| ttaattgtca ctagctactt tagcatggat ggtgaggtat tgtatacctg tgtaagacaa | 1740 |
| gcttggctgg tttttaatat tttaatttgt ttattagttt gctca | 1785 |

<210> SEQ ID NO 65
<211> LENGTH: 1622
<212> TYPE: DNA
<213> ORGANISM: Glycine max

<400> SEQUENCE: 65

| | | |
|---|---|---|
| ccgggccccc ccatgacgcg tacgtattcg gctcgagccc aattcttccc cctccaccca | 60 |
| cccagcatat ctctctattc ctatttatta gcacccctca cattaccttg tgtcaccaac | 120 |
| tactttgact cctttaccat accattacaa taattatcaa acctaaccag taaaaatggt | 180 |
| gaccgtggag gaaatccgca acgctcagcg ttcccatgga cccgccacca tcttggcctt | 240 |
| cggcaccgcc acgccgtcca actgcgtctc ccaagccgat taccctgact actacttccg | 300 |
| cattaccaac agcgaacaca tgactgatct caaagaaaag ttcaagcgca tgtgtgaaaa | 360 |
| gtccatgata aagaagcgat acatgcacct gacggaggac tttctgaaag agaacccgaa | 420 |
| catgtgcgag tacatggcgc catcgctgga cgtgagacaa gacgtagtgg tgatggaggt | 480 |
| gccgaagctg ggaaaacaag ccgcaacgaa agcgattaag gagtgggtc aaccaaagtc | 540 |
| aaagatcaca caccttgtgt tctgcaccac ttcaggcgtg acatgcccg gagcagatta | 600 |
| ccagctcacg aagcttctcg gcctgaggcc ctccgtgaag cgcctcatga tgtatcagca | 660 |
| gggctgcttc gccggcggca ccgtactccg cctcgcgaag gacctcgccg agaacaacaa | 720 |
| gggtgcgagg gtgctcgttg tctgctccga gataaccgcc gtgacgttcc gcggcccctc | 780 |
| ggacacgcac ctcgactcgc tcgtgggaca ggcactgttc ggagatggcg ccgcagcgtt | 840 |
| gatcatcgga tcagaccccg acccagcagt ggagcggccg atattcgaga tgatatcggc | 900 |
| cgcccagaca atcctgcccg actctgacgg tgctatagat gggcaccttc ggggaggtggg | 960 |
| actcacgttc cacctcttga agatgtgcc cgggatcatc tcgaagaaca ttgagaagag | 1020 |
| tcttgttgaa gcttttgagc ccatcgggat cagcgactgg aactctatct tctggatcgc | 1080 |
| acatcccggt ggtccgcgca tcctcgatca agtcgaggag aagctccggc tcaagccgga | 1140 |
| gaaactccag tccacccggc atgtgctgag tgagtacgga acatgtcaa gcgcgtgtgt | 1200 |
| tttgttcatt ctggatgaaa tgaggaagaa gtctaaggag aagggaaga gtaccactgg | 1260 |
| agaagggtta gagtgggggg tgctattcgg attcggccg ggtctaaccg ttgagaccgt | 1320 |
| tgttcttcac agtgttccct tggagggata aatcatgctg atgcggtgac tagtgattta | 1380 |

-continued

```
agagtgatca ataaggaacc ctcggaaata ccagggaaag tttgttatta ttactagttt    1440
cacttgtgga tttatcgtag cataatgttg tacaagaata atttaatatg aacaagatcg    1500
tgtgtttgtt attgattttt tcaaagttat atagtccgta cttattcggc attgcatttc    1560
gtttaaacag gacagagcgg ctctagatct acagagtctc acgcatgcgt gcatgtgaag    1620
tc                                                                  1622
```

<210> SEQ ID NO 66
<211> LENGTH: 1634
<212> TYPE: DNA
<213> ORGANISM: Glycine max

<400> SEQUENCE: 66

```
ttgttgtctc gtgtgctgct agctccaata gggtttgaat atcaccattt ccaattgcaa      60
accacagctt aattctctct actactgcta gctgtgactt gttttgagtt caatcaaatc     120
gcattggtat ctgaaatcag gaaagatggt tagcgtagct gagatcaggc aggcacaaag     180
ggcagaaggc ccagcaacca tccttgccat tggaactgca aacccaccaa accgtgttga     240
tcagagcacc tatcctgatt actacttcag aatcaccaac agtgaccaca tgaccgagct     300
caaagagaaa tttcagcgca tgtgtgacaa gtctatgatc aagacgagat atatgtacct     360
aaacgaagag atcttgaaag agaatccaaa catgtgtgct tacatggcac cttcttttga     420
tgctaggcaa gacatggtgg tggtagaggt accaaagcta gggaaagagg ctgcagtaaa     480
ggccataaag gagtggggcc agccaaagtc aaagattacc cacttgatct ctgcaccac     540 tagcggtgtg gacatgcctg gtgctgatta ccaactcacc aaacaattgg gccttcgccc     600
ttatgtgaag aggtacatga tgtaccaaca aggttgcttt gcaggtggca cggttcttcg     660
tttggccaag gatttggctg agaacaacaa gggtgcacgt gtgcttgttg tctgctctga     720
gatcactgca gtcacattcc gtgggccaag tgacactcac cttgatagtc ttgtgggcca     780
agcattgttt ggagatggag ctgctgcagt cattgttggt tctgacccaa ttccacaagt     840
tgagaagcct ttgtatgagc ttgtttggac tgcacaaaca attgctccag acagtgaagg     900
tgctattgat ggacaccttc gtgaagttgg actcacattt cacctcctca aggatgttcc     960
cgggattgtc tcaaagaaca ttgataaggc actttttgag gctttcaacc cattgaacat    1020
ctctgattac aactccatct tttggattgc acaccctggt gggcctgcga ttttagacca    1080
agttgagcaa agttgggtc tcaaacctga gaagatgaag gccactagag atgtgcttag    1140
tgaatatggg aacatgtcaa gtgcttgtgt tcttttcatc ttggatgaga tgaggaggaa    1200
atctgctgaa aatggacata aaccacagg tgaaggactt gaatggggtg tgttgttcgg    1260
ttttggacct ggacttacca ttgaaactgt tgttttgcat agtgtggcca tctgagatgc    1320
ctcatatatt atttcattat tgtgtaccac ttttcaaact tgcttggggt ttgtaacaac    1380
aacaaccacc aaaaaaaaaa aaactcgttt agagtttgtt tgtgtacgtt tatattaaaa    1440
taataatacg tgtttggtgg cttttttagcc taattatcaa taacaggcat tgttttttaa    1500
agtttgtaat tgtgtacgtt tatattcaaa taataataca tgttcgatgg ccttttagcc    1560
taatttcatg ataacaaaaa tttgtctgaa aaaaataat tctttcatga tttatattat    1620 aaatttatc ttag                                                       1634
```

<210> SEQ ID NO 67
<211> LENGTH: 1517
<212> TYPE: DNA

<213> ORGANISM: Glycine max

<400> SEQUENCE: 67

```
ggtagtagac ggtggaaaaa tgtatatgtt ggtgtacatt ggtgcatgca cgtgatgata      60
ctcacctacc cttcaacccct cacatacata taaaatgcca tctcctcaaa caagttcaaa    120
gcacaccttc atttcaacct ctctgatttt gtaattgagt tcgatcaaat agctcccagt    180
actttaattg atttctgaat atcatcactt aatttgaagg aaagatggtg agcgtagctg    240
agatccgcca ggcacaaagg gcagaaggcc cagcaaccat ccttgccatt ggaactgcaa    300
acccaccaaa ctgtgttgat cagagcacct atcctgacta ctacttcaga atcaccaaca    360
gtgagcacat gaccgagctc aaagagaaat tccagcgcat gtgtgacaag tctatgatca    420
agaggagata tatgtaccta acgaagaga tcttgaaaga aatccaaac atgtgtgctt      480
acatggcacc ttctttggat gctaggcaag acatggtggt ggtagaggta ccaaagctag    540
ggaaagaggc tgcagtaaag gccataaagg agtggggcca gccaaagtca agattaccc     600
acttgatctt ctgcaccacc agtggtgttg acatgcctgg tgctgattac caactgacca    660
aacaattggg ccttcgcccc tatgtgaaga ggtatatgat gtaccaacaa ggttgctttg    720
caggtggcac ggttcttcgt ttggccaagg atttggctga gaacaacaag ggtgcacgtg    780
tgcttgttgt ctgttctgag atcactgcag tcacattccg tggaccaagt gacactcacc    840
ttgatagtct tgtgggccaa gcattgtttg gagatggagc tgctgctgtc attgttggtt    900
ctgacccaat tccacaagtt gagaagcctt gtatgagct tgtttggact gcacaaacaa    960
ttgctccaga cagtgaaggt gctattgatg gacaccttcg tgaagttgga ctcacatttc   1020
acctcctcaa ggatgttccc gggattgtct caaagaacat tgataaggca ctttttgagg   1080
cttttcaaccc attgaacatc tctgattaca actccatctt ttggattgca caccctggtg   1140
ggcctgcgat tttagaccaa gttgagcaaa agttgggtct caaacctgag aagatgaagg   1200
ccactagaga tgtgcttagt gaatatggga acatgtcaag tgcttgtgtt cttttcatct   1260
tggatgagat gaggaggaaa tctgctgaaa atggacataa aaccacaggt gaaggacttg   1320
aatgggggtgt gttgttcggt tttggacctg gacttacact tttcaaactt gcttggggtt   1380
tgtaacaaca acaaccacca aaaaaaaaaa aactcgttta gagtttgttt gtgtacgttt   1440
atattaaaat aataatacgt gttttggtggc cttttagcct aattatcaat aacaggcatt   1500
tgttttagaa aaaaaag                                                  1517
```

<210> SEQ ID NO 68
<211> LENGTH: 540
<212> TYPE: DNA
<213> ORGANISM: Glycine max

<400> SEQUENCE: 68

```
cacctatcct gattactact tcagaatcac caacagtgac cacatgaccg agctcaaaga     60
gaaatttcag cgcatgtgtg acaagtctat gatcaagatc tcttcgttta ggtacatata    120
tctcgtcttg atcttgaaag agaatccaaa catgtgtgct tacatggcac cttcttttgga  180
tgctaggcaa gacatggtgg tggtagaggt accaaagcta gggaaagagg ctgcagtaaa    240
ggccataaag gagtggggcc agccaaagtc aagattacc cacttgatct ctgcaccac     300
tagcggtgtg gacatgcctg gtgctgatta ccaactcacc aaacaattgg gccttcgccc    360
ttatgtgaag aggtacatga tgtaccaaca aggttgcttt gcaggtggca cggttcttcg    420
tttggccaag gatttggctg agaacaacaa gggtgcacgt gtgcttgttg tctgctctga    480
```

-continued gataattgta gtcacattcc gtgggcccaa gtgacactta ccttggatag tcttgtgggc    540

<210> SEQ ID NO 69
<211> LENGTH: 1823
<212> TYPE: DNA
<213> ORGANISM: Glycine max

<400> SEQUENCE: 69
gtgaaaactt aattgcatta atagtaatat aacatgttct tatttactga tataaaaaaa     60
gaagcatgtg agggaagcag ggaaaaaaag gaagagaaag aatacatttt tcaaactcaa    120
catgaaagaa tgaataagaa agaaaaggac ttggtcttgc acaagatata tggattagac    180
agtgacactg cggagcacaa cagtctcaac ggtgagtcca gggccgaaac caaatagcac    240
accccagtca aggccttcac cggttgtgcc aagtccattt tctattgatt tcttcctcat    300
ttgatccaag atgaatagca cacatgcact tgacatgtta ccatactcgc tgagcacatg    360
tctagtagct tccattttt caggctttaa gcctaactta gcctcaactt ggtccaaaat    420
tgcgggtcca ccagggtgtg caatccagaa gatagaattg taatcggaga ttcccaaggg    480
tgggaaggct tcaaccaagg ccttctcaat attcttggag atgagtccag gaacatcctt    540
gaggagatgg aaagtgagac caacttcgcg aaggtgtcca tcaatagccc cttcactgtc    600
tggaaggatt gtctgggcag tccagacaag ctgaaacaaa ggcttttcaa ctggtaaggg    660
gtctgatcca acaatgacag cggctgcacc atctccaaac aaggcttgac ccacaaggct    720
atcaagatgg gtgtcagttg ggccgcgaaa tgtgactgct gtgatctcag aacaaacccc    780
aagcacgcga gcacccttgt tgttttcggc gaggtctttg gccaaacgaa gcaccgtgcc    840
accggcaaag cagccttgtt ggtacatcat gtaacgcttg acgagggac gaaggcccag    900
tagtttagtg agctgataat cagcaccagg catgtcgaca ccactagtgg tgcaaaagat    960
gagatgggta atcttggact tgggttgacc ccattccttg attgccttag ttgcagcctc   1020
ttttcccaac tttggtacct ccacaaccac catgtcttgc cttgcatcca acgaaggtgc   1080
catatatgca caaacactgg gattctcctt caggatctct tcatttaagt acatgtatcg   1140
cttcttaatc attgacttat cacctgatcc aaacaataaa ttaaatttca ttaatatcac   1200
taatcaaatc aaaggaatat gttgaaaata acaatatac atattgtata aagaaatgaa   1260
gaaaggagag agatatatat cttacacatg cgcttgaatt tttctttgag ctcggtcatg   1320
tgctcgctgt tggtgatgcg gaaataatag tcaggatagg tactctgatc cacgcagttg   1380
ggaggagtgg cggtgccaat agccatgaca gtggcagggc cttctgcacg ttgcgcctta   1440
cgaatctctt caacactcac catcctagct ggttaagaaa agaatggaag tgggaagtag   1500
caagtaggat agaaagggta tgatatgatg atgggggtgg atgttggaaa gtgatttgga   1560
aggtggata tatatagata gttgatattg gtaggtaggc taaggtacgt agatgctatg   1620
catgcttcct ctgactcgtg gctgcgcttt gtttcaacta tgtggtgccc cgcatggcta   1680
cgtagactga tgactactct cttattttaa caacccaata ttttttggttt tttgtttatt   1740
ttttaatcaa cacgttttca ttaggagaag ccacgaaagt atgaattatg attaggaaaa   1800
gtcaatggtg aaggtcatag agg                                           1823

<210> SEQ ID NO 70
<211> LENGTH: 1729
<212> TYPE: DNA
<213> ORGANISM: Glycine max

<400> SEQUENCE: 70

```
atatagataa cttgtgtgta agcttaattg aaaaaatagt ataacaagtt gttatttact        60
agtatacaaa cagaagcatt tgcagggcag gggaaaaaaa atcgaaacac aatacgtttt       120
ttcaaaccgg ccagccaaga atacatatga aaaagaaag atttgttctc ttgctcaata        180
tatatgatca gagagtgaca ctgcggagca acagtctc aacggtgagt ccagggccga         240
aaccaaatag cacaccccag tcaagacctt caccggttgt gccaagtcca ttttctattg       300
atttcttcct catttgatcc aagatgaata gcacgcatgc acttgacatg ttaccatact       360
cgctgagcac atgtctagta gcttccattt tttcaggctt caggcctaac ttagcctcaa       420
cttggtccaa aattgcgggt ccaccagggt gtgcaatcca aagatagaa ttgtaatcgg        480
agattcccaa gggttggaag gcttcaacca aggccttctc aatattcttg agatgagtc        540
caggaacatc cttgaggaga tggaaagtga gaccaacttc gcgaaggtgt ccatcaatag       600
ccccttcact gtctggaagg attgtctggg cagtccagac aagctgaaac aaaggctttt       660
caactggtaa ggggtctgat ccaacaatga cagcggctgc accatctcca aacaaggctt       720
gacccacaag gctatcaaga tgggtgtcag ttgggccgcg aaatgtgact gcggtgatct       780
cagaacaaac gacaagcacg cgagcaccct tgttgttttc agcgaggtct ttggccaaac       840
gaagcaccgt gccaccggca aagcagcctt gttggtacat catgtaacgc ttgacggagg       900
ggcgaaggcc taatagtta gtgagccgat aatcagcacc aggcatgtcg acaccactag       960
tggtgcaaaa gatgagatgg gtaatcttgg acttgggttg accccattcc ttgattgcct      1020
tagttgcagc ctctttttccc aactttggta cctccacaac caccatgtct tgccttgcat    1080
ccaacgaagg tgccatatat gcacaaacac tgggattctc cttcaggatc tcttcgttta     1140
agtacatgta tcgcttctta atcatcgact tatcacacat gcgcttgaac ttttctttga     1200
gctcagtcat gtgctcactg ttggtaatgc ggaaataata gtcaggataa gtactctgat     1260
cgacgcagtt tggaggagtg gcagtgccga tggccatgac ggtggcaggg ccttctgcac     1320
gttgtgcctt acgggattgc ttcaacactc accattgtta taaatttat gaatcaacta      1380
atgaagctag cttgcaccaa agaatgaaac taattagtaa ttaaggagta gctagctacg     1440
aaagcatata tcacctgctt tccgtgtgaa ggaaggagat cacgttatta ttggtcaatg     1500
caggccactt tctaagactg tgaggttcaa tgtgttgaaa gtgatcccag ctggatcttc     1560
tagcggtgca aagaaggctt ttactggaat gtgagctttg atttccagtt tttattgaag     1620
ataaatgtta ccttattaat tattatatct gatttctttt ctggatgata acaaatatga     1680
aaaccttgtc aattttggat tttctttgag gtttaaaaaa aaaaaaaaa                  1729
```

<210> SEQ ID NO 71
<211> LENGTH: 1592
<212> TYPE: DNA
<213> ORGANISM: Glycine max

<400> SEQUENCE: 71

```
ttttttttttt ttttttttttt ttttttaatga agatgaaatt ggacaaaagc tattcacttt     60
gcaactgtat atatagatca attatgtgtt aagcttaatt gcatttatga catgacatgt       120
tcttatttac ttgtataaaa aaagaagcat atgagaaaga cggaaaaaaa agcaaaagga      180
gaaagaatac attttcaaa cagacgtgtc agacataaga aaggatatga ttagactgtg      240
acactgcgaa gcacaacagt ctcaacagtg agtccagggc caaaaccaaa tagcacaccc      300
cattcaagcc cttcaccagt ggtgccaagt ccattttcta ttgacttctt cctcatttga     360
```

-continued

| | |
|---|---|
| tccaagatga acaacacgca tgcacttgac atgttaccat actcgctgag cacatgtcta | 420 |
| gtagcttcca ttttttcagg tttcaagcct aacttagcct caacttggtc caatattgct | 480 |
| ggtccaccag ggtgtgcaat ccaaaagata gagttgtaat catcaattcc caagggttgg | 540 |
| aaggcttcaa ccaaggcctt ttggatgttc ttcgagatga gtccaggaac atccttgagg | 600 |
| agatggaaag tgagtcctac ttcgcgaagg tggccatcaa tagccccttc actgtctgga | 660 |
| aggattgttt gtgcagtcca cacaagctca acaaaggct tttcagcagg caaagggtct | 720 |
| gatccaacaa tgcacagcagc tgcaccatct ccaaacaagg cttgcccaac aaggctatca | 780 |
| agatgggtgt cactcgggcc gcgaaatgtg actgctgtga tctctgaaca cacgacgagc | 840 |
| acacgagcac ccgtgttgtt ttcggccaag tctttcgcca gacgaagcac cgtgccaccg | 900 |
| gcaaagcagc cttgttggta catcatgtaa cgcttgacgg aggggcgaag gcctaatagt | 960 |
| ttagtgagct gataatcagc accaggcatg tcgacaccac tagtggtgca aaagatgaga | 1020 |
| tgggtaatct tggacttggg ttgaccccat tccttgattg ccttagttgc agcctctttt | 1080 |
| cccaactttg gtacctccac aaccaccatg tcttgccttg catccaacga aggtgccatg | 1140 |
| taagcacaaa cactcggatt ctctttcagg atttcttcat ttaagtacat gtatcgcttc | 1200 |
| ttaatcattg acttatcacc tgatcgaaat aataaattaa atttcattaa tatcactaat | 1260 |
| caaatcaaag gaatatgttg aaaataagca atatacatat tgtataaaga aatgaagaaa | 1320 |
| ggagagagat atatatctta cacatgcgct tgaattttc tttgagctcg gtcatgtgct | 1380 |
| cgctgttggt gatgcggaaa taatagtcag gataggtact ctgatcgaca cagtttggag | 1440 |
| gagttgcggt gccaatagcc atgacagtgg cagggccctc tgcacgttgt gcattacgga | 1500 |
| tctcttcaac actgaccatc ctagctagtt aattttctga agcaaagaat gaaagtgtag | 1560 |
| tagctaggaa agaaaaggct tggatggatg tt | 1592 |

<210> SEQ ID NO 72
<211> LENGTH: 1310
<212> TYPE: DNA
<213> ORGANISM: Glycine max
<220> FEATURE:
<221> NAME/KEY: misc_feature
<222> LOCATION: (823)..(836)
<223> OTHER INFORMATION: n = unknown

<400> SEQUENCE: 72

| | |
|---|---|
| gaaaaagcaa aagagaaaga atatattttt caaactaaac aagcaacaat acataagaaa | 60 |
| aaaaaaggat ttgtgatctt ctgtataatt tttctgacac acccagataa ctcatacaca | 120 |
| acactcgtta cacaattgac ccataaataa acctggttcc agacagttct atagttcaat | 180 |
| ttatgctcaa tcacaaagaa tctttcaatg aagataaaat tggacaaaag atattcactt | 240 |
| tgcaactgca tatatagatt acttgtgtgt aagcttaaat gaattaatag taaaacaagt | 300 |
| tcttatttat tggtatacaa aaagaagcat tgatgaagg cagggcaggg aaaaaaaatc | 360 |
| aaaagacaga ataagccttg atcagccaac aatacatatg aaaaaagaaa gatttgttgt | 420 |
| cttgacaaaa tatgattact gattagacac tgacactgcg gagcacaacc gtctcaacag | 480 |
| tgagtccagg gccaaaacca aagagcacac cccaatcaag gccttcacca gttgtgccaa | 540 |
| gtccattttc tatagacttc ttcctcatct gatccaagat gaataacaca catgcacttg | 600 |
| acatattacc atactcgctg agcacatgtc tagtagcttc cattttttca ggcttcaagc | 660 |
| ctaacttagc ctcgacttgg tctaaaattg ccggtccacc agggtgtgca atccagaaga | 720 |

-continued

| | |
|---|---|
| tagagttgta atcagagatt cccaagggtt ggaaggcttc aactaaggcc ttttcgatat | 780 |
| tcttagagat gagtccagga acatccttga ggagatggaa agngagtcca acttcncgaa | 840 |
| ggtgtccatc aatagcccct tcactgtctg gaaggattgt ctgggcagtc cagacaagct | 900 |
| gaaacaaagg ctttcaaatg gtaaggtggt ctgatccacc aatgaaagca gttgcaccat | 960 |
| ctcccaaaca aggtttaccc cccaaggcta tcaagatggg tgtccagttg gccccaggaa | 1020 |
| cgtccacttc agtgattttc agaccaaaac cacaagcacg gggagcaccc ttgttgtttc | 1080 |
| tggctaggtc tttgcccaga cgaagcactg tgccgccggc aaagcagcct tgttggtaca | 1140 |
| tcatgtaacg cttgacgcag ggacgaaggc ccagtagttt agtgagctgg taatcagcac | 1200 |
| caggcatgtc gacaccgctg gtggtgcaaa aaatgagatg gagtaatctg gtcacttgga | 1260 |
| gttgacccca ttccttgatg gccttagtgg cagcctgttt tcccaacttt | 1310 |

<210> SEQ ID NO 73
<211> LENGTH: 1455
<212> TYPE: DNA
<213> ORGANISM: Glycine max

<400> SEQUENCE: 73

| | |
|---|---|
| attggacaaa agctattcac tttgcaaatg tatacataga taatttatgt gttaagctta | 60 |
| attgcattaa taacatgaca tgttcttatt tactggtata caaaatgaag caaaagagaa | 120 |
| ggaatacatt tttcaaacag aacttacaag acatgagaaa gaatataatt agacagtgac | 180 |
| actgcgtagc acaacagtct caacagtgag tccagggcca aaaccaaata acacaccccca | 240 |
| ttcaagtcct tcaccagttg tgccaagtcc attttctatt gacttcttcc tcatttgatc | 300 |
| caagatgaac agcacacatg cacttgacat gttaccatac tcgctaagca cgtgtctagt | 360 |
| agcttccatt ttttcatgct tcaatcctaa cttagcctca acttggtcca aaattgctgg | 420 |
| tccaccaggg tgtgcaatcc aaaagataga gttgtaatca tcaatttcta agggtttgaa | 480 |
| ggcttcaacc aaggcctttt cgatgttctt ggagatgagt ccaggaacat ccttgaggag | 540 |
| atggaaagtg agtcctactt ggcgaaggtg gccatcaata cgccttcgc tgtctggaag | 600 |
| gattgtttgt gcagtccaca caagctcaaa caaaggcttt tcagctggca gaggatctga | 660 |
| tccaacaatg acagcagctg caccatctcc aaacaaggct tgccccacaa ggctgtcaag | 720 |
| atgtgtgtca ctcgggccac gaaatgtgac tgctgtgatc tccgaacaca ccacaagcac | 780 |
| acgagcactt gttgttttca gccaagtctt tgccagacga agcaccgtgc caccagcaaa | 840 |
| acagccttgt tggtacatca tgtaacgctt caccgatgga cgaagtccta gtagttttgt | 900 |
| gagctgataa tcagcaccag gcatgtccac accactggtt gtgcagaaga tgagatgagt | 960 |
| aatcttggac ttggattgac cccattcctt gattgccttt gttgcagcct cttttcccaa | 1020 |
| ctttggtacc tccacaacaa ccatgtcttg ccttgcatcc aatgaaggtg ccatataggc | 1080 |
| accaacactc ggattctcct tcaggatctc ttcatttaag tacatgtatc gtttcttaat | 1140 |
| cattgactta tcacaaatgc gcttgaactt ttctttgagc tcggtcatgt ggtcactgtt | 1200 |
| ggtgatgcgg aaataatagt caggataggt actctgatcc acgcagttgg gaggagtggc | 1260 |
| cgtgccaata gccatcacgg tggcagggcc ttccgcacgt tgtgccttac gaatctcttc | 1320 |
| aacactcacc attttcctaa ttttcaatct ctgcaaccaa caactaagct tctttgaacc | 1380 |
| caagaattaa tgaaactcaa gtagtagtag ctacgaaaga aaggctatga tatgaatgat | 1440 |
| ggggatcgat gctat | 1455 |

<210> SEQ ID NO 74
<211> LENGTH: 669
<212> TYPE: DNA
<213> ORGANISM: Glycine max

<400> SEQUENCE: 74

| | | |
|---|---|---|
| gcaactgaat atatagatga attttgtgaa aacttaattg cattaatagt aatataacat | 60 |
| gttcttattt actggtataa aaaagaagc atgtgaggga agcagggaaa aaaggaaga | 120 |
| gaaagaatac attttcaaa ctcaacatga agaatgaat aagaaagaaa aggacttggt | 180 |
| cttgcacaag atatatggat tagacagtga cactgcggag cacaacagtc tcaacagtga | 240 |
| gtccagggcc aaaaccaaac agcacacccc attcaaggcc ttcacctgtt gtgccaagtc | 300 |
| cattttctaa tgacttcctc ctcatttgat ccaagatgaa tagcacacat gcacttgaca | 360 |
| tgttaccata ctcgctgagc acatgcctag tagcttccat tttttcaggc ttcaagccta | 420 |
| acttagcctc cacttggtcc aaaattgcgg gtccaccagg gtgtgcaatc cagaagatag | 480 |
| aattgtaatc ggagattccc aagggttgga aggcttcaac caaggccttc tcaatattct | 540 |
| tggagatgag tccaggaaca tccttgagga tggaaagt gagaccaact tcgcgaaggt | 600 |
| gtccatcaat agccccttca ctgtctggaa ggattgtctg gcagtccag acaagctgaa | 660 |
| acaatacaa | 669 |

<210> SEQ ID NO 75
<211> LENGTH: 912
<212> TYPE: DNA
<213> ORGANISM: Glycine max

<400> SEQUENCE: 75

| | | |
|---|---|---|
| cccacgcgtc cggatactta ttgatctgtt tcatataatg ttgtatatca cagtcaaata | 60 |
| actcacccaa gacagaaaat tttaagctaa actggactaa gttaatcggc acaactctct | 120 |
| ttacacaaac cacataattc caaacagttc tacagtccaa tttatacaca atcacgaaga | 180 |
| atcttttgtt ggagatgaaa ttggtaaaaa taaatagaa gatattcact ttgcaactgt | 240 |
| atagtataga tcaattgtgt ataagcttaa ttgcattaat aataagatgt gttctcgttt | 300 |
| agtgtttact ggtatacaaa aagaagaat gtgagaaagc aaaagagaaa gaatacattt | 360 |
| ttcaaactaa aaagcaata atacataaga agaaagaag gatctgtgtt cttgctcaat | 420 |
| atatatgatt agacagtgac actgcggagt acaacagtct caacagtgag tccaggaccg | 480 |
| aaaccaaata gcacacccca gtcaaggcct tcgccggttg tgccaagtcc attttctatt | 540 |
| gatttcttcc gcatttgatc caagatgaat agcacacatg cacttgacat gttaccatac | 600 |
| tcgctgagca catgcctagt agcttccatt ttttcaggct tcaagcctaa cttagcctcc | 660 |
| acttggtcca aaattgcggg tccaccaggg tgtgcaatcc agaagataga attgtaatcg | 720 |
| gagattccca agggttggaa ggcttcaacc aaggccttct caatattctt ggagatgagt | 780 |
| ccaggaacat ccttgaggag atggaaagtg agaccaactt cgcgaaggtg tccatcaata | 840 |
| gccccttcac tgtctggaag gattgtctgg cagtccaga caagctgaaa caaaggcttt | 900 |
| tcaactggta ag | 912 |

<210> SEQ ID NO 76
<211> LENGTH: 753
<212> TYPE: DNA
<213> ORGANISM: Glycine max

<400> SEQUENCE: 76

-continued

| | |
|---|---|
| ggatagatca attatgtata agcttaatag cattaataac acgacttgtt cttatttact | 60 |
| ggtatacaaa aagaagcatt tgatgaaatc agggggaaaa ttcaaaagac aaagaataca | 120 |
| tttttcaaac tgaacagcaa agaatacata agaaaagaga aagatttgct gtcttaagaa | 180 |
| aatactatta ctgattagac actgactcaa ttactgatta gacagtgaca ctgcggagca | 240 |
| caacagtctc aacggtgagt ccagggccga aaccaaatag cacacccag tcaaggcctt | 300 |
| caccggttgt gccaagtcca ttttctattg atttcttcct catttgatcc aagatgaata | 360 |
| gcacacatgc acttgacatg ttaccatact cgctgagcac atgtctagta gcttccattt | 420 |
| tttcaggctt caagcctaac ttagcctcaa cttggtccaa aattgcgggt ccaccagggt | 480 |
| gtgcaatcca aagatagaa ttgtaatcgg agattcccaa gggttggaag gcttcaacca | 540 |
| aggccttctc aatattctta gagatgagtc caggaacatc cttgaggaga tggaaagtga | 600 |
| gtccaacttc gcgaaggtgg ccatcaatag ccccttcact gtctggaagg attgtttggg | 660 |
| cagtccagat aagctgaaac aaaggctttt caactggtaa ggggtctgat ccaacaatga | 720 |
| cagcggctgc accatctcca aacaaggcta aac | 753 |

<210> SEQ ID NO 77
<211> LENGTH: 805
<212> TYPE: DNA
<213> ORGANISM: Glycine max

<400> SEQUENCE: 77

| | |
|---|---|
| ccacgcgtcc gggcagaagg cccagcaacc atccttgcca ttggaactgc aaacccacca | 60 |
| aaccgtgttg atcagagcac ctatcctgat tactacttca gaatcaccaa cagtgaccac | 120 |
| atgaccgagc tcaaagagaa atttcagcgc atgtgtatgt actgccatac tctcatctta | 180 |
| attttttccat atttctcact tctacaaaat tgttttttcta catccgtttt aatttataca | 240 |
| aataacactt gttaatttgg cacatcttaa ttctgtcttc tcgttacatt atattatcta | 300 |
| tcacgtcgat ctgcgaatca ttcttgaaat aaataaataa ataaatctaa ttgggtgcaa | 360 |
| atattaaaat ggcatcaagg ttttttataag ttacttagtc taaatagtta aaaattaaat | 420 |
| tgataggttt ttgcatttca atagtagcta gtcattatgt atagttagag attattagtc | 480 |
| ttttaactct cccttttcaaa aaaaaaaaaa aagagggtga taattcgtta tggtgtttgt | 540 |
| tgtcttgatt atacaatata gatcgttgac attattattt ctttatgact aattttcagg | 600 |
| tgacaagtct atgatcaaga cgagatatat gtacctaaac gaagagatct tgaaagagaa | 660 |
| tccaaacatg tgtgcttaca tggcaccttc tttggatgct aggcaagaca tggtggtggt | 720 |
| agaggtacca aagctaggga aagaggctgc agtaaaggcc ataaggagt ggggccagcc | 780 |
| aaagtcaaag attacccact tgatc | 805 |

<210> SEQ ID NO 78
<211> LENGTH: 540
<212> TYPE: DNA
<213> ORGANISM: Glycine max

<400> SEQUENCE: 78

| | |
|---|---|
| ctcgagccct ttctatccta cttgctactt cccacttcca ttctttttctt aaccagctag | 60 |
| gatggtgagt gttgaagaga ttcgtaaggc gcaacgtgca gaaggccctg ccactgtcat | 120 |
| ggctattggc accgccactc ctcccaactg cgggtgtcaa agatcctctc ctggctgtta | 180 |
| cgttcacatg agcttctgcg ggcacataaa caggctgatc cattccttat ctctcatgag | 240 |
| gcattgcccg tacatttacc ttcgatacac gtgcttaaac gggcagatcc tgcaagagaa | 300 |

```
tccgagtgtt tgcgcttaca tggcaccttc gatggatgca aggcaagaca tggtggttgt      360
ggcggtacca aagttgggaa aagaggctgc aactcacgca atcatggaat ggggtcaacc      420
ccagtccaag attacccatc tgatcttctg caccactagt ggtgtcgaca tgcctggtgc      480
tgattatcag ctcactaaac tattaggcct tcgccctac gtcaagcgtt acatgatgta      540
```

<210> SEQ ID NO 79
<211> LENGTH: 1310
<212> TYPE: DNA
<213> ORGANISM: Brassica napus

<400> SEQUENCE: 79

```
gacaactcag ctccggactc tttacctaga tcggaaaccg ccgtcaccta cgactctccg      60
tacccgctct acgcgatgtc cttctcctcc tccacccacc gaatcgccgt cgggagcttc     120
ctcgaggact acaacaaccg catcgacatc tctccttcg actccgactc catgtccctc      180
aagccccttc catccctctc cttcgagcac ccttaccctc ccaccaagct catgttcagt     240 ccccctccc tccgccgcag cggcgggggc gacctcctcg cctcctccgg cgacttcctc      300
cgcctctggg aggtcaacga agactcctcc tccgcggagc cagtatcggt cctcaacaac     360
agcaagacga gcgagttctg cgcgccgctg acctccttcg actggaacga cgtggagccg     420
aagcggttag gcacgtgcag catcgacacc acgtgcacga tctgggacgt ggagaggtcc     480
gtggtggaga cgcagctcat cgcgcacgac aaggaggtcc acgacatcgc gtggggggag     540
gctagggttt tcgcctcggt ctccgccgac ggatcggtga ggatcttcga tctgcgcgac     600
aaggagcact ccaccatcat ctacgagagc ccccagcccg atacgccgct cctgaggctc     660
gcgtggaaca agcaggactt gcggtgtatg ccacgattc tgatggattc gaataaggtt      720
gtcattctcg acattcgatc gccgacgatg ccggtcgccg agcttgaaag gcaccagggg     780
agtgtgaacg cgattgcgtg ggcgccgcag agctgtaagc atatctgctc gggtggggat     840
gacgcgcagg ctcttatctg ggagttgccg acgatggctg ggccgaatgg gattgatccc     900
atgtcggttt actcggccgg ttcggagatt aaccagttgc agtggtcggc ttctctgcct     960
gattggattg gcattgcgtt tgctaacaaa atgcagctcc tcagagtttg agatgcaggt    1020
ggggaagtga tcaaaaatca gagatagcat agacccgtgt aaccagtgcg taagcttagt    1080
agggtttggt tggtgcaaag cacattctgg tttctttgat tcgcaatgcc tctatgcatc    1140
tatgtgatcg taactaagac tttattcgct tggtgtacca aatgctctac tatttttatta    1200 tctctgtttg tgtataaacc aaaccaggat aataatgtta ttgcggtggt ttctggtgtt    1260
tggattaaaa aaaaaaaaaa aaaaaaaaaa aaaaaaaaaa aaaaaaaaaa                1310
```

<210> SEQ ID NO 80
<211> LENGTH: 584
<212> TYPE: DNA
<213> ORGANISM: Glycine max

<400> SEQUENCE: 80

```
aggtgcttat taatggacac cttcgtgagg ttggactcac atttcacctt ctcaaggatg      60
tccccgggat tgtctcaaag acatgataag gcacttttg aggctttcaa cccattgaac      120
atctctgatt acaactccat cttttggatt gcacaccccg tgggcctgc tattcttgac      180 caagttgagc aaaagttagg tctcaaacct gagaagatga aggccactag agatgtgctt     240
agtgaatatg ggaacatgtc aagtgcttgt gttcttttca tcttggatga gatgaggagg     300
```

```
aaatctgctg aaaatggact taaaaccaca ggtgaaggac ttgaatgggg tgtgttgttc    360
ggttttggac ctggacttac cattgaaact gttgttctgc gcagtgtggc catctgagat    420
gcctaatata ttatttcatt attgtgtacc acttttcaaa cttgctggag tttgtaacaa    480
caacaacaac aaaaaaaaaa aaactcgttt agagtttgta attgtgtacg tttatattca    540
aataataata catgttcgat ggccttttag cctaatttca tgat                    584
```

<210> SEQ ID NO 81
<211> LENGTH: 1527
<212> TYPE: DNA
<213> ORGANISM: Glycine max

<400> SEQUENCE: 81

```
acacttcagc tacgtaggcc ccccccccaa aaagtatttt gaaatatttt caaaagacct     60
atatttggta agccaatcaa attggacatt aataaaggaa tggagagggc agaacaaatt    120
ggaggaggca aagctgtggc cacagtccta gccattggca cagcaaatcc acccaatttc    180
atccttcagg aggattatcc tgacttctac tttcgggtca ccaatagcga ccatttgcac    240
cgcttgaagc aaaagttcaa gcgcatttgc gagaattcaa agatagaaaa gcgacacata    300
gtccacacgg aagaatacct aaagcagaac tcagacagcg gcacgtacga tggccttccc    360
ttggagacac gacagaatgt ccccacggaa caggtaataa aattaggtat ggaagcagca    420
tcaaaggcca ttaaggaatg gggcgaaccc ttatcagaaa tcacacacct catcttctac    480
accacttctt gcttcggctc cgttcccggt cctgaccact acctctccaa acaacttgga    540
ctccgctcaa cggtcaaccg cctcatgctc ttcagccacg gttgccacgc tggcggcacc    600
attctccgcg ttgccaaaga tatcgcggag aacaaccctg gctcacgtgt tcttgccgtc    660
tgttccgaga ccatgtttgc ctcgtttcgc gctcctagcg aatccaacgt tgaggttctc    720
gtaggacagg ctctgttcgg agacggtgcc gccgccgtca tcattggcgc ggatcctaag    780
cactccatcg agcatccact cttcgaactc gtgttggctt ctcaaaccac tgtgcctgac    840
accgagaatg cgatcaaagg aagtcaacaa gagaataggt tggtttatta tttggataag    900
gacattccca atattgtaac taacaatgtg aagaagtgtt tggttgatga gttgggtgaa    960
gttggtttcg tcgacgaaat tgattggaac aagttttttct atgcaattca tccgggtggg   1020
gctgttattg tgagtggggt tgaagagaag ctagggttag agaaagagaa gctgagtgcg   1080
acatggcacg tgctgagcca acacgggaac atgtggagtc caactgtgat ttttatcttg   1140
gatgagatga ggaacaggtc caagactgag gggaagagca caaccggtga agggttagag   1200
tgggggattt tattagggtt tggtcctggt gtggcaatgg aaactgtgct tttacgtagt   1260
tatccatgtt gataaatagt tacaaggagt tacaaatact actactgcta ctcatgttta   1320
tgtatttatg ggtattttt ttaagaataa atgtggtaac tttcttagta agagaaatta   1380
aatgtaacat aatcgttgta tgtcacgatt gttttaagag tttggatatt gtaataatga   1440
tttagacaac acggactagt aaaatcgaga atttactatt ttagaatcaa aaaaaaaaa    1500 aaaaaaaaaa actgagacta gtctctc                                       1527
```

<210> SEQ ID NO 82
<211> LENGTH: 1421
<212> TYPE: DNA
<213> ORGANISM: Lycopersicon esculentum

<400> SEQUENCE: 82

```
cgtgattttc tcttcttgac ttgctaaaat ttgtataata ttttttgtat tttcatatac     60
```

```
ataaatctta gtcaagaaaa agggaaaatc cgcgaaaatg gtcaccgttc ccgaggttcg    120
aagggcgcat cgtgcaaagg gaccagctac tatcatggcc ataggcacgg cgactccttc    180
gaactgtgtt gatcaaagca cttatcctga ttattatttt cgaatcacta atagtgaaca    240
tatgactgag cttaaggaga atttaagcg catgtgtgat aaatcgatga ttaataagag    300
atatatgcat ttaactgaag aaattttaaa agaaaaccca atatttgtg aatacatggc    360 tccttctttg gatgctagac aagatatagt ggtggttgaa gtgccaaaac ttggcaaaga    420
agcagcccaa aaggccatta agaatgggg tcagcccaag tccaagatca cccatgtggt    480
cttttgcacc actagtgggg tggacatgcc tggggccgac taccaactca ccaagcttct    540
tgggcttcga ccttcggtta agcggctcat gatgtatcaa caaggttgct ttgctggtgg    600
gaccgttatc cgactggcaa aggacttagc tgagaacaac aagggtgctc gagttcttgt    660
tgtttgctca gagatcactg cagttacttt tcgtggtcca agtgatactc atttggatag    720
tatggttgga caagcccttt ttggtgatgg ggcagccgca atgattatag gttcagatcc    780
attaccagaa gttgaaaggc ctttgtttga actcgtctct gcagcccaaa ctctactccc    840
tgatagcgaa ggtgctattg atggtcacct tcgcgaagtt gggctaacat ttcacttgct    900
caaagatgtt cctggattga tctcgaaaaa cattgaaaag agtttaattg aagcattcca    960
accgttaggc atttctgatt ggaattccat cttttggatc gcgcaccctg gtgggccggc   1020
gattctagat caagttgaac taaaactgag cctaaagccc gaaaaacttc gggctactag   1080
gcaagtttta agtgactatg gaaatatgtc tagtgcttgt gttctattta ttttagatga   1140
aatgagaaag gcctcatcca agaagggct tagtaccaca ggtgaaggcc ttgattgggg   1200
tgtacttttt ggatttgggc ctgggcttac tgttgagact gttgtgctcc atagtgtgtc   1260
tacttagtat ataatattac taaaggggt tataagttaa atagattatc tatgtaatct   1320
tatattatat ttcttatatt tggtgtatca tgtatttatt ttgttttcaa ttgaaaaaaa   1380
aaaaaaaaaa actcgataag aaaaagttca ttttcccttt g                       1421
```

<210> SEQ ID NO 83
<211> LENGTH: 1416
<212> TYPE: DNA
<213> ORGANISM: Lycopersicon esculentum

<400> SEQUENCE: 83

```
cttcccccaa actgcaccaa gacaattatc actctttcat tcacgtagtc ctaaacacaa     60
aaaaacctag catatccacc attttttccg gcgaaaatgg tcaccgtgga ggagtatcgt    120
aaggcgcaac gtgcagaggg tccagctacg atcttagcca ttggaacatc tacgccttct    180
aactgtgttg atcagagtac ttatcctgat tattattttc gtatcactaa cagtgagcac    240
aagactgagc tgaaagagaa atttaagcgc atgtgtgata aatcaatgat taagaagaga    300
tatatgcact taaccgaaga aatcttgaaa gagaaccta acatgtgtgc atacatggca    360
ccttcccttg atgcaaggca agacatagtt gttgttgaag tgcctaaact tggaaaagaa    420
ggcagcccaa aaggccatca agaatgggg ccagcccaaa tccaagatta cccatttggt    480
cttttgtacc actagtggtg tggacatgcc cgcgtgtgac taccaactcg ctaagctcct    540 acccettcgc ccatcagtca agcgactcat gatgtaccaa caaggttgct ttgccggggg    600
aacagtactt cggctagcca aggacttggc tgagaacaac aagggtgcta gagtccttgt    660
tgtttgctct gagatcactg cagttacgtt ccgtggaccc agtgaatctc acttagatag    720
```

-continued

```
cttggtaggc caagcccttt ttggtgatgg ggcggccgca attattatag gttcggaccc      780
aattatoggg gtcgaaagac ctttatttga actcgtctca gcagcccaaa ctcttgtccc      840
cgatagcgaa ggcgctattg acggacacct acgtgaggtt gggcttacat tccacttact     900
caaggatgtt cctgggctta tctcgaaaaa catcgaaaag agccttctag aagcatttca     960
acctctaggt atatctgact ggaactctct attttggatc gctcaccctg gcgggcctgc    1020
gattttggac caagttgaat tgaagttggg cctaaagcct gagaaactta gggctacaag    1080
agaagtacta agtaactatg gcaatatgtc aagtgcttgt gtgttgttta ttttggatga    1140
aatgagaaag gcctctacaa aagaaggcct aggaactact ggtgaagggc ttgaatgggg    1200
tgtccttttt ggatttgggc ctgggcttac agttgagact gttgtccttc acagtgttgc    1260
tgcttagtgg gctgggctta cattgtgggc ctctaaaatt tcttggttat taatgtgttt    1320
gctatatttt gttgtttaat gtttatgttg tcttttttca aataaagata tttataatga    1380
gaactatacc taaaaaaaaa aaaaaaaaaa actcga                              1416
```

<210> SEQ ID NO 84
<211> LENGTH: 685
<212> TYPE: DNA
<213> ORGANISM: Triticum aestivum

<400> SEQUENCE: 84

```
accacaccac accacgccac cagtacaagc ggcgcctgtc atttgtctac cacctgctag      60
ctgcttccct ctgcgtcccg caaacttaga cttcacacag ccggccactg gtgcgacaac     120
tactagctcg tcggccgctg gtacgtacgt agatcccatc gatggcggcc accatgaccg     180
tggaggaggt gaggaaggcg cagcgggcgg agggccggc caccgtgctc gccatcggta     240
cggcgacgcc cgcgaactgc gtgtaccagg ccgactaccc cgactactac ttcaagatca     300
ccaagagcga ccacatggcc gacctcaagg agaagttcaa gaggatgtgt gacaagtcgc     360
agatcaggaa gagatacatg cacctaacgg aggagatcct tcaggagaac cccaacatgt     420
gcgcctacat ggcgcccctcc ctggacgcgc gccaggacat cgtcgtcgtg gaggtcccca     480
agctcggcaa ggcggcggcg cagaaggcca tcaaggagtg gggacagccg cggtccaaga     540
tcacccacct cgtcttctgc accacctccg gcgtcgacat gccgggggcc gactaccagc     600
tcaccaagat gctcggcctg cgcccgtccg tgaagcgcct catgatgtac cagcagggct     660
gcttcgccgg cggcacggtg ctccg                                          685
```

<210> SEQ ID NO 85
<211> LENGTH: 929
<212> TYPE: DNA
<213> ORGANISM: Triticum aestivum
<220> FEATURE:
<221> NAME/KEY: misc_feature
<222> LOCATION: (3)..(39)
<223> OTHER INFORMATION: n = unknown

<400> SEQUENCE: 85

```
ggnacaatgt tccagnagnn atgtgtgaca ggtgcgatng atccgaaaga ggtacatgca      60
cgtgacggag gagatcctta aggagaaccc caacgtctgc gcgtacatgg cgccgtctct     120
ggatgcgcgc caagacatgg tgctcggcga ggtcccgaag ctcgggaagg aggcggcaca     180
taaggccata aaggaatggg gccagccact gtccaagatc acgcacctcg tcttctgcac     240
cacctccggc gtagacatgc cggtgccga ctatcagcta accaagatgc tcggactcca     300
cccgtccgtg aggcgcgtca tgctgtacca gcaaggctgc tttgctggcg gcacggtgct     360
```

```
ccgcgtggcc aaggaccttg cagagaacaa ccgtggcgcg cgtgtgctcg tcgtctgctc      420
agagatcaca gccgtgactt ttcgggggcc atgtgacacc cagctagatt ccatgggtgg      480
ccaggcactc tttggcgatg gggcagctgc cgtggtcgtg ggcgctgacc ccgacgtgct      540
tgttgaaagg ccactgttcc aacttgtctc ggcgagccag acaatactgc cggacacgga      600
tggcttcatc aagggccacc tccgggaggg tgggctcacc ttccacctcc acaaggatgt      660
gcctgtagcc atctcaaaaa acatccaaca agcgctagag gacgccttcg ctccactcgg      720
catcgatgac tggaactcca tcttttgggt ggctcaccct ggtggtccgg ccatccttga      780
catggtggag gcagaggcca agctggacaa aaggcggatg cgtgccacca ggcacatcct      840
atccgagtac ggcaacatgt ccagcgcttg tgtgctcttc atcctcgacg agatgcgtaa      900
gcgctctgct gaggacggac acgccacca                                         929

<210> SEQ ID NO 86
<211> LENGTH: 469
<212> TYPE: DNA
<213> ORGANISM: Triticum aestivum
<220> FEATURE:
<221> NAME/KEY: misc_feature
<222> LOCATION: (400)..(414)
<223> OTHER INFORMATION: n = unknown

<400> SEQUENCE: 86
aaacatacat acataacttg cttattacgc aaagtaacac atcgatcaaa ctttagttaa       60
aacctagttg gtttaatatg gtgatggggc cttcttcgtt ggatgagatc agaaaggcac      120
agagagcaga cggtcctgca ggcatcttag cgataggtac ggccaaccct gcgaaccatg      180
tgctccaagc tgagtatcca gactactact tccgcatcac caacagtgaa cacatgaccg      240
accttaagga gaagttcaag cgcatgtgcg ataagtcgac cataagaaaa cgccacatgc      300
acttgaccga ggagttcttg aaagagaacc ctaacatgtg cgcctacatg gctccttctc      360
tcgacgctag acaagacctc gtggtggttg aagtccctan nctaggtaaa gatngcagca      420
gtgaaggcca tcaaggagtg gggtcagctt aagtcaaaga tcacacacg                  469

<210> SEQ ID NO 87
<211> LENGTH: 563
<212> TYPE: DNA
<213> ORGANISM: Triticum aestivum
<220> FEATURE:
<221> NAME/KEY: misc_feature
<222> LOCATION: (13)..(18)
<223> OTHER INFORMATION: n = unknown

<400> SEQUENCE: 87
ccttgctact tanctagnaa ctccttggtg ctgatcaatg gcggcggtga aattggagga       60
agtgagaagg gcacagcggg cggtgggtct ggcgaccgtg ctggcaatcg gcacggccgt      120
cccggccaac tgcgtgtacc aggccaccta cccggactac tatttcagag tcaccaagag      180
cgagcacctc ccggacctca aggagaagtt cgagaggat tgcgagaagt ccacgatcag      240
gaagaggcac atgcacctca ccgaagagat cctgacaaag aaccctagca tctgctccca      300
catggagccg tcgctggaca cgcgccacga cattgtcgtc gtggaggtgc ccaaacttcg      360
gaaagaggcg gcagagaggg ccatcaagga gtggggccag ccgcagtcaa agatcaccca      420
cgttgtcttc tgcaccacct ccggcgtgga catgccaggt gccgactacc agttgacgag      480
gctgctcggc ctctcgccga cggtcaaacg cctcatgatg taccagcaag gctgctttgg      540
```

```
tggtgccacg gtgctccgca tgg                                            563
```

<210> SEQ ID NO 88
<211> LENGTH: 483
<212> TYPE: DNA
<213> ORGANISM: Triticum aestivum

<400> SEQUENCE: 88

```
acaccacacc acgccaccag tacaagcggc gcctgtcatt tgtctaccac ctgctagcta    60
gctgcttccc tctgcgcccc gcaaacttag acttcacaca gccggccact ggtgcgacaa   120
ctactagctc gtcggccgct ggtacgtacg tagatcccat cgatggcggc caccatgacc   180
gtggaggagg tgaggaaggc gcagcgggcg gaggggccgg ccaccgtgct cgccggcggc   240
accgtgctcc gcctcgccaa ggacctcgcc gagaacaacc gcggcgcgcg cgtgctcgtc   300
gtctgctccg agatcaccgc ggtcaccttc cgcggcccgc acgagtccca cctcgactcg   360
ctggtcggcc aggcgctctt tggcgatggc gcggccgcgg tgatcgtcgg cgccgacccc   420
gacgtgtccg tggagcgtcc cctgttccag ctcgtgtccg cgagccagac gatcctgccg   480
gac                                                                  483
```

<210> SEQ ID NO 89
<211> LENGTH: 1452
<212> TYPE: DNA
<213> ORGANISM: Triticum aestivum
<220> FEATURE:
<221> NAME/KEY: misc_feature
<222> LOCATION: (673)..(673)
<223> OTHER INFORMATION: n = unknown

<400> SEQUENCE: 89

```
gacagacaca gcccggtctt cctgcgtctc tcttgtacct ggacgccctc ggagcagcta    60
gctgcatctc tacaaaccat ccagtatagt aggcagcagt tgtttggagg agagatggcg   120
ccggcggcat tgacggcgtt ggacgcgagg gcgccacggg cggagggcct ggcgacggtg   180
ctggccatcg gcacggcggc accggacaac tgcgtgtacc aggccgacta cccggactac   240
tacttccggg tcaccaacag cgaccacctc cccgagctca agcagaagtt caagcagata   300
tgtgagggt ccatgatccg gaagaggcac atgcacatga ccgagaagct gcttgagcaa   360
aaccccagca tgtgcgagtt caacgccccg tcactggacg tgcgccaggg catcctcctc   420
accgaggtcc ccaagctcgg gatggctgcg gcgcagaagg caatcaagga gtggggccaa   480
ccgttgtcga agatcacaca ccttgtgttc tgcacccggc aatccgtggg cttgccgggt   540
gccgactacc atctcataaa gatgcttggc ctcaaccccg tcggtgaggc gcgtcatgtt   600
gtacctacaa ggctgcttcg ccggcgctac agcgatccgt gtggcaaagg acattgccga   660
gaacaaccat ggnagcacgc gtcctcatcg tctgctcgga gatcacagcc gccaccttcc   720
gtggcccctc agccacgggg tcccaccttg ataatctcgt ctcccaggcg ctcttcggtg   780
acggcgccgc cgcgatggtt gttggtgctg accccaagga gcccatggag aagccaattt   840
tccagttggt ctcaacaagc cagaccatcc tgcccgagtc ggatggtctc atcgaagtaa   900
acctcttgga ggttgggctc accatccaca tcgacaagga cgtgcctagg atcatctcaa   960
aaaatattga gcatgcgttg accaacgcct ttgcgccact cggcatcgat gactggaact  1020
ccatcttctg ggtggcgcac cccggtgggc cggcaattct tgacatgatc gaggccaagg  1080
tcaacctgaa caaaaagcgg atgagtgcca gcaggcacgt cctgtccgaa tacgcaacca  1140
ttgccggcgc cactgtcctc ttcattctgg atgagatgcg taagcgctct gccgaggaga  1200
```

```
accatgccac tactggcgag ggcatggact ggggcgtcct cttcggattt ggccccggca    1260
tcaccctcga gaccgtcgtc atccggagca tgcctatcaa caccaccaca tgatccatac    1320
tagtggagag catgtgtggt ggcagaaacg tttctttcct ggataagtca ccttatcagc    1380
attttcattg ttgaataagt taccttctct tgaagtgtat taggctctcg ttgctaatca    1440
agttgtattg tg                                                        1452
```

<210> SEQ ID NO 90
<211> LENGTH: 1885
<212> TYPE: DNA
<213> ORGANISM: Triticum aestivum

<400> SEQUENCE: 90

```
cgtgcgcgcc acgcgtacgc tctcgccttg tttgctttgt tcttcacaag gtacctcgat      60
cgtgcccact tcatacaact ctcgggttca gctatctatc tatcaagtgg aataagagta    120
gaaagtgaag gggttttga acctaaaaaa cgatcgcttt tcaacgatct gattctactt    180
aatattgcat gcaggaaagt caccatggca agcagcagca gcatcccacc caccaccgtc    240
cgtgagatcc gtgttgcgca acgtgcggac aggcccgcgg cccacaagtc acatgaatcg    300
tttgatcagc ctctcgcctt gtttgctttg ttctttgtaa ggtggagtag gtagctcgct    360
caatacatac ctctctcgat cgtctctgct ttatccaatt taggcacttg tgttcagcta    420
tctatcgagt aggataggag tacaaggaaa gccaccatgg caagcaacag cagcatccca    480
gccaccacct tgagcgagtc cgtgagatcc gtgttggcga acgcgccggc ggcgccgctc    540
ccgtgctggc cagcggcccc gcgaacccgc ccactgcgt gccctgggc gacctccccg    600 tccactactt ccgcgtgacc aacagcgacc acctcaccga ccacaagccc accttcgcgc    660
aggtatgcgg gatgacaggc atcggcaggc gtttcttcca ccacacagat gacctcctcg    720
ccgggcacgc ccccctgttc ctcgacgccc ggcttgacgt cgtggctacc gccgcgcccg    780
acctcgccgc gtcggctgcc gcgcgcgcca tggccgagtg gggccgtccg gtgggcgaca    840
tcacccatct cgacgtcagc accaacgcgg gcgcgcacgc cccgggcacc gatgtccgct    900
tggtctccct cctcggcctc cgccatgatg tcctgcgcac cgtgctccag ctcaacggct    960
gcgcttccgg gtgcgccgcc ctacgcctag ccaaggacct cgccgagaac aaccgcggcg    1020
cgcgcgtcct cgtggtctgc gtcgagctca ccgtcaccgc cttcgcggc ccccacgagg    1080 gggacacctt cgacccctc atcccccagg ggctcttcgg tgacggcgcc ggcgcggtca    1140
tcgtcggtgc cgacccaac gcccacgagc gcccgctgtt tgagatggtg tcggcctcgc    1200
agtacgtgat accggacacc gagcacatgc tcaccatgca gctcggcaat ggtggcatcg    1260
gcgggaccat cgccaccgga ctgccaagac tggcggcggg catcgttgag cggtgcctgc    1320
tggatgcgtt cggcaaccac ctagccgtca tcggaggcgt cgtcgaatgg aacaacctct    1380
tctgggccgt gcatcccggc agcagtgtga tgttggacca catcgtcagg gcactccggc    1440
ttgctccggg gaagctggcg gcgagcagaa ccgtggtgag agagtatggg aacatgctgg    1500
gcgccacggt gatcttcgtg ctcgatgagg tcaggcgcca aagagaagat cctcaaggag    1560
agggagctgg ccatgatgaa ggctgggggg tgatgatggg atttggaccg gggttcactg    1620
tggaggcgat gctgctgcac gccgctacct aggtaattag aaagaacaaa taaaaaacac    1680
atggcatata tattcaataa agtgcatgaa atgcaacctt ttatatttcc atatccacat    1740
atcacctata tatacgtaag tgtaagaaat gtgaacatgt ggtgtgagag tggttaagtc    1800
```

-continued

| ctgtaagagt gatctacaat atatggttat aaataaaatt ttagctactt gcaagttgct | 1860 |
| tcaaaaaaaa aaaaaaaaaa aaaaa | 1885 |

<210> SEQ ID NO 91
<211> LENGTH: 605
<212> TYPE: DNA
<213> ORGANISM: Triticum aestivum
<220> FEATURE:
<221> NAME/KEY: misc_feature
<222> LOCATION: (25)..(41)
<223> OTHER INFORMATION: n = unknown

<400> SEQUENCE: 91

| cacaacaaaa gtgaaaaacc agggnataaa ggaaattcag naacagccat cacaccgtcg | 60 |
| ctctcgtaac cacttgtagt actggtgatt ttatgttgtt ggcgaataaa taataaagtt | 120 |
| tggtttgctg atcgatcatg caatggttga caatgggacg ctgtagagga cgagtgtctc | 180 |
| gacagtgagg ccggggccaa agccgaagag gacaccccac tccttaccct ctccagtggt | 240 |
| tgcttggcca tcctgggaag aggtcttacg catcacgtca aggacgaaga ggacacatgc | 300 |
| gctggacata ttgccgtact ccgacaggac ctctcggctc gcgcgcatgc gttccttgtc | 360 |
| aaggccaact ttctcctcaa ccatgtccag gatcgccggc ccgccagggt gtgcaatcca | 420 |
| gaagatggag ttccagtcgt ggatgcccag aggcttgaat gcgtcctcga gcgcctgctc | 480 |
| gatgttcttg gagatgagcc cgggaacgtc cttgagaagg tggatggtga gccctgcctc | 540 |
| cgtaaggtgg ccgttgatgg caccctcgga gtcgggcagg atggtctggc tcgctgatac | 600 |
| cagct | 605 |

<210> SEQ ID NO 92
<211> LENGTH: 1721
<212> TYPE: DNA
<213> ORGANISM: Triticum aestivum

<400> SEQUENCE: 92

| cccacgcgtt cgagtttcgc cgggtccaga tcgtgaattc aggggtagcc gaccgactac | 60 |
| tccgctctgg cccggccgcc gcagccgcgt tcgtcggcac agcaccgcac ctcggtgccg | 120 |
| atgcggccgt gacgccgccg ggcctggggg aagcgcggca gcgacggcgt cgctcgcttg | 180 |
| gaccggcggc acgctcaggt ccgctgcgaa tagtgatgtc tctaccatca atgattataa | 240 |
| agctcacttt gggtttgctc tggtgcatca tccacttagc aatcagtctt ttaagcgcat | 300 |
| attctggtgg gataccccgc accacccccc cgccacaccg ggcgccgccg gttgttatac | 360 |
| ttcctccttc gggctggccg cgctcctctg cgcgccacgt accgatacac gaccccgccg | 420 |
| ccgacggcgg cgacaactac taccgcgccg gcggctggtc cgtgcgcaac tctcatcgat | 480 |
| ggcggccccc ccgccccagg aggttgtggg gatggcgcag ccggccgtgg cgaccaccac | 540 |
| cctggctggc gtaccaggc ggcccacccc ccatgactt ggcggaggcc aatgtacgcc | 600 |
| tcatcacgga gcggatacc gcgaccacgc atttccccctc cgagtacggc aacatgtcca | 660 |
| gagcctgtgt cctcttcatc atggatgaga tgcgcaagcg ctccgccggg gatggccacg | 720 |
| ccacaaccgg cgaggcaatg gactgggcg tcctcttcgc cttcggcccc cgcctcacgg | 780 |
| tggagaccgt cgtcccccac agcgtcccca tcactgccgg cgccaccgcg tgatcgctcc | 840 |
| ttctccattt attatcttcc tctcatggaa aaacatacaa ctacagcttc tactgccgag | 900 |
| tttgtttgta caatatatat tctaccgtgc gtggtttgta tgtgttggta gatgcattct | 960 |
| gctgttagtc tgtgtcgcgc acgccgtcgc atacttacta gtagtaacac aaccgagctt | 1020 |

-continued

| | |
|---|---|
| ttacaggttt attataagca aagtgtggtc ataatgtgga gtgtgaggtg tattacctgt | 1080 |
| gtacgaaaag ataggctgtt caattcgacc cttatgtggt tcgaaagcac atgggagata | 1140 |
| atgcagaggg gcgtcctctt cggcttcgcc ccgcccgca cggggagac ccccggcccc | 1200 |
| cacaccggcc ccatcaccgc cggcgcaacc gcatgatcat cgctccttct ccatttgtct | 1260 |
| tccccatgca tggctggcta ccgccccag gcggcccgcc gctccttgac atggtcgagg | 1320 |
| caaaggtaaa cctccacaag gagcggatgc gtgcgaccag gcatgtcctc tccgaatacg | 1380 |
| gcaacatgtc cagtgcctgc gtcctcttca tcatggatga gatgcgcaag cgctccgccg | 1440 |
| aggatggcca cgccacaacc ggcgagggaa tggactgggg cgtcctcttc ggcttcggcc | 1500 |
| ccggcctcac ggtggagacc gtcgtcctcc acagcgtccc catcaccgcc ggggcaaccg | 1560 |
| catgatcatc gctccttatc catttatctt cctcatgcat ggaaaaaacc tacgtactac | 1620 |
| gtacagcagc ttctacactg ccgatcgagt ttgtaccata tatattctac cgtacgtgcg | 1680 |
| tggtttgtat gtgttgtttc aatttaacct gtcggcttat t | 1721 |

<210> SEQ ID NO 93
<211> LENGTH: 795
<212> TYPE: DNA
<213> ORGANISM: Triticum aestivum
<220> FEATURE:
<221> NAME/KEY: misc_feature
<222> LOCATION: (13)..(13)
<223> OTHER INFORMATION: n = unknown

<400> SEQUENCE: 93

| | |
|---|---|
| ttcggcacga ggnagtcgta gaagcaccga atagcaacag gggaagaaga aaattgcctt | 60 |
| aagctcattg tgtctcctcg atcgtgattt agtactggac gacggggaag aagagggaaa | 120 |
| aacattgaga gattttgcca gtggccggct aattgaaaag agagttcttt ggagatgggg | 180 |
| ttttgcgcga cgcccaccag cgccccgggc gggggggccag gcgccgccgt gcctccattc | 240 |
| gtccccctc gacggccctt ctcggactac tctttggtgc caccagttag cgctcccgtg | 300 |
| gtgcgcctct cgcccgtggg cgctaatgca ggtgagaaga caatgattga gaagagacat | 360 |
| ttgtacatgt ctgatgagtt cattaggagc agcccttcta ttacggccta caattcccca | 420 |
| tcgctcaacc ttcgtcaagg gctagcggat gccgctatac cacaactcgg tgcggaagct | 480 |
| gcacggcatg ccatcgcgga ctggggccgg caggcatcga acatcacaca cctcgtcttc | 540 |
| tgcacgacgg tgagtgggtg catgcccggt gccgactttg agctcatcaa gctcctcgac | 600 |
| ctccctctct ccactagacg tttcatgcta taccaggctg gctgccatgg tgccggcatc | 660 |
| tccatgcgtc tagccaagga ccttgctgaa aataaccatg gctcccgtgt acttgtggtt | 720 |
| tgctctgagg tgatcaccat ggcttttcgt ggcccctcga aaagccacat ggggaacctt | 780 |
| gttgggcagg ccatc | 795 |

<210> SEQ ID NO 94
<211> LENGTH: 566
<212> TYPE: DNA
<213> ORGANISM: Triticum aestivum

<400> SEQUENCE: 94

| | |
|---|---|
| gacatcttca attactctgt tagtcccact gtaaacccgt gagactgatg catgctcgcg | 60 |
| cgtttgctcc catcccatgc atggctgcgt acgtgtttga tcaggtgaca ggtcggccat | 120 |
| caagaagcgc tacttccacc acacggagga gttgctgcag catcacccgg agttcatcga | 180 |

| | |
|---|---|
| ccgcacgttg ccatccctag atgcccggat ggacatcgcg gccaccgccg ttccggacct | 240 |
| cgcggcagcg gcagcgggca aggccatcgc ggagtggggc cgcccagccg ccgacatcac | 300 |
| ccacctcgtc gtcagcacct actccggcgc ccacatgccg ggcgtcgacc tccgcctggc | 360 |
| ctccctcctc ggcctcgacc cgtccgtccg ccgcaccatg ctctacctca acggctgctc | 420 |
| cagcgggtcc gccgcgctcc gcgtcgccaa ggacatcgcc gagaacaacc gcggtgcccg | 480 |
| cgtcctcgtc gcctgcgccg agctcaccct catcttgttc cgcgcgcccg acgaggccca | 540 |
| cgtcgacacg atcatcatgc aggctc | 566 |

<210> SEQ ID NO 95
<211> LENGTH: 258
<212> TYPE: DNA
<213> ORGANISM: Helianthus annuus

<400> SEQUENCE: 95

| | |
|---|---|
| aggataatcc caacatgtgt gcatacaatg ccccgtcctt agacgataga caagatattg | 60 |
| tggtcgtgga agtaccgaag ctcggtaaag aggctgcaac acgcgccatc aaggaatggg | 120 |
| gccaaccgaa gtcgaagatc acacacctcg tgttttgcac gacaagcggt gttgacatgc | 180 |
| ccggagccga ttatcaactc actaagctcc taggccttcg gtcttcggtc aagcggttta | 240 |
| tgatgtacca acaaggct | 258 |

<210> SEQ ID NO 96
<211> LENGTH: 1400
<212> TYPE: DNA
<213> ORGANISM: Nicotiana tabacum

<400> SEQUENCE: 96

| | |
|---|---|
| atcactagcc atttgaaaac cctagtaatc gtccatcatt ttttccgcaa aaatggtgac | 60 |
| cgtcgaggaa tttcgtaggg cgcaatgtgc cgagggtccg gccacggtca tggctatcgg | 120 |
| aacagccaca ccttccaact gtgttgatca agcactttat cctgattatt attttcgtat | 180 |
| cactaatagc gagcataagg ttgagcttaa ggaaaaattt aagcgcatgt gtgaaaaatc | 240 |
| aatgattaag aaaaggtaca tgcacttaac agaggaaatc ttgaaagaga atcctaatat | 300 |
| ttgtgcatac atggcacctt cccttgatgc tagacaagac atagtggtgg ttgaagtgcc | 360 |
| aaaacttggc aaagaggcag cccaaaaagc catcaaagaa tggggccagc ccaagtccaa | 420 |
| aattactcat ttggtctttt gtacaactag tggtgtagac atgcccgggt gtgactacca | 480 |
| actcactaag ctactcgggc tccgtccatc ggtcaagcgg ttcatgatgt accaacaagg | 540 |
| ttgctttgcc ggtggcacgg tactccggat ggctaaggac ttggccgaaa caacaaggg | 600 |
| cgctcgagtc cttgttgttt gttcagagat caccgctgtc acgtttcgtg acccaatga | 660 |
| cacccacttg gatagtttag ttgggcaagc ccttttttggt gatggggcag ccgcggtcat | 720 |
| tataggttct gatccaattc cagaggtcga gaggcctttg ttcgagcttg tctctgcagc | 780 |
| ccaaactctt ctccccgata gcgaaggcgc tatcgacggt caccttcgtg aagttgggct | 840 |
| tacattccac ttactcaaag atgttcctgg gctaatctca aaaaacattg agaaaagcct | 900 |
| tgtggaagca ttccaacctt gggaatttc tgattggaac tctttattttt ggattgctca | 960 |
| tcctggtggg cctgcaattt tggaccaagt tgaactaaaa ttgggcctaa agcaagaaa | 1020 |
| actaaaggct acaagaaaag tattaagtaa ctatggcaac atgtctagtg cttgtgtgtt | 1080 |
| gtttatttg gatgaaatga ggaaagcctc tgcaaaagaa ggtttgggaa ctactggtga | 1140 |
| agggcttgaa tggggtgtgc ttttttggatt tgggcctggg cttacagttg agactgttgt | 1200 |

-continued

```
tctccacagt gttgctactt agtgggcttg ggcttatatt gtgggaagat tttaagtgtt    1260
ataattgttt attttgtttc ttgtggttga atttattttg tttgtaatga atgtatttgc    1320
tctattttgc tatttcatct tgcaaataat gaaatttgta atgtgaacta tttaatcaaa    1380
gaactgaatt tctttctctt                                                1400
```

<210> SEQ ID NO 97
<211> LENGTH: 38
<212> TYPE: DNA
<213> ORGANISM: Artificial
<220> FEATURE:
<223> OTHER INFORMATION: F7H19.60_1 Forward Primer

<400> SEQUENCE: 97

```
tgtaaaacga cggccagttt ggccatacca tttgttga                              38
```

<210> SEQ ID NO 98
<211> LENGTH: 38
<212> TYPE: DNA
<213> ORGANISM: Artificial
<220> FEATURE:
<223> OTHER INFORMATION: F7H19.60_1 Reverse Primer

<400> SEQUENCE: 98

```
caggaaacag ctatgaccgc acattgggga tactttgg                              38
```

<210> SEQ ID NO 99
<211> LENGTH: 38
<212> TYPE: DNA
<213> ORGANISM: Artificial
<220> FEATURE:
<223> OTHER INFORMATION: F7H19.60_2 Forward Primer

<400> SEQUENCE: 99

```
tgtaaaacga cggccagttc ctcttgttcc ttcccaaa                              38
```

<210> SEQ ID NO 100
<211> LENGTH: 38
<212> TYPE: DNA
<213> ORGANISM: Artificial
<220> FEATURE:
<223> OTHER INFORMATION: F7H19.60_2 Reverse Primer

<400> SEQUENCE: 100

```
caggaaacag ctatgaccca acgagtgagt acgcgaag                              38
```

<210> SEQ ID NO 101
<211> LENGTH: 38
<212> TYPE: DNA
<213> ORGANISM: Artificial
<220> FEATURE:
<223> OTHER INFORMATION: F7H19.60_3 Forward Primer

<400> SEQUENCE: 101

```
tgtaaaacga cggccagtgc atcacaatcg aatcagga                              38
```

<210> SEQ ID NO 102
<211> LENGTH: 38
<212> TYPE: DNA
<213> ORGANISM: Artificial
<220> FEATURE:
<223> OTHER INFORMATION: F7H19.60_3 Reverse Primer

<400> SEQUENCE: 102
caggaaacag ctatgaccac gatcaagcca ctggaaag                                    38

<210> SEQ ID NO 103
<211> LENGTH: 38
<212> TYPE: DNA
<213> ORGANISM: Artificial
<220> FEATURE:
<223> OTHER INFORMATION: F7H19.60_4 Forward Primer

<400> SEQUENCE: 103
tgtaaaacga cggccagtcc ggaaccatgt tgtgtaga                                    38

<210> SEQ ID NO 104
<211> LENGTH: 38
<212> TYPE: DNA
<213> ORGANISM: Artificial
<220> FEATURE:
<223> OTHER INFORMATION: F7H19.60_4 Reverse Primer

<400> SEQUENCE: 104
caggaaacag ctatgaccat ggagcgtgtc aagaaagc                                    38

<210> SEQ ID NO 105
<211> LENGTH: 38
<212> TYPE: DNA
<213> ORGANISM: Artificial
<220> FEATURE:
<223> OTHER INFORMATION: F7H19.60_5 Forward Primer

<400> SEQUENCE: 105
tgtaaaacga cggccagtgt cgctagcaaa cgaagaca                                    38

<210> SEQ ID NO 106
<211> LENGTH: 38
<212> TYPE: DNA
<213> ORGANISM: Artificial
<220> FEATURE:
<223> OTHER INFORMATION: F7H19.60_5 Reverse Primer

<400> SEQUENCE: 106
caggaaacag ctatgaccag ctcgagagca tcaacgat                                    38

<210> SEQ ID NO 107
<211> LENGTH: 38
<212> TYPE: DNA
<213> ORGANISM: Artificial
<220> FEATURE:
<223> OTHER INFORMATION: F7H19.60_6 Forward Primer

<400> SEQUENCE: 107
tgtaaaacga cggccagtca ctccccaatc caaagatg                                    38

<210> SEQ ID NO 108
<211> LENGTH: 38
<212> TYPE: DNA
<213> ORGANISM: Artificial
<220> FEATURE:
<223> OTHER INFORMATION: F7H19.60_6 Reverse Primer

<400> SEQUENCE: 108
caggaaacag ctatgaccca gtcaacccaa ccatcctc                                    38

<210> SEQ ID NO 109
<211> LENGTH: 38
<212> TYPE: DNA
<213> ORGANISM: Artificial

-continued

<220> FEATURE:
<223> OTHER INFORMATION: F7H19.60_7 Forward Primer

<400> SEQUENCE: 109
tgtaaaacga cggccagtcg agctcttctt ttggacga                    38

<210> SEQ ID NO 110
<211> LENGTH: 38
<212> TYPE: DNA
<213> ORGANISM: Artificial
<220> FEATURE:
<223> OTHER INFORMATION: F7H19.60_7 Reverse Primer

<400> SEQUENCE: 110
caggaaacag ctatgaccga ggtgaacacg tggagaca                    38

<210> SEQ ID NO 111
<211> LENGTH: 38
<212> TYPE: DNA
<213> ORGANISM: Artificial
<220> FEATURE:
<223> OTHER INFORMATION: F7H19.60_8 Forward Primer

<400> SEQUENCE: 111
tgtaaaacga cggccagtgg atggttgggt tgactgat                    38

<210> SEQ ID NO 112
<211> LENGTH: 38
<212> TYPE: DNA
<213> ORGANISM: Artificial
<220> FEATURE:
<223> OTHER INFORMATION: F7H19.60_8 Reverse Primer

<400> SEQUENCE: 112
caggaaacag ctatgacctc agaatatcca cgtcagca                    38

<210> SEQ ID NO 113
<211> LENGTH: 38
<212> TYPE: DNA
<213> ORGANISM: Artificial
<220> FEATURE:
<223> OTHER INFORMATION: F7H19.60_9 Forward Primer

<400> SEQUENCE: 113
tgtaaaacga cggccagtcg ctatcaacgt gttcttcg                    38

<210> SEQ ID NO 114
<211> LENGTH: 40
<212> TYPE: DNA
<213> ORGANISM: Artificial
<220> FEATURE:
<223> OTHER INFORMATION: F7H19.60_9 Reverse Primer

<400> SEQUENCE: 114
caggaaacag ctatgacctt ggagggaaga aattaggaga                  40

<210> SEQ ID NO 115
<211> LENGTH: 38
<212> TYPE: DNA
<213> ORGANISM: Artificial
<220> FEATURE:
<223> OTHER INFORMATION: F7H19.60_10 Forward Primer

<400> SEQUENCE: 115
tgtaaaacga cggccagttg tctccacgtg ttcacctc                    38

<210> SEQ ID NO 116
<211> LENGTH: 41
<212> TYPE: DNA
<213> ORGANISM: Artificial
<220> FEATURE:
<223> OTHER INFORMATION: F7H19.60_10 Reverse Primer

<400> SEQUENCE: 116
caggaaacag ctatgaccgt gagcttctca ggtttcttct g                41

<210> SEQ ID NO 117
<211> LENGTH: 38
<212> TYPE: DNA
<213> ORGANISM: Artificial
<220> FEATURE:
<223> OTHER INFORMATION: F7H19.60_11 Forward Primer

<400> SEQUENCE: 117
tgtaaaacga cggccagtcc ggatatttaa tgctgacg                    38

<210> SEQ ID NO 118
<211> LENGTH: 39
<212> TYPE: DNA
<213> ORGANISM: Artificial
<220> FEATURE:
<223> OTHER INFORMATION: F7H19.60_11 Reverse Primer

<400> SEQUENCE: 118
caggaaacag ctatgacccg aatccaaatg gctttgtaa                   39

<210> SEQ ID NO 119
<211> LENGTH: 37
<212> TYPE: DNA
<213> ORGANISM: Artificial
<220> FEATURE:
<223> OTHER INFORMATION: F7H19.60_12 Forward Primer

<400> SEQUENCE: 119
tgtaaaacga cggccagtca gctcagccct ggaaaat                     37

<210> SEQ ID NO 120
<211> LENGTH: 38
<212> TYPE: DNA
<213> ORGANISM: Artificial
<220> FEATURE:
<223> OTHER INFORMATION: F7H19.60_12 Reverse Primer

<400> SEQUENCE: 120
caggaaacag ctatgaccag ggcaaaacat tgctatcg                    38

<210> SEQ ID NO 121
<211> LENGTH: 2304
<212> TYPE: DNA
<213> ORGANISM: Arabidopsis thaliana

<400> SEQUENCE: 121
gatttctctt attttttcct tcctctcatc ctcataatca gaatatccac gtcagcatta     60
aatatccggt tttcttaaac aaaacaaaaa cttaaaatag agaaagaca taattttagg     120 ctttgattat acaataaaaa aaatactgtg agatgagtaa aagatttttt ttttcgaaac    180
atggtgattt tttaaaaaaa tttgacatgt agtatgtgta gttgaattca gctgataata    240
tactttagta caaaccatta aaataaaaat gagttccaaa ttttaaaaaa caaacaagat    300
aaataattta gttttccaaa agaattattg atccacatac aattgtctat ttgaaattga    360

-continued

```
aaaccagtca aattgttttt ttagtaattg atttccaaac tacaaaaaga aaatgtggtt      420
agtagaagaa ctagtagagg tgaacacgtg gagacacgct taaagcacgc gacgaagaac      480
acgttgatag cgattatggg tttaattcta ttgggccttt tctggagtc tagacccaag       540 cccatatagt agtaatcttt tgaccaatc agtcaaccca accatcctct cccgttgacc       600
gtgaagtgag tcacgcactt acctcacaac aatagcacta accaccggta gctctacaat      660
gtctcttagt tcggtaacaa actcttctaa ctaaaagtat agtaaaaact ttgctatata      720
agaaagagtc tttgcacatt tcatttactt gcaaccaatt acaaaaaaga gtgtaagaag      780
aaaaacaaaa caaatccatt ttttttatta ctctgttttt tcccctgttt ttaagtttat      840
ttacttctta ctctgttttc tgctctgttt tagctttaaa cagaagacta aagaagatgg      900
ttgcggttga aagagttgag agtctagcaa aaagcggaat catatcgatt ccaaaagaat      960
atattcgtcc aaaagaagag ctcgagagca tcaacgatgt tttcctagaa gagaagaaag     1020
aagacggtcc tcaagttccc acaatcgatc taaagaacat cgagtcagac gatgaaaaga     1080
tccgtgagaa ttgtattgag gagctgaaaa aggcatcttt ggattgggga gtgatgcatt     1140
tgatcaacca tggaatacca gctgatctaa tggagcgtgt caagaaagcc ggagaagagt     1200 tttcagttt gtctgtggaa gagaaggaga agtatgcaaa cgatcaagcc actggaaaga     1260 tcaaggcta tggaagtaaa ttggctaaca acgcgagtgg acaattggaa tgggaagatt     1320
acttctttca tcttgcgtat cctgaagaga agagagatct atcaatttgg cctaagacac     1380
caagtgatta catgtaagct ttgaattgtt ttactaaaga aaacaaaatc ttgttttggt     1440
tttagaatct tttattaacg tttttcgatg attgtagaga agcaacgagt gagtacgcga     1500
agtgtcttcg tttgctagcg actaaagtct tcaaggctct ctctgtcggt ctaggtttag     1560
agcctgaccg tctagagaaa gaagttggtg gtttagaaga gcttcttcta caaatgaaga     1620
taaattacta tccaaaatgt cctcagcctg agctagcact cggtgtggaa gctcacaccg     1680
atgtaagcgc tttaactttc attctacaca acatggttcc gggtttgcag cttttctacg     1740
agggcaaatg ggtcactgca aaatgtgttc ctgattcgat tgtgatgcac attggggata     1800 cttttggagat tcttagtaat gggaagtata agagtatact tcatcgtggg ttggtgaata     1860
aggagaaggt taggatttct tgggctgtgt tttgtgaacc cccaaaggat aagattgttc     1920
ttaagccgtt gccggagatg gtgagtgttg agtctccggc taagtttcct ccacggactt     1980
ttgctcaaca tattgagcat aagttgtttg ggaaggaaca agaggaattg gtatccgaga     2040
aaaatgatta agtttctgtg tttactctta tttttgaaac tctatgtgcg agtttctttt     2100
ataatgtgtt tgtgtctttc tcatgaattt gatgtgtttg tgcctttat agtgaatatt     2160 gcggagctta acaagcaaac tttaatttaa agaaacaaag ttctaaaata aaatataaaa     2220
ataaaaccca aacaaactac atgcaaacca aactttgatt cccctgaatt agttaacttt     2280
tgtatctacg aaagcattag tgtg                                            2304
```

<210> SEQ ID NO 122
<211> LENGTH: 2316
<212> TYPE: DNA
<213> ORGANISM: Arabidopsis thaliana

<400> SEQUENCE: 122

```
gatttctctt attttttcct tcctctcatc ctcataatca gaatatccac gtcagcatta       60
aatatccggt tttcttaaac aaaacaaaaa cttaaaatag agaaaagaca taattttagg      120
```

```
ctttgattat acaataaaaa aaatactgtg agatgagtaa gaagattttt ttttcgaaac      180
atggtgattt tttaaaaaaa tttgacatgt agtatgtgta gttgaattca gctgataata      240
tactttagta caaaccatta aaataaaaat gagttccaaa ttttaaaaaa caaacaagat      300
aaataattta gttttccaaa agaattattg atccacatac aattgtctat ttgaaattga      360
aaaccagtca aattgttttt ttagtaattg atttccaaac tacaaaaaga aaatgtggtt      420
agtagaagaa ctagtagagg tgaacacgtg agacacgct  taaagcacgt gtgcacacaa      480
acgacgaaga acacgttgat agcgattatg ggtttaattc tattgggcct tttccgggag      540
tctagaccca agcccatata gtagtaatct ttttgaccaa tcagtcaacc caaccatcct      600
ctcccgttga ccgtgaagtg agtcacgcac ttacctcaca acaatagcac taaccaccgg      660
tagctctaca atgtctctta gttcggtaac aaactcttct aactaaaagt atagtaaaaa      720
ctttgctata taagaaagag tctttgcaca tttcatttac ttgcaaccaa ttacaaaaaa      780
gagtgtaaga agaaaaacaa aacaaatcca ttttttttat tactctgttt tttcccctgt      840
ttttaagttt atttacttct tactctgttt tctgctctgt tttagcttta aacagaagac      900
taaagaagat ggttgcggtt gaaagagttg agagtctagc aaaaagcgga atcatatcga      960
ttccaaaaga atatattcgt ccaaaagaag agctcgagag catcaacgat gttttcctag     1020
aagagaagaa agaagacggt cctcaagttc cacaatcga  tctaaagaac atcgagtcag     1080
acgatgaaaa gatccgtgag aattgtattg aggagctgaa aaaggcatct ttggattggg     1140
gagtgatgca tttgatcaac catggaatac cagctgatct aatggagcgt gtcaagaaag     1200
ccggagaaga gtttttcagt ttgtctgtgg aagagaagga gaagtatgca aacgatcaag     1260
ccactggaaa gattcaaggc tatggaagta aattggctaa caacgcgagt ggacaattgg     1320
aatgggaaga ttacttcttt catcttgcgt atcctgaaga gaagagagat ctatcacttt     1380
ggcctaagac accaagtgat tacatgtaag ctttgaattg ttttactaaa gaaaacaaaa     1440
tcttgttttg gttttagaat cttttattaa cgttttcga  tgattgtaga gaagcaacga     1500
gtgagtacgc gaagtgtctt cgtttgctag cgactaaagt cttcaaggct ctctctgtcg     1560
gtctaggttt agagcctgac cgtctagaga aagaagttgg tggtttagaa gagcttcttc     1620
tacaaatgaa gataaattac tatccaaaat gtcctcagcc tgagctagca ctcggtgtgg     1680
aagctcacac cgacgtaagc gctttaactt tcattctaca caacatggtt ccgggttttgc    1740
agcttttcta cgagggcaaa tgggtcactg caaaatgtgt tcctgattcg attgtgatgc     1800
acattgggga tactttggag attcttagta atgggaagta taagagtata cttcatcgtg     1860
ggttggtgaa taaggagaag gttaggattt cttgggctgt gttttgtgaa cccccaaagg     1920
ataagattgt tcttaagccg ttgccggaga tggtgagtgt tgagtctccg gctaagtttc     1980
ctccacggac ttttgctcaa catattgagc ataagttgtt tgggaaggaa caagaggaat     2040
tggtatccga gaaaatgat  taagtttctg tgttactct  tatttttgaa actctatgtg     2100
cgagtttctt ttataatgtg tttgtgtctt tctcatgaat ttgatgtgtt tgtgcctttt     2160
atagtgaata ttgcggagct taacaagcaa actttaattt aaagaaacaa agttctaaaa     2220
taaaatataa aaataaaacc caaacaaact acatgcaaac caaactttga ttcccctgaa     2280
ttagttaact tttgtatcta cgaaagcatt agtgtg                               2316
```

<210> SEQ ID NO 123
<211> LENGTH: 2316
<212> TYPE: DNA
<213> ORGANISM: Arabidopsis thaliana

<400> SEQUENCE: 123

```
cacactaatg ctttcgtaga tacaaaagtt aactaattca ggggaatcaa agtttggttt      60
gcatgtagtt tgtttgggtt ttattttat attttatttt agaactttgt ttctttaaat     120
taaagtttgc ttgttaagct ccgcaatatt cactataaaa ggcacaaaca catcaaattc     180
atgagaaaga cacaaacaca ttataaaaga aactcgcaca tagagtttca aaaataagag     240
taaacacaga aacttaatca tttttctcgg ataccaattc ctcttgttcc ttcccaaaca     300
acttatgctc aatatgttga gcaaaagtcc gtggaggaaa cttagccgga gactcaacac     360
tcaccatctc cggcaacggc ttaagaacaa tcttatcctt tgggggttca caaacacag      420
cccaagaaat cctaaccttc tccttattca ccaacccacg atgaagtata ctcttatact     480
tcccattact aagaatctcc aaagtatccc caatgtgcat cacaatcgaa tcaggaacac     540
attttgcagt gacccatttg ccctcgtaga aaagctgcaa acccggaacc atgttgtgta     600
gaatgaaagt taaagcgctt acgtcggtgt gagcttccac accgagtgct agctcaggct     660
gaggacattt tggatagtaa tttatcttca tttgtagaag aagctcttct aaaccaccaa     720
cttctttctc tagacggtca ggctctaaac ctagaccgac agagagagcc ttgaagactt     780
tagtcgctag caaacgaaga cacttcgcgt actcactcgt tgcttctcta caatcatcga     840
aaaacgttaa taaagattc taaaaccaaa acaagatttt gttttcttta gtaaaacaat     900
tcaaagctta catgtaatca cttggtgtct taggccaaag tgatagatct ctcttctctt     960
cagaatacgc aagatgaaag aagtaatctt cccattccaa ttgtccactc gcgttgttag    1020
ccaatttact tccatagcct tgaatctttc cagtggcttg atcgtttgca tacttctcct    1080
tctcttccac agacaaactg aaaaactctt ctccggcttt cttgacacgc tccattagat    1140
cagctggtat tccatggttg atcaaatgca tcactcccca atccaaagat gccttttca     1200
gctcctcaat acaattctca cggatctttt catcgtctga ctcgatgttc tttagatcga    1260
ttgtgggaac ttgaggaccg tcttctttct tctcttctag aaaacatcg ttgatgctct     1320
cgagctcttc ttttggacga atatattctt ttggaatcga tatgattccg cttttgcta    1380
gactctcaac tctttcaacc gcaaccatct tctttagtct tctgtttaaa gctaaaacag    1440
agcagaaaac agagtaagaa gtaaataaac ttaaaaacag gggaaaaaac agagtaataa    1500
aaaaaatgga tttgttttgt ttttcttctt acactctttt ttgtaattgg ttgcaagtaa    1560
atgaaatgtg caaagactct ttcttatata gcaaagtttt tactatactt ttagttagaa    1620
gagtttgtta ccgaactaag agacattgta gagctaccgg tggttagtgc tattgttgtg    1680
aggtaagtgc gtgactcact tcacggtcaa cgggagagga tggttgggtt gactgattgg    1740
tcaaaaagat tactactata tgggcttggg tctagactcc cggaaaaggc ccaatagaat    1800
taaacccata atcgctatca acgtgttctt cgtcgtttgt gtgcacacgt gctttaagcg    1860
tgtctccacg tgttcacctc tactagttct tctactaacc acatttctct tttgtagttt    1920
ggaaatcaat tactaaaaaa acaatttgac tggttttcaa tttcaaatag acaattgtat    1980
gtggatcaat aattcttttg gaaaactaaa ttatttatct tgtttgtttt ttaaaatttg    2040
gaactcattt ttattttaat ggtttgtact aaagtatatt atcagctgaa ttcaactaca    2100
catactacat gtcaaatttt tttaaaaaat caccatgttt cgaaaaaaaa atcttcttac    2160
tcatctcaca gtattttttt tattgtataa tcaaagccta aaattatgtc ttttctctat    2220
tttaagtttt tgttttgttt aagaaaaccg gatatttaat gctgacgtgg atattctgat    2280
```

-continued tatgaggatg agaggaagga aaaaataaga gaaatc                                    2316

<210> SEQ ID NO 124
<211> LENGTH: 355
<212> TYPE: PRT
<213> ORGANISM: Arabidopsis thaliana

<400> SEQUENCE: 124

Met Val Ala Val Glu Arg Val Glu Ser Leu Ala Lys Ser Gly Ile Ile
1               5                   10                  15

Ser Ile Pro Lys Glu Tyr Ile Arg Pro Lys Glu Leu Glu Ser Ile
            20                  25                  30

Asn Asp Val Phe Leu Glu Glu Lys Glu Asp Gly Pro Gln Val Pro
            35                  40              45

Thr Ile Asp Leu Lys Asn Ile Glu Ser Asp Asp Glu Lys Ile Arg Glu
    50                  55                  60

Asn Cys Ile Glu Glu Leu Lys Lys Ala Ser Leu Asp Trp Gly Val Met
65                  70                  75                  80

His Leu Ile Asn His Gly Ile Pro Ala Asp Leu Met Glu Arg Val Lys
                85                  90                  95

Lys Ala Gly Glu Glu Phe Phe Ser Leu Ser Val Glu Glu Lys Glu Lys
            100                 105                 110

Tyr Ala Asn Asp Gln Ala Thr Gly Lys Ile Gln Gly Tyr Gly Ser Lys
            115                 120                 125

Leu Ala Asn Asn Ala Ser Gly Gln Leu Glu Trp Glu Asp Tyr Phe Phe
    130                 135                 140

His Leu Ala Tyr Pro Glu Lys Arg Asp Leu Ser Ile Trp Pro Lys Thr
145                 150                 155                 160

Pro Ser Asp Tyr Ile Glu Ala Thr Ser Glu Tyr Ala Lys Cys Leu Arg
                165                 170                 175

Leu Leu Ala Thr Lys Val Phe Lys Ala Leu Ser Val Gly Leu Gly Leu
            180                 185                 190

Glu Pro Asp Arg Leu Glu Lys Glu Val Gly Gly Leu Glu Glu Leu Leu
            195                 200                 205

Leu Gln Met Lys Ile Asn Tyr Tyr Pro Lys Cys Pro Gln Pro Glu Leu
    210                 215                 220

Ala Leu Gly Val Glu Ala His Thr Asp Val Ser Ala Leu Thr Phe Ile
225                 230                 235                 240

Leu His Asn Met Val Pro Gly Leu Gln Leu Phe Tyr Glu Gly Lys Trp
                245                 250                 255

Val Thr Ala Lys Cys Val Pro Asp Ser Ile Val Met His Ile Gly Asp
            260                 265                 270

Thr Leu Glu Ile Leu Ser Asn Gly Lys Tyr Lys Ser Ile Leu His Arg
    275                 280                 285

Gly Leu Val Asn Lys Glu Lys Val Arg Ile Ser Trp Ala Val Phe Cys
        290                 295                 300

Glu Pro Pro Lys Asp Lys Ile Val Leu Lys Pro Leu Pro Glu Met Val
305                 310                 315                 320

Ser Val Glu Ser Pro Ala Lys Phe Pro Pro Arg Thr Phe Ala Gln His
                325                 330                 335

Ile Glu His Lys Leu Phe Gly Lys Glu Gln Glu Glu Leu Val Ser Glu
            340                 345                 350

Lys Asn Asp
        355

```
<210> SEQ ID NO 125
<211> LENGTH: 356
<212> TYPE: PRT
<213> ORGANISM: Arabidopsis thaliana

<400> SEQUENCE: 125

Met Val Ala Val Glu Arg Val Glu Ser Leu Ala Lys Ser Gly Ile Ile
1               5                   10                  15

Ser Ile Pro Lys Glu Tyr Ile Arg Pro Lys Glu Leu Glu Ser Ile
            20                  25                  30

Asn Asp Val Phe Leu Glu Glu Lys Lys Glu Asp Gly Pro Gln Val Pro
            35                  40                  45

Thr Ile Asp Leu Lys Asn Ile Glu Ser Asp Glu Lys Ile Arg Glu
    50                  55                  60

Asn Cys Ile Glu Glu Leu Lys Lys Ala Ser Leu Asp Trp Gly Val Met
65                  70                  75                  80

His Leu Ile Asn His Gly Ile Pro Ala Asp Leu Met Glu Arg Val Lys
                85                  90                  95

Lys Ala Gly Glu Glu Phe Phe Ser Leu Ser Val Glu Glu Lys Glu Lys
            100                 105                 110

Tyr Ala Asn Asp Gln Ala Thr Gly Lys Ile Gln Gly Tyr Gly Ser Lys
        115                 120                 125

Leu Ala Asn Asn Ala Ser Gly Gln Leu Glu Trp Glu Asp Tyr Phe Phe
    130                 135                 140

His Leu Ala Tyr Pro Glu Glu Lys Arg Asp Leu Ser Ile Trp Pro Lys
145                 150                 155                 160

Thr Pro Ser Asp Tyr Ile Glu Ala Thr Ser Glu Tyr Ala Lys Cys Leu
                165                 170                 175

Arg Leu Leu Ala Thr Lys Val Phe Lys Ala Leu Ser Val Gly Leu Gly
            180                 185                 190

Leu Glu Pro Asp Arg Leu Glu Lys Glu Val Gly Gly Leu Glu Glu Leu
        195                 200                 205

Leu Leu Gln Met Lys Ile Asn Tyr Tyr Pro Lys Cys Pro Gln Pro Glu
    210                 215                 220

Leu Ala Leu Gly Val Glu Ala His Thr Asp Val Ser Ala Leu Thr Phe
225                 230                 235                 240

Ile Leu His Asn Met Val Pro Gly Leu Gln Leu Phe Tyr Glu Gly Lys
                245                 250                 255

Trp Val Thr Ala Lys Cys Val Pro Asp Ser Ile Val Met His Ile Gly
            260                 265                 270

Asp Thr Leu Glu Ile Leu Ser Asn Gly Lys Tyr Lys Ser Ile Leu His
        275                 280                 285

Arg Gly Leu Val Asn Lys Glu Lys Val Arg Ile Ser Trp Ala Val Phe
    290                 295                 300

Cys Glu Pro Pro Lys Asp Lys Ile Val Leu Lys Pro Leu Pro Glu Met
305                 310                 315                 320

Val Ser Val Glu Ser Pro Ala Lys Phe Pro Pro Arg Thr Phe Ala Gln
                325                 330                 335

His Ile Glu His Lys Leu Phe Gly Lys Glu Gln Glu Leu Val Ser
            340                 345                 350

Glu Lys Asn Asp
        355

<210> SEQ ID NO 126
```

```
<211> LENGTH: 356
<212> TYPE: PRT
<213> ORGANISM: Arabidopsis thaliana

<400> SEQUENCE: 126
```

| | | | | | | | | | | | | | | |
|---|---|---|---|---|---|---|---|---|---|---|---|---|---|---|
| Met | Val | Ala | Val | Glu | Arg | Val | Glu | Ser | Leu | Ala | Lys | Ser | Gly | Ile | Ile |
| 1 | | | | 5 | | | | | 10 | | | | | 15 | |
| Ser | Ile | Pro | Lys | Glu | Tyr | Ile | Arg | Pro | Lys | Glu | Glu | Leu | Glu | Ser | Ile |
| | | | 20 | | | | | 25 | | | | | 30 | | |
| Asn | Asp | Val | Phe | Leu | Glu | Glu | Lys | Glu | Asp | Gly | Pro | Gln | Val | Pro |
| | | 35 | | | | | 40 | | | | | 45 | | |
| Thr | Ile | Asp | Leu | Lys | Asn | Ile | Glu | Ser | Asp | Asp | Glu | Lys | Ile | Arg | Glu |
| | 50 | | | | | 55 | | | | | 60 | | | | |
| Asn | Cys | Ile | Glu | Glu | Leu | Lys | Lys | Ala | Ser | Leu | Asp | Trp | Gly | Val | Met |
| 65 | | | | | 70 | | | | | 75 | | | | | 80 |
| His | Leu | Ile | Asn | His | Gly | Ile | Pro | Ala | Asp | Leu | Met | Glu | Arg | Val | Lys |
| | | | | 85 | | | | | 90 | | | | | 95 | |
| Lys | Ala | Gly | Glu | Glu | Phe | Phe | Ser | Leu | Ser | Val | Glu | Lys | Glu | Lys |
| | | | 100 | | | | | 105 | | | | | 110 | | |
| Tyr | Ala | Asn | Asp | Gln | Ala | Thr | Gly | Lys | Ile | Gln | Gly | Tyr | Gly | Ser | Lys |
| | | | 115 | | | | | 120 | | | | | 125 | | |
| Leu | Ala | Asn | Asn | Ala | Ser | Gly | Gln | Leu | Glu | Trp | Glu | Asp | Tyr | Phe | Phe |
| | 130 | | | | | 135 | | | | | 140 | | | | |
| His | Leu | Ala | Tyr | Ser | Glu | Glu | Lys | Arg | Asp | Leu | Ser | Ile | Trp | Pro | Lys |
| 145 | | | | | 150 | | | | | 155 | | | | | 160 |
| Thr | Pro | Ser | Asp | Tyr | Ile | Glu | Ala | Thr | Ser | Glu | Tyr | Ala | Lys | Cys | Leu |
| | | | | 165 | | | | | 170 | | | | | 175 | |
| Arg | Leu | Leu | Ala | Thr | Lys | Val | Phe | Lys | Ala | Leu | Ser | Val | Gly | Leu | Gly |
| | | | 180 | | | | | 185 | | | | | 190 | | |
| Leu | Glu | Pro | Asp | Arg | Leu | Glu | Lys | Glu | Val | Gly | Gly | Leu | Glu | Glu | Leu |
| | | 195 | | | | | 200 | | | | | 205 | | | |
| Leu | Leu | Gln | Met | Lys | Ile | Asn | Tyr | Tyr | Pro | Lys | Cys | Pro | Gln | Pro | Glu |
| 210 | | | | | 215 | | | | | 220 | | | | | |
| Leu | Ala | Leu | Gly | Val | Glu | Ala | His | Thr | Asp | Val | Ser | Ala | Leu | Thr | Phe |
| 225 | | | | | 230 | | | | | 235 | | | | | 240 |
| Ile | Leu | His | Asn | Met | Val | Pro | Gly | Leu | Gln | Leu | Phe | Tyr | Glu | Gly | Lys |
| | | | | 245 | | | | | 250 | | | | | 255 | |
| Trp | Val | Thr | Ala | Lys | Cys | Val | Pro | Asp | Ser | Ile | Val | Met | His | Ile | Gly |
| | | | 260 | | | | | 265 | | | | | 270 | | |
| Asp | Thr | Leu | Glu | Ile | Leu | Ser | Asn | Gly | Lys | Tyr | Lys | Ser | Ile | Leu | His |
| | | 275 | | | | | 280 | | | | | 285 | | | |
| Arg | Gly | Leu | Val | Asn | Lys | Glu | Lys | Val | Arg | Ile | Ser | Trp | Ala | Val | Phe |
| | 290 | | | | | 295 | | | | | 300 | | | | |
| Cys | Glu | Pro | Pro | Lys | Asp | Lys | Ile | Val | Leu | Lys | Pro | Leu | Pro | Glu | Met |
| 305 | | | | | 310 | | | | | 315 | | | | | 320 |
| Val | Ser | Val | Glu | Ser | Pro | Ala | Lys | Phe | Pro | Pro | Arg | Thr | Phe | Ala | Gln |
| | | | | 325 | | | | | 330 | | | | | 335 | |
| His | Ile | Glu | His | Lys | Leu | Phe | Gly | Lys | Glu | Gln | Glu | Glu | Leu | Val | Ser |
| | | | 340 | | | | | 345 | | | | | 350 | | |
| Glu | Lys | Asn | Asp |
| | | | 355 |

```
<210> SEQ ID NO 127
<211> LENGTH: 1346
<212> TYPE: DNA
```

<213> ORGANISM: Arabidopsis thaliana

<400> SEQUENCE: 127

| | |
|---|---|
| gaaaaacaaa acaaatccat tttttttatt actctgtttt ttcccctgtt tttaagttta | 60 |
| tttacttcac ttgcaaccaa ttacaaaaaa gagtctttaa acagaagact aaagaagatg | 120 |
| gttgcggttg aaagagttga gagtctagca aaaagcggaa tcatatcgat tccaaaagaa | 180 |
| tatattcgtc caaaagaaga gctcgagagc atcaacgatg ttttcctaga agagaagaaa | 240 |
| gaagacggtc ctcaagttcc cacaatcgat ctaaagaaca tcgagtcaga cgatgaaaag | 300 |
| atccgtgaga attgtattga ggagctgaaa aaggcatctt tggattgggg agtgatgcat | 360 |
| ttgatcaacc atggaatacc agctgatcta atggagcgtg tcaagaaagc cggagaagag | 420 |
| tttttcagtt tgtctgtgga agagaaggag aagtatgcaa acgatcaagc cactggaaag | 480 |
| attcaaggct atggaagtaa attggctaac aacgcgagtg gacaattgga atgggaagat | 540 |
| tacttctttc atcttgcgta tcctgaagag aagagagatc tatcaatttg gcctaagaca | 600 |
| ccaagtgatt acatagaagc aacgagtgag tacgcgaagt gtcttcgttt gctagcgact | 660 |
| aaagtcttca aggctctctc tgtcggtcta ggtttagagc ctgaccgtct agagaaagaa | 720 |
| gttggtggtt tagaagagct tcttctacaa atgaagataa attactatcc aaaatgtcct | 780 |
| cagcctgagc tagcactcgg tgtggaagct cacaccgatg taagcgcttt aactttcatt | 840 |
| ctacacaaca tggttccggg tttgcagctt ttctacgagg gcaaatgggt cactgcaaaa | 900 |
| tgtgttcctg attcgattgt gatgcacatt ggggatactt tggagattct tagtaatggg | 960 |
| aagtataaga gtatacttca tcgtgggttg gtgaataagg agaaggttag gatttcttgg | 1020 |
| gctgtgtttt gtgaaccccc aaaggataag attgttctta gccgttgcc ggagatggtg | 1080 |
| agtgttgagt ctccggctaa gtttcctcca cggacttttg ctcaacatat tgagcataag | 1140 |
| ttgtttggga aggaacaaga ggaattggta tccgagaaaa atgattaagt ttctgtgttt | 1200 |
| actcttatttt ttgaaactct atgtgcgagt ttcttttata atgtgtttgt gtctttctca | 1260 |
| tgaatttgat gtgtttgtgc cttttatagt gaatattgcg gagcttaaca agcaaacttt | 1320 |
| aatttaaaga aaaaaaaaaa aaaaaa | 1346 |

<210> SEQ ID NO 128
<211> LENGTH: 895
<212> TYPE: DNA
<213> ORGANISM: Hordeum vulgare

<400> SEQUENCE: 128

| | |
|---|---|
| ggcacgagag agacttgtca atttggccta aaatccccag cgcgtcctcg gggagccaca | 60 |
| tgtgtcggcg cgaggcaact gcgagcccta gcgagcagaa tcctggcagc actatcaatg | 120 |
| cgcttgggat tagaagaagg aaggctacag aaggaagttg gtggcgtgga agagcttctt | 180 |
| cttcaattga aaatcaatta ctaccccaag tgtccacaac cagaactcgc tctcggtgtc | 240 |
| caagctcaca ccgatataag ggcactcact ttcattctcc acaacatgcg tcctgccctc | 300 |
| caactctttc accacggcaa gtgggtgacc gctaactgtg ctcctaactc catcatcatg | 360 |
| cacattggag acaccatcga gatcctcagt catggacagt tcaacagcgt tctccacagg | 420 |
| ggtctggcca ataaggagaa ggccaggatc tcggggccag gttcctgtgc gccccccag | 480 |
| gtgatggtca ccctttgccc cctctcccag actctctccc cggccccgcc tccgcccgtc | 540 |
| ccccccagcg cccctgcgct gctcctcgcg cgcacgcgct gccccagcc cccgggcttt | 600 |
| ctcgcccccc gtgaccccga gtcccttttc tccggcggac ctatggctcc ctggcctctg | 660 |

```
ctgggtgctg tttcccgggg gggctgaacc cctcgggtcg gcgggcggtg tggtcggctt    720
ggcgccccgg ggcccgcggg tgggcctatt ggggcgccgg gggccgcgtc ggcggagggg    780
ggcggaggtg aggggccgg tgggcggctg tctcgccgcg ccccgagggc cctggccggc    840
cctcgacgcg ggtggggggg ccgcggcggg ggcctcctgg tggggccttt atagg         895

<210> SEQ ID NO 129
<211> LENGTH: 1440
<212> TYPE: DNA
<213> ORGANISM: Brassica napus

<400> SEQUENCE: 129
gtcggagtaa cgtccgccca cgcgtcgacc cacgcgtccg gtactctgtt tttcccctgt     60
tctaagcttc tttccttacc tttctctgtt ttcatcttta aaaccagcc aaaacgaaga    120 tggttgaagt ggaaagagtc gagaatttag caaagagcgg aatcaaatcg atcccaaaag    180
aatacatccg tccaaaagaa gagctggaga gcatcaacga cgttttccaa gaagagaaga    240
aagaagacgg ccctcaagtc cccaccatcg acttacaaaa catcgagtca gaagacgaaa    300
cggtccgtga gcaatgcata gaggagctca agaaggctgc tatggactgg ggagtgatgc    360
atttgatcaa ccacggcgta ccggttgacc tgatggagcg tgtgaagaaa gcaggagaag    420
agttcttcgg tttgccgtg gaggagaagg agaagtatgc aaacgatcaa gccaccggaa    480
agatccaagg gtatggaagt aaattagcta caacgcgag tggacagcta gagtgggaag    540
actacttctt ccatcttgtt tatcctgaag acaagagaga tctctcactt tggcccaaga    600
caccaagtga ttacgttgaa gccacgagtg agtacgctaa gtgtcttcgt ttgctagcaa    660
caaaagtttt caaagctctc tctatcggtc taggcttaga gcctgaccgt ctagagaaag    720
aagttggtgg tttagaagag cttcttctac aaaagaagat aaactattac ccgaaatgcc    780
ctcagcctga gctagcactt ggcgtggaag ctcacaccga tgtaagcgct ttgaccttca    840
ttctacacaa catggttcct ggtctgcagc ttttctacga gggcaaatgg gttattgcaa    900
aatgtgttcc tgattccatt gtgatgcaca ttggcgatac gttggagatt cttagtaatg    960
gcaagtttaa gagtatactg caccgtggtt tggtgaataa ggagaaggtt aggatctctt   1020
gggctgtgtt ttgtgagcca cccaaggata agatcgttct taagccgttg ccggagatgg   1080
tgagtgctga gactccggct aagtttcctc caaggacatt ttctcaacat attgagcata   1140
agttgtttag aaaaaacgaa caagaggagt tggtgcctga gaaaaagac gattaagttt   1200 gagtctatat atatgttaaa ctatgtgttc aagtctctct tttcttttgt gtgtttgtgt   1260
cttaatcctg tgtcagtctt attgaagatg tgaagacata tgtctacaga atgtgtcact   1320
gatatatatg ttagtaaaaa cgagtaacac atgaagatat atgaaccaca tgttgtatta   1380
agagcttgag aatattttct gatttaaaaa aaaaaaaaaa aaaaaaaaaa gggcggccgc   1440

<210> SEQ ID NO 130
<211> LENGTH: 397
<212> TYPE: DNA
<213> ORGANISM: Brassica napus

<400> SEQUENCE: 130
cacgcgaccg accacgcgtc cgatgcattt gatcaaccat ggtatacctg ttgaactaat     60
ggagcgtgtg aagaagtcag gagaagagtt cttcagtttg cccgtggaag agaaggagaa    120
gtatgcaaac gatcaagcca gcggaaagat tcaagggtat ggaagcaagt tggctaataa    180
```

| | |
|---|---|
| cgcgagtgga caacttgagt gggaagatta cttctttcat cttgtttatc ctgaagacaa | 240 |
| gagagatcta tcactttggc ctaagacacc aactgattac attgaagcta cgagtgagta | 300 |
| cgctaagtgt cttcgtttgc tagcaacaaa agtcttcaag gctctctcta tcgccctagg | 360 |
| cttagagcct gaccgtccag agaaagaagt tggtggg | 397 |

<210> SEQ ID NO 131
<211> LENGTH: 3239
<212> TYPE: DNA
<213> ORGANISM: Zea mays

<400> SEQUENCE: 131

| | |
|---|---|
| ccgccggcgg ggtcggtgtt cggcagctga ctgcaggtgg gcagcgatcg tgaggcatcg | 60 |
| gttaatgggg cgcctgtccg cgcggtaagg gtcagtcttc agcctctgcc tcggggtgca | 120 |
| cagacctggt ggtagtatcc gagccgtgcc tagccacgga ggtgctgcac acgcaagggg | 180 |
| tggagttagg ctttgtgagc accaagcatc tttaataatc ctatatttgt ttgttcatga | 240 |
| gggttccatg ggtatattgt acctcttgta aactgaagca cacgattaat tctttgttaa | 300 |
| agaatgccat gataatagtt tgctctaatt gaaattaatg ttcaatcaat ttgttaaagc | 360 |
| ttatggtttc ttctgaattt agttattgcc gacagagaaa aaacagtgaa agattataca | 420 |
| catcatatac ggctgaattt agttattgat cctctctatt tttatatttt ctttgttcgg | 480 |
| caactacacg cttatttac ttcaccctgt ttgttacttt agtcactaga ttaaacttta | 540 |
| gtttaatcgc taaagtacct cgttggtttc agtgactaaa ccagactaaa gagcattaat | 600 |
| tgatgtaaat aatgactatg ttgtccatat taattagtgg atatttgctg caaacagaaa | 660 |
| gtgaagaggg caaataaggt gaaaatccta ctttaatccc ttttagccat cccttggtga | 720 |
| ctaaagaatt aaagtttagt cacaacactt tagtcaccat atttaattct ttagggacta | 780 |
| aaagtgacta aactttagtc accccaaact aaacggtacc ttagatctat ttatttgagg | 840 |
| aatgcaagtg tttgaataac tattctattt aaataagatc tacctaacga cgtacggaca | 900 |
| tctaactagt atagaattaa cgtacacatg tattgatttg agtgacccat ggctgattcc | 960 |
| agtgatcaac aataatcctg ccaagcatca agctaatccc aaggtgccac ggaatggtct | 1020 |
| cgcccgccgc cgctggccac atataccagc aggtgaccgt cggattgggt ggcgcttggc | 1080 |
| acggaaaaaa atttggtgca gcactgctgc aaaccagagt ggtttgcagc ccctcacaaa | 1140 |
| aaggaggata gacccacct gcaggtccag cagataacgt tttagttgta ttattgttgc | 1200 |
| tgcgggtggg gtctatcctc ttttttgtga ggggctgcaa acactctggt ttgcagcagt | 1260 |
| gctgcaccaa attttttcc cttggcacgt gttcgggtgg tagctggctc ctccatgcaa | 1320 |
| tgcctatgcc tgtcgtcgcg atcgcaacca ccagtcaaga cgaatggcag gcagctaagt | 1380 |
| agctaacaac aacaggcttg tattgtatgt acagcaatat atatacatct cgagaagctc | 1440 |
| ctagcagaga tgcatccatc tcgacgacga tccatccatc ttaaagcaag cagagacatg | 1500 |
| gagtcgtcgc cgctgctgca gctgccggcg gcacgcgtgg aggctctgag cctcagcggc | 1560 |
| ctctccgcca tccgcccga gtacgtccgc cccgccgacg agcgagccgg cctcggggat | 1620 |
| gccttcgacc tggcgcgcac ccatgccaac gaccacaccg cgccgaggat ccccgtcgtc | 1680 |
| gacatctccc cgttcctcga cagcagcagc cagcagcagc agcgggacga atgcgtggag | 1740 |
| gccgtgcgtg ccgccgccgc cgactgggc gtcatgcaca tcgccggcca cggcatcccc | 1800 |
| gccgagctca tggaccgcct gcgcgccgca ggaaccgcct tcttcgccct ccccgtccag | 1860 |
| gacaaggagg cctacgccaa cgaccccgcc gccggccgcc tgcagggcta cggcagccgc | 1920 |

```
ctcgccacca acacctgcgg gcagcgcgag tgggaggact acctcttcca ccttgtgcac   1980
cccgacgggc tcgccgacca cgcgctctgg cctgcgtacc cgcccgacta catcgccgcc   2040
acccgcgact tcgccgccg aacgcgggac ctggcctcca cgctgctcgc catcctctcc    2100
atgggcctcc ttggcacaga ccgtggcgac gcgctagaga aggcgctcac caccaccacc   2160
accaggacag cagctgacga cgacctcctc ctgcagctca agatcaacta ctacccgagg   2220
tgcccgcagc cggagctggc cgtcggcgtg gaggcccaca cggacgtcag cgccctctcc   2280
ttcatcctcc acaacggcgt gccgggcctg caggtgctcc acggcgcccg ctgggtgacg   2340
gcgcgccacg agccgggcac catcatcgtc cacgtggggg acgccctgga gatcctcagc   2400 aacgccgct acaccagcgt cctccaccgc ggcctcgtca accgggaggc cgtgcgcatc    2460
tcctgggtcg tcttctgcga gccgccacca gactccgtgc tgctgcaccc gctgccggag   2520
cttgtcacgg aaggccaccc cgcaaggttc acgccgcgca cattcaagca gcacctggat   2580
cgcaagcttt tcaagaagaa acagcagcac aaagcaaaag cagaggaaga ggatggcggc   2640
aatggtgacc accaccgcca cgagccgccg ccgcagacca actgatgggc tgcacatgtc   2700
tttccatccg cccacgcata tcttctctcg cgaaattaat aaggatccat cagcattttc   2760
catatattta tattagtttc atgctcctac gttactacga gaaaaaaat agtatctatg    2820 atatatagaa tccatgtgtt aaaatatcac tgtaacacta atattatata tgttgttacg   2880
aaatcaatat aataaaataa tttgatatac caaaacacta attattattc tatagttttg   2940
ttagagtaac taaaagttaa gatttatata ctttaaaaga tatataagat tgtaccatca   3000
ctagtaaaaa ataaacaata ccaatatttt ataaatatga gtatgttggg ccacaatggg   3060
tcaactagtt gggccttgta actagctgtg tgagaagacg attctcagag accatatagg   3120
ctctgagggc atcaggcaac agggtatcga gaaaatacca acgaactatt gtacctcatc   3180
ctctccgtgt cgacgctgtt attggttttc tcgcaagaca tccttattct tcaaccttc    3239
```

<210> SEQ ID NO 132
<211> LENGTH: 1371
<212> TYPE: DNA
<213> ORGANISM: Gossypium hirsutum

<400> SEQUENCE: 132

```
cccagcgtcc gccccgcgtc ccccccccc ccccccgcg tccgaaaaaa attgtttttg      60 ttttttaaaat ataaacttac gacatctaca aatggtgacc tcagtgctac ctagagtaga   120
aagcttggca agcagtggga ttcaatcaat cccgaaagaa tatatcaggc ctcaagaaga   180
gcttacaagc ataggtaacg tgtttgaaga agagaaaaaa gaggaagggc ctcaggttcc   240
gaccatcgat ttgacagaaa tcgagtcgga ggacaaagag gtccgggaaa gatgtcagca   300
ggagctgaaa aaggctgcca tggaatgggg tgtgatgcac cttgttaacc atggcatctc   360
cgaggagctc atggatcgtg ttaggaaagt tgggcagaaa ttctttgaac tccctgtgga   420
ggagaaagag aagtatgcca acgaccagag ctctgggaat gttcagggct atggtagcaa   480
gcttgctaat aatgctagtg ggcagcttga gtgggaggac tacttcttcc atctaatttt   540
tcctgaggat aagagagact tgtcaatttg gcctaaaatc cccagcgaat acactgaagt   600
tacaagtgag tatgcaaggc aactgcgagg cctagcgagc aaaatacttt cagcactatc   660
aatttgcttg ggattagaag aaggaaggct agagaaggaa gttggtggcg tggaagagct   720
tcttcttcaa ttgaaaatca attactaccc caagtgtcca caaccagaac tcgctctcgg   780
```

```
tgtcgaagct cacaccgata taagtgcact cactttcatt ctccacaaca tggttcctgg      840
cctccaactc ttttaccaag gcaagtgggt gaccgctaaa tgtgttccca actccatcat      900
catgcacatt ggagacacca tcgagatcct cagcaatgga aagttcaaga gcattctcca      960 cagggtctg gttaataagg agaaggttag gatctcatgg gcagttttct gtgagccacc     1020
gaaggataag atcatcctta agccactccc ggagactgtc tctgagaccg aacctccact     1080
gttccctcct cgtacctttg ctcagcatat cgagcataag ctgttcagga gacccagga     1140 taatctgtcc aactgaaact agtattttta tttgtcgcga taacctattt ctttctgtac     1200
tctgatgaat gctatatttc gttgggggt taaacccttg gttgtggcgt ctgtctccac      1260
tccttggctc ctctttacct gttttatttg aataatgaga gctgatttgg ttctttttt      1320 taaaaaaaa aaaaaaaaa aaaaaaaaa aaaaaaaaa aaaaaaaaa a                    1371

<210> SEQ ID NO 133
<211> LENGTH: 441
<212> TYPE: DNA
<213> ORGANISM: Gossypium hirsutum

<400> SEQUENCE: 133
caaatggtga cctcagtgct acctagagta gaaagcttgg caagcagtgg gattcaatca       60
atcccgaaag aatatatcag gcctcaagaa gagcttacaa gcataggtaa cgtgtttgaa      120
gaagagaaaa agaggtccg ggaaagatgt cagcaggagc tgaaaaaggc tgccatggaa       180
tggggtgtga tgcaccttgt taaccatggc atctccgagg agctcatgga tcgtgttagg      240
aaagttgggc agaaattctt tgaactccct gtggaggaga aagagaagta tgccaacgac      300
cagagctctg ggaatgttca gggctatggt agcaagcttg ctaacaatgc tagtgggcag      360
cttgagtggg aggactactt cttccatctt atttttcctg aggataagag agacttgtca      420
atttggccta aaatccccag c                                                441

<210> SEQ ID NO 134
<211> LENGTH: 430
<212> TYPE: DNA
<213> ORGANISM: Gossypium hirsutum

<400> SEQUENCE: 134
cccacgcgtc cggttctaga tcgcgagcgg ccgcccgcga tctagaaccc cacgcgtccg       60
gaaagaatat atcaggcctc aagaagagct acaagcata ggtaacgtgt ttgaagaaga      120 gaaaaagag gaagggcctc aggttccgac catcgatttg acagaaatcg agtcggagga       180
caaagaggtc cgggaaagat gtcagcagga gctgaaaaag gctgccatgg aatggggtgt      240
gatgcacctt gttaaccatg gcatctccga ggagctcatg gatcgtgtta ggaaagttgg      300
gcagaaattc tttgaactcc ctgtggagga gaaagagaag tatgccaacg accagagctc      360
tgggaatggt cagggctatg gtagcaagct tgtaacaatg ctagtgggca gcttgagtgg      420
gaggactact                                                             430

<210> SEQ ID NO 135
<211> LENGTH: 862
<212> TYPE: DNA
<213> ORGANISM: Allium porrum

<400> SEQUENCE: 135
gttccccccc cccgtccccc aattaccccgt catcgacctc tcaaagggta gccaagagaa       60
tgtggttgag caaataaggg aggcagcaga ggagtacggt atatttcagt tggtcaatca      120
```

-continued

```
cgggataccg aatgaagtga taagtgagtt gcagagagta gggaaggagt tctttgagct      180
gccgcaggag gagaaggagg tttacgcaac ggtcccggat tcggggagct ttgaaggtta      240
tgggacgaag ttgcagaagg atttggaagg gaagaaggct tgggttgatt acttgtttca      300
taatgtgtgg cccaagcaca agattaatta aagtttttgg cctcagaatc ctcctgctta      360
caggaaggca aacgaggagt acacaaagca tctacaggac gtagtggaca aaatgcacgg      420
ctacttatca cttggactag gattggaaag ccatgttctt aaagaagcag tcggaggaga      480
cgacctcgaa tatctgttga agataaaacta ctaccctcct tgtcctcgcc ctgatttggc      540
cttaggcgtt gtagcgcaca ctgacatgtc cagcctcacc attcttgtgc caaatgaagt      600
tcctgggctt caggtcttca aagatgatca ctggtttgat gccaagtata tccctaatgc      660
ccttatctgc catattggtg atcaaattga gattctgagc aatgggaagt acaaaagcgt      720
gctacacagg acaacggtaa acaaggaaaa gtcgcggatg tcgtggccgg tgttctgctc      780
gccgcctggg gacttggtga taggtccttt gccccagctt gtgaatgatg agaatcctcc      840
aaagttcaag ctcgtgccga at                                              862

<210> SEQ ID NO 136
<211> LENGTH: 864
<212> TYPE: DNA
<213> ORGANISM: Allium porrum

<400> SEQUENCE: 136
tgccgcgttg cgagaagtcc actgaacctt atcatttaga ggaggagaag acacaaaaaa      60
aaaaaagcag gttccctcaa aaacagcttc gttctgtggc acatcgtaaa tggcgacaag     120
attaattata agttttggcc taagaatcct cctgcttaca ggaaggcgaa cgaggagtac     180
acaaagcatc tacagcacgt agtggacaaa atgcacagct acttatcact tggcctagga     240
ttggaaagcc atgttcttaa agaagcagtc ggaggagacg acctcgaata tctgttgaag     300
ataaactact accctccttg tcctcgccct gatttggcct taggcgttgt agcgcacact     360
gacatgtcca gcctcaccat tcttgtgcct aatgaagttc ctgggcttca ggtcttcaaa     420
gatgatcact ggtttgatgc taagtatatc cctaatgccc ttatctgcca tattggtgat     480
caaattgaga ttctgagcaa tgggaagtac aaaagcgtgc tacacaggac aacggtaaac     540
aaggaaaagt cgcggatgtc gtggccggtg ttctgctcgc cgcctggaga cttggtgata     600
ggtcctttgc cccagctgtt gaatgatgag aatcctccaa agttcaagac caagaaatac     660
aaagattatg cttattgcaa aattaataaa cttcctcagt gaggctgttt gtgtgctgaa     720
gtatggtgct taatattatt tgttcctgtg gttacttaag tctgtttttt tttctaataa     780
gattgattca tgattgatag tttgtgctga atgttatgta gagtctcctg ccgtattgaa     840
atatatgtcg ttaatgtttc ctct                                            864

<210> SEQ ID NO 137
<211> LENGTH: 1606
<212> TYPE: DNA
<213> ORGANISM: Oryza sativa

<400> SEQUENCE: 137
atcgagtacg tgtgcacgca gctcatctac tagcctacac tccgggaggg cgacatgacg      60
gacgcggagc tgagagtgga ggccctcagc ctcagcggcg cctccgccat cccgccggag     120
tacgtccgcc cggaggagga gcgcgccgac ctcggcgacg ccctgagctt cgcccgggcc     180
```

-continued

```
gcgtccgacg acgacgccac cgcccgcatc cccgtcgtcg acatctccgc gttcgacaac      240
gacggcgacg gcaggcacgc gtgcgtggag gcggtgcgcg cggcggccga ggagtggggc      300
gtcatgcaca tcgccggcca cggcctcccg ggcgacgtcc tcggccgcct gcgcgccgcg      360
ggcgaggcgt tcttcgcgct gcccatcgcg gagaaggagg cgtacgccaa cgacccggcg      420
gcggggcggc tgcaggggta cggcagcaag ctcgccgcca acgccagcgg gaagagggag      480
tgggaggact acctgttcca cctcgtccac ccggaccacc tcgccgacca ctcgctctgg      540
ccggcgaacc cgccggagta cgtccccgtg tcgcgcgact cggcggccg cgtccggacc       600 ctcgcgtcca agctgctcgc catcctctcc ctcggcctcg gcctgccgga agagacgctg      660
gaacgccgcc tgagaagaca tgatcagcac ggcgtcgacg acgacctgct tctccagctc      720
aagatcaact actacccgag gtgcccgcgg cctgacctcg ccgtcggcgt cgaggcacac      780
accgacgtca gcgcgctctc cttcatcctc cacaacggcg tgccgggact gcaggcgcac      840
cacgccggga cctgggtcac cgcgcgctcc gaacagggca ccatcgtcgt ccacgtcggc      900
gacgccctgg agatcctcac caacggccgg tacaccagcg tgctccaccg cggcctcgtc      960
agccgcgacg cagtgcgcct ctcctgggtc gtcttctgcg agccgccgcc tgagtccgtg     1020
ctgctgcagc cggtgcagga gctgctcgcc gacggcgccg gcaagccgct cttcgcgccg     1080
cgcacattca gcagcacgt gcaacgcaag ctgttcaaga agctcaagga tcagcaagac      1140
aacaatgccg cagctgcatc gaacggaatg ataactaaat aattgcaatt agtcgatcta     1200
tcggcgagac aacccaatat tttgaaaaat tgatggacac acaaaaaaaa cttttttata     1260
taagaatatg catttggttg attcaacatg aaaaatattt tcaaaccatt atattttaa      1320 ttggttatga ataaactata aaaataattg cattcgtctg aatttcagat aaaggagaac     1380
aaataatgtt caacggaagc gaaagccggg gaaatgtacg gatgttatat cgagagctta     1440
acttatgaga tgtcttatat tttgttgtct atgtattgca gtcgacttgt acaccgagtc     1500
tttccatccc tattaagagc tggagctcaa tattatgatg ggatttgcta taaatgtgtc     1560
accatatttt tcataaaaaa taatcaccat gtaaaaaaaa aaaaaa                    1606
```

<210> SEQ ID NO 138
<211> LENGTH: 1476
<212> TYPE: DNA
<213> ORGANISM: Oryza sativa

<400> SEQUENCE: 138

```
ttcacgttcc cgtgtttttg agtgcgcgga gcgcaccgga ccccgcccgc cgggcgtacg       60
aggggaggaa gagctgaggc atactccgaa cccagccaga gagctagctc agtgagcagt      120
acacagtaca ctccccgggt tatctctccc agcacgccag ctagcttttg cttgcaatgg      180
cggactgcat gcaggagtgg ccggagcccg tggtccgcgt gcaggcgctc gccgatagcg      240
gcctggaggc catcccgcgc tgctacgtca accaccgtg cgaccgcccc gccccgagg        300 cggacgacgc gtcctccggc gccagcattc cggtggtcga cctcggcaac ggcggcgacg      360
acgagggcgg ccagctcgcg gaggccgtgg cggcggcgtg ccggggctgg ggcttcttcc      420
agtggtaaaa ccacggggtg cggccggagc tgatgcgcgc ggcgcgggag gcgtggcacg      480
gcttcttccg cctgccgctc caggagaagc agaagtacgc caactcgccg cggacgtacg      540
aggggtacgg cagccggctc ggcgtcgaga agggcgccat cctcgactgg ggagactact      600
acttcctcgt cctctcgccg gacgccgcca agagcccggc caaatactgg ccggccaatc      660
ccggcatctg caaggaggtg tccgaggagt acgggagaga ggtgatcaag ctgtgcgagc      720
```

-continued

```
ggctgatgag gttgctgtca gcgagcctgg ggctggacga gacgcggttc caggaggcgt      780
tcggtggggc ggactgcggc gcgggcctgc gcgccaacta ctacccgcgg tgcccgcagc      840
cggacctcac gctgggcctc tccgcccact ccgatcccgg catcctcacc gtcctcctcg      900
ccgacgacca cgttcgcggc ctccaggtac gccgccgtga cggccactgg gtcaccgtgc      960
agcccctccc cgacgccttc atcgtcaacg tcggcgacca gattgagatc ttgagcaact     1020
cgatgtacaa gagcgtggag caccgcgtga tcgtgaacgc cgaggaggag cgcatctcgc     1080
tcgcactctt ctacaacccg agaggcgacg tcccggtggc gccggcgccg gagctggtga     1140
cgccggagcg gccgtcgctc tactaccgtc cgatgacctt cgacgagtac agggtgtacg     1200
tcaggaagaa tggccccaag ggcaatgcac agcttgaggc tctcaagggc cagtcaatca     1260
cccaaaacaa cgaataataa ataattagta attaattaac taattaagct acaccgatcg     1320
atccaacagc gacggcatgc taatccatgg atcgaactag caagctagct agctagcagt     1380
cagcattaat tatcccatgt atgatctgaa tcggaataac acatgcatga gtgtgtgtac     1440
atgggctact taatttacgc aacatatata gttata                               1476
```

<210> SEQ ID NO 139
<211> LENGTH: 1285
<212> TYPE: DNA
<213> ORGANISM: Sorghum bicolor

<400> SEQUENCE: 139

```
gcacgaggcg gagtaggtgc agcagagcag acgcagagcg gcacagcaat ggcggaggct      60
cgtaactacg acagtattgt caacaggaat gagatcacgg acgctgcggc ttcggcgttc     120
gccaaccccg agcagatccc ggagaagtac gtccgaaccg aggaggtcct cgacggcgtc     180
gtcgtcggtg aggacgagcg ctacgagctg ccggtcgtcg acatggccag gctcctcgac     240
ccggagctgt cggcgtcgga gatcgccaag cttggcgatg cctgcagaaa ctggggtttc     300
tttcagctga caaaccatgg agttgacgaa gaagtggtac agcgaatgaa agacagtgcc     360
cggcggttct tcagcttgcc gctggaaagc aaggccaaag tggccgtccg aggaaacggc     420
ttcgaaggat tcgggcacca ctacagcaga gcgtccagtg gtaagctgga ctgggcggag     480
agcatgatcc tcgtcacgca gccagtccac gacaggaaca tggaaatgtg gcctacaaat     540
ccacccacgt tcagggacgc gcttgaggtt tactctgtgg agatgatcga cctggcaatg     600
aagctcctgg gtttcatggc ggccgacctc ggggtggagc aggaggcgct cctggacgcc     660
ttcacgggga agcggcagag catggcgatc cactcctacc cgccgtgccg ccaccgggag     720
aaggtgatgg gcatcacgcc gcacacggac gggctgggac tgacgctgct gctgcacgtc     780
gacgacacgc cgggcctgca gatccgcaag gacggcaggt ggttccccgt gcgcccgctg     840
ccgggcgcct tcgtcgtcaa cgtcgccgac atcctggacg tgctcaccaa cggcgcctac     900
gccagcgtcg agcacagggt gctcccggac gccgagggg gccggaccac cgtcgtgata     960
ttccaggagg cgtccgtcgg cggcctggtg gcgccgctgc cggggctcct cctcgaggag    1020
ggcggcgccc acgcgcggta cagatccatc gagattgagg agtacatcaa gggaaacttc    1080
aacgcgctgg agcacgggac acggttcatc gagagcctca ggatatagta gagtcgtcat    1140
cgtctgtgga ttctcgcacg cgtcaaaaca gatgtactag ttgctccttc agttcgaaaa    1200
taattgctca actcatattt caacgagcca accaatctta aaacatatct gtatcttcta    1260
tatcttgctc taatattatt ttttc                                          1285
```

<210> SEQ ID NO 140
<211> LENGTH: 1411
<212> TYPE: DNA
<213> ORGANISM: Glycine max

<400> SEQUENCE: 140

```
agttgagagt tgaaagacat gggtacggtg gctcccagag ttgaaagctt ggcgaacatg      60
ggtacggtgg ctccaagagt tgaaagcttg gcgagcagcg ggataaagtg tatcccgaag     120
gaatacgtga ggcctcaaga agagctcaag agcataggga acgtgtttga ggaggaaaag     180
aaggaaggge tacaggttcc gacaattgac ttgagagaga tagattcgga ggacgaggtt     240
gttcgaggga atgtcgtga gaagctgaag aaagcggcgg aggagtgggg tgtgatgcac     300
ttggtgaacc atgggatccc cgatgagctg atagagcggg tgaagaaagc aggggaaacg     360
ttctttggtc tggcggttga ggaaaaggag aagtacgcga atgatttgga gtctggcaag     420
attcaaggct atggaagcaa gctggccaac aatgccagtg ccaactcga gtgggaagat     480
tacttcttcc accttgcttt ccctgaggac aagcgtgacc tctccttctg gccaaagaaa     540
cccgctgatt atattgaggt cacaagcgag tatgcaaagc gactgagggg gcttgcgacc     600
aagatattgg aggcactctc tattggattg gggttggaag gatggaggtt ggagaaggaa     660
gttggtggga tggaagagct tctacttcaa ttgaagatca actactaccc tatttgtccc     720
cagccagaac ttgctctggg agttgaagcc cacactgatg tgagttcact cactttcctc     780
cttcacaaca tggtgccagg tctgcagcta ttctacgaag gccaatgggt cacagcaaaa     840
tgtgtccccg attccattct catgcacatt ggtgacacca ttgagatcct gagcaacggc     900
aagtacaaga gcattcttca tagggggttg gtgaacaagg aaaaggttag aatatcgtgg     960
gcagtgttct gtgaaccccc caaggagaag atcatcctgc agccacttcc cgagcttgtc    1020
actgagacag agccagcacg ctttccacct cgcacttttg ctcagcatat tcaccacaaa    1080
ctattcagaa aggatcagga aggtctccca aattgatcac tgcaggcatc acatttgtat    1140
ttgtttgctt gtcttatgaa ttacttctta gttcttatgg gttgtactaa taaactaggc    1200
cttgcatgtc ggtgtggcct catcaatcat catgctaagt ttgtttatc ctttattaaa     1260
tactattgat attattcttg tttgagttta attctcgatt tgattaacat gggcgttcat    1320
gattattatc caaatcaagt tgaagtcctt tactccttcc aaaaaaaaaa aaaaaaaaa     1380
aaaaaaaaaa gcggccgctc tagaggatcc a                                    1411
```

<210> SEQ ID NO 141
<211> LENGTH: 5777
<212> TYPE: DNA
<213> ORGANISM: Arabidopsis thaliana

<400> SEQUENCE: 141

```
gatctttttc atgttttgtt tttattcata catatccaag agactttaaa tatttgttta      60
tcaatattac aaattatcac ataatatatt cgtgttttgc ttttattcat atgattccaa     120
aaatcactta ttaaaagcta ttcattttaa acttgttcca acctaaacat ctttattttt     180
aaagtctttt cagaatatta gaccaaaaat ataaatacat tttaataata tatatgacca     240
aattaattat ttaaaacttt tgcagatgca tcatctatat atacattttt gcagccactt     300
tgtgaaataa atcctggagt tgggatttat ttacagcggc tgccactgga atttaataat     360
tattttttgat aattagaaag aaaatcttct aattaaatat ttgacattta acaatcttcc    420
caaaatctct ctaccttaac tacacgatta attactaaaa taaaacttcc aaaatattta     480
```

```
atattattta attactacaa aattatcatt tttgatattg cttttctaca tgattataat        540
catcaaaccg tagagatctt tgatagcatt taattactac aaaattacaa aatatttaga        600
caataattca taaacatatc ataaataaga tcaacattaa taaaataaat gagttttttt        660
tagaggacgg gttggcggga cgggtttggc aggacgttac ttaataacaa ttgtaaacta        720
taaaataaaa acattttata actatataca atttacaaac ttttatatat attaatttaa        780
aaaataaatt gttcccgcgg tgtaccgcgg gttaaaatct agttatattt taaaaatcga        840
gatgttacat atgtgttaaa ctttcttttt tgtcttctta tgtgatatca aattttatga        900
tcttatcgat tttaatcagg tatatcttgg tatagcctta gatttcataa tcgcatataa        960
aaatcataaa ttatgtagaa actagttata atcaaataat atttatttca tatggtatac       1020
caaaattaag tattcaattg ctacgtggat attaataatt tgaattcggt aacatactct       1080
ttttcttttt gttaaaccaa agaatctcaa acaaaagttt ttgatcatag ttactaaatc       1140 attttttggtg aataaccgag agaatgtctc ccgacttcta ttaaaaaaca aaaataacaa       1200
ttacacaatc actcgtcttg aacaaacagg tctagaaaca tcatcccgta agatttcatc       1260
cgcacaccgg agaacataaa caagagcata aaagcttaaa gacaagcata gtttgttaac       1320
atgtccgtaa aatgattagc ctctctatat gtgaaacacg gtcaatctag tttttcgata       1380
aaaaactata gcgcaaacgt actagaaatg atagcagatg agagtcccat aactttgtct       1440
tcaaaatctc aaccaccatt taccacaaat atggggatga aaacaggcaa acggtctcat       1500
acgtcgtaaa taagcattct taatgtcaag ttggtagata ggccataaaa taagcatcct       1560
tatgtttagc gcatagcctc cacaccattc accctcctca ttacgtatca gaccaccacc       1620
agccgcgagt ctcgaattgc cataaaatac cccatcagta tttaatttaa accagcccat       1680
agacgagata agccatttta tcagcttctc aacccgacca gcccttttgtg ttgcctttcc      1740 gctactagct ctcgcctcca atacctcctt agctaactct cttatgaacc gcaccctatt       1800
cttccatact ttattctccc caaaaactag ctaattgaat taccaacatt tgatcaagat       1860
aatatactag gtagctaatt aatgagctca tttttttttt gtcgtcaatg ggctaattta       1920
ttaattacag tatgaactat tgactattat tctaaataag tgaatatcac gagtatgtac       1980
gaattattgg atgtatctat ttgtattgat tgatgtaata tcaaatagta agaatttgga       2040
gtaaacgtgg gtttggggtt gaagcaggta gggcatgtca aagtagggcg tctttcgtta       2100 tgtcccttc ctctaaattt gaacctctgt cattgtttac agaaaaatcg taataaccca       2160
taaatgtgtt ttaaaaaaca ttatttcgag ttttctacac atattctagt catgtttaat       2220
ttgaatcttt tcttatttaa gtaagcttta gacatttta acctaagttt tcttctccct        2280
tcataaattt tgagatctat ataatgttct tacattttgg atcaagatct tcatattctc       2340
attccaatta gtaaaagatt tttcacctt taatctctt atcttttatt tatattcttt         2400
agttatgttt atgcttttca tcatatttag tggttagttt ttattattta tttattgatt       2460
catgacttat gctagattat gataagaatt tatgttacca cttgataaat cctccatttg       2520
acatgtgttt aatgctagat ttatattgtc tccaaattta caactttgat gtcttatgat      2580
aaatgccaac aaccaaattt cagataaaga ttagcagact aactaagctt attattcact       2640
tgcaaggtgg agtgatgttg aaagaaccct cacagacacg tcattgggaa gactaaatct       2700 cttttagca cgttacacct ttgagatcgc gttattccca tatggagaga gagcaacaat       2760
acgagacatg gagaggcacc attaccgccg gcgcaactgc ttccaaatat tgacaaacaa       2820
```

-continued

```
atttgaatct ggatcttctc tattcgtgaa caaggagata gaagctacga tgaatgcatg    2880
gaagcttggt ttgctttaat ataaacacta aggggagta gaactttctt gaaaaattgt     2940
atgcaaatta tttaccgaat gttaaaagct ttttttcgaat aaattttaca ttttcttaat   3000
aataataata aaaaggatt gttgattatc ttaatcacaa acaatttatt ttagctgaat     3060
tagacaattg ttagtaaaat gattagagtg tcacatatta atgttgttag tgtttcatgt   3120
catcctagtg atccaataat taggccattc tatagctcgt aacgttaaaa taaaaggccc   3180
attatctgaa tatacagaag cccattatca atagatacat taaaagatac tgattaatcc   3240
agagggttta tatctacgcc gtctccattg attatttctc cgtctcttga aaaatccgac   3300
tgacactgac ctcaaaactc tcctctcact ttcgtcgtga agaagccaaa tctcgaatcg   3360
aatcagcacc acacatttcc atggataatt cagctccaga ttcgttatcc agatcggaaa   3420
ccgccgtcac atacgactca ccatatccac tctacgccat ggctttctct tctctccgct   3480
catcctccgg tcacagaatc gccgtcggaa gcttcctcga agattacaac aaccgcatcg   3540
acattctctc tttcgattcc gattcaatga ccgttaagcc tctcccgaat ctctccttcg   3600
agcatcctta tcctccaaca aagctaatgt tcagtcctcc ttctctccgt cgtccttcct   3660
ccggagatct cctcgcttcc tccggcgatt tcctccgtct ttgggaaatt aacgaagatt   3720
catcaaccgt cgagccaatc tcggttctca acaacagcaa aacgagcgag ttttgtgcgc   3780
cgttgacttc cttcgattgg aacgatgtag agccgaaacg tctcggaact tgtagtattg   3840
atacgacgtg tacgatttgg gatattgaga agtctgttgt tgagactcag cttatagctc   3900
atgataaaga ggttcatgac attgcttggg gagaagctag ggttttcgca tcagtctctg   3960
ctgatggatc cgttaggatc tttgatttac gtgataagga acattctaca atcatttacg   4020
agagtcctca gcctgatacg cctttgttaa gacttgcttg gaacaaacaa gatcttagat   4080
atatggctac gattttgatg gattctaata aggttgtgat tctcgatatt cgttcgccga   4140
ctatgcctgt tgctgagctt gaaagacatc aggctagtgt gaatgctata gcttgggcgc   4200
ctcagagctg taaacatatt tgttctggtg gtgatgatac acaggctctt atttgggagc   4260
ttcctactgt tgctggaccc aatgggattg atccgatgtc ggtttattcg gctggttcgg   4320
agattaatca gttgcagtgg tcttcttcgc agcctgattg gattggtatt gcttttgcta   4380
acaaaatgca gctccttaga gtttgaggtg agagtttctc tttcgctaca taattctcat   4440
ttgctaggcc tagattctaa tgaggaagca ttgattattg gtttagattg tgttgcatta   4500
cagatagttc tctaggtttg gtaactaaac gttttttcga ttcttgataa caaagccact   4560
agagatttga cactaactcg ttttagattt acctgaatca atatctctgt taaaatcaat   4620
tactttgtta tgcatacata aatcacagtt tagtagtcat atatattggc tcttattagc   4680
gacaggtctc acacttgctg taatggctga tagtgtagta gtcatatgtt ggctttcatc   4740
taagttgatg tatcatatga tgaatagttg tacactcgtc aggttctaat ttttacccat   4800
aattcttcag tctatttttt tttgagacaa tctattctta atttaacgaa gccactagct   4860
acgtatacaa atattgttaa tttaacgaag tatctgagaa ttgtttactg ctgactctgc   4920
tgtatgccct cagaaacata tagaagtgga attggaaact tcatgctggt ttgaacatct   4980
ttgtatgtgt gcttcaggtt tttgtaactc atttagacaa cagcattgca tatatacacg   5040
cacatatgca acctagaaaa tcaaataacc tttccttata attactatcc atttcacttg   5100
atgtcaggtg cagatgtgaa gtgatcaata aggattttag catagacccg tataatcgtc   5160
atgtgcgtaa gtaggtttgg tttgcgctcc ctctcgcttt taggtccgca atgactctgt   5220
```

```
atctatctga ttgtaactaa aactgaattc atttgatgaa ccaaatgata ctattatctt      5280
atgttgtgta taaaacccaa ccaggatata ttgcggtttc tggtgtttag atttggtaat      5340
tggagcttag tacaatgcaa ccctgtcttg ctttattgga cgtctctaag ataaatcagc      5400
ttgcaatgaa ttccaatgga gtttgtcagt ttgaattaac ttctttgcat aattaacaca      5460
aagatttgca gtataaattc cattggaaga cttatttgtt tatttgacac agatttaaat      5520
tgaatttcaa tggagtttca gtcgactatg tgacacaaag atttgaaatg aactccaatg      5580
ggaatttgat gagtaaatta ttataaacaa tccaatgttt gacacaaata ttttagaatc      5640
ttcacatctg aagtcttata aatcgtagca aaattttcaa tcttgaaaat tataaaaaat      5700
gagaattaat ttaaatcact gatccgataa tctcctctag aaatataaga atctataaac      5760
cattaatagt agaattc                                                     5777
```

<210> SEQ ID NO 142
<211> LENGTH: 28
<212> TYPE: DNA
<213> ORGANISM: Artificial
<220> FEATURE:
<223> OTHER INFORMATION: Primer Sequence ttg-5'

<400> SEQUENCE: 142

```
ccctgcaggt caaactctga ggagctgc                                           28
```

<210> SEQ ID NO 143
<211> LENGTH: 34
<212> TYPE: DNA
<213> ORGANISM: Artificial
<220> FEATURE:
<223> OTHER INFORMATION: Primer Sequence ttg-5'

<400> SEQUENCE: 143

```
ggtcgacgcc accatggaca actcagctcc ggac                                    34
```

<210> SEQ ID NO 144
<211> LENGTH: 1381
<212> TYPE: DNA
<213> ORGANISM: Brassica napus

<400> SEQUENCE: 144

```
ccacgcgtcc gcccacgcgt ccgcccacgc gtccggtact ctgttttcat ctttaaaaac        60
cagccaaaac gaagatggtt gaagtggaaa gagtcgagaa tttagcaaag agcggaatca      120
aatcgatccc aaaagaatac atccgtccaa agaagagct ggagagcatc aacgacgttt        180
tccaagaaga gaagaaagaa gacggccctc aagtccccac catcgactta caaaacatcg      240
agtccgaaga cgaaacgctc cgtgagaaat gcacagagga gctcaagaag gctgctatgg      300
actggggagt gatgcatctg atcaaccacg gcgtaccggt tgacctgatg gagcgtgtga      360
agaaagcagg agaagagttc ttcggttttgc ccgtggagga aaggagaag tatgcaaacg      420 atcaagccac cggtaagatc caagggtatg gaagtaaatt agctaacaac gcgagtggac      480
agctagagtg ggaagactac ttcttccatc ttgtttatcc tgaagacaag agagatctct      540
cactttggcc caagacacca agtgattatg tccacgagtg agtacgctaa gtgtcttcgt      600
ttgctagcaa caaaggtttt caaagctctc tctatcggtc taggcttaga gcctgaccgt      660
ctagagaaag aagttggtgg tttagaagag cttcttctac aaaagaagat aaactattac      720
ccgaaatgcc ctcagcctga gctagcactt ggcgtggaag ctcacaccga tgtaagcgct      780
```

```
ttgaccttca ttctacacaa catggttcct ggtctgcagc ttttctacga gggcaaatgg      840
gttattgcaa aatgtgttcc tgattccatt gtgatgcaca ttggcgatac gttggagatt      900
cttagtaatg gcaagtttaa gagtatactg caccgtggtt tggtgaataa ggagaaggtt      960
aggatctctt gggctgtgtt ttgtgagcca cccaaggata agatcgttct taagccgttg     1020
ccggagatgg tgagtgctga gactccggct aagtttcctc aaggacatt ttctcaacat     1080 attgagcata agttgtttag aaaaaacgaa caagaggagt tggtgcctga gaaaaaagac     1140
gattaagttt gagtctatat atatgttaaa ctatgtgttc aagtctctct tttcttttgt     1200
gtgtttgtgt cttaatcctg tgtcagtctt attgaagatg tgaagacata tgtctacaga     1260
atgtgtcact gatatatatg ttagtaaaaa cgagtaacac atgaagatat atgaaccaca     1320
tgttgtatta agagcttgag aatattttct gatttacatt aaaaaaaaaa aaaaaaaaa     1380 g                                                                    1381

<210> SEQ ID NO 145
<211> LENGTH: 1346
<212> TYPE: DNA
<213> ORGANISM: Arabidopsis thaliana

<400> SEQUENCE: 145
gaaaaacaaa acaaatccat tttttttatt actctgtttt ttcccctgtt tttaagttta      60
tttacttcac ttgcaaccaa ttacaaaaaa gagtctttaa acagaagact aaagaagatg     120
gttgcggttg aaagagttga gagtctagca aaaagcggaa tcatatcgat tccaaaagaa     180
tatattcgtc aaaagaaga gctcgagagc atcaacgatg ttttcctaga agagaagaaa     240
gaagacggtc ctcaagttcc cacaatcgat ctaaagaaca tcgagtcaga cgatgaaaag     300
atccgtgaga attgtattga ggagctgaaa aaggcatctt tggattgggg agtgatgcat     360
ttgatcaacc atggaatacc agctgatcta atggagcgtg tcaagaaagc cggagaagag     420
tttttcagtt tgtctgtgga agagaaggag aagtatgcaa acgatcaagc cactggaaag     480
attcaaggct atggaagtaa attggctaac aacgcgagtg acaattggaa tgggaagat     540 tacttcttc atcttgcgta tcctgaagag aagagagatc tatcaatttg gcctaagaca     600
ccaagtgatt acatagaagc aacgagtgag tacgcgaagt gtcttcgttt gctagcgact     660
aaagtcttca aggctctctc tgtcggtcta ggtttagagc ctgaccgtct agagaaagaa     720
gttggtggtt tagaagagct tcttctacaa atgaagataa attactatcc aaaatgtcct     780
cagcctgagc tagcactcgg tgtggaagct cacaccgatg taagcgcttt aactttcatt     840
ctacacaaca tggttccggg tttgcagctt ttctacgagg gcaaatgggt cactgcaaaa     900
tgtgttcctg attcgattgt gatgcacatt ggggatactt tggagattct tagtaatggg     960
aagtataaga gtatacttca tcgtgggttg gtgaataagg agaaggttag gatttcttgg    1020
gctgtgtttt gtgaacccc aaaggataag attgttctta gccgttgcc ggagatggtg    1080 agtgttgagt ctccggctaa gtttcctcca cggactttg ctcaacatat tgagcataag    1140
ttgtttggga aggaacaaga ggaattggta tccgagaaaa atgattaagt ttctgtgttt    1200
actcttattt ttgaaactct atgtgcgagt ttcttttata atgtgtttgt gtctttctca    1260
tgaatttgat gtgtttgtgc cttttatagt gaatattgcg gagcttaaca agcaaacttt    1320
aatttaaaga aaaaaaaaa aaaaaa                                          1346

<210> SEQ ID NO 146
<211> LENGTH: 38
```

```
<212> TYPE: DNA
<213> ORGANISM: Artificial
<220> FEATURE:
<223> OTHER INFORMATION: NotI-oligo(dT) primer

<400> SEQUENCE: 146
aacccggctc gagcggccgc tttttttttt tttttttt                              38

<210> SEQ ID NO 147
<211> LENGTH: 1035
<212> TYPE: DNA
<213> ORGANISM: Brassica napus

<400> SEQUENCE: 147
gtcgacgcca ccatggacaa ctcagctccg gactctttac ctagatcgga aaccgccgtc      60
acctacgact ctccgtaccc gctctacgcg atgtccttct cctcctccac ccaccgaatc     120
gccgtcggga gcttcctcga ggactacaac aaccgcatcg acatcctctc cttcgactcc     180
gactccatgt ccctcaagcc ccttccatcc ctctccttcg agcaccctta ccctcccacc     240
aagctcatgt tcagtccccc ctccctccgc cgcagcggcg ggggtgacct cctcgcctcc     300
tccggcgact tcctccgcct ctgggaggtc aacgaagact cctcctccgc ggagccagta     360
tcggtcctca acaacagcaa gacgagcgag ttctgcgcgc cgctgacctc cttcgactgg     420
aacgacgtgg agccgaagcg gttaggcacg tgcagcatcg acaccacgtg cacgatctgg     480
gacgtggaga ggtccgtggt ggagacgcag ctcatcgcgc acgacaagga ggtccacgac     540
atcgcgtggg gggaggctag ggttttcgcc tcggtctccg ccgacggatc ggtgaggatc     600
ttcgatctgc gcgacaagga gcactccacc atcatctacg agagccccca gcccgatacg     660
ccgctcctga ggctcgcgtg gaacaagcag gacttgcggt gtatggccac gattctgatg     720
gattcgaata aggttgtcat tctcgacatt cgatcgccga cgatgccggt cgccgagctt     780
gaaaggcacc aggggagtgt gaacgcgatt gcgtgggcgc cgcagagctg taagcatatc     840
tgctcgggtg gggatgacgc gcaggctctt atctgggagt tgccgacgat ggctgggccg     900
aatgggattg atcccatgtc ggtttactcg gccggttcgg agattaacca gttgcagtgg     960
tcggcttctc tgcctgattg gattggcatt gcgtttgcta acaaaatgca gctcctcaga    1020
gtttgacctg caggg                                                    1035

<210> SEQ ID NO 148
<211> LENGTH: 3864
<212> TYPE: DNA
<213> ORGANISM: Arabidopsis thaliana
<220> FEATURE:
<221> NAME/KEY: misc_feature
<222> LOCATION: (3827)..(3827)
<223> OTHER INFORMATION: n = unknown

<400> SEQUENCE: 148
aagcttgaca ttctttctct gatgccattt ggtttgcaat ttccggtata acaccaccac      60
gagcctggaa gctactctca acatcactca aaatttgatc agcttcaacc caaaaatcaa     120
tctcatccat aacatcacaa ctaggaatca tctcaacatc ttcccacttg aagaatccac     180
aagctccaaa tccctaacac aatttcttaa acaatgttta accagaatta tcaactatga     240
gctttaaact tgcgaacgag tcaaaacctt tttgatgcag catatcaggt aagctctacc     300
ggaaacgtct ttaactctcc ggcaaggtcc agcaccgcag gaacaaatcg ggatggtgaa     360
ggcaggacgg aatttgatat cttcgtcggt tactttgtca caccatttga agaaacagca     420
```

-continued

```
attctgagcc tgcgaatttc aaatgtcgtc agtaacaaat tcaaatttcc tcgcgaattt    480
tgcaggagat gaagaatcag taaagaaagc gagtacgaac cgttggacac ttgtagaact    540
tccttccggg attttctcga gtattcgcga ccttgatttc acagaaacct ccgccgcatg    600
ggcattggat cgccggtgga ggatcatcgg tgtaggattt gagaggacaa tcgttgatcc    660
agtggccagc ctgacggcat cggaagcaat ttccggtctg cattgtgccg ttaagcattc    720
gtcgaacatt ctccttctcg ggatgttaat atgggccagg tcatctttt taagcccaca    780 taatttattt ttagctatga ctaaacaaaa catgctgaat atgggacggg cttaatgggc    840
ctgaagactt aagcagatt aacgaaacaa gtgtgttgtg tataatatga gaaccatgtc    900
gttctgatcg gttaaaaact acagctgacc aaataacacc tataggcttc tgcggatatg    960
actctacggc gtctacgcct cgcatgccta tcatatttaa ccgtcaataa tggatttggc   1020
ggttttggta ggccgggtca accggattaa aagaaacgg tttggagtcc ttccttgcaa   1080 ttgaatttc acgcatcggg ttttgtgatt tctctgtcat aatgggcccg gcacatatgg   1140
ttcataaccc atgtgggcct atggtataat ttttccaatt aaaactattg ttaggtcgat   1200
aaaacaaaaa acaataaaaa cgagtggaat acacatacca aaagaatgt gatgaacatt   1260 agtaatttta ttttgatggt taatgaaaaa caaaataatg catcttgaca tcttccgttg   1320
gaaagcgcaa atagggcaga ttttcagaca gatatcacta tgatgggggg tgggagaaag   1380
aaaacgaggc gtacctaatg taacactact taattagtcg ttagttatag gactttttt   1440 ttgtttgggc ctagttatag gatcataagg taaaaatgaa gaatgaatat tagattagta   1500
ggagctaatg atggagttaa gtagtatgca cgtgtaagaa ctgggaagtg aaacctcctg   1560
tatggtgaag aaactataca acaaagcct ttgttggtgt atacgtatta attttttattc   1620 ttttatcaca agcgatacgt atcttaagac ataataaata tatatcttac tcataataaa   1680
tatcttaaga tatatataca gtatacacct gtatatatat aataaatagg catatagtag   1740
aaattaatat gagttgttgt tgttgcaaat atataaatca atcaaaagaa ttaaaaccca   1800
ccattccaat cttggtaagt aacgaaaaaa cagggaagca agaagaacca cagaaaaggg   1860
ggctaacaac tagacacgta gatcttcatc tgcccgtcca tctaacctac cacactctca   1920
tcttcttttt cccgtgtcag tttgttatat aagctctcac tctccggtat atttccaaat   1980
acacctaact tgtttagtac acaacagcaa catcaaactc taatataccc aagttggtgt   2040
atactataat ggtgatggct ggtgcttctt ctttggatga gatcagacag gctcagagag   2100
ctgatggacc tgcaggcatc ttggctattg gcactgctaa ccctgagaac catgtgcttc   2160
aggcggagta tcctgactac tacttccgca tcaccaacag tgaacacatg accgacctca   2220
aggagaagtt caagcgcatg tgtacgtctt attaacttct actttcattt cctttggcat   2280
atatcttcat tcacatagtt tagctaacaa gtatttacta ttcacaggcg acaagtcgac   2340
aattcggaaa cgtcacatgc atctgacgga ggaattcctc aaggaaaacc cacacatgtg   2400
tgcttacatg gctccttctc tggacaccag acaggacatc gtggtggtcg aagtccctaa   2460
gctaggcaaa gaagcggcag tgaaggccat caaggagtgg ggccagccca agtcaaagat   2520
cactcatgtc gtcttctgca ctacctccgg cgtcgacatg cctggtgctg actaccagct   2580
caccaagctt cttggtctcc gtccttccgt caagcgtctc atgatgtacc agcaaggttg   2640
cttcgccgga ggtactgtcc tccgtatcgc taaggatctc gccgagaaca accgtggagc   2700
acgtgtcctc gttgtctgct ctgagatcac agccgttacc ttccgtggtc cctctgacac   2760
ccaccttgac tccctcgtcg gtcaggctct tttcagtgat ggcgccgccg cactcattgt   2820
```

```
ggggtcggac cctgacacat ctgtcggaga gaaacccatc tttgagatgg tgtctgccgc   2880
tcagaccatc cttccagact ctgatggtgc catagacgga catttgaggg aagttggtct   2940
caccttccat ctcctcaagg atgttcccgg cctcatctcc aagaacattg tgaagagtct   3000
agacgaagcg tttaaacctt tggggataag tgactggaac tccctcttct ggatagccca   3060
ccctggaggt ccagcgatcc tagaccaggt ggagataaag ctaggactaa aggaagagaa   3120
gatgagggcg acacgtcacg tgttgagcga gtatggaaac atgtcgagcg cgtgcgttct   3180
cttcatacta gacgagatga ggaggaagtc agctaaggat ggtgtggcca cgacaggaga   3240
agggttggag tggggtgtct tgtttggttt cggaccaggt ctcactgttg agacagtcgt   3300
cttgcacagc gttcctctct aaacagaacg cttgccttct atctgcctac ctacctacgc   3360
aaaactttaa tcctgtctta tgttttatat aatataatca ttatatgttt acgcaataat   3420
taaggaagaa ttcatttgat gtgatatgtg ctggacaggt ctattcgact gtttttgtac   3480 tctcttttt gtgtcttttt acaatattaa atctatgggt cttgaatgac atcaaatctt   3540
tgttacatcc acaaggtctc aaactcatca taccgagatt gaaaacgttc ctcctttgct   3600
gtaagttcat cttgaggatt catttgaggc tctgtcgctg ttgtatcctc gtcttcatat   3660
tctccacctt gtcttgcctt gagtaccatc tcttccgtag ttgtccccat tatctcgttt   3720
gcttccttca tttccacgca tctatacttg tcttctgaat cctgaccagc cctcacaata   3780
tttacttaac tgaacatatt cagaggaaca ttctgattag aagagantat agcaagggac   3840
tcacacgaga tacaatccaa gctt                                          3864

<210> SEQ ID NO 149
<211> LENGTH: 681
<212> TYPE: DNA
<213> ORGANISM: Brassica napus

<400> SEQUENCE: 149
gtcgacccac gcgtccgata acttgcttat tacgcaaagt aacacatcga tcaaacttta     60
gttaaaacct agttggttta atatggtgat ggggccttct tcgttggatg agatcagaaa    120
ggcacagaga gcagacggtc ctgcaggcat cttagcgata ggtacggcca accctgcgaa    180
ccatgtgctc caagctgagt atccagacta ctacttccgc atcaccaaca gtgaacacat    240
gaccgacctt aaggagaagt tcaagcgcat gtgcgataag tcgaccataa gaaaacgcca    300
catgcacttg accgaggagt tcttgaaaga gaaccctaac atgtgcgcct acatggctcc    360
ttctctcgac gctagacaag acctcgtggt ggttgaagtc cctaagctag gcaaagatgc    420
agcagtgaag gccatcaagg agtggggtca gcctaagtca aagatcacac acgttgtctt    480
ctgcaccacc tctggagttg acatgcctgg tgctgactac cagctcacca agctccttgg    540
ccttcgccct tccgtgaagc gtctcatgat gtaccagcaa gggttgcttt cgccggcggc    600
acttgtctcc gtctcgccaa ggacctcgct gagaacaacc gtggcgcacg tgtcctcgtg    660
gtctgctctg agatcacagc c                                              681

<210> SEQ ID NO 150
<211> LENGTH: 1465
<212> TYPE: DNA
<213> ORGANISM: Brassica napus

<400> SEQUENCE: 150
ggtaccggtc cggaattccc gggtcgaccc acgcgtccga taacttgctt attacgcaaa     60
```

-continued

```
gtaacacatc gatcaaactt tagttaaaac ctagttggtt taatatggtg atggggcctt    120
cttcgttgga tgagatcaga aaggcacaga gagcagacgg tcctgcaggc atcttagcga    180
taggtacggc caaccctgcg aaccatgtgc tccaagctga gtatccagac tactacttcc    240
gcatcaccaa cagtgaacac atgaccgacc ttaaggagaa gttcaagcgc atgtgcgata    300
agtcgaccat aagaaaacgc cacatgcact tgaccgagga gttcttgaaa gagaacccta    360
acatgtgcgc ctacatggct ccttctctcg acgctagaca agacctcgtg gtggttgaag    420
tccctaagct aggcaaagat gcagcagtga aggccatcaa ggagtggggt cagcctaagt    480
caaagatcac acacgttgtc ttctgcacca cctctggagt tgacatgcct ggtgctgact    540
accagctcac caagctcctt ggccttcgcc cttccgtgaa gcgtctcatg atgtaccagc    600
aaggttgctt cgccggcggc actgtcctcc gtctcgccaa ggacctcgct gagaacaacc    660
gtggcgcacg tgtcctcgtg gtctgctctg agatcacagc cgtcaccttc cgtggcccctt    720 ctgacaccca ccttgactca ctcgtgggac aagctctctt cagcgacggt gcagccgcgc    780
tcattgtcgg ctcggaccct gatgtctctg ctggagagaa gcccatcttc gagatggtgt    840
ctgctgctca gaccatcctc ccagactcgg acggtgccat agatggacac ttaagggaag    900
tgggactcac cttccatctc ctcaaggacg tcccccggact catctccaag aacattgaga    960
agagtctaga cgaagcgttt aaacccttag ggataagtga ctggaactcc ctcttctgga   1020
tagctcaccc tggtggtcca cgatccttg acgacgttga agaagaagcta ggactcaagg   1080 cagagaagat gagagccacg cgtcacgtgt tgagcgagta tggaaacatg tctagcgcct   1140
gtgtcctctt tatattggat gagatgagga ggaagtctaa ggaagatggt gtggccacga   1200
caggtgaagg gttagaatgg ggtgtcttgt ttgggttcgg accaggtctc accgtggaga   1260
cagttgtcct acacagcgtt cctgtctaaa cagaaagctc tcttcctata aatgcctacc   1320 taccttttcac atacttacct catatcatgt ctttatgttt ttttttttca atttaagata   1380
atatttgtaa tgcaataatt aaaaaaaaaa aattcattag tgtgacaaaa aaaaaaaaa    1440 aagggcggcc gctctagagg atcca                                         1465
```

<210> SEQ ID NO 151
<211> LENGTH: 2209
<212> TYPE: DNA
<213> ORGANISM: Arabidopsis thaliana

<400> SEQUENCE: 151

```
atggagatta acggggcaca caagagcaac ggaggaggag tggacgctat gttatgcggc     60
ggagacatca agacaaagaa catggtgatc aacgcggagg atcctctcaa ctggggagct    120
gcagcggagc aaatgaaagg tagccatttg gatgaagtga agagaatggt tgctgagttt    180
aggaagccag ttgtgaatct tggtggtgag actctgacca ttggacaagt ggctgcgatc    240
tcaactattg gtaacagtgt gaaggtggag ctatcggaga cagctagagc cggtgtgaat    300
gctagtagtg attgggttat ggagagtatg aacaaaggca ctgatagtta tggtgttact    360 actggtttg tgctacttc tcatcggaga accaaaaacg gtgtcgcact tcagaaggaa    420
cttattagat tccttaacgc cggaatattc ggaagcacga agaaacaag ccacacattg    480 ccacactccg ccacaagagc cgccatgctt gtacgaatca acactctcct ccaaggattt    540
tccggtatcc gatttgagat tctcgaagca attaccagtt tcctcaacaa caacatcact    600
ccatctctcc ccctcgtgg tacaatcacc gcctccggag atctcgttcc tctctcctac    660
atcgccggac ttctcaccgg tcgtcccaat tccaaagcta ctggtcccaa cggtgaagct    720
```

-continued

```
ttaacagcag aggaagcttt caaattagca ggaatcagct ccggattctt tgatctccag      780
cctaaggaag gtctcgcgct agtcaatggc acggcggttg gatctggaat ggcgtcaatg      840
gtgttattcg aaacgaatgt tctctctgtt ttggctgaga ttttgtcggc ggttttcgca      900
gaggtgatga gtggtaagcc tgagttcacc gatcatctca ctcacagact aaacatcat      960
cccggtcaaa tcgaagcggc ggcgataatg gagcatatcc tcgacggaag ctcgtacatg     1020
aaattagctc agaagcttca cgagatggat ccgttacaga aacctaaaca agatcgttac     1080
gctcttcgta cttctcctca atggttaggt cctcaaatcg aagtgatccg ttacgcaacg     1140
aaatcgatcg agcgtgagat taactccgtc aacgataatc cgttgatcga tgtttcgagg     1200
aacaaggcga ttcacggtgg taacttccaa ggaacaccaa tcggagtttc aatggataac     1260
acgagattgg cgatagcagc gattggtaaa ctcatgtttg ctcaattctc agagcttgtg     1320
aatgatttct acaacaatgg tttaccctcg aatctaaccg cttcgaggaa tccaagtttg     1380
gattatggat tcaagggagc tgagattgca atggcttctt attgttcaga gcttcaatac     1440
ttagctaatc ctgtgactag ccatgttcaa tcagcagagc aacataacca agatgtcaac     1500
tctttgggac taatctcgtc tcgcaaaact tctgaagctg ttgatattct caagcttatg     1560
tcaacaacgt tcctcgttgc gatttgtcaa gctgtggatt tgagacattt ggaggagaat     1620
ttgagacaga ctgtgaagaa cactgtctct caagtggcga gaaagttct tactactgga     1680
gtcaatggtg agcttcatcc ttctcgcttc tgcgaaaagg atttactcaa agttgtagac     1740
cgtgaacaag tctacacata cgcggatgat ccttgtagcg caacgtaccc gttgattcag     1800
aagctgagac aagttattgt tgaccatgct ttgatcaatg gtgagagtga aagaatgca     1860
gtgacttcaa tcttccataa gattggagct ttcgaggagg agcttaaggc agtgctaccg     1920
aaagaagtgg aagcagcaag agcagcctac gataacggaa catcggctat cccgaacagg     1980
atcaaggaat gtaggtcgta tccattgtat agattcgtga gggaagagct tggaacagag     2040
cttttgaccg gagagaaagt gacgtcgcct ggagaagagt tcgacaaggt tttcacggcg     2100
atttgtgaag gtaaaatcat tgatccgatg atggaatgtc tcaacgagtg gaacggagct     2160
cccattccaa tatgttaaga gtatagtcct ctgtttttt cttaccata              2209
```

<210> SEQ ID NO 152
<211> LENGTH: 4507
<212> TYPE: DNA
<213> ORGANISM: Arabidopsis thaliana

<400> SEQUENCE: 152

```
aaacattttg aaactaatta cgttcacatc taccatcgat gattgacaag cttattgtca       60
ccttttatgt taaagtgaca tggtcttgac cgttaatttg catgttattc tacatctata      120
gtccaaagat agcaaaccaa agaaaaaaat tgtcacagag ggttcaatgt tacttagata      180
gaaatggttc tttacaataa taaatttatg ttccattctt catggaccga tggatatata      240
tgactatata tatgttacaa gaaaacaaa aacttatatt ttctaaatat gtcttcatcc      300
agtgcactag ctcattgtgt atacatttac ttgcttcttt ttgttctatt tcatttcctc      360
taacaaatta ttcccttata ttttgtgatg tactgaatta ttatgaaaaa aaacctttac      420
acttgataga gaagcatatt tggaaacgta tataatttgt ttaattggag tcaccaaaat      480
tatacaaatc ttgtaatatc attaacataa tagcaaacta attaaatata tgttttttgag     540
gtcaaatgtt cggtttagtg ttgtttctga aaaaaattat tggttaataa aatttcaaat      600
```

-continued

```
aaaaaggaca ggtctttcaa ataaaaggac aggtctttct caccaaaaca aatttcaagt      660
atagataaga aaaatataat aagataaaca attcatgctg gtttggttcg acttcaacta      720
gttagttgta taagaatata ttttttttaat acatttttt agcaactttt gtttttgata      780
catataaaca aatattcaca ataaaaccaa actacaaata gcaactaaaa taattttttg      840
aaaacgaaat tagtggggac gaccttgaat tgactgaact acattcctac gttccacaac      900
tactcccatt tcattcccaa accataatca atcactcgta taaacatttt tgtctccaaa      960
aagtctcacc aaccgcaaaa cgcttattag ttattacctt ctcaattcct cagccaccaa     1020
gccacggact acctttcga tgcttgaggt tgatatttga cggaacacac aaatttaacc     1080
caaaccaaac caaaaccaaa cgcgttttaa atctaaaaac taattgacaa actcttttg     1140 cgactcaaac caaattcacg ttttccatta tccaccatta gatcaccaat cttcatccaa     1200
cggtcatcat taaactctca cccaccctc atacttcact tttttctcc gaaaaaatcg     1260 aaaacttgtg ttctctcttc tctcttctct tgtccttacc taacaacaac actaacattg     1320
tccttcttat ttaaacgtct cttctctctt cttcctcctc agaaaaccaa aaaccaccaa     1380
caattcaaac tctctctttc tccttcacc aaacaataca agagatctga tctcattcac     1440
ctaaacacaa acttcttgaa aaccaatgga tcaaatcgaa gcaatgttgt gcggcggagg     1500
agagaagaca aaagtggcgg ttactacgaa gactttggca gatccattga attgggggttt     1560 agcagcggat caaatgaaag gaagtcattt agatgaagtg aagaagatgg tcgaagagta     1620
tcgtagacca gtcgtgaatc ttggcggaga aacactgacg atcggacaag ttgctgccat     1680
ctccaccgta ggaggcagcg ttaaggttga gttagcggag acttcaagag ccggtgtgaa     1740
agctagcagt gattgggtta tggagagcat gaacaaaggt actgacagtt acggagtcac     1800
caccggcttt ggtgctactt ctcaccggag aaccaaaaac ggcaccgcat acaaacaga     1860 actcattagg taattaatta aatcctatac cttatattat ataactaatt aataattaga     1920
gaactcatta ggaatgtgat cagagaaata aataaattag tggcttaagt ggataacgca     1980
tactcacgag tatacaattt gcatgggaga tataccgggt cggtgatacc ggtcgggtcg     2040
ggtctatttt aattaattaa agtttatttc cgatttcaga ttttttgaacg ccggaatatt     2100 cggaaacacg aaggagacat gtcacacact gccgcaatcc gccacaagag ccgccatgct     2160
cgtcagagtc aacactcttc tccaaggata ctccgggatc cgattcgaga tcctcgaagc     2220
gattacaagt ctcctcaacc acaacatctc tccgtcacta cctctccgtg gaaccattac     2280
cgcctccggg catctcgttc ctctctctta catcgccgga cttctcaccg gccgtcctaa     2340
ttccaaagcc accggtcccg acggtgaatc gctaaccgag aaagaagctt ttgagaaagc     2400
cggaatcagt actggattct tcgatttaca acctaaggaa ggtttagctc tcgttaatgg     2460
cacggcggtt ggatctggaa tggcgtcgat ggttctattc gaagcgaatg tccaagcggt     2520
gttagcggag gttttatcag cgatcttcgc ggaggttatg agcgggaaac ctgagtttac     2580
cgatcatctg actcatcgtt taaacatca tcccggacaa atcgaagcgg cggcgataat     2640
ggagcacata ctcgacggaa gctcatacat gaaattagct caaaaggttc acgagatgga     2700
tccattgcag aaaccaaaac aagatcgtta cgctcttcgt acatctcctc aatggctagg     2760
tcctcaaatt gaagtaatcc gtcaagctac gaaatcgata gagcgtgaaa tcaactccgt     2820
taacgataat ccgttgatcg atgtttcgag gaacaaggcg attcacggtg gtaacttcca     2880
aggaacacca atcggagttt ctatggataa cacgagattg gcgattgctg cgattgggaa     2940
gctaatgttt gctcaattct ctgagcttgt taatgatttc tacaacaatg gacttccttc     3000
```

-continued

```
gaatctaact gcttcgagta atccaagttt ggattatgga ttcaaaggag cagagattgc   3060
tatggcttct tattgttctg agcttcaata cttggctaat ccagtcacaa gccatgttca   3120
atcagctgag caacataatc aagatgtgaa ctctcttggt ttgatctcgt ctcgtaaaac   3180
atctgaagct gtggatattc ttaagctaat gtcaacaacg ttccttgtgg ggatatgtca   3240
agctgttgat ttgagacatt tggaggagaa tctgagacaa actgtgaaga acacagtttc   3300
tcaagttgct aagaaagtgt taaccactgg aatcaacggt gagttacatc cgtcaaggtt   3360
ttgcgagaag gacttgctta aggttgttga tcgtgagcaa gtgttcacgt atgtggatga   3420
tccttgtagc gctacgtacc cgttgatgca gagactaaga caagttattg ttgatcacgc   3480
tttgtccaac ggtgagactg agaagaatgc agtgacttcg atctttcaaa agattggagc   3540
ttttgaagag gagcttaagg ctgtgcttcc aaaggaagtt gaagcggcta gagcggctta   3600
tgggaatgga actgcgccga ttcctaaccg gattaaggaa tgtaggtcgt atccgttgta   3660
taggttcgtg agggaagagc ttggaacgaa gttgttgact ggagaaaagg ttgtgtctcc   3720
gggagaggag tttgataagg tcttcactgc tatgtgtgaa ggtaaactta ttgatccgtt   3780
gatggattgt ctcaaggaat ggaacggagc tccgattccg atttgctaag agagcattcc   3840
tctgtttctg ttctgtgttt ttgtgttttg ttttcaattt taattttgct gtgttaatgt   3900
ttgaattgag ttttttgattg taatgtgaat ggtgtcacac cttgtatgat atatatgata   3960
taaaaactta cgtgtaaaac tcgttgttaa cttgttactt tttatgttgg taaatgtgga   4020
tttgacaccg ttgacaaaag actttatgat ttatttgtgt ttggcttcaa aatgtatgtt   4080
tctggccttt ctctaaacat ttcgaatcct tttatgtgag tttctctttt tagatattag   4140
actaatatct atcctatgca tctcatggcc atttcttgga gcctatcgtg caataacaaa   4200
cacattatat cttctttgtc ataatctttc atttgcgagt aacaaaaaaa tcttacttct   4260
tgacattcat ccatttaat gatgtagaat aatacagata caattgatag aaactggaag   4320
ttgtgtctgt tctctgacaa tatctgcatc agaaaagagt tcaagtttgc tctaaactcg   4380
aataagatag ctgcaaactc attcccttg gctagtcaag acaattgcta gaaactgaaa   4440
gttgtttgat ttctgacaat atctacatca gagaagttca agttttttct atgacacaga   4500
acagaag                                                            4507
```

<210> SEQ ID NO 153
<211> LENGTH: 2097
<212> TYPE: DNA
<213> ORGANISM: Arabidopsis thaliana

<400> SEQUENCE: 153

```
atggagtttc gtcaaccaaa cgcaacagca ttgagcgacc cacttaactg gaatgtagcg    60
gcggaggctt taaagggag ccacctggag gaggtgaaga agatggtgaa ggattatagg   120
aaaggaacgg tgcagctagg cggagagacg ctgaccatcg gtcaggttgc ggcagtagcg   180
agtggaggac cgacagtgga gctttctgag gaggctcggg gcggtgtgaa ggcgagtagt   240
gactgggtga tggagagcat gaaccgtgat acggacacat atgggatcac cactggatt   300 ggttcatctt ctcgtaggag gactgaccaa ggtgctgctc ttcaaaaga gcttattagg   360 tatttgaacg ccgggatatt cgctaccggc aacgaagatg acgacaggtc aaacacgctt   420
ccccggccgg ctactagagc agcgatgctc atccgtgtaa acaccctcct ccaaggctac   480
tctggtatac gctttgagat cctcgaagcc atcacaacac tcctcaactg caaaattaca   540
```

-continued

```
ccgctccttc ctctccgagg caccattacc gcctccgggg atctcgttcc gttatcctat      600
atcgctggat tcctcatcgg gcgccccaac tcccgatccg tgggcccctc tggcgagatc      660
ctcactgcct tggaggcctt caagctcgct ggagtatcgt cttttttcga actcaggcct      720
aaagaagggc ttgcgctcgt gaatgggact gcggtggggt ctgctttagc ctctacggta      780
ctgtacgatg ccaacatttt ggtggttttc tccgaagttg cttccgccat gtttgcagag      840
gttatgcagg ggaaaccaga gtttaccgat catcttacgc ataaactcaa gcaccatcct      900
ggtcagatcg aagccgccgc tatcatggag catattctag acggaagctc ttatgtaaaa      960
gaagctctac atctccacaa gattgatccg cttcagaaac taaacaaga tcggtatgtt     1020 cttggttacg ctctgcgaac atctccgcaa tggcttggac cgcagattga ggtgataaga     1080
gcagcgacta agatgatcga acgtgagata aactcagtaa cgataaccc tttgatcgat     1140 gtttcaagaa acaaagctat ccatggtggg aacttccagg ggacaccaat tggtgtcgcc     1200
atggataaca ctcgtctagc acttgcttct atcgggaagc taatgttcgc tcagttcact     1260
gaactcgtaa atgatttcta caacaacggg ttaccctcta atctatctgg tggtagaaac     1320
cctagtcttg attacgggtt aaaaggcgca gaagtcgcca tggcttctta ttgctcagag     1380
cttcagttcc tagcaaatcc tgtgacgaac catgtcgaaa gcgcttctca acacaatcaa     1440
gatgttaact ctcttgggct gatctcgagc cgaacgacag cagaagctgt ggttatcctc     1500
aagctcatgt caacgactta cttggtagct ttgtgccaag cctttgatct gagacacctt     1560
gaagaaattc tcaagaaagc ggttaatgag gttgtgagcc acactgccaa aagcgttcta     1620
gcaatcgaac cattccgcaa acacgacgat attcttggag ttgtcaaccg cgaatacgtc     1680
ttctcctatg ttgatgaccc aagcagcctc actaaccctt taatgcagaa gctgagacat     1740
gtcctcttcg acaaagcttt agctgaaccg gaaggcgaga ccgacacggt ttttcggaaa     1800
atcggagcgt tcgaggccga gctgaaattt ctcctcccta aagaagtgga acgagtcagg     1860
acagagtacg agaacggtac atttaatgtg gctaaccgaa tcaagaagtg tcgatcgtat     1920
ccgctgtacc ggtttgtgcg gaatgaactc gagacgaggt tgctaaccgg agaggatgtt     1980
cggtcaccgg gagaggattt tgacaaagtc ttcagggcta tatctcaagg aaaactcata     2040
gatcctctgt tgaatgtct gaaagagtgg aacggtgctc cgatttctat ctgctaa       2097
```

<210> SEQ ID NO 154
<211> LENGTH: 548
<212> TYPE: DNA
<213> ORGANISM: Zea mays

<400> SEQUENCE: 154

```
gtaaaagaaa aattgttcat ttgagaactt acaatgagtt ttacacacaa atttaaatta       60
gacagacata aaaccacttc acagacaatc atttggtaaa attattcaga catgtaaaaa      120
aaaaaagact ttatggtaag aaaaaaacag aggactatac tcttaacata ttggaatggg      180
agctccgttc cactcgttga gacattccat catcggatca atgatttac cttcacaaat      240 cgccgtgaaa accttgtcga actcttctcc aggcgacgtc actttctctc cggtcaaaag      300
ctctgttcca agctcttccc tcacgaatct atacaatgga tacgacctac attccttgat      360
cctgttcggg atagccgatg ttccgttatc gtaggctgct cttgctgctt ccacttcttt      420
cggtagcact gccttaagct cctcctcgaa agctccaatc ttatggaaga ttgaagtcac      480
tgcattcttc tcactctcac cattgatcaa agcatggtca acaataaccct tgtctcaagc      540 ttctgaat                                                                548
```

<210> SEQ ID NO 155
<211> LENGTH: 2354
<212> TYPE: DNA
<213> ORGANISM: Zea mays

<400> SEQUENCE: 155

| | | | | | |
|---|---|---|---|---|---|
| ccgggcaaga | agagcagcac | catccagtgc | atcacgagct | cttctgcacc | agattagcag | 60 |
| gccatcgcct | acttttggct | tccaaatcat | ttatttacgg | cgtacgtgcc | ttctgttcaa | 120 |
| accccagccc | cgctgcaatg | gagtgcgaca | acggccgcgt | cgctgctacc | aacggcgact | 180 |
| ccctgtgcat | ggcgctgccc | cgcgccgccg | acccgcttaa | ctgggggaag | gcggcggagg | 240 |
| agatgatggg | cagccacctc | gacgaggtga | agcggatggt | ggccgagtac | cgccagcccc | 300 |
| tggtgaagat | cgagggcgcc | agcctccgca | tcgcgcaggt | ggccgcagtc | gccgccggcg | 360 |
| cgggcgaggc | ccgggtcgag | ctcgacgagt | ccgcccgcgg | ccgggtcaag | gcgagcagcg | 420 |
| actgggtcag | ggacagcatg | atgaacggca | ccgacagcta | cggcgtcacc | acaggtttcg | 480 |
| gcgccacctc | ccaccgccgc | accaaggagg | cggcgctct | ccagagggag | ctcatcaggt | 540 |
| tcctcaacgc | cggcgccttt | ggcatcggca | ccgacgccgg | ccacgtcctg | ccggccgagg | 600 |
| ccacgcgcgc | ggccatgctc | gtccgcatca | acaccctcct | ccagggctac | tccggcatcc | 660 |
| gcttcgagat | cctcgaggcc | atcgtcaagc | tgctcaacgc | caacgtcacg | ccgtgcctgc | 720 |
| cgctgcgcgg | caccggtcac | cgcgtccggc | acctcgtgcc | gctctcctac | attgcgggcc | 780 |
| tcgtcaccgg | gcgcgagaac | gccgtggcgg | tggctcccga | tggcacgaag | gtgaacgccg | 840 |
| cggaggcgtt | caggatcgcc | ggcatccaaa | gcggcttctt | cgagctgcag | cccaaggaag | 900 |
| gtctcgccat | ggtgaacggc | actgccgtgg | gctccggcct | tgcctccacg | gtgctctttg | 960 |
| aggcaaacgt | acttgccgtc | cttgccgagg | tcctgtccgc | cgtgttctgc | gaggtcatga | 1020 |
| acggtaagcc | ggagtacacc | gaccacctga | cctacaagct | gaagcaccac | ccaggacaga | 1080 |
| tcgaggcggc | tgccatcatg | gagcacatct | tggaaggcag | ttcctacatg | aagcttgcta | 1140 |
| agaagctcgg | tgagctcgac | ccgttgatga | agcccaagca | ggacaggtac | gcgctccgta | 1200 |
| cgtcgccgca | gtggctcggc | ccgcagattg | aggttatccg | tgcctccacc | aagtccattg | 1260 |
| agcgcgagat | caactccgtc | aatgacaacc | cgctcatcga | cgtcgcccga | agcaaggccc | 1320 |
| ttcacggtgg | caacttccag | ggcacgccca | tcggggtgtc | catggacaac | acccgcctcg | 1380 |
| ccgtcgcagc | catcggcaag | ctcatgtttg | cgcagttctc | tgagctcgtc | aacgactact | 1440 |
| acaacaacgg | cttgccctcc | aacctgtccg | gcgggcgcaa | ccccagcttg | gactacggct | 1500 |
| tcaagggcgc | cgagatcgcc | atggcgtcct | actgctctga | gctgcagttc | ctggggaatc | 1560 |
| cggtcaccaa | ccacgtccag | agcgcggagc | agcacaacca | ggacgtgaac | tcgctcgggc | 1620 |
| tcatctcctc | caggaagact | gctgaagcca | tcgagatcct | caagctcatg | tcatccacgt | 1680 |
| tcctgatcgc | cctgtgccag | gcagtcgacc | tgcgccacat | cgaggagaac | gtcaagagcg | 1740 |
| ccgtcaagag | ctgcgtgatg | acggtggcca | agaagactct | gagcaccaac | tccaccggtg | 1800 |
| gcctccacgt | cgcccgcttc | tgcgagaagg | acctgctcca | ggagatcgag | cgcgaggcgg | 1860 |
| tgttcgcgta | tgccgacgac | ccctgcagcg | ctaactaccc | gctgatgaag | aagcttcgca | 1920 |
| acgtgctcgt | ggagcgcgcc | ctcgccaatg | gcaccgccga | gttcgacgcc | gagacatccg | 1980 |
| tgttcgctaa | ggtcgcccag | ttcgaggagg | agctgcgcac | ggcgctgccc | agtgcggtgg | 2040 |
| aggctgcacg | ggcggctgtc | gaaaacggca | cggcagcgat | accgaacaga | atcaccgagt | 2100 |

-continued

| | |
|---|---|
| gccgctccta cccgctctac cgcttcgtac gcgaggagct cggagcagtg tacctcaccg | 2160 |
| gcgagaagac gcggtctccc ggcgaggagc ttaacaaggt gctcgttgcc atcaaccagg | 2220 |
| gcaagcacat cgacccgctg ctcgagtgcc tcaaggagtg gaacggcgag cccctgccca | 2280 |
| tctgctgaac agagaaaata caaggagcag aagactgtat tttctagcta atacgtattt | 2340 |
| tttattccta attg | 2354 |

<210> SEQ ID NO 156
<211> LENGTH: 2678
<212> TYPE: DNA
<213> ORGANISM: Zea mays

<400> SEQUENCE: 156

| | |
|---|---|
| cggacgcgtg ggctagctag ctttccccag ctcttcttcc acagcactgt ctgtctcgca | 60 |
| attagctgta ctaatccgct agtggcactg ctgctactct cgtgtactcc cagctatctc | 120 |
| ctctctatac tcttgtacgt acgcacgtgt cgcaaccgca atggagtgcg agaccgggct | 180 |
| tgtccgctcc ctgaacggcg agggcctgtg catgtcggcg gcggcggcgg cgccgcgcgc | 240 |
| cgacgccctg aactggggca aggccgcgga ggacctgtcc gggagccacc tggacgaggt | 300 |
| gaagcggatg gtggtggagt ccgcgagcc gctggtgagg atccagggcg ccagcctgag | 360 |
| catcgggcag gtggccgccg tggcgcgggg cgccggcggc gaggcccgcg tggagctgga | 420 |
| cgagtccgcc cgcggccacg tcaaggccag cagcgactgg gtcatgagca gcatgatgaa | 480 |
| cggcaccgac agctacggcg tcaccaccgg cttcggcgcc acgtcgcaca ggaggaccaa | 540 |
| ggagggcggc gcgctccaga gggagctcat cagattcctc aatgctggcg cgttcggcac | 600 |
| cggcgccgac ggccacgtgc tgccggccga ggccacgcgc gcggcgatgc tcgtgcgcat | 660 |
| caacaccctc ctccagggct actccggcat ccgcttcgag atcctcgagg ccatcgccaa | 720 |
| gctgctcaac gccaacgtca cgccgtgcct gccgctccgg ggcaccatca ccgcgtcggg | 780 |
| cgacctcgtc ccgctctcct acatcgccgg cctcatcacg ggccgccaga actccgtcgc | 840 |
| ggtgggcccc gacggcagga aggtgggcgc cgccgaggcg ttcaggatcg ccggcatcga | 900 |
| gcacgggttc ttcgagctgc agcccaagga gggcctcgcc atggtcaacg gcaccgccgt | 960 |
| gggctccggc ctcgcctcca ccgtgctctt cgaggccaac gttctcgccg tcatggccga | 1020 |
| ggtcatctcc gcggtgttct gcgaggtcat gaccggcaag cccgagttca ccgaccacct | 1080 |
| gacgcacaag ctgaagcacc accccggaca gatcgaggcc gccgctatca tggagcacgt | 1140 |
| cctggaaggc agctcgtaca tgaagctggc caagaagctc ggcgagctcg acccgctgat | 1200 |
| gaagccgaag caggacagat acgcgctccg cacctccccg cagtggctgg gcccgcagat | 1260 |
| cgaagtgatc cgcttcgcca ccaagtccat cgagcgcgag atcaactccg tcaacgacaa | 1320 |
| cccgctcatc gatgtgtccc gtggcaaggc gctccacggc ggcaacttcc agggaactcc | 1380 |
| catcggcgtg tccatggaca acaccgtct cgcccttgcc gccatcggca agctcatgtt | 1440 |
| cgcgcagttc tcggagctgg tgaacgacta ctacaacaac ggcctcccgt ccaacctgtc | 1500 |
| gggcgggcgc aaccccagct ggactacgcttcaagggc gccgagatcg ccatggcctc | 1560 |
| ctactgctcg gagctccagt tcctgggcaa cccggtgacc aaccacgtcc agagcgcgga | 1620 |
| gcagcacaac caggacgtga actccctggg cctcatctcg tccaggaaga ccgccgaggc | 1680 |
| agtggacatc ctgaagctga tgacgtccac gttcctgatc gcgctgtgcc aggccatcga | 1740 |
| cctgcggcac ctcgaggaga acgtgaaggc cgcggtgaag aactgcgtga cgcaggtggc | 1800 |
| caagaagtcg ctgagcctga acgcccgggg cgggctccac aacgcgcgct ctgcgagaa | 1860 |

-continued

```
ggacctgcag acggcgatcg accgcgaggc ggtgttcgcg tacgcggacg acccgtgcag   1920
ccccaactac ccgctgatgc agaagctccg cgcggtgctg gtcgagcacg cgctggccaa   1980
cggcgacgcc gagcgcgccg cggagacgtc catcttcgcc aaggtggccg agttcgagca   2040
gcaggtccgc gcggcgctgc ccaaggaggt ggaggccgcg cgcgcggccg tggagagcgg   2100 cagcccctg gtccccaaca ggatcaggga gtgccggtcc tacccgctgt accggttcgt    2160
gcgcgaggag gtcggcaccg agtacctgac cggcgagagg accaggtccc cggcgaggga   2220
gctcaacaag gtgctcgtgg ccatcaacca gcgcaagcac atcgacccgc tgctcgagtg   2280
cctcaaggag tggaacggcg cgcccctgcc gctctgctga gctcagctga gctgcacgca   2340
cctgctccgc acaaagaagg aaaaacaaaa gtatagcggc tcaagacagc gtttcaagat   2400
cgtttattta caaccagact agcagaagat gctctctata tctaccgtcg ccttgtatta   2460
ttagtagctg aagtaagttc atgtgaatgt tgtcgtgttc ccgcagctgc gacgccatgg   2520
cgtgcgacgt gcgcgttctt ggctgtcgca gctgctgaaa cttttgatgg tttttaacct   2580
gtaagctggg ggggatgaag taaattattt tgttctacaa aaaaaaaaa aaaaaaaaa     2640 aaaaaaaaaa aaaaaactcg aaaaggggc ccggtacc                            2678
```

<210> SEQ ID NO 157
<211> LENGTH: 2423
<212> TYPE: DNA
<213> ORGANISM: Zea mays

<400> SEQUENCE: 157

```
tcgagggccg gccggagga agagcagcac tagatctctc ctctacagct tcccagcaag    60
ccagttgcat acatttcact gctgttatct ttctcagctt gatcagtgct ttagttttct   120
ctagttccaa tggcttgcga ttccccgtgc atggcgacgc cccgcgccga cccgcttaac   180
tgggggaagg cggcggagga gctgatgggc agccacctgg acgaggtcaa gcggatggtg   240
gccgagtacc gccaacccctt ggtgaagatc gagggcgcca gcctcaacat cgcgcaggtg   300
gccgctgtgg ccgccggcgc tggcgaggcc cgggtcgagc tggacgagtc cgcccgtggc   360
cgggtcaagg caagcagcga ctgggtcatg agcagcatga tgaacggcac cgacagctac   420
ggcgtcacca ccgcttcgg cgccacgtcg cacaggagga ccaaggaggg cggcgcgctc   480
cagagggagc tcatcaggtt cctcaacgca ggcgccttcg gcaccggcgc ggacggccac   540
gtcctgccgg ccgatgcgac gcgcgcggcc atgctcgtcc gcatcaacac cctcctccag   600
gggtactccg ggatccgctt cgagatcctc gaggcgatcg tcaagctgct caacgccaac   660
gtcacgccgt gcctgccgct ccgcggcacg gtcaccgcgt ccggcgacct cgtgccgctc   720
tcctacattg ccggcctcgt caccgggcgt gagaactctg ttgcggtcgc tccagacggc   780
agcaaggtga acgctgccga ggcattcaag attgccggaa tccagggcgg cttcttcgag   840
ctgcagccca aggagggtct tgcgatggtg aacggcacgg ccgtgggctc tggcctcgcc   900
tccactgtgc tcttcgaggc taacatcctt gccatcctcg ccgaggtcct gtccgccgtg   960
ttctgcgaag tcatgaacgg caagccggag tacaccgacc acctgaccca aagctcaag   1020 caccacccgg gacagattga ggctgctgcc atcatggagc acatcttgga gggcagctcc   1080
tacatgaagc ttgccaagaa gctcggcgag ctcgaccccct tgatgaagcc caagcaggac   1140
cggtacgcgc tccgcacgtc gccgcagtgg ctttggcccac aaattgaggt tatccgcgcc   1200
gccaccaaat ccattgagcg cgagatcaac tccgtcaacg caacccgct catcgatgtc   1260
```

-continued

```
gcccgaagca aggcacttca cggtggcaac ttccagggca cgcccatcgg ggtatctatg    1320
gacaacaccc gtctcgccat cgcagccatc ggcaagctca tgtttgcgca gttctctgag    1380
ctcgtcaacg actactataa caacggcttg ccctccaacc tgtccggtgg gcgcaacccc    1440
agcttggact acggctttaa gggcgccgag atcgccatgg cgtcctactg ctccgagctg    1500
cagtttctgg ggaacccggt caccaaccac gtccagagcg cagagcagca caaccaggac    1560
gtcaactcgc tggggctcat ctcctccagg aagactgctg aggccatcga gatcctgaag    1620
ctcatgtcct cgacgttcct gatcgccctg tgccaggccg tggacctgcg ccacatcgag    1680
gagaatgtca gagcgccgt caagagctgc gtgatgacgg tggcgaagaa gactctgagc    1740
accgactcca ccggtggcct ccacgtcgcc cgcttctgcg agaaggacct gctccaagag    1800
atcgagcgcg aggcggtgtt cgcgtatgcc gacgacccct gcagcgctaa ctacccgctg    1860
atgaagaagc ttcgtaacgt gctcgtggag gcgcccctcg ccaacggcgc tgctgagttc    1920
aacgcggaga cctccgtgtt cgccaaggtc gcccagttcg aggaggacct gcgcgcggcg    1980
ctgcccaagg cggtggaggc tgcacggggcg gctgtcgaga acggcacggc agcgataccg    2040
aacagaatca ccgactgccg ctcctacccg ctctaccgct tcgtgcgcga ggagctcgga    2100
gccgtgtacc tcaccggcga agacgcgc tctcccggcg aggagctgaa caaagtgctc    2160
attgccatca accaaggcaa gcacatcgat ccgctgctcg agtgccttaa ggagtggaac    2220
ggcgagcccc tgcccatctg ctaaacagag aaacggatag gaagaagact ggagtgttca    2280
ttgttcagta gttttgcgtg gttggtagca aaggctaatg actgtttatc tggtcatact    2340
ctacttatga aacgttatat tttcaagaaa tgtgtattcc attcttgtta taaaaaaga    2400 aaaaaaaaaa aaaaaaagcg gcc                                           2423
```

<210> SEQ ID NO 158
<211> LENGTH: 2656
<212> TYPE: DNA
<213> ORGANISM: Zea mays

<400> SEQUENCE: 158

```
gcacgagacc attacctaga acatcctaat cgaaaaagga cgaagagcct acctttcccc      60
agctcttcgt ctacagcact gccacattag tagttagtta ccagcagtac tactcttgtg    120
tagtagcttt taatttcccc cagctagcta gctagtttct acttccgtcc gcgcgcgctc    180
atctgcgcac gcacgtgtcc ccgtccgcaa tggagtccga ggccggcctg cttgtccgct    240
cctccctgaa cggcgagggc ctgtgcatgc cggcgccgcg cgccgacccg ctgaactggg    300
gcaaggccgc ggagggcctg tccgggagcc acctggacga ggtgaagcgg atggtggcgg    360
agttccgcga gccgctggtg aagatccagg cgccagcct gagcgtcgcg caggtggccg    420
ccgtggccgt gggcgccggg ggcggcgagg cccgcgtgga gctggacgag tccgctcgcg    480
agcgcgtcag ggccagcagc gactgggtca tgggcagcat gatgaacggc accgacagct    540
acggcgtcac caccggcttc ggcgctacct cccaccgccg caccaaggaa ggcggcgcgc    600
tccagaggga gctcatcaga ttcctcaatg ccggcgcctt cggcaccggc gccgacggcc    660
acgtgctgcc ggcggaggcc acccgcgcgg cgatgctcgt gcgcgtcaac ccctcctcc    720 agggctactc cggaatccgc ttcgagatcc tcgaggccat cgccaagctg ctcaacgcca    780
acgtcacgcc gtgcctgccg ctccggggca ccatcaccgc gtcgggcgac ctcgtcccgc    840
tctcctacat cgccggcctc ataacggcc gccagaactc catggcggtg gcccccgatg    900
gcaggaaggt gggcgccgcg gaggcgttca gatcgcggg catcgagcac ggcttcttcg    960
```

-continued

| | |
|---|---|
| agctgcagcc caaggaaggt ctcgccatgg tcaacggcac ggccgtgggc tctggccttg | 1020 |
| cgtccaccgt gctcttcgag gccaacgtgc tcgccgtcct ggccgaggtc atctccgcgg | 1080 |
| tgttctgcga ggtcatgacg ggcaagccgg agttcaccga ccacctcacg cacaagctga | 1140 |
| agcaccaccc cggacagatc gaggccgccg cggtcatgga gcacatcttg gaaggcagct | 1200 |
| cctacatgaa gctggcgaag aggctcggcg agctcgaccc gctgatgaag ccgaagcagg | 1260 |
| acaggtacgc gctccgcacc tccccgcagt ggctcggccc acagatcgaa gtcatccgct | 1320 |
| tcgccaccaa gtccatcgag cgcgagatca actccgtcaa cgacaacccg ctcatcgacg | 1380 |
| tgtcccgtgg caaggcgctc cacggcggca acttccaggg gacacccatc ggtgtgtcca | 1440 |
| tggacaacac tcgtctcgcg ctcgccgcta tcggcaagct catgttcgcg cagttctcgg | 1500 |
| agctggtgaa cgactactac aacaacggcc ttccctccaa cctgtccggt gggcgtaacc | 1560 |
| cgagcttgga ctacgttttc aagggtgccg agatcgccat ggcctcctac tgctccgagc | 1620 |
| tccagttcct gggcaacccg gtgaccaacc acgtccagag cgctgagcag cacaaccagg | 1680 |
| acgtgaactc cctgggcctc atctcctcca ggaagaccgc cgaggccatc gacatcctga | 1740 |
| agctgatgtc gtccacgttc ctgatcgccc tgtgccaggc catcgacctg cggcacctcg | 1800 |
| aggagaacgt gaaggccgcg gtgaagaact gcgtgacgca ggtggccaag aagtccctga | 1860 |
| gcctgaacgc caggggcggg ctccacaacg cgcgcttctg cgagaaggac ctgcagacgg | 1920 |
| cgatcgaccg cgaggcggtg ttcgcgtacg cggacgaccc gtgcagcccc aactacgcgc | 1980 |
| tgatgcagaa gctccgcgcg gtgctggtcg agcacgcgct ggccaacggc gacgccgagc | 2040 |
| gcgacgtgga cacgtccatc ttcgccaagg tggccgagtt cgagcagcag gtccgcgcgg | 2100 |
| cgctgcccaa ggaggtggag gccgcgcgcg cggccgtgga aacggcagc cctctggtcc | 2160 |
| ccaacaggat caaggagtgc cggtcctacc cgctgtaccg gttcgtgcgc gaggaggtcg | 2220 |
| gcaccgagta cctgaccggc gagaagacga ggtcgcccgg cgaggagctg aacaaggtgc | 2280 |
| tcgtggccat caaccagcgc aagcacatcg acccgctgct cgagtgcctc aaggagtgga | 2340 |
| acggcgagcc cctgccgctc tgctgagctg caccagcaga gaaagacaat gtatacagaa | 2400 |
| ggaaaacaaa gtatagcag cacaaaacag agcgtttcaa ggtcgttgtg aagtgtttta | 2460 |
| cgatcatact agcaggagaa ctctatattt accgttgccc tgtaccagta gctaaagttc | 2520 |
| atgtgaatgt tgttgtgttc ccgcagctgc gacgccatgg cctgcgatgt gcatggtctt | 2580 |
| ggctgctgca gctactgaaa cttttgatgg ttttaacttg taagctagcg ggggataaag | 2640 |
| taaattactt tgctcc | 2656 |

<210> SEQ ID NO 159
<211> LENGTH: 2502
<212> TYPE: DNA
<213> ORGANISM: Zea mays

<400> SEQUENCE: 159

| | |
|---|---|
| ccggccggga ggaagagcag caccatcacc agctcttctc catcaagagt aacaggccat | 60 |
| cgccttacta gttctgatcc caaatcattt acggcgtagg tgcctcttgc tcataaccca | 120 |
| gccccacagc aatggagtgc gagaacggcc gcggcgttgc tgcaaccaac agcgattccc | 180 |
| tgtgcatggc gacgccccgc gccgacccgc ttaactgggg caaggcggcg gaggagctga | 240 |
| tgggcagcca cctggacgag gtcaagcgga tggtggccga gtaccgccaa cccttggtga | 300 |
| agatcgaggg cgccagcctc agcatcgcgc aggtggccgc cgtggccacc ggcgctggcg | 360 |

-continued

```
aggcccgggt cgagctggac gagtctgccc gtagccgggt caaggcaagc agcgactggg    420
tcatgaccag catgatgaac ggcaccgaca gctacgcgcg caccaccggc ttcggcgcca    480
cgtcgcacag gaggaccaag gagggcggcg cgctccagag ggagctcatc aggttcctca    540
acgccggcgc cttcggcacc ggcgcggacg gccacgtcct gccggccgag acgacgcgcg    600
cggccatgct cgtccgcatc aacaccctcc tccaggggta ctctggcatc cgcttcgaga    660
tcctcgaggc gatcgtcaag ctgctcaacg ccaacgtcac gccgtgcctg ccgctccgcg    720
gcacggtaac cgcgtccggc gacctcgtgc cgctctccta cattgcgggc ctcgtcaccg    780
ggcgtgagaa ctctgttgcg gttgccccag acggcagcag ggtcaacgcc gccgaggcat    840
tcaagattgc cggaatccag ggcggcttct tcgagctgca gcccaaggag ggtcttgcga    900
tggtgaacgg cacggccgtg ggctctggcc ttgcctccac tgtgctcttc gaggctaata    960
tccttgccat cctcgccgag gtcctgtctg ccgtgttctg cgaggtcatg aacggcaagc    1020
cggagtacac tgaccacctg acccacaagc tcaagcacca cccgggacag atcgaggctg    1080
ctgccatcat ggagcacatc ttggagggca gctcctacat gaagcttgcc aagaagctcg    1140
gcgagctcga tcccttgatg aagcccaagc aggaccggta cgcgctccgc acgtcgccgc    1200
agtggcttgg cccccagatt gaggttatcc gcgccgccac caagtccatt gagcgcgaga    1260
tcaactccgt caacgacaac ccgctcatcg atgtcgcccg aagcaaggct cttcacggtg    1320
gcaacttcca gggcacgccc atcggggtgt ccatggacaa cacccgtctc gccatcgcag    1380
ccatcggcaa gctcatgttt gcgcagttct ctgagctcgt caacgactac tacaacaacg    1440
gcttgccctc caacctgtcc ggtgggcgca accccagctt ggactacggc tttaagggtg    1500
ccgagatcgc catggcgtcc tactgctccg agctgcagtt cctggggaac ccggtcacca    1560
accacgtgca gagcgcggag cagcacaacc aggacgtcaa ctcactggga ctcatctcct    1620
ccaggaagac tgctgaggcc atcgagatcc taaagctcat gtcctcgacg ttcctgatcg    1680
ccctgtgcca ggccgtggac ctgcgccaca tcgaggagaa cgtcaagagc gctgtcaaga    1740
gctgcgtgat gacggtggcg aagaagaccc tgagcaccaa ctccaccggt ggtctccacg    1800
tcgcccgctt ctgcgagaag gacctgctcc aggagatcga gcgcgaggcg gtgttcgcgt    1860
atgccgacga cccctgcagc gctaactacc cgctgatgaa gaagcttcgc aacgtgctcg    1920
tggagcgcgc cctcgccaac ggcgctgccg agttcaacgc ggagacatcc gtgttcgcca    1980
aggtcgccca gttcgaggag gacctgcgcg cggcgctgcc aaaggcggtg gaggctgcac    2040
gggcggctgt cgagaacggc acggcaggga taccgaacag aatcgccgag tgccgctcct    2100
acccgctcta ccgcttcgtg cgcgaggagc tcggagccgt gtacctcacc ggcgagaaga    2160
cgcgctctcc cggcgaggag ctgaacaagg tgctcgttgc catcaaccag ggcaagcaca    2220
tcgacccgtt gctcgagtgc ctcaaggagt ggaacggcga gccactgccc atctgctgaa    2280
cagagaaaat acaaggagca gaagactgta tttttagcta ataatgcttt ttattcccaa    2340
tttatttatt gtcgttgata tgctacggat tcttgtcata cagctgcaac gccctgtaac    2400
caacttcgaa catgtaatag gttttcgagt atgcgaatca tatttgcagt taattaaatc    2460
caagtgttac ttttttccaa aaaaaaaaa aaaaagcgg cc                         2502
```

<210> SEQ ID NO 160
<211> LENGTH: 2550
<212> TYPE: DNA
<213> ORGANISM: Zea mays

<400> SEQUENCE: 160

-continued

```
cattgggtac ctcgaggccg gccgggagga agagctgcac catcaccagc tcttctccat      60
caagagtaac aggccatcgc cttactagtt ctgatcccaa atcatttacg gcgtaggtgc     120
ctcttgctca aaacccagcc ccacagcaat ggagtgcgag aacggccgcg ttgctgcaac     180
caacagcggt tccctgtgca tggcgacgcc ccgcgccgac ccgcttaact gggggaaggc     240
ggcggaggag ctgatgggca gccacctgga cgaggtcaag cggatggtgg ccagtaccg      300
ccaacccttg gtgaagatcg agggcgccag cctcagcatc gcgcaggtgg ccgccgtggc     360
caccggcgct cgcgaggccc gggtcgagct ggacgagtcc gcccgtggcc gggtcaaggc     420
aagcagcgac tgggtcatga gcagcatgat gaacggcacc gacagctacg gcgtcaccac     480
cggcttcggt gccacgtcgc acaggaggac taaggagggc ggcgcgctcc agagggagct     540
catcaggttc ctcaacgcag gcgccttcgg caccggcgcg gatggccacg tcctgccggc     600
cgaggcgacg cgcgcggcca tgctcgtccg catcaacacc ctcctccagg ggtactccgg     660
catccgcttc gagatcctcg aggcgattgt caagctgctc aacgccaacg tcacgccgtg     720
cctgccgctc cgcggcacgg tcaccgcgtc cggcgacctc gtgccgctct cctacattgc     780
cggcctcgtc accgggcgtg agaactctgt tgcgctcgcc ccaaacggca gcaaggtcaa     840
cgccgccgag gcattcaaga ttgccggaat ccaggtggc ttcttcgagc tgcagcccaa      900
ggagggtctt gcgatggtga acggcacggc cgtgggctct ggccttgcct ccactgtgct     960
cttcgaggct aatatccttg ccatcctcgc cgaggtcttg tccgccgtgt tctgcgaggt    1020
catgaacggc aagccggagt acaccgacca cctgacccac aagctcaagc accacccggg    1080
acagatcgag gctgctgcca tcatggagca catcttggag ggcagctcct acatgaagct    1140
tgccaagaag ctcggcgagc tcgatccctt gatgaagccc aagcaggacc ggtacgcgct    1200
ccgcacgtcg ccgcagtggc ttggcccca gattgaggtt atccgcgccg ccaccaagtc     1260
cattgagcgc gagatcaatt ccgtcaacga caacccgctc atcgatgtcg cccgaagcaa    1320
ggctcttcac ggtggcaact tccagggcac gcccatcggg gtgtccatgg acaacacccg    1380
tctcgccatc gcagccatcg gcaagctcat gtttgcgcag ttctctgagc tcgtcaacga    1440
ctactacaac aacggcttgc cctccaacct gtccggtggg cgcaaccccta gcttggacta    1500
cggctttaag ggcgccgaga tcgccatggc gtcctactgc tccgagctgc agttcctggg    1560
gaacccggtc accaaccacg tgcagagcgc ggaacagcac aaccaggacg tcaactcgct    1620
gggactcatc tcctctagga agactgctga ggccatcgag atcctgaagc tcatgtcctc    1680
gacgttcctg atcgccctgt gccaggccgt ggacctgcgc cacatcgagg agaacgtcaa    1740
gagcgctgtc aagagctgcg tgatgacggt ggcgaggaag accctgagca ccaactccac    1800
cggtggtctc cacgtcgccc gcttctgcga gaaggacctg ctccaggaga ttgagcgcga    1860
ggcggtgttc gcgtatgccg acgaccctg cagcgctaac tacccactga tgaagaagct     1920
tcgcaacgtg ctcgtggagc gcgccctcgc caacggcgct gccgagttca acgcggagac    1980
atccgtgttc gccaaggtcg cccagttcga ggacgacctg cgtgcggcgc tgcccaaggc    2040
ggtggaggct gcacgggcgg ctgtcgagaa cggcacggca gggataccga acagaatcgc    2100
cgactgccgc tcctacccgc tctaccgctt cgtgcgcgag gagctcggag ccgtgtacct    2160
caccggcgag aagactcgct ctcccggcga ggagctgaac aaggtgctcg ttgccatcaa    2220
ccagggcaag cacatcgacc cgttgctcga gtgcctcaag gagtggaacg gcagccact    2280
gcccatctgc tgaacagaga aaatacaagg agcagaagac tgtatttta gctaataatg     2340
```

-continued

| | |
|---|---|
| cttttttattc ccaatttatt tattgtcgtt gatatgctac ggattcttgt catacagctg | 2400 |
| caaaacgccc tgtaaccaac ttcgaacatg caataggttt tcgagtatgc gaatcatatt | 2460 |
| tgcagttaat taaaaaaaaa aaaaaaaaaa aaaaaaaaaa aaaaaaaaaa aaaaaaaaaa | 2520 |
| aaaaaaaaaa ccgagaaggg ggccggtacc | 2550 |

<210> SEQ ID NO 161
<211> LENGTH: 2357
<212> TYPE: DNA
<213> ORGANISM: Oryza sativa
<220> FEATURE:
<221> NAME/KEY: misc_feature
<222> LOCATION: (2245)..(2336)
<223> OTHER INFORMATION: n = unknown

<400> SEQUENCE: 161

| | |
|---|---|
| cccacgcgtc cgtcagcttc caactcgagc tcttcttcta cttaaaagaa aaaaaacacg | 60 |
| catatctagt agtactgttc tagtgttctt gtacttctat tcgtgtgcta ctactgcatc | 120 |
| tgtgagtctg tgtgactgta cacatctgta atggagtgcg aaaccgggct tgttcgttcc | 180 |
| ctgaacggcg acggccacgt tctgccggcg gaggcgacgc gcgcggcgat gctcgtccgc | 240 |
| atcaacaccc tcctccaggg ttactccggc atccgcttcg agatcctcga ggccatcacc | 300 |
| aagctgctca atgccaacgt cacgccgtgc ctgccgctcc ggggcaccat caccgcctcc | 360 |
| ggtgacttgg tcccactgtc ctacattgcc ggcctcatca ccggccgcca gaactccgtg | 420 |
| gccgtcgccc cggatggccg caaggtgacc gccgccgagg cattcaagat tgccggcatt | 480 |
| gagcacggct tcttcgagtt gcagcctaag gaaggtcttg ccatggtgaa cggcacggcc | 540 |
| gtcggctctg gccttgcatc gaccgtgctc tttgaggcca acgtccttgc catcctcgcc | 600 |
| gaggtcctgt ccgccgtgtt ctgtgaggtc atgaccggca agccggagta caccgaccac | 660 |
| ctgacacaca agctgaagca ccaccctgga cagatcgagg ctgccgccat catggagcac | 720 |
| atcttggaag gcagctcgta catgaagctg gcgaagaagc tcggcgagct cgaccgttg | 780 |
| atgaagccga agcaggacag gtacgcgctc cgcacgtcgc gcagtggct cggcccacag | 840 |
| atcgaggtca tccgcttcgc caccaagtcg atcgagcgcg agatcaactc cgtcaacgac | 900 |
| aacccgctga tcgatgtctc ccgtggcaag gcgcttcacg gtggcaactt ccagggcacg | 960 |
| cccatcggcg tgtccatgga caacacccgc ctcgccctcg ctgccatcgg caagctcatg | 1020 |
| ttcgcgcagt tctctgagct cgtgaacgac ttctacaaca acgggcttcc ttccaacctg | 1080 |
| tccggtggac gcaaccccag cttggactat gggttcaagg gcgcggagat cgccatggcg | 1140 |
| tcgtactgct ccgagctcca gttcttgggc aacccggtga ccaaccatgt ccagagcgcg | 1200 |
| gagcagcaca accaggacgt gaactcgctt ggtctcatct cctccaggaa gaccgccgag | 1260 |
| gccatcgaca tcctgaagct catgtcctcc acgttcttga tcgccctgtg ccaggccatc | 1320 |
| gacctgcgcc acctcgagga gaacatgaag accgcggtga gaactgcgt gatgcaggtg | 1380 |
| gccaagaaat ccctgagcat gaaccacatg gcgccctcc acatcgctcg cttctgcgag | 1440 |
| aaggacctgc tcaccgcgat cgaccgcgag gccgtgttcg cctacgccga cgacccctgc | 1500 |
| agcgccaact acccgttgat gcagaagctc cgcgcggtgc tcatcgagca cgcgctcgcc | 1560 |
| aacggcgacg ccgagcgcgt cctggagacc tccatcttcg ccaaggtggc cgagttcgag | 1620 |
| cagcacgtcc gcgcgcgct gcccaaggag gtggaggccg cgcgcgtcgc cgtcgagaac | 1680 |
| ggcacccgc tcgtccccaa ccggatcaag gagtgccgct cgtacccgct ctaccggttc | 1740 |
| gtgcgcgagg aggtcggcac cgagtacctc accggcgaga agacgcggtc gccggcgag | 1800 |

-continued

```
gagctgaaca aggtgctcgt cgccatcaac gagcgcaagc acatcgaccc gctgctcgaa    1860
tgcctcaagg aatggaatgg cgcgccactg ccactctgct gaacagaaat ggaatactaa    1920
aaaaaatgca aaacaagaag acgtatagca acacaaaact gaaagataga gagcatttcg    1980
agagtgtgaa tgttttctac tatgtctaga tgaacatggt gatgatacta ttttacggtt    2040
ctttgtagtt aacttgatgt tactgttgct gtttcagctt ctgcggttgc cataacctgc    2100
agttccgcat ggcctggcac gcagctttct gaaacttttg gtgctgtaaa tttgtataag    2160
ttgggggact aaagtaaatt attttgtttt aaaaaaaaaa aaaaaaaaaa aaaaaatgaa    2220
tgaatgaatc ttagtgtgaa aaaannnnnn nnnnnnnnnn nncncccccn cnccttgatt    2280
ggatggacct taggggggaaa aaaaaaaaaa aaaaaaaaag gcggcccccaa aaaanncggg    2340 ggggggggcc cttgggg                                                   2357
```

<210> SEQ ID NO 162
<211> LENGTH: 2535
<212> TYPE: DNA
<213> ORGANISM: Oryza sativa

<400> SEQUENCE: 162

```
cggcgacatc tacggcgtca ccaccggctt cggcggcacc tcccaccgcc gcaccaagga     60 cggcccccgcc ctccaagtcg agctcctcag gcatctcaac gccggaatct tcggcactgg    120
ctccgatggc cacacgctgc cgtcggagac ggtgcgggcg ccatgctcg tgcgcatcaa     180 caccctcctc cagggctact ccggcatccg gttcgagatc ctcgaggcca tcaccaagct    240
gctcaacacc ggcgtcacgc cgtgcctgcc gctccgtggc accatcaccg cgtccggtga    300
cctggttccc ctgtcctaca ttgccggcct catcaccggc cgccccaacg cgcaggccat    360
ctcgcccgac ggcaggaagg tggacgccgc cgaggcgttc aagctcgccg gcatcgaggg    420
tggcttcttc acgctgaacc ccaaggaagg tctcgccatc gtcaatggca cgtccgtggg    480
gtcggcgctc gcggccaccg tgatgttcga cgccaacatc ctcgccgtcc tgtccgaggt    540
gctctcggcg gtgttctgcg aggtgatgaa cggcaagccg gagtacaccg accacctgac    600
ccacaagctg aagcaccacc ctgggtcgat cgaggccgcc gccatcatgg agcacatcct    660
cgccgggagc tcgttcatga gccacgccaa gaaggtgaac gagatggacc cgctgctgaa    720
gccgaagcag gacaggtacg cgctccgcac gtcgccgcag tggctcggcc gcagatcga    780 ggtcatccgc gccgccacca gtccatcga gcgcgaggtc aactccgtga cgacaaccc    840 ggtgatcgac gtccaccgcg gcaaggcgct ccacggcggc aacttccagg gcacccccat    900
cggtgtgtcc atggacaacg cccgtctcgc catcgccaac atcggcaagc tcatgttcgc    960
gcagttctcc gagctcgtga cgagttcta caacaacggg ctgacctcca acctggccgg    1020
cagccgcaac ccgagcttgg actacggggtt caagggcacc gagatcgcca tggcctccta    1080
ctgctctgag ctccagtacc tcgccaaccc catcaccaac catgtccaga gcgcggagca    1140
gcacaaccag gacgtgaact cgctgggtct cgtctcggcc aggaagaccc tggaggcggt    1200
ggacatcctc aagctcatga cctccaccta catcgtcgcc ctgtgccagg ccgtcgacct    1260
tcgccacctc gaggagaaca tcaagagctc cgtcaagaac tgcgtcaccc aggtggccaa    1320
gaaggtgctc accatgaacc ccaccggcga cctctccagc gcgcgcttca gcgagaagaa    1380
cctcctcacc gccatcgacc gcgaggccgt gttcagctat gccgacgacc cgtgcagcgc    1440
caactacccg ctcatgcaga agctccgcgc cgtgctcgtc gagcacgccc tcaccagcgg    1500
```

-continued

```
cgacgccgag cccgaggcct ccgtgttctc caagatcacc aagttcgagg aggagctccg    1560
ctctgcgctg ccccgggaga tcgaggccgc ccgcgtcgcc gtcgccaacg gcaccgcccc    1620
cgtcgccaac cggatcgtcg agagccggtc gttcccgctc taccgcttcg tccgcgagga    1680
gctcggctgc gtattcctca ccggcgagaa gctcaagtcc cccggcgagg agtgcaacaa    1740
ggtgttcctc ggcatcagcc agggcaagct catcgacccc atgctcgact gcctcaagga    1800
gtggaacggc gagccccttc ccatcaacta agccaagatc ccatcgccat tgccattgcc    1860
atacacccat catcgaggag gagaggagac taaaaataaa agaaaacgaa ccgcttcgtg    1920
tatcttcaga caaaaaagac cctgtatttt cttcgttcgt tgccgtttgg tttatagtga    1980
tctcgtgttc tttgtgttag ctgctctgct cagcttgcca gccatggcgg caaagcaagc    2040
ggcttttcta agatattgtc gctaaactgt attttgggt gaaagtattg ctactcaatt    2100
ccatccttaa aaagttgtgg taatagaaat gttttgatcc tataaaaaaa aaaaaaaaa    2160 actgaggggg gggcccggtg cccaatgggc ctttaatgag tcggtttccc gccctaactg    2220
ggcggggtga ccacgggagg attggaaaac gctgggtagc caattaatgg gttgggggac    2280
tgcgctttgg ggctttgggt ttaggaaaag ccaacactgc ccttggacag ggccgacgaa    2340
tggggatggc acacgctgta ggtgatagcc ggggtttac gaccagagct acctgcctgc    2400
cagactaggc gtcctctcct tagttggtgc gcccgctatg gcttacctt tcatagctct    2460 ggtagtcagt ctctagtggc catattgttg agtgttttgt tacctgcgtg tagagtacac    2520
actcgcatca cgcaa                                                     2535
```

<210> SEQ ID NO 163
<211> LENGTH: 1717
<212> TYPE: DNA
<213> ORGANISM: Oryza sativa
<220> FEATURE:
<221> NAME/KEY: misc_feature
<222> LOCATION: (1711)..(1711)
<223> OTHER INFORMATION: n = unknown

<400> SEQUENCE: 163

```
gccccggacg gcagcaaggt ggacgccgct gaggcgttca ggatcgccgg catcgagcac      60
gggttcttcg cgttgcagcc caaggaaggg ctcgccatcg tcaacggcac ggccgtgggc     120
tccggcctcg cggcgatcgt gctcttcgag gccaacgtct tggccgtcct tgccgaggtc     180
ctctcggcgg tgtactgcga ggtgatggcc ggcaatccgg agtacaccga ccacctcatc     240
cacgcgctga agcaccaccc tggacagatc gaagctgcgg ccatcatgga gcacatactg     300
gaaggcagct cctacatgag gcttgccaag gagcagggcg aagcttgacc gtgttgacga     360
agctgaggca ggacaggtac gccatccgca cggcgccgca gtggctcggc ccgcaggtcg     420
aggtcatccg cttcgccacc aagtcgatcg agcgggagat caactccgtc aacgacaacc     480
cggtcatcga cgtcgcccgc cgcaaggcgc tccaacggcg gcaacttcca gggcactccc     540
atcggggtgt ccatggacaa cacccgcctc gccatcgctg ccatcggcaa gctcatgttc     600
gcgcagttct cggagctcgt gaacgacttc tacaacaacg gctgccatc caacctgtct     660 ggcggtcgca acccgagctt ggactacggg ttcaagggcg ccgagatcgc catggcctcc     720
tactgctccg agctgcagtt cttggcaac ccagtgacca accacgtcca gagcgccgag     780
cagcacaacc aggacgtcaa ctctcttgga ctcatctcct ccaggaagac cgccgaggca     840
atcgacatcc tgaagctcat gtcctccacg ttccttgatcg ccctctgcca ggccgtcgac     900
ctgcggcaca tcgaggagaa cgtcaagagc gccgtcaaga gctgcgtcat gacggtggcc     960
```

-continued

```
aagaagacac tcagcaccaa ctccaccggc gatctccacg tcgcacgctt ctgcgagaag    1020
gacctgctca aggagatcga ccgcgaggcg gtgttcgcgt acgcggacga cccgtgcagc    1080
cacaactacc cgctgatgaa gaagctgcgc aacgtgctcg tggagcgcgc cctcgccaac    1140
ggcgcggccg agttcaacgc cgacacctcg gtgttcgcca aggtcgcgca gttcgaggag    1200
gagctgcgcg cgactctgcc aggtgcgatc gaggccgcac gtgcggctgt ggagaacggc    1260
acggcggcga ttcccagcag aatcaccgag tgcaggtcgt atccgctcta ccggttcgtg    1320
cgcgaggagc tcggaacaaa gtacctgacc ggcgagaaga cacgatcgcc tggcgaggag    1380
ctgaacaagg ttcttgtggc tatcaacgaa ggcaagcaca tcgacccgtt gctcgagtgc    1440
ctcaaggagt ggaacggcga gcccctgcca atctgctgaa ctagtgaacc gattagctga    1500
ataacagtgg agtgtggagg cgtgcggtgt tgtttttatc tggtgaatat tttattttta    1560
cacttatctt tgtgttactc aaaagaattc ttcgttgcat agcggcaagc atgcacagca    1620
aaccttggta ccgagtgcag gtttcaaaag caactagtgt tgtaacatat aagttttgga    1680
tatcagagtg ttgcaaatca ttaaaaaaaa naaaaaa                             1717
```

<210> SEQ ID NO 164
<211> LENGTH: 1273
<212> TYPE: DNA
<213> ORGANISM: Oryza sativa

<400> SEQUENCE: 164

```
ctcgtcccgc tgtcctacat tgccggcctt gtcactgggc gcgagaacgc cgtggcggtt     60
gcaccagatg gcagcaaggt gaacgccgct gaggcgttca agattgctgg catccagggc    120
ggcttcttcg agctgcagcc caaggaaggc cttgccatgg tcaatggcac tgccgtgggc    180
tctggccttg catcgaccgt gctctttgag gctaacattc ttgccatcct cgccgaggtc    240
ctctcggccg tgttctgcga ggtgatgaac ggcaagccgg agtacaccga ccacctgact    300
cacaagctca agcaccatcc aggacagatc gaggccgccg ccatcatgga gcacatcttg    360
gagggaagct cctacatgaa gcatgccaag aagcttggtg agctcgaccc actgatgaag    420
ccgaagcaag accggtacgc gctccggaca tccccacagt ggctcggccc tcaaattgag    480
gttatccgcg ccgccaccaa gtccattcga gcgtgagatc aactccgtga acgacaaccc    540
gctcattgac gtctcccgtg caaggggctc cacggcggc aacttccagg gcacacccat    600
cggcgtgtcc atggacaaca ccaggctcgc cattgccgcg atcggtaagc tcatgttcgc    660
gcagttctct gagctcgtga acgatttcta caacaacggc ctgccgtcca acctgtccgg    720
tgggcgcaac ccgagcttgg actacggggtt caaggtgcgc cgagatctgc catgcgtcg    780 tactgctctg agctgcagtt cctggtgcaa cccggtcacc aaccacgtcc agagcgccga    840
gcagcacaac caggacgtga actccctcgg actcatctcc tccaggaaga cggccgaggc    900
catcgagatc ctgaagctca tgtcctcgac gttcctgatc gcgctgtgcc aggccgtgga    960
cctgcgccac atcgaggaga acgtcaagag cgccgtcaag agctgcgtga tgacggtggc    1020
gaagaagacc ctgagcacca actccaccgg cggcctccac gtcgcccgct tctgcgaaaa    1080
ggacctgctc caggagatcg agcgcgaggc ggtgttcgcc tacgccgacg acccctgcag    1140
cgccaactac ccgctcatga agaagctgcg caacgtgctc gtggagcgcg ccctcgccaa    1200
cggcacggcc gagttcgacg ccgagacctc cgtcttcgcc aaggtcgccc ggttcgagga    1260
ggagctccgc gcg                                                      1273
```

<210> SEQ ID NO 165
<211> LENGTH: 1334
<212> TYPE: DNA
<213> ORGANISM: Oryza sativa

<400> SEQUENCE: 165

| | | | | | |
|---|---|---|---|---|---|
| gcacgagccg | gtcatcgacg | tgcaccgcgg | caaggccctg | cacggcggca | acttccaggc | 60 |
| acgccggatc | ggcgtgtcca | tggacaacac | ccgcctcgcc | atcgccaaca | tcggcaagct | 120 |
| catgttcgcc | cagttctccg | agctggtcaa | cgagttctac | aacaacgggc | tcacgtcaaa | 180 |
| cctggccggc | agccgcaacc | cgagcttgga | ctacggcttc | aagggcaccg | agatcgccat | 240 |
| ggcctcctac | tgctcggagc | tccagttcct | cgccaacccg | gtcaccaacc | acgtccagag | 300 |
| cgcggagcag | cacaaccagg | acgtcaactc | cctcggcctc | gtctccgcca | ggaagaccgc | 360 |
| cgaggcggtg | gacatcctca | agctcatgtc | ctccacctac | ctggttgcgc | tctgccaggc | 420 |
| cgtcgacctg | cgccacctgg | aggagaacct | caagagcgcc | gtcaagaact | gcgtgacgac | 480 |
| ggtggccaag | aaggtgctca | ccacgggccc | cgccggcggc | ctccacagcg | cgcgcttcag | 540 |
| cgagaaggcc | ctgctcaccg | ccatcgaccg | cgaggccgtg | tacagctacg | ccgacgaccc | 600 |
| gtgcagcgcc | aactacccgc | tgatgaccaa | gatccgcgcc | gtgctcgtcg | agcacgccct | 660 |
| cgccaacggc | cccgccgaga | aggacgacgg | ctcctccgtg | ttctccaaga | tcaccgcgtt | 720 |
| cgaggaggag | ctccgcgagg | cgctgcccag | ggagatggag | gcggcgcgcg | tggcgttcga | 780 |
| gaccggcacc | gcgccgatca | ccaacaggat | caaggagagc | aggtcgttcc | cgctgtaccg | 840 |
| cttcgtccgc | gaggagctcg | gctgcgtgta | cctcaccgga | gagaagctca | gtcccccgg | 900 |
| cgaggagtgc | aacaaggtgt | tcctggccat | cagcgagcgc | aagctcatcg | acccgatgct | 960 |
| cgagtgcctc | aaggagtgga | acggcgagcc | cctgcccatc | tgctgatcga | accagtccac | 1020 |
| ccgcgaacgc | gacaagatcc | aggaagagac | gatacgtgca | ccgaaataag | aaagggagga | 1080 |
| attcaggatc | ctgaaggctt | ctcgtacgct | catcagcaga | ttacgttgtt | tctccgtccg | 1140 |
| tgtttttttt | ttccttttg | agcttgctgt | atttatccgt | gttgtaatcg | tgtgagattg | 1200 |
| ctgctgcaat | gccgtggcgc | ctgcagcgtt | catggccttg | gctggcagct | ttctgattcc | 1260 |
| gttgttgtat | tttgcaagtg | aaatatacta | atatagcgct | atcttgatta | catgtgttga | 1320 |
| aaaaaaaaa | caaa | | | | | 1334 |

<210> SEQ ID NO 166
<211> LENGTH: 33
<212> TYPE: DNA
<213> ORGANISM: Artificial
<220> FEATURE:
<223> OTHER INFORMATION: Primer WER_Nco

<400> SEQUENCE: 166
ttcccatggt ttttgtttct tgaatgata gac    33

<210> SEQ ID NO 167
<211> LENGTH: 38
<212> TYPE: DNA
<213> ORGANISM: Artificial
<220> FEATURE:
<223> OTHER INFORMATION: Primer wer_5' #2

<400> SEQUENCE: 167
gtttaaacgg cgcgccgtca aagtgtcaaa ccatcttc    38

-continued

```
<210> SEQ ID NO 168
<211> LENGTH: 395
<212> TYPE: PRT
<213> ORGANISM: Arabidopsis thaliana

<400> SEQUENCE: 168

Met Val Met Ala Gly Ala Ser Ser Leu Asp Glu Ile Arg Gln Ala Gln
1               5                   10                  15

Arg Ala Asp Gly Pro Ala Gly Ile Leu Ala Ile Gly Thr Ala Asn Pro
            20                  25                  30

Glu Asn His Val Leu Gln Ala Glu Tyr Pro Asp Tyr Tyr Phe Arg Ile
        35                  40                  45

Thr Asn Ser Glu His Met Thr Asp Leu Lys Glu Lys Phe Lys Arg Met
    50                  55                  60

Cys Asp Lys Ser Thr Ile Arg Lys Arg His Met His Leu Thr Glu Glu
65                  70                  75                  80

Phe Leu Lys Glu Asn Pro His Met Cys Ala Tyr Met Ala Pro Ser Leu
                85                  90                  95

Asp Thr Arg Gln Asp Ile Val Val Glu Val Pro Lys Leu Gly Lys
            100                 105                 110

Glu Ala Ala Val Lys Ala Ile Lys Glu Trp Gly Gln Pro Lys Ser Lys
        115                 120                 125

Ile Thr His Val Val Phe Cys Thr Thr Ser Gly Val Asp Met Pro Gly
    130                 135                 140

Ala Asp Tyr Gln Leu Thr Lys Leu Leu Gly Leu Arg Pro Ser Val Lys
145                 150                 155                 160

Arg Leu Met Met Tyr Gln Gln Gly Cys Phe Ala Gly Gly Thr Val Leu
                165                 170                 175

Arg Ile Ala Lys Asp Leu Ala Glu Asn Asn Arg Gly Ala Arg Val Leu
            180                 185                 190

Val Val Cys Ser Glu Ile Thr Ala Val Thr Phe Arg Gly Pro Ser Asp
        195                 200                 205

Thr His Leu Asp Ser Leu Val Gly Gln Ala Leu Phe Ser Asp Gly Ala
    210                 215                 220

Ala Ala Leu Ile Val Gly Ser Asp Pro Asp Thr Ser Val Gly Glu Lys
225                 230                 235                 240

Pro Ile Phe Glu Met Val Ser Ala Ala Gln Thr Ile Leu Pro Asp Ser
                245                 250                 255

Asp Gly Ala Ile Asp Gly His Leu Arg Glu Val Gly Leu Thr Phe His
            260                 265                 270

Leu Leu Lys Asp Val Pro Gly Leu Ile Ser Lys Asn Ile Val Lys Ser
        275                 280                 285

Leu Asp Glu Ala Phe Lys Pro Leu Gly Ile Ser Asp Trp Asn Ser Leu
    290                 295                 300

Phe Trp Ile Ala His Pro Gly Gly Pro Ala Ile Leu Asp Gln Val Glu
305                 310                 315                 320

Ile Lys Leu Gly Leu Lys Glu Lys Met Arg Ala Thr Arg His Val
                325                 330                 335

Leu Ser Glu Tyr Gly Asn Met Ser Ser Ala Cys Val Leu Phe Ile Leu
            340                 345                 350

Asp Glu Met Arg Arg Lys Ser Ala Lys Asp Gly Val Ala Thr Thr Gly
        355                 360                 365

Glu Gly Leu Glu Trp Gly Val Leu Phe Gly Phe Gly Pro Gly Leu Thr
    370                 375                 380
```

```
Val Glu Thr Val Val Leu His Ser Val Pro Leu
385                 390                 395
```

<210> SEQ ID NO 169
<211> LENGTH: 29
<212> TYPE: DNA
<213> ORGANISM: Artificial
<220> FEATURE:
<223> OTHER INFORMATION: Primer Sequence

<400> SEQUENCE: 169
accatggttg cggttgaaag agttgagag                                29

<210> SEQ ID NO 170
<211> LENGTH: 30
<212> TYPE: DNA
<213> ORGANISM: Artificial
<220> FEATURE:
<223> OTHER INFORMATION: Primer Sequence

<400> SEQUENCE: 170
gtcgacgcgg ccgctcattt ttctcggata                               30

<210> SEQ ID NO 171
<211> LENGTH: 30
<212> TYPE: DNA
<213> ORGANISM: Artificial
<220> FEATURE:
<223> OTHER INFORMATION: Primer Sequence

<400> SEQUENCE: 171
gcggccgctc agaagatagg agcgtttgag                               30

<210> SEQ ID NO 172
<211> LENGTH: 23
<212> TYPE: DNA
<213> ORGANISM: Artificial
<220> FEATURE:
<223> OTHER INFORMATION: Primer Sequence

<400> SEQUENCE: 172
acgctaacag atcggaaccg gag                                      23

<210> SEQ ID NO 173
<211> LENGTH: 25
<212> TYPE: DNA
<213> ORGANISM: Artificial
<220> FEATURE:
<223> OTHER INFORMATION: Primer Sequence

<400> SEQUENCE: 173
acgcgtttct gcgagaaaga cttac                                    25

<210> SEQ ID NO 174
<211> LENGTH: 25
<212> TYPE: DNA
<213> ORGANISM: Artificial
<220> FEATURE:
<223> OTHER INFORMATION: Primer Sequence

<400> SEQUENCE: 174
gacgtccaaa ggatacgacc tacac                                    25

<210> SEQ ID NO 175
<211> LENGTH: 24
<212> TYPE: DNA

```
<213> ORGANISM: Artificial
<220> FEATURE:
<223> OTHER INFORMATION: Primer Sequence

<400> SEQUENCE: 175
gacgtccatc ctcaagctta tgtc                                           24

<210> SEQ ID NO 176
<211> LENGTH: 24
<212> TYPE: DNA
<213> ORGANISM: Artificial
<220> FEATURE:
<223> OTHER INFORMATION: Primer Sequence

<400> SEQUENCE: 176
gtcgactctc agtctcaccg ttag                                           24
```

PRODUCTION OF INCREASED OIL AND PROTEIN IN PLANTS BY THE DISRUPTION OF THE PHENYLPROPANOID PATHWAY

This application claims priority to U.S. Provisional Application No. 60/427,313, filed Nov. 18, 2002, herein incorporated by reference in its entirety.

The present invention relates to the fields of nucleic acid chemistry and agricultural biotechnology. In particular, the present invention is directed at methods and compositions for increasing oil levels in plants.

Currently, levels of oil in oilseed crops have been increased incrementally by traditional breeding and selection methods. There exist few references to transgenic plants with increased levels of oil. In contrast, increases in the proportions of some strategic fatty acids have been achieved by the introduction or manipulation of various plant fatty acid biosynthesis genes in oilseeds. For instance, Voelker et al. demonstrated that expression in *Brassicaceae* of a medium chain fatty acyl-ACP thioesterase from California Bay increased the lauric acid (12:0) content (*Science*, 257: 72-74 (1992)). Hitz et al. increased proportions of oleic acid in *Glycine max* by co-suppression using a sense construct encoding a plant microsomal FAD-2 (delta-12) desaturase (Proc. 9th International Cambridge Rapeseed Congress UK, pp. 470-472 (1995)). Although the use of plant transgenes resulted in altered proportions of sn-2 lauric acid in canola and oleic acid in soy, there was no evidence of increased total fatty acid content, or increased oil yield in these transgenics.

Certain workers have attempted to increase or modulate the oil content of plants by manipulation of oil biosynthetic pathway genes. For example, U.S. Pat. No. 6,268,550 to Gengenbach et al. provides maize acetyl CoA carboxylase nucleic acids for altering the oil content of plants. Additionally, U.S. Pat. No. 5,925,805 to Ohlrogge et al. provides an *Arabidopsis* acetyl CoA carboxylase gene that can be used to increase the oil content of plants. However, the oil content was not increased substantially in these experiments.

A need therefore exists for an improved method to alter the oil content of plants, and in particular to increase the oil content of plants and seeds.

SUMMARY OF INVENTION

The present invention includes materials and provides a method for increasing the oil content of a plant by disrupting the function of a phenylpropanoid pathway protein in that plant. In the present invention, the phenylpropanoid pathway protein is selected from the group consisting of chalcone synthase (CHS), leucoanthocyanidin dioxygenase (LDOX), phenylalanine ammonia lyase (PAL) and the transcription factor TTG1. In one embodiment, the function of the phenylpropanoid pathway protein is disrupted by suppressing the expression of the gene for that protein. In a further embodiment, the function of the phenylpropanoid pathway protein is disrupted by causing a mutation in the coding or regulatory sequence for that protein.

The present invention also includes and provides a method for increasing the protein content of a plant by disrupting the function of a phenylpropanoid pathway protein in that plant. In the present invention, the phenylpropanoid pathway protein is selected from the group consisting of CHS, PAL, TTG1, and LDOX. In one embodiment, the function of the phenylpropanoid pathway protein is disrupted by suppressing the expression of the gene for that protein. In a further embodiment, the function of the phenylpropanoid pathway protein is disrupted by causing a mutation in the coding sequence for that protein. In another embodiment the increased protein is in the seed of the plant.

The present invention also includes and provides a method for altering the fiber content of a plant by disrupting the function of a phenylpropanoid pathway protein in that plant. In the present invention the phenylpropanoid pathway protein is selected from the group consisting of CHS, PAL, TTG1, and LDOX. In one embodiment the function of the phenylpropanoid pathway protein is disrupted by suppressing the expression of the gene for that protein. In a further embodiment the function of the phenylpropanoid pathway protein is disrupted by causing a mutation in the coding or regulatory sequence for that protein. In another embodiment, the altered fiber content is in the seed of the plant.

The present invention also provides isolated polynucleotides encoding transcription factors that are operative in the phenylpropanoid pathway in a plant. In one embodiment of the present invention, the isolated polynucleotides encoding transcription factors are selected from the group consisting of SEQ ID NOs: 2, 3, and 147, and complements thereof. In a further embodiment, the isolated polynucleotides encoding transcription factors are isolated from corn, canola or soybean.

In another embodiment, the present invention provides vectors comprising at least 50 base pairs from one polynucleotide selected from the group consisting of SEQ ID NOs: 4 through 17, 29, 30, 32 through 96, 128 through 140, 144, 149, 150, and 154 through 165, wherein the polynucleotide can be expressed in both the sense and antisense orientations. Expression of both sense and antisense orientations can be accomplished by expression of polynucleotides in the sense and antisense orientation in the same or distinct T-DNAs, or by the expression of self-complementary (i.e., hairpin) RNAs. In a further embodiment, the present invention provides expression cassettes comprising said vectors, wherein the polynucleotide of interest is operably linked to a promoter. The invention further includes and provides plants comprising said expression cassettes.

The present invention further provides a method of producing a plant with increased oil content, comprising disrupting the function of a protein in the phenylpropanoid pathway. In a further embodiment of the present invention, the protein in the phenylpropanoid pathway is selected from the group consisting of CHS, PAL, TTG1, and LDOX. In another embodiment, the increased oil content is in the seed of the plant.

The present invention further provides a method of producing a plant with increased protein content, comprising disrupting the function of a protein in the phenylpropanoid pathway. In a further embodiment of the present invention, the protein in the phenylpropanoid pathway is selected from the group consisting of CHS, PAL, TTG1, and LDOX. In another embodiment, the increased protein content is in the seed of the plant.

The present invention further provides a method of increasing phenylpropanoid pathway products in a plant by increasing the expression of phenylpropanoid pathway proteins. In a further embodiment of the present invention the proteins in the phenylpropanoid pathway are selected from the group consisting of CHS, PAL, TTG1, and LDOX.

The invention further provides plants derived from said method and grain derived from said plants. The present invention further provides oil, feed and meal derived from said grain.

DESCRIPTION OF THE FIGURES

FIG. 3 shows alignment of predicted protein sequences of LDOX from two wild type *Arabidopsis* ecotypes Columbia (SEQ ID NO: 124) and Landsberg (SEQ ID NO: 125) and the oil 4 mutant from *Arabidopsis* (SEQ ID NO: 126).

BRIEF DESCRIPTION OF THE SEQUENCES

Figure 1:
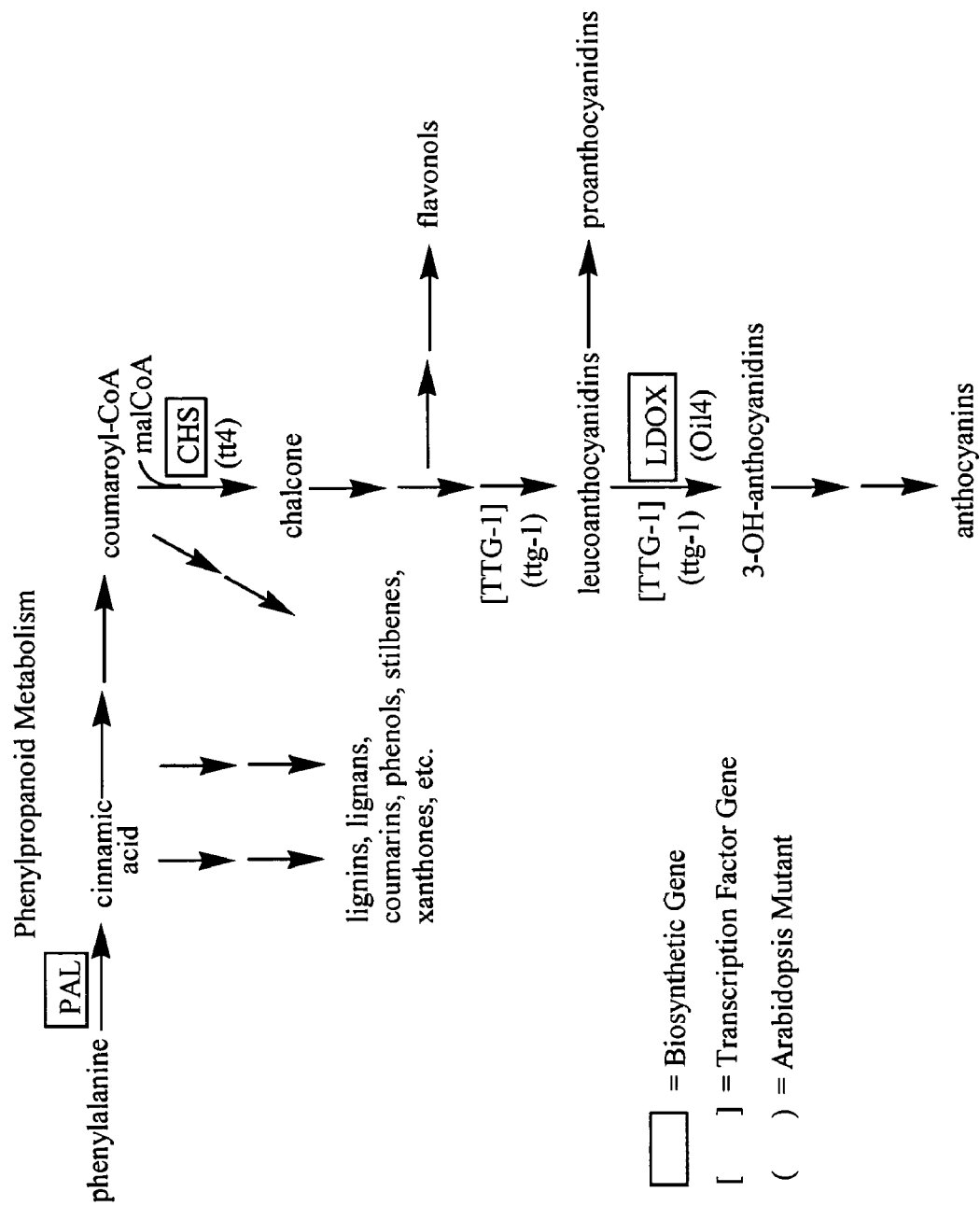
FIG. 1 shows a schematic representation of the phenylpropanoid pathway in plants.

SEQ ID NO: 1 is a TTG1 protein from *Arabidopsis thaliana*.

SEQ ID NO: 2 is a polynucleotide encoding a TTG1 from soybean.

SEQ ID NO: 3 is a polynucleotide encoding a TTG1 from corn.

SEQ ID NOs: 4 through 8 are polynucleotides encoding CHS from corn.

SEQ ID NOs: 9 through 11 are polynucleotides encoding CHS from soybean.

SEQ ID NOs: 12 and 13 are polynucleotides encoding CHS from corn.

SEQ ID NOs: 14 through 28 are polynucleotides encoding CHS from soybean.

SEQ ID NO: 29 is a polynucleotide encoding CHS from *Brassica napus*.

SEQ ID NO: 30 is a partial polynucleotide sequence encoding CHS from *Brassica napus*.

SEQ ID NO: 31 is a polynucleotide encoding CHS from *Arabidopsis thaliana*.

SEQ ID NO: 32 is a polynucleotide encoding CHS from barley.

SEQ ID NOs: 33 through 36 are polynucleotides encoding CHS from *Brassica napus*.

SEQ ID NOs: 37 through 49 are polynucleotides encoding CHS from corn.

SEQ ID NOs: 50 through 58 are polynucleotides encoding CHS from cotton.

SEQ ID NOs: 59 and 60 are polynucleotides encoding CHS from potato.

SEQ ID NOs: 61 and 62 are polynucleotides encoding CHS from rice.

SEQ ID NOs: 63 and 64 are polynucleotides encoding CHS from sorghum.

SEQ ID NOs: 65 through 78 are polynucleotides encoding CHS from soybean.

SEQ ID NO: 79 is a full length sequence of a polynucleotide encoding CHS from *Brassica napus*.

SEQ ID NOs: 80 and 81 are polynucleotides encoding CHS from soybean.

SEQ ID NOs: 82 and 83 polynucleotides encoding CHS from tomato.

SEQ ID NOs: 84 through 94 are polynucleotides encoding CHS from wheat.

SEQ ID NO: 95 is a polynucleotide encoding a CHS from sunflower.

SEQ ID NO: 96 is a polynucleotide encoding a CHS from tobacco.

SEQ ID NOs: 97 through 120 are primers used for PCR amplification.

SEQ ID NOs: 121 through 123 are polynucleotide sequences encoding LDOX from *Arabidopsis thaliana* cultivars Columbia, Landsberg and an oil4 mutant, respectively.

SEQ ID NOs: 124 through 126 are the encoded protein sequences of LDOX from *Arabidopsis thaliana* cultivars Columbia, Landsberg and an oil4 mutant, respectively.

SEQ ID NO: 127 is a polynucleotide encoding LDOX from *Arabidopsis thaliana*.

SEQ ID NO: 128 is a polynucleotide encoding LDOX from barley.

SEQ ID NOs: 129 and 130 are polynucleotides encoding LDOX from *Brassica napus*.

SEQ ID NO: 131 is a polynucleotide encoding LDOX from corn.

SEQ ID NOs: 132 through 134 are polynucleotides encoding LDOX from cotton.

SEQ ID NOs: 135 and 136 are polynucleotides encoding LDOX from onion.

SEQ ID NOs: 137 and 138 polynucleotides encoding LDOX from rice.

SEQ ID NO: 139 is a polynucleotide encoding LDOX from sorghum.

SEQ ID NO: 140 is a polynucleotide encoding LDOX from soybean.

SEQ ID NO: 141 is a polynucleotide encoding a TTG1 from *Arabidopsis thaliana*.

SEQ ID NOs: 142 and 143 are primer sequences used in PCR amplification reactions.

SEQ ID NO: 144 is a polynucleotide encoding a full length sequence of LDOX from *Brassica napus*.

SEQ ID NO: 145 is a polynucleotide encoding LDOX from *Arabidopsis thaliana*.

SEQ ID NO: 146 is a primer sequence used in PCR amplification reactions.

SEQ ID NO: 147 is a polynucleotide encoding TTG1 from *Brassica napus*, contained with the plasmid pMON65420.

SEQ ID NO: 148 is a polynucleotide encoding a CHS from *Arabidopsis thaliana*.

SEQ ID NOs: 149 and 150 are polynucleotides encoding CHS from *Brassica napus*.

SEQ ID NO: 151 is a polynucleotide encoding PAL1 from *Arabidopsis thaliana*.

SEQ ID NO: 152 is a polynucleotide encoding PAL2 from *Arabidopsis thaliana*.

SEQ ID NO: 153 is a polynucleotide encoding PAL3 from *Arabidopsis thaliana*.

SEQ ID NOs: 154 through 160 are polynucleotides encoding PAL from corn.

SEQ ID NOs: 161 through 165 are polynucleotides encoding PAL from rice.

SEQ ID NOs: 166 and 167 are primers used in PCR amplification reactions.

SEQ ID NO: 168 is a CHS protein from *Arabidopsis thaliana*.

SEQ ID NOs: 169 and 170 are primers used in PCR amplification reactions.

SEQ ID NOs: 171 through 176 are primers used in PCR amplification reactions.

DETAILED DESCRIPTION OF THE INVENTION

The present invention provides isolated polynucleotides encoding transcription factors and enzymes important in the phenylpropanoid biosynthetic pathway in a plant. The invention also provides gene constructs that disrupt the function of proteins in the phenylpropanoid biosynthetic pathway. The result of disrupting the function of these proteins in plants is increased oil levels in the plant. Additionally, disrupting the function of these proteins results in increased protein and altered fiber levels in the plant.

Nucleic Acids of Present Invention

A "phenylpropanoid" compound is a compound having a 3-carbon side chain on an aromatic ring, a common structural element shared by all of the metabolites in the monolignol pathway as well as other subclasses of plant phenolics such as flavonoids. A schematic representation of the phenylpropanoid pathway is shown in FIG. 1. This figure provides only a condensed overview of a complex pathway and is intended to further illustrate the current invention. It in no way should be construed as a limitation in scope of the described invention.

Flavonoids consist of various groups of compounds, which include chalcones, flavonones, isoflavanones, aurones, catechins, anthocyanidins, and flavonols. These plant metabolites influence many plant-animal interactions and also function to protect plants against UV-B irradiation. The first committed step of flavonoid biosynthesis from the phenylpropanoid pathway is catalyzed by the enzyme chalcone synthase (CHS). Three molecules of acetate-derived malonyl-CoA and one molecule of p-coumaryl-CoA are condensed to generate one molecule of tetrahydroxychalcone. Details of the phenylpropanoid pathway can be found in most plant biochemistry references (see for example, *Biochemistry and Molecular Biology of Plants*, Buchanan, Gruissem, and Jones. eds., American Society of Plant Physiology (2000)).

In one embodiment, the present invention provides constructs that disrupt the function of phenylpropanoid pathway enzymes such as CHS, PAL and LDOX. In further embodiments, the instant invention provides constructs that disrupt the function of transcription factors, such as TTG1 (TRANSPARENT TESTA GLABRA1, see, Walker et al., *The Plant Cell*, 11:1337-49 (1999)), which regulate the transcription of phenylpropanoid pathway genes.

In some embodiments, the polynucleotides of the present invention are cloned, amplified, or otherwise constructed from plants generally regarded as oilseed crops. In preferred embodiments, the plants are soybean, canola or corn.

The present invention includes a plurality of polynucleotides that encode for the identical amino acid sequence. The degeneracy of the genetic code allows for several trinucleotide codons to encode the same amino acid. Additionally, the present invention includes isolated nucleic acids comprising allelic variants. The term "allelic" as used herein refers to a polynucleotide that encodes an alternative amino acid sequence that has the same or similar function of the original form of the same gene.

The nucleic acids and vectors of the present invention need not have the exact nucleic acid sequences described herein. Instead, the sequences of the nucleic acids and vectors can vary, so long as the nucleic acid either performs the function for which it is intended or has some other utility, for example as a nucleic acid probe for complementary nucleic acids. For example, some sequence variability in any part of the TTG1 nucleic acid sequence is permitted so long as the variant retains at least 10% of the activity observed under similar conditions for analogous wild-type transcription factors.

Fragment and variant nucleic acids are also encompassed by this invention. Nucleic acid fragments encompassed by the invention are of two types. First, fragment nucleic acids that are not full length but do perform their intended function are encompassed within this invention. Second, fragments of the nucleic acids identified herein are useful as hybridization probes or in one of the gene suppression strategies useful in down regulation of enzyme activity.

"Substantially similar" nucleic acid fragments refers to fragments wherein changes in one or more nucleotide bases result in substitution of one or more amino acids but do not substantially affect the functional properties of the polypeptide encoded by the nucleotide sequence. "Substantially similar" also refers to nucleic acid fragments wherein changes in one or more nucleotide bases do not affect the ability of the nucleic acid fragment to mediate alteration of gene expression by gene suppression strategies useful in down regulation of enzyme activity. "Substantially similar" also refers to modifications of the nucleic acid fragments of the instant invention, such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the present invention, wherein one or more nucleotides are substituted, deleted or inserted, for their ability to affect the level of the polypeptide encoded by the unmodified nucleic acid fragment in a plant or plant cell. For example, a substantially similar nucleic acid fragment comprising a fragment with a change of at least 1 of 25 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, untranslated region, or intron and by nucleic acid fragments that do not share 100% the entire coding region of a gene, untranslated region, or intron and by nucleic acid fragments that do not share 100% sequence identity with the gene to be suppressed. Moreover, alterations in a nucleic acid fragment that result in the production of a chemically equivalent amino acid at a given site, but do not affect the functional properties of the encoded polypeptide, are well known in the art.

The present invention also provides methods for detection and isolation of derivative or variant nucleic acids encoding the proteins provided herein. The methods involve hybridizing at least a portion of a nucleic acid comprising any part of SEQ ID NOs: 4 through 17, 29, 30, 32 through 96, 128 through 140, 144, 149, 150, and 154 through 165, to a sample nucleic acid, thereby forming a hybridization complex, and detecting the hybridization complex. The presence of the complex correlates with the presence of a derivative or variant nucleic acid that can be further characterized by nucleic acid sequencing, expression of RNA or protein and testing to determine whether the derivative or variant retains activity. In general, the portion of a nucleic acid comprising any part of SEQ ID NOs: 4 through 17, 29, 30, 32 through 96, 128 through 140, 144, 149, 150, and 154 through 165, used for hybridization is at least 15 nucleotides, and hybridization is under hybridization conditions that are sufficiently stringent to permit detection and isolation of substantially homologous nucleic acids. Such conditions are well known to one of skill in the art. Exemplary high stringency conditions include hybridization in 50% formamide, 5×SSC, 50 mM sodium phosphate, pH 7.0, 5 mM EDTA, 0.1% SDS, 5× Denhardt's with 100 µg/mL denatured salmon sperm DNA at 42° C., and a wash in 0.1×SSC, 0.1% SDS at 60 to 65° C. An extensive guide to the hybridization of nucleic acids is found in Tijssen, *Laboratory Techniques in Biochemistry and Molecular Biology-Hybridization with Nucleic Acid Probes*, Part 1, Chapter 2 (Elsevier, N.Y.: 1993); Ausubel et al., eds., *Current Protocols in Molecular Biology*, Chapter 2 (Greene Publishing and Wiley-Interscience, N.Y.: 1995). See Sambrook et al., *Molecular Cloning: A Laboratory Manual* (2d ed., Cold Spring Harbor Laboratory Press, Plainview, N.Y.: 1989). Using these references, those of ordinary skill can generate variants of the present nucleic acids.

Computer analyses can also be utilized for comparison of sequences to determine sequence identity. Such analyses include, but are not limited to, CLUSTAL in the PC/Gene program (available from Intelligenetics, Mountain View, Calif.); the ALIGN program (Version 2.0) and GAP, BEST-FIT, BLAST, FASTA, and TFASTA in the Wisconsin Genetics Software Package, Version 8 (available from Genetics Computer Group (GCG), 575 Science Drive, Madison, Wis.). Alignments using these programs can be performed using the default parameters. The CLUSTAL program is well described by Higgins et al., *Gene*, 73:237-244 (1988); Higgins et al., *CABIOS*, 5:151-153 (1989); Corpet et al., *Nucleic Acids Res.*, 16:10881-10890 (1988); Huang et al., *CABIOS*, 8:155-165 (1992); and Pearson et al., *Meth. Mol. Biol.*, 24:307-331 (1994). The BLAST programs of Altschul et al., *J. Mol. Biol.*, 215:403 (1990), are based on the algorithm of Karlin and Altschul, *Proc. Natl. Acad. Sci.* (U.S.A.), 87:2264-2268 (1990). To obtain gapped alignments for comparison purposes, Gapped BLAST (in BLAST 2.0) can be utilized as described in Altschul et al., *Nucleic Acids Res.*, 25:3389 (1997). Alternatively, PSI-BLAST (in BLAST 2.0) can be used to perform an iterated search that detects distant relationships between molecules. When utilizing BLAST, Gapped BLAST, PSI-BLAST, the default parameters of the respective programs can be used. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see, Henikoff & Henikoff, *Proc. Natl. Acad. Sci.*(U.S.A.), 89:10915 (1989)). Alignment may also be performed manually by inspection.

For purposes of the present invention, comparison of nucleotide sequences for determination of percent sequence identity to the nucleic acid sequences disclosed herein is preferably made using the BLASTN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program. In the present invention, it is anticipated that the nucleotides herein could be useful at about 70%, about 80%, about 90%, about 95%, or about 99% identity, in addition to the recited usefulness at 100% identity.

Isolation of Nucleic Acids Encoding Phenylpropanoid Pathway Proteins

Nucleic acids encoding phenylpropanoid pathway proteins can be identified and isolated by standard methods as described by Sambrook et al., *Molecular Cloning: A Laboratory Manual*, Cold Spring Harbor, N.Y. (1989). For example, a DNA sequence encoding a target protein can be identified by screening a genomic DNA or cDNA library generated from nucleic acid derived from a particular cell type, cell line, primary cells, or tissue.

Screening for DNA fragments that encode a target phenylpropanoid pathway protein and regulators can be accomplished by screening plaques from a genomic or cDNA library for hybridization to a probe of an available phenylpropanoid pathway protein from other organisms or by screening plaques from a cDNA expression library for binding to antibodies that specifically recognize the target phenylpropanoid pathway protein. DNA fragments that hybridize to phenylpropanoid pathway protein probes from other organisms or plaques carrying DNA fragments that are immunoreactive with antibodies to phenylpropanoid pathway proteins can be subcloned into a vector and sequenced or used as probes to identify other cDNA or genomic sequences encoding all or a portion of the desired phenylpropanoid pathway protein gene.

A cDNA library can be prepared, for example, by random oligo priming or oligo dT priming. Plaques containing DNA fragments can be screened with probes or antibodies specific for phenylpropanoid pathway proteins. DNA fragments encoding a portion of the target gene can be subcloned and sequenced and used as probes to identify a genomic copy of the gene. DNA fragments encoding a portion of the target protein can be verified by determining sequence homology with other known genes encoding the target protein or by hybridization to messenger RNA specific to the target protein. Once cDNA fragments encoding portions of the 5', middle and 3' ends of a target protein are obtained, they can be used as probes to identify and clone a complete genomic copy of the gene for the target protein from a genomic library.

Portions of the genomic copy or copies of a phenylpropanoid pathway protein gene can be sequenced and the 5' end of the gene identified by standard methods including either DNA sequence homology to analogous genes or by RNAase protection analysis, as described by Sambrook et al., *Molecular Cloning: A Laboratory Manual*, Cold Spring Harbor Press, Cold Spring Harbor, N.Y. (1989). The 3' and 5' ends of the target gene can also be located by computer searches of genomic sequence databases using known coding regions specific to the target protein. Once portions of the 5' end of the gene are identified, complete copies of the target gene can be obtained by standard methods, including cloning or polymerase chain reaction (PCR) synthesis using oligonucleotide primers complementary to the DNA sequence at the 5' end of the gene. The presence of an isolated full-length copy of the target phenylpropanoid pathway gene can be verified by hybridization, partial sequence analysis, or by expression of the protein.

A further embodiment of the present invention is the isolation from an EST library of nucleic acids encoding proteins in the phenylpropanoid pathway. EST libraries may be prepared as described in Cooke et al., "EST and genomic sequencing projects", In *Plant Gene Isolation: Principles* and *Practice*, ed. Foster and Twell, pp. 401-419: John Wiley & Sons LTD (1996), and references included therein.

Gene Suppression

Gene suppression may be effective against a native plant gene associated with a trait, e.g., to provide plants with reduced levels of a protein encoded by the native gene or with enhanced or reduced levels of an affected metabolite.

As used herein "gene suppression" means any of the well-known methods for suppressing a transcript or a protein from a gene including post-transcriptional gene suppression and transcriptional suppression. Post transcriptional gene suppression is mediated by transcribed RNA having homology to a gene targeted for suppression. The RNA transcribed from the suppressing transgene can be in the sense orientation to effect what is called co-suppression, in the anti-sense orientation to effect what is called anti-sense suppression or in both orientations producing a double-stranded RNA to effect what is called RNA interference (RNAi). Transcriptional suppression is mediated by a transcribed double-stranded RNA having homology to promoter DNA sequence to effect what is called promoter trans suppression.

More particularly, post-transcriptional gene suppression by anti-sense oriented RNA to regulate gene expression in plant cells is disclosed in U.S. Pat. No. 5,107,065 (Shewmaker et al.) and U.S. Pat. No. 5,759,829 (Shewmaker et al.). Post-transcriptional gene suppression by sense-oriented RNA to regulate gene expression in plants is disclosed in U.S. Pat. No. 5,283,184 (Jorgensen et al.) and U.S. Pat. No. 5,231,020 (Jorgensen et al.). Post transcriptional gene suppression by double-stranded RNA to suppress genes in plants by RNAi is disclosed in PCT Publication WO 99/53050 (Waterhouse et al.) using recombinant DNA constructs comprising sense-oriented and anti-sense-oriented elements of a targeted gene in separate transcription units or in a single transcription unit. See, also PCT Publication WO 99/49029 (Graham et al.), U.S. Publication 2003/0175965 A1 (Lowe et al.), U.S. patent application No. 10/465,800 (Fillatti), and U.S. Pat. No. 6,506,559 (Fire et al.). See, also Titia Sijen et al., *The Plant Cell*, 8:2277-2294, December 1996, which discloses the use of constructs carrying inverted repeats of a cowpea mosaic virus gene in transgenic plants to mediate virus resistance. Another DNA construct for RNAi gene suppression comprising a singly-oriented gene element bordered by oppositely-oriented promoters is disclosed in U.S. Publication 2003/0061626 A1 (Plaetinck et al.) and U.S. Pat. No. 6,326,193. See, also U.S. patent application No. 10/393,347, which discloses constructs and methods for simultaneously expressing one or more recombinant genes while simultaneously suppressing one or more native genes in a transgenic plant. See also U.S. Pat. No. 6,448,473, which discloses multigene expression vectors for use in plants. All of the above-described patents, applications and international publications disclosing materials and methods for post-transcriptional gene suppression in plants are incorporated herein by reference.

A preferred method of post transcriptional gene suppression in plants employs either sense-oriented or anti-sense-oriented, transcribed RNA that is stabilized, e.g., with a terminal hairpin structure. A preferred DNA construct for effecting post transcriptional gene suppression is transcribed to a segment of anti-sense oriented RNA having homology to a gene targeted for suppression, where the anti-sense RNA segment is followed at the 3' end by a contiguous, complementary, shorter segment of RNA in the sense orientation. The use of self-stabilized anti-sense RNA oligonucleotides in plants is disclosed in PCT Publication WO 94/01550 (Agrawal et al.). See also PCT Publication WO 98/05770 (Werner et al.), where the anti-sense RNA is stabilized by hairpin forming repeats of poly(CG) nucleotides. See also U.S. Publication 2002/0048814 A1 (Oeller), where sense or anti-sense RNA is stabilized by a poly(T)-poly(A) tail. See also U.S. Publication 2003/0018993 A1 (Gutterson et al.), where sense or anti-sense RNA is stabilized by an inverted repeat of a subsequence of an NOS gene. See also U.S. Publication 2003/0036197 A1 (Glassman et al.), where RNA having homology to a target is stabilized by two complementary RNA regions. All of the above-described patents, applications and international publications disclosing materials and methods for employing stabilized RNA and its use in gene suppression in plants are incorporated herein by reference.

Transcriptional suppression such as promoter trans suppression can be effected by a expressing a DNA construct comprising a promoter operably linked to inverted repeats of promoter DNA for a target gene. Constructs useful for such gene suppression mediated by promoter trans suppression are disclosed by Mette et al., The *EMBO Journal*, 18(1): 241-148 (1999), and by Mette et al., *The EMBO Journal*, 19(19):5194-5201 (2000), both of which are incorporated herein by reference.

Yet another strategy for gene down-regulation or suppression contemplated by this invention is the use of ribozymes. Ribozymes, or catalytic RNA molecules capable of cleaving target mRNA at specific sites, are well know in the art. (See, for example, Gibson and Shillitoe, *Molecular Biotechnology*, 7(2):125-137 (1997)).

Another method for abolishing the expression of a gene is by insertion mutagenesis using the T-DNA of *Agrobacterium tumefaciens*. After generating the insertion mutants, the mutants can be screened to identify those containing the insertion in a phenylpropanoid pathway protein gene. Plants containing a single transgene insertion event at the desired gene can be crossed to generate homozygous plants for the mutation (Koncz et al., In: *Methods in Arabidopsis Research*, World Scientific (1992)).

Alternatively, a plant phenotype can be altered by eliminating phenylpropanoid pathway protein genes, such as CHS, PAL, TTG1, and LDOX, e.g., by homologous recombination (Kempin et al., *Nature*, 389:802 (1997)).

A plant trait can also be modified by using the cre-lox system (U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

One of ordinary skill in the art will recognize that a number of methods can be used to inactivate, abolish or suppress gene expression or the activity of the phenylpropanoid pathway proteins of the present invention.

Expression Cassettes and Vectors

An "expression cassette" refers to a nucleic acid construct that when introduced into a host cell, results in transcription or translation of an RNA or polypeptide, respectively. Anti-sense or sense constructs that are not or cannot be translated are expressly included by this definition. An expression cassette may be a combination of nucleic acid elements that perform specific functions and are maintained as a clonable unit.

A "vector" refers to a nucleic acid molecule capable of carrying inserted nucleic acid sequences and being perpetuated in a host cell.

The expression cassettes and vectors of the invention include nucleic acids encoding phenylpropanoid pathway proteins, in sense and antisense configuration. Additionally, this invention contemplates vectors and cassettes constructed to disrupt the function of proteins in the phenylpropanoid biosynthetic pathway. In addition, this invention sets forth the expression cassettes and vectors for overexpressing novel transcription factor genes (such as TTG1) in plants to increase products in the phenylpropanoid pathway.

A transgene comprising a phenylpropanoid pathway protein can be subcloned into an expression cassette or vector, and its expression can be detected or quantified. This method of screening is useful to identify transgenes providing for an expression of a phenylpropanoid pathway protein, and expression of a phenylpropanoid pathway protein in a transformed plant cell.

Plasmid vectors that provide for easy selection, amplification, and transformation of the transgene in prokaryotic and eukaryotic cells include, for example, pUC-derived vectors, pSK-derived vectors, pGEM-derived vectors, pSP-derived vectors, pBS-derived vectors, pFastBac (Invitrogen) for baculovirus expression and pYES2 (Invitrogen) for yeast expression. Additional elements may be present in such vectors, including origins of replication to provide for autonomous replication of the vector, selectable marker genes, preferably encoding antibiotic or herbicide resistance, unique multiple cloning sites providing for multiple sites to insert DNA sequences or genes encoded in the transgene, and sequences that enhance transformation of prokaryotic and eukaryotic cells. One vector that is useful for expression in both plant and prokaryotic cells is the binary Ti plasmid (Schilperoort et al., U.S. Pat. No. 4,940,838) as exemplified by vector pGA582. This binary Ti plasmid vector has been previously characterized by An, *Methods in Enzymology*, 153:292 (1987). This binary Ti vector can be replicated in bacteria, such as *E. coli* and *Agrobacterium*. The *Agrobacterium* plasmid vectors can also be used to transfer the transgene to plant cells. The binary Ti vectors preferably include the nopaline T-DNA right and left borders to provide for efficient plant cell transformation, a selectable marker gene, unique multiple cloning sites in the T border regions, the colE1 replication of origin and a wide host range replicon. The binary Ti vectors carrying a transgene of the invention can be used to transform both prokaryotic and eukaryotic cells but are preferably used to transform plant cells. See, for example, Glassman et al., U.S. Pat. No. 5,258,300.

A vector or expression cassette of the present invention can contain a transgene encoding a phenylpropanoid pathway protein in sense or antisense configuration. The vectors and expression cassettes of the present invention are constructed according to whether the strategy is to overexpress or suppress the function of the phenylpropanoid pathway protein. The term "expression", as used herein, refers to the transcription and stable accumulation of sense (mRNA) or antisense RNA derived from the nucleic acid fragment of the invention. Expression may also refer to translation of mRNA into a polypeptide.

In general, the expression vectors and cassettes of the invention contain at least a promoter capable of expressing RNA in a plant cell and a terminator, in addition to a nucleic acid encoding a phenylpropanoid pathway protein. Other elements may also be present in the expression cassettes of the invention. For example, expression cassettes can also contain enhancers, introns, untranslated leader sequences, cloning sites, matrix attachment regions for silencing the effects of chromosomal control elements, and other elements known to one of skill in the art.

Nucleic acids encoding phenylpropanoid pathway proteins are operably linked to regulatory elements such as promoter, termination signals and the like. Operably linking a nucleic acid under the regulatory control of a promoter or a regulatory element means positioning the nucleic acid such that the expression of the nucleic acid is controlled by these sequences. In general, promoters are found positioned 5' (upstream) to the nucleic acid that that they control. Thus, in the construction of heterologous promoter/nucleic acid combinations, the promoter is preferably positioned upstream to the nucleic acid and at a distance from the transcription start site of the nucleic acid that the distance between the promoter and the transcription start site approximates the distance observed in the natural setting. As is known in the art, some variation in this distance can be tolerated without loss of promoter function. Similarly, the preferred positioning of a regulatory element with respect to a heterologous nucleic acid placed under its control is the natural position of the regulatory element relative to the structural gene it naturally regulates. Again, as is known in the art, some variation in this distance can be accommodated.

Expression cassettes have promoters that can regulate gene expression. Promoter regions are typically found in the flanking DNA sequence upstream from coding regions in both prokaryotic and eukaryotic cells. A promoter sequence provides for regulation of transcription of the downstream gene sequence and typically includes from about 50 to about 2,000 nucleotide base pairs. Promoter sequences also contain regulatory sequences, such as enhancer sequences, that can influence the level of gene expression. Some isolated promoter sequences can provide for gene expression of heterologous genes, that is, a gene different from the native or homologous gene. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue-specific or developmental regulation. An isolated promoter sequence that is a strong promoter for heterologous genes is advantageous because it provides for a sufficient level of gene expression to allow for easy detection and selection of transformed cells and provides for a high level of gene expression when desired. Transcription initiation regions that are preferentially expressed in seed tissue and that are undetectable in other plant parts are considered desirable for seed oil modifications in order to minimize any disruptive or adverse effects of the gene product.

Promoters of the instant invention will generally include, but are not limited to, promoters that function in plant cells. Useful promoters include the napin promoter (Kridl et al., *Seed Sci. Res.*, 1:209-219 (1991)), the WEREWOLF promoter (Lee and Schiefelbein, *Cell*, 99:473-483 (1999)), the e35S CaMV promoter for the 35S transcript RNA derived from Cauliflower Mosaic Virus modified as described by Kay et al., *Science*, 235:1299-1302 (1987), the 35S promoter (Odell et al., *Nature*, 313:810 (1985)), the CaMV 19S (Lawton et al., *Plant Mol. Biol.*, 9, 31F (1987)), nos (Ebert et al., *Proc. Nat. Acad. Sci.* (U.S.A.), 84:5745 (1987)), Adh (Walker et al., *Proc. Nat. Acad. Sci.* (U.S.A.), 84:6624 (1987)), sucrose synthase (Yang et al., *Proc. Nat. Acad. Sci.* (U.S.A.), 87:4144 (1990)), tubulin, actin (Wang et al., *Mol. Cell. Biol.*, 12:3399 (1992)), cab (Sullivan et al., *Mol. Gen.*

*Genet.*, 215:431 (1989)), PEPCase promoter (Hudspeth et al., *Plant Mol. Biol.*, 12:579 (1989)), the 7S-alpha'-conglycinin promoter (Beachy et al., *EMBO J.*, 4:3047 (1985)), or those associated with the R gene complex (Chandler et al., *The Plant Cell*, 1:1175 (1989)). Other useful promoters include the tomato E8, patatin, ubiquitin, mannopine synthase (mas), soybean seed protein glycinin (Gly), soybean vegetative storage protein (vsp) promoters, and the *Arabidopsis* banyuls promoter.

Indeed, in an embodiment, the promoter used is a seed coat—specific promoter. Examples of seed coat—regulated genes and transcriptional regions are disclosed herein. Other promoters known to function, for example, in maize include the promoters for the following genes: waxy, Brittle, Shrunken 2, Branching enzymes I and II, starch synthases, debranching enzymes, oleosins, glutelins, sucrose synthases, and globulin 1. Other promoters useful in the practice of the invention that are known to those of skill in the art are also contemplated by the invention.

Moreover, transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924). As the DNA sequence between the transcription initiation site and the start of the coding sequence, i. e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability or by preventing inappropriate initiation of translation. The choice of such sequences is at the discretion of those of skill in the art. Sequences that are derived from genes that are highly expressed in higher plants, and in soybean, corn, and canola in particular, are contemplated.

Expression cassettes of the present invention will also include a sequence near the 3' end of the cassette that acts as a signal to terminate transcription from a heterologous nucleic acid and that directs polyadenylation of the resultant mRNA. Some 3' elements that can act as termination signals include those from the nopaline synthase gene of *Agrobacterium tumefaciens* (Bevan et al., *Nucl. Acid Res.*, 11:369 (1983)), a napin 3' untranslated region, a globulin 3' untranslated region, the tumor large locus (tml) from *Agrobacterium tumefaciens* (Barker et al., *Plant Mol. Biol.*, 2:335-350 (1983)), or one from a zein gene, such as, for example Z27. Other 3' elements known to those of skill in the art also can be used in the vectors of the present invention.

Regulatory elements, such as Adh intron 1 (Callis et al., *Genes Develop.*, 1:1183 (1987)), a rice actin intron (McElroy et al., *Mol. Gen. Genet.*, 231 (1):150-160 (1991)), sucrose synthase intron (Vasil et al., *Plant Physiol.*, 91:5175 (1989)), the maize HSP70 intron or TMV omega element (Gallie et al., *The Plant Cell*, 1:301 (1989)), may further be included where desired. Other such regulatory elements useful in the practice of the present invention are known to those of skill in the art and can also be placed in the vectors of the present invention.

The vectors of the present invention can be optimized for expression in plants by having one or more codons replaced by other codons encoding the same amino acids so that the polypeptide is optimally translated by the translation machinery of the plant species in which the vector is used. See, for example Perlak et al., *Proc. Natl. Acad. Sci. (U.S.A.)*, 88(8):3324-3328 (1991)) or Moriyama and Powell, *Journal of Molecular Evolution*, 45(5):514-523 (1997).

Plant Transformation

In a preferred embodiment of the invention, a transgenic plant expressing the desired protein is to be produced. Various methods for the introduction of a desired polynucleotide sequence encoding the desired protein into plant cells are available and known to those of skill in the art and include, but are not limited to, (1) physical methods such as microinjection (Capecchi, *Cell*, 22(2):479-488 (1980)), electroporation (Fromm et al., *Proc. Natl. Acad. Sci. (U.S.A.)*, 82(17):5824-5828 (1985); U.S. Pat. No. 5,384,253), and microprojectile mediated delivery (biolistics or gene gun technology) (Christou et al., *Bio/Technology*, 9:957 (1991); Fynan et al., *Proc. Natl. Acad. Sci. (U.S.A.)*, 90(24):11478-11482 (1993)); (2) virus mediated delivery methods (Clapp, *Clin. Perinatol.*, 20(1):155-168 (1993); Lu et al., *J. Exp. Med.*, 178(6):2089-2096 (1993); Eglitis and Anderson, *Biotechniques*, 6(7):608-614 (1988 )); (3) *Agrobacterium*-mediated transformation methods.

The most commonly used methods for transformation of plant cells are the *Agrobacterium*-mediated DNA transfer process (Fraley et al., *Proc. Natl. Acad. Sci. (U.S.A.)*, 80:4803 (1983)) and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide for certain plant species such as tobacco, *Arabidopsis*, potato, and *Brassica* species.

*Agrobacterium*-mediated transformation is achieved through the use of a genetically engineered soil bacterium belonging to the genus *Agrobacterium*. Several *Agrobacterium* species mediate the transfer of a specific DNA known as "T-DNA", which can be genetically engineered to carry any desired piece of DNA into many plant species. The major events marking the process of T-DNA mediated pathogenesis are induction of virulence genes, processing and transfer of T-DNA. This process is the subject of many reviews (Ream, *Ann. Rev. Phytopathol.*, 27:583-618 (1989); Howard and Citovsky, *Bioassays*, 12:103-108 (1990); Kado, *Crit. Rev. Plant Sci.*, 10:1-32 (1991); Zambryski, *Annual Rev. Plant Physiol. Plant Mol. Biol.*, 43:465-490 (1992); Gelvin, In *Transgenic Plants*, Kung and Wu, eds., Academic Press, San Diego, Calif., pp.49-87 (1993); Binns and Howitz, In *Bacterial Pathogenesis of Plants and Animals* (Dang, ed.) Berlin: Springer Verlag, pp. 119-138 (1994); Hooykaas and Beijersbergen, *Ann. Rev. Phytopathol.*, 32:157-179 (1994); Lessl and Lanka, *Cell*, 77:321-324 (1994); Zupan and Zambryski, *Annual Rev. Phytopathol.*, 27:583-618 (1995)).

*Agrobacterium*-mediated genetic transformation of plants involves several steps. The first step, in which the virulent *Agrobacterium* and plant cells are first brought into contact with each other, is generally called "inoculation". The *Agrobacterium*-containing solution is then removed from contact with the explant by draining or aspiration. Following the inoculation, the *Agrobacterium* and plant cells/tissues are permitted to be grown together for a period of several hours to several days or more under conditions suitable for growth and T-DNA transfer. This step is termed "co-culture". Following co-culture and T-DNA delivery, the plant cells are treated with bactericidal or bacteriostatic agents to prevent further growth of the *Agrobacterium* remaining in contact with the explant or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps. Both the "delay" and "selection" steps typically include bactericidal or bacteriostatic agents to prevent further growth of any remaining Agrobacterium cells because the growth of Agrobacterium cells is undesirable after the infection (inoculation and co-culture) process.

A number of wild-type and disarmed strains of Agrobacterium tumefaciens and Agrobacterium rhizogenes harboring Ti or Ri plasmids can be used for gene transfer into plants. The Agrobacterium hosts contain disarmed Ti and Ri plasmids that do not contain the oncogenes that cause tumorigenesis or rhizogenesis, respectfully, which are used as the vectors and contain the genes of interest that are subsequently introduced into plants. Preferred strains would include but are not limited to Agrobacterium tumefaciens strain C58, a nopaline-type strain that is used to mediate the transfer of DNA into a plant cell, octopine-type strains such as LBA4404 or succinamopine-type strains, e.g., EHA101 or EHA105. The nucleic acid molecule, prepared as a DNA composition in vitro, is introduced into a suitable host such as E. coli and mated into the Agrobacterium, or directly transformed into competent Agrobacterium. These techniques are well-known to those of skill in the art.

The Agrobacterium can be prepared either by inoculating a liquid such as Luria Burtani (LB) media directly from a glycerol stock or streaking the Agrobacterium onto a solidified media from a glycerol stock, allowing the bacteria to grow under the appropriate selective conditions, generally from about 26° C.-30° C., and taking a single colony or a small loop of Agrobacterium from the plate and inoculating a liquid culture medium containing the selective agents. Those of skill in the art are familiar with procedures for growth and suitable culture conditions for Agrobacterium as well as subsequent inoculation procedures. The density of the Agrobacterium culture used for inoculation and the ratio of Agrobacterium cells to explant can vary from one system to the next, and therefore optimization of these parameters for any transformation method is expected.

Typically, an Agrobacterium culture is inoculated from a streaked plate or glycerol stock and is grown overnight and the bacterial cells are washed and resuspended in a culture medium suitable for inoculation of the explant.

With respect to microprojectile bombardment (U.S. Pat. Nos. 5,550,318; 5,538,880; and 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

For microprojectile bombardment, one will attach (i.e., "coat") DNA to the microprojectiles such that it is delivered to recipient cells in a form suitable for transformation thereof. In this respect, at least some of the transforming DNA must be available to the target cell for transformation to occur, while at the same time during delivery the DNA must be attached to the microprojectile. Therefore, availability of the transforming DNA from the microprojectile may comprise the physical reversal of bonds between transforming DNA and the microprojectile following delivery of the microprojectile to the target cell. This need not be the case, however, as availability to a target cell may occur as a result of breakage of unbound segments of DNA or of other molecules which comprise the physical attachment to the microprojectile. Availability may further occur as a result of breakage of bonds between the transforming DNA and other molecules, which are either directly or indirectly attached to the microprojectile. It further is contemplated that transformation of a target cell may occur by way of direct recombination between the transforming DNA and the genomic DNA of the recipient cell. Therefore, as used herein, a "coated" microprojectile will be one that is capable of being used to transform a target cell, in that the transforming DNA will be delivered to the target cell, yet will be accessible to the target cell such that transformation may occur.

Any technique for coating microprojectiles that allows for delivery of transforming DNA to the target cells may be used. Methods for coating microprojectiles that have been demonstrated to work well with the current invention have been specifically disclosed herein. DNA may be bound to microprojectile particles using alternative techniques, however. For example, particles may be coated with streptavidin and DNA end labeled with long chain thiol cleavable biotinylated nucleotide chains. The DNA adheres to the particles due to the streptavidin-biotin interaction but is released in the cell by reduction of the thiol linkage through reducing agents present in the cell.

Alternatively, particles may be prepared by functionalizing the surface of a gold oxide particle, providing free amine groups. DNA, having a strong negative charge, binds to the functionalized particles. Furthermore, charged particles may be deposited in controlled arrays on the surface of mylar flyer disks used in the PDS-1000 Biolistics device, thereby facilitating controlled distribution of particles delivered to target tissue.

As disclosed above, it further is proposed that the concentration of DNA used to coat microprojectiles may influence the recovery of transformants containing a single copy of the transgene. For example, a lower concentration of DNA may not necessarily change the efficiency of the transformation but may instead increase the proportion of single copy insertion events. In this regard, approximately 1 ng to 2000 ng of transforming DNA may be used per each 1.8 mg of starting microprojectiles.

Microprojectile bombardment techniques are widely applicable and may be used to transform virtually any plant species. Examples of species that have been transformed by microprojectile bombardment include monocot species such as maize (PCT Publication WO 95/06128), barley, wheat (U.S. Pat. No. 5,563,055, specifically incorporated herein by reference in its entirety), rice, oat, rye, sugarcane, and sorghum; as well as a number of dicots including tobacco, soybean (U.S. Pat. No. 5,322,783, specifically incorporated herein by reference in its entirety), sunflower, peanut, cotton, tomato, and legumes in general (U.S. Pat. No. 5,563,055, specifically incorporated herein by reference in its entirety).

For microprojectile bombardment transformation in accordance with the current invention, both physical and biological parameters may be optimized. Physical factors are those that involve manipulating the DNA/microprojectile precipitate or those that affect the flight and velocity of either the macro- or microprojectiles. Biological factors include all steps involved in manipulation of cells before and immediately after bombardment, such as the osmotic adjustment of target cells to help alleviate the trauma associated with bombardment, the orientation of an immature embryo or other target tissue relative to the particle trajectory, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as DNA concentration, gap distance, flight distance, tissue distance, and helium pressure. It further is contemplated that the grade of helium may effect transformation efficiency. One also may optimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation.

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kananycin and tetracycline.

Particularly preferred selectable marker genes for use in the present invention would include genes that confer resistance to compounds such as antibiotics like kanamycin (nptII), hygromycin B (aph IV) and gentamycin (aac3 and aacC4) (Dekeyser et al., *Plant Physiol.*, 90:217-223 (1989)), and herbicides like glyphosate (Della-Cioppa et al., *Bio/Technology*, 5:579-584 (1987)). Other selection devices can also be implemented including but not limited to tolerance to phosphinothricin, bialaphos, and positive selection mechanisms (Joersbo et al., *Mol. Breed.*, 4:111-117 (1998)) and are considered within the scope of the present invention.

The regeneration, development, and cultivation of plants from various transformed explants is well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. In an exemplary embodiment, MS and N6 media may be modified by including further substances such as growth regulators. A preferred growth regulator for such purposes is dicamba or 2,4-D. However, other growth regulators may be employed, including NAA, NAA +2,4-D or perhaps even picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened off, e.g., in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are preferably matured either in a growth chamber or greenhouse. Plants are regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants are preferably grown at about 19 to 28° C. After the regenerating plants have reached the stage of shoot and root development, they may be transferred to a greenhouse for further growth and testing.

Note, however, that seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/L agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant.

Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, *Physiol. Plant*, 15:473-497 (1962)) or N6-based media (Chu et al., *Scientia Sinica*, 18:659 (1975)) supplemented with additional plant growth regulators including but not limited to auxins such as picloram (4-amino-3,5,6-trichloropicolinic acid),2,4-D (2,4-dichlorophenoxyacetic acid) and dicamba (3,6-dichloroanisic acid); cytokinins such as BAP (6-benzylaminopurine) and kinetin; ABA; and gibberellins. Other media additives can include but are not limited to amino acids, macroelements, iron, microelements, vitamins and organics, carbohydrates, undefined media components such as casein hydrolysates, with or without an appropriate gelling agent such as a form of agar, such as a low melting point agarose or Gelrite if desired. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Examples of such media would include but are not limited to Murashige and Skoog (Murashige and Skoog, *Physiol. Plant*, 15:473-497 (1962)), N6 (Chu et al., *Scientia Sinica*, 18:659 (1975)), Linsmaier and Skoog (Linsmaier and Skoog, *Physio. Plant.*, 18:100 (1965)), Uchimiya and Murashige (Uchimiya and Murashige, *Plant Physiol.*, 15:473 (1962)), Gamborg's B5 media (Gamborg et al., *Exp. Cell Res.*, 50:151 (1968)), D medium (Duncan et al., *Planta*, 165:322-332 (1985)), McCown's Woody plant media (McCown and Lloyd, *HortScience*, 16:453 (1981)), Nitsch and Nitsch (Nitsch and Nitsch, *Science*, 163:85-87 (1969)), and Schenk and Hildebrandt (Schenk and Hildebrandt, *Can. J. Bot.*, 50:199-204 (1972)) or derivations of these media supplemented accordingly. Those of skill in the art are aware that media and media supplements such as nutrients and growth regulators for use in transformation and regeneration and other culture conditions such as light intensity during incubation, pH, and incubation temperatures can be optimized for the particular variety of interest.

Any of the nucleic acid molecules of the invention may be introduced into a plant cell in a permanent or transient manner in combination with other genetic elements such as vectors, promoters, enhancers, and the like. Furthermore, any of the nucleic acid molecules of the invention may be introduced into a plant cell in a manner that allows for expression or overexpression of the protein or fragment thereof encoded by the nucleic acid molecule.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Backcrossing to a parental plant and out-crossing with a non-transgenic plant are also contemplated, as is vegetative propagation.

Transgenic plants may find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs or may be crossed or bred to plants of related crop species. Improvements encoded by the recombinant DNA may be transferred, e.g., from cells of one species to cells of other species, e.g., by protoplast fusion.

Plants

Plants for use with the vectors of the invention include dicots and monocots, preferably oil producing species including but not limited to, corn (*Zea mays*), *Brassica* sp., particularly those *Brassica* species useful as sources of seed oil (e.g., *B. napus, B. rapa, B. juncea*), sunflower (*Helianthus annuus*), safflower (*Carthamus tinctorius*), rice (*Oryza sativa*), soybean (*Glycine max*), tobacco (*Nicotiana tabacum*), peanuts (*Arachis hypogaea*), cotton (*Gossypium barbadense, Gossypium hirsutum*), coconut (*Cocos nucifera*), cocoa (*Theobroma cacao*), oil palm (*Elaeis guineensis*), flax (*Linum usitatissimum*); *Cuphea* species; castor (*Ricinus communis*), olive (*Olea europaea*), cashew (*Anacardium occidentale*), macadamia (*Macadamia integrifolia*), and almond (*Prunus amygdalus*)).

The plants described in the present invention can be used to generate seeds containing valuable commercial products, such as oil and animal feed. The processing and milling of such seed is well known in the art (see, for example, Watson in *Corn and Corn Improvement*, Holt, Nelson, and Keeney, eds., American Society of Agronomy pp. 881-940 (1988); and *Soybeans: Improvement, Production and Uses*, Wilcox, ed. (1987)).

The present invention will be further described by reference to the following detailed examples, which are not to be viewed as limiting the scope of the invention as further described herein. It is understood that there are many extensions, variations, and modifications on the basic theme of the present invention beyond that shown in the examples and description, which are within the spirit and scope of the present invention.

EXAMPLE 1

This example sets forth the identification and sequence analysis of a chalcone synthase ortholog from *Brassica napus* and TTG1 orthologs from corn, soybean and canola.

The *Arabidopsis thaliana* chalcone synthase (CHS) nucleic acid sequence (GenBank Accession M20308, SEQ ID NO: 31) was used as a BLAST query against proprietary *Brassica napus* sequence libraries. A single EST clone from a sequence library that was derived from whole seeds at 30 days after pollination, LIB4156-020-R1-K1-E4 (SEQ ID NO: 149), was identified as having high homology. A 944-base pair fragment containing the CHS coding sequence was removed from LIB4156-020-R1-K1-E4 by digestion with SmaI and XbaI. The fragment was purified and sequenced using methodology well known in the art. This purified fragment containing the *Brassica napus* CHS ortholog (BnCHS) (SEQ ID NO: 33) was then cloned in the antisense orientation between the e35S promoter and the tml 3' UTR in a backbone vector. The resulting plasmid, containing the e35S::BnCHS::tml 3' UTR, was named KAHADF032096 and was subsequently used in the construction of plant transformation vectors.

The *Arabidopsis thaliana* TTG1 nucleic acid sequence (GenBank Accession AJ133743, SEQ ID NO: 141) was used as a BLAST query against proprietary *Brassica napus* sequence libraries. A single EST clone that was derived from silique walls at 10 days after pollination, LIB3169-025-P1-K2-B5 (SEQ ID NO: 79), was identified as having high homology. This sequence was used as a query against all *Arabidopsis* DNA sequences in GenBank®, the NIH genetic sequence database containing an annotated collection of all publicly available DNA sequences (*Nucleic Acids Research* 30(1):17-20 (2002)). The BLAST search identified *Arabidopsis thaliana* TTG1 as having the highest homology, thus confirming the *Brassica* sequence as a TTG1 ortholog.

The coding sequence for *Brassica napus* TTG1 (BnTTG1) was PCR amplified from the EST clone LIB3169-025-P1-K2-B5 (SEQ ID NO: 30) using the primers ttg-3' (SEQ ID NO: 142) and ttg-5' (SEQ ID NO: 143).

These primers were designed to add SalI and PstI restriction sites as well as a Kozak consensus sequence to the TTG1 sequence to facilitate further cloning. Sequencing was done using the protocol and equipment supplied by ABI PRISM (ABI PRISM BigDye Terminators (v 3.0) Ready Reaction Cycle Sequencing Kit and the ABI PRISM 377 Automated DNA Sequencer, Foster City, Calif.). Alignments with the predicted *Arabidopsis* TTG1 peptide revealed that clone LIB3169-025-P1-K2-B5 started at base pair +3 of the predicted coding sequence. This was the reason that a Kozak consensus translation initiation site was also added by the primers described above. The resulting PCR product was isolated, purified, and cloned into pCR2.1TOPO, purchased from Invitrogen (Carlsbad, Calif.), following the manufacturer's instructions. The resulting plasmid containing the full-length coding sequence of TTG1 was named pMON65420 and was subsequently used in the construction of plant transformation vectors.

EXAMPLE 2

This example describes the construction of plant transformation vectors with the BnCHS and BnTTG1 coding sequences described above.

pMON75051 (e35S::BnCHS(antisense)::tml)

A 3470-base pair fragment containing the e35S promoter, the BnCHS (SEQ ID NO: 33) in antisense orientation and the tml 3' UTR was removed from the vector KAHADF032096 by digestion with NotI. The fragment was ligated into the vector pCGN11121, which had been digested with NotI. The vector pCGN11121 contains a nopaline T-DNA right border sequence and octopine T-DNA left border sequence, in between which are the promoter from the Figwort Mosaic Virus (FMV) and the intron from *Z. mays* HSP70 driving the expression of the CP4 EPSP synthase gene containing a CTP, linked to a synthetic EPSP synthase coding region and the 3' UTR from the pea rbsc E9 gene and the recognition sites for the recombinase. The resulting plasmid was named pMON75051. The nucleic acid sequence was determined using standard sequencing methodology and confirmed the integrity of the cloning junctions.

pMON75052 (napin::BnCHS(antisense)::napin)

A 1280-base pair fragment containing BnCHS (SEQ ID NO: 33) coding sequence was removed from LIB4156-020-R1-K1-E4 by digestion with NotI and PstI. The fragment was isolated and purified using methodology well known in the art and then cloned in the antisense orientation between the napin promoter and napin 3' UTR in pMON67163 which had been digested with NotI-Sse8387I. The resulting plasmid was named pMON75052. The nucleic acid sequence was determined using standard sequencing methodology and confirmed the integrity of the cloning junctions.

pMON75053 (pBAN::BnCHS(antisense)::napin)

The NotI/PstI fragment described above was also cloned in the antisense orientation down stream of the banyuls promoter (pBAN) by ligating it into a NotI/Sse387I digested pMON70905 and upstream of the napin 3' UTR, for transformation into canola. The resulting plasmid was named pMON75053, and is notated as pBAN::BnCHS(antisense)::napin.

pMON75702 (35S::BnTTG1(antisense)::tml)

Figure 2:
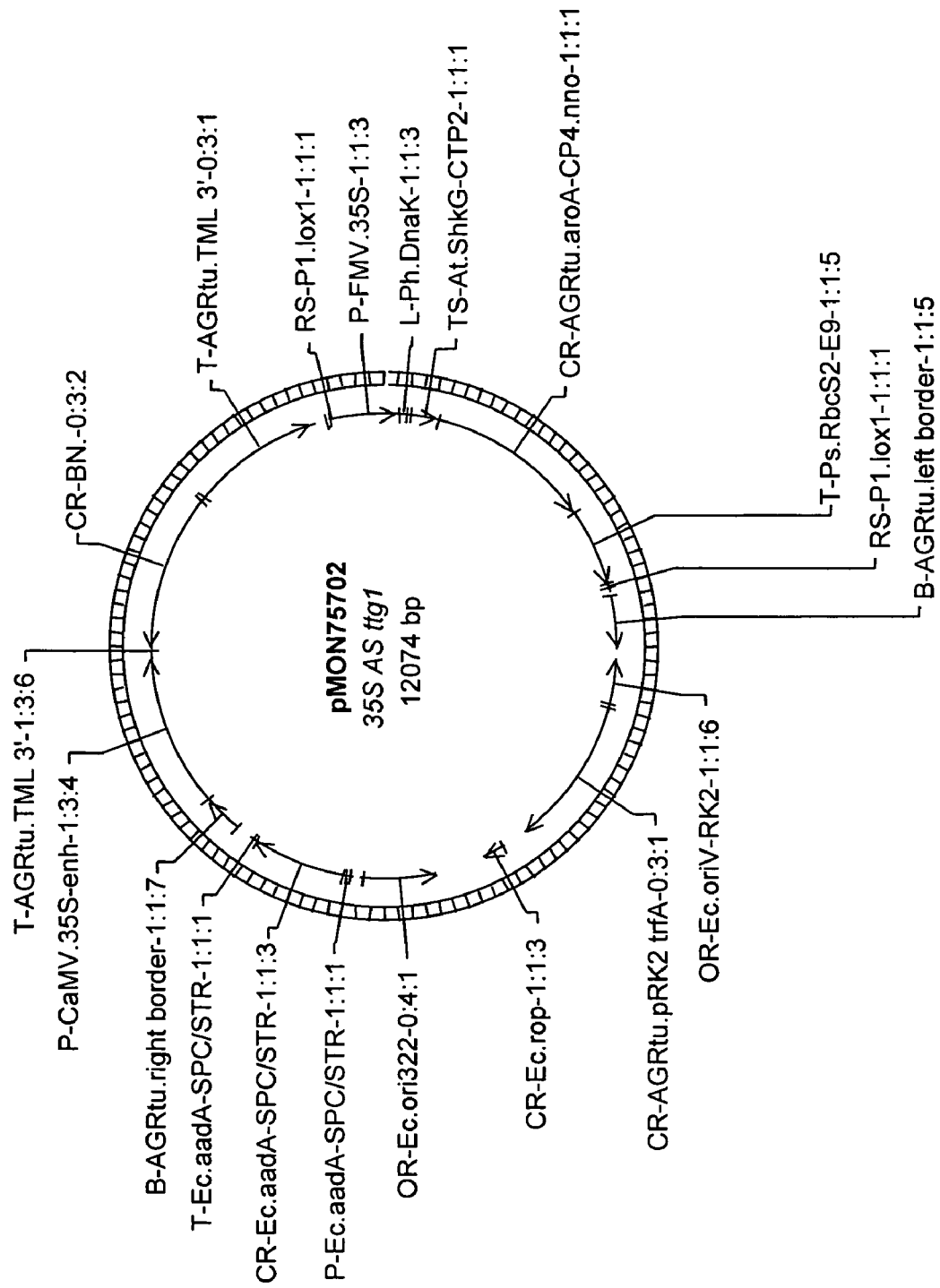
FIG. 2 shows a schematic representation of pMON75702.

The *Brassica napus* TTG1 ortholog (BnTTG1) from pMON65419 is cloned, in the antisense orientation, downstream of the e35S promoter and upstream of the tml 3' UTR, for transformation into canola. The resulting plasmid is named pMON75702 (FIG. 2).

pMON70906 (pBAN::BnTTG1 (antisense)::napin)

The vector pMON67163 contains a nopaline T-DNA right border sequence and an octopine T-DNA left border sequence. Between the two T-DNA border sequences are the 35S promoter driving expression of an CP4 EPSP synthase coding sequence consisting of the first exon of the *Arabidopsis* EPSP synthase gene (containing a chloroplast targeting sequence) linked to a synthetic EPSP synthase coding region and the 3' UTR from the pea rbcS E9 gene; the napin promoter and 3' UTR and recognition signals for cre recombinase.

The napin promoter was removed from pMON67163 by sequential digestion with PacI followed by NotI. The PacI overhang was blunt ended using Pfu polymerase according to the manufacturer's instructions (Stratagene, La Jolla, Calif.). The resulting 9503-base pair fragment was ligated to a 994-base pair BamHI-NotI fragment from pMON69809, which contained the *Arabidopsis* banyuls promoter (pBAN). The BamHI overhang was blunt ended using Pfu polymerase according to the manufacturer's instructions (Stratagene). The resulting plasmid was named pMON70905. The nucleic acid sequence was determined using standard sequencing methodology and confirmed the integrity of the cloning junctions.

The vector pMON65419 contains EST clone LIB3169-025-P1-K2-B5 in a pSPORT1 (Invitrogen) background. A 1362-base pair NotI-PstI fragment containing the coding sequence of BnTTG1 (SEQ ID NO: 79) was ligated into a 10477-base pair NotI-Sse8387I fragment from pMON70905. The resulting plasmid, which contains the BnTTG1 coding sequence in antisense orientation being driven by the pBAN promoter, was named pMON70906. The nucleic acid sequence was determined using standard sequencing methodology (ABI PRISM BigDye Terminators (v 3.0) Ready Reaction Cycle Sequencing Kit and the ABI PRISM 377 Automated DNA Sequencer, (Foster City, Calif.) and confirmed the integrity of the cloning junctions.

pMON65423 (e35S::BnTTG1(sense)::tml)

The TTG1 coding sequence of pMON65420 (SEQ ID NO: 147) was found to contain a single nucleotide change (C273T), relative to that shown in SEQ ID NO: 30, that does not result in a change in the predicted protein sequence. A 1031-base pair fragment containing the BnTTG1 coding sequence (SEQ ID NO: 147) was removed from pMON65420 by digestion with SalI and PstI. The resulting fragment was ligated into the vector pCGN9977, which had been sequentially digested with SalI and PstI. The vector pCGN9977 contains a nopaline T-DNA right border sequence and an octopine T-DNA left border. Between the two T-DNA border sequences are (a) the e35S promoter, (b) a polylinker to facilitate cloning, (c) the 3' untranslated region of the tumor large locus from *Agrobacterium tume*-

*faciens* (tml), (d) the 35S promoter, driving expression of the bar gene from *Streptomyces hygroscopicus*, encoding phosphinothricin acetyl transferase (EMBL:X17220), and (e) the 3' untranslated region of the nopaline synthase gene of *Agrobacterium tumefaciens* (nos). The resulting plasmid, containing the BnTTG1 coding sequence in sense orientation between the e35S promoter and the tml 3' UTR, was named pMON65423. This vector was designed for complementation studies in *Arabidopsis* ttg1 mutants. The nucleic acid sequence was determined using standard sequencing methodology and confirmed the integrity of the cloning junctions.

pMON65440 (pBAN::BnTTG1(sense)::napin)

The coding region of the *Brassica napus* TTG1 ortholog was removed from pMON65423, as above, by digestion with NcoI and PstI. The DNA fragment is ligated between the pBAN promoter and napin 3' UTR in NcoI-Sse8387I digested pMON70905. The resulting plasmid, pMON65440, contains the BnTTG1 coding sequence in sense orientation being driven by the pBAN promoter and using the napin 3' UTR. This vector was designed for complementation studies in *Arabidopsis* ttg1 mutants.

pMON65442 (pWER::BnTTG1 (sense)::tml)

An *E. coli* culture containing the BAC clone T9L3 was obtained from the Arabidopsis Biological Resource Center (ABRC, Columbus, Ohio). The BAC clone DNA was isolated by standard methods known to one of skill in the art.

The promoter of the *Arabidopsis* WEREWOLF gene (Lee and Schiefelbein, *Cell* 99:473-483 (1999)) was isolated by PCR from BAC clone T9L3 using the primers WER_Nco (SEQ ID NO: 166) and were 5' #2 (SEQ ID NO: 167).

The reaction conditions for the PCR reaction followed a protocol recommended by the enzyme manufacturer (PE Applied Biosystems, Foster City, Calif.). pWEREWOLF was amplified using 1.5 µL of T9L3 DNA as template, 30 nanomoles each of the primers WER_Nco (SEQ ID NO: 166) and were 5' #2 (SEQ ID NO: 167), 10 micromoles each of dATP, dCTP, dGTP and TTP, 2.5 units of AmpliTaq Gold (PE Applied Biosystems) in 1× Opti-Prime™ Buffer 3 (Stratagene). After an initial incubation at 95° C. for 10 minutes, 28 cycles of PCR were performed with 94° C. for 15 seconds, 62° C. for 10 seconds, 52° C. for 10 seconds, and 72° C. for 3 minutes followed by 1 cycle of 72° C. for 7 minutes. The product of the PCR reaction was purified according to standard methodology well known in the art and cloned into pCR2.1 Topo (Invitrogen) according to manufacturer's instructions. The resulting plasmid was named pMON69835. The sequence of this clone was determined using standard sequencing methodologies as set forth by PE Applied Biosystems (Foster City, Calif.).

The Banyuls promoter was removed from pMON65423 by digestion with PvuII and NcoI. The resulting 10966-bp fragment was ligated to a 1098-bp fragment from pMON69835, which contained the *Arabidopsis* WEREWOLF promoter. The resulting plasmid contained the BnTTG1 coding sequence in sense orientation between the WEREWOLF promoter and the tml 3' UTR. This vector was designed for complementation studies in *Arabidopsis* ttg1 mutants.

Table 1 summarizes the vectors described above.

TABLE 1

Summary of Constructs for Plant Transformations

| Plasmid | Promoter Coding | Sequence Orientation | 3' UTR | Crop |
|---|---|---|---|---|
| pMON65423 | e35S | BnTTG1 Sense | tml | *Arabidopsis* |
| pMON65440 | pBAN | BnTTG1 Sense | napin | *Arabidopsis* |
| pMON65442 | pWEREWOLF | BnTTG1 Sense | tml | *Arabidopsis* |
| pMON70906 | pBAN | BnTTG1 Antisense | napin | Canola |
| pMON75702 | e35S | BnTTG1 Antisense | tml | Canola |
| pMON75051 | e35S | BnCHS Antisense | tml | Canola |
| pMON75052 | napin | BnCHS Antisense | napin | Canola |
| pMON75053 | pBAN | BnCHS Antisense | napin | Canola |

EXAMPLE 3

This example describes the transformation of canola and *Arabidopsis* plants.

*Arabidopsis* Transformation

*Arabidopsis* seeds, mutant and wild type, are sown onto 2¼ inch pots containing reverse osmosis water (ROW) saturated MetroMix 200 (The Scotts Company, Columbus, Ohio). The plants are vernalized by placing the pots in a flat, covered with a humidity dome, in a growth chamber at 4-7° C., 8-hrs light/day for 4-7 days. The flats are transferred to a growth chamber at 22° C., 55% relative humidity, and 16-hrs light/day at an average intensity of 160-200 µEinstein/s/m$^2$. After germination, the dome is lifted and slid back about 1 inch to allow for mild air circulation without desiccation. The humidity dome is removed once true leaves have formed. The plants are bottom watered, as needed, with ROW until well established, generally 2-3 weeks after germination. Plants are then bottom watered, as needed, with Plantex 15-15-18 solution at 50 ppm N$_2$. Pots are thinned so that 1 plant remains per pot at 2-3 weeks after germination. Once plants begin to bolt, the primary inflorescence is trimmed to encourage the growth of axillary bolts.

The vectors are introduced into *Agrobacterium tumefaciens* strain ABI using methodologies well known in the art.

Transgenic *Arabidopsis thaliana* plants are obtained essentially as described by Bent et al. (*Science* 265:1856-1860 (1994)) or Bechtold et al. (*C.R. Acad. Sci., Life Sciences*, 316:1194-1199 (1993)). Cultures containing the desired vector are grown overnight in Luria Broth (10% bacto-tryptone, 5% yeast extract, and 10% NaCl) with kanamycin (75 mg/L), chloramphenicol (25 mg/L), and spectinomycin (100 mg/L). The bacterial culture is centrifuged and resuspended in 5% sucrose+0.05% Silwet-77. The aerial portions of whole *Arabidopsis thaliana* (CS89; ttg1) plants (at ~5-7 weeks of age) are immersed in the resulting solution for 2-3 seconds. The excess solution is removed by blotting the plants on paper towels. The dipped plants are placed on their side in a covered flat and transferred to a growth chamber at 19° C. After 16 to 24 hours, the dome is removed and the plants are set upright. When plants have reached maturity, water is withheld for 2-7 days prior to seed harvest. Harvested seed is passed through a stainless steel mesh screen (40 holes/inch) to remove debris. Seed is stored in paper coin envelopes at room temperature.

Seeds are sown onto flats containing ROW saturated MetroMix 200. The plants are vernalized and germinated as described above. After true leaves have emerged, the aerial portions of the seedlings are sprayed with a solution containing a 1:200 dilution of Finale herbicide (The Scotts Company) in ROW. Approximately 1 week after the first application, the plants are sprayed a second time. Up to 16 Finale resistant seedlings are transplanted to a 2¼" pot, one seedling per pot, containing MetroMix 200 and are grown under the conditions described above.

Alternatively, transformed plants are selected on media. *Arabidopsis* seeds are surface sterilized using a vapor phase sterilization protocol. An open container of seeds is placed in a dessicator with a beaker containing 100 mL of household bleach. Immediately prior to sealing the dessicator, 3 mL of concentrated HCl is added to the bleach. The dessicator is sealed and a vacuum is applied to allow sterilization by chlorine fumes. Seeds are incubated for several hours. Sterilized seed are sprinkled onto *Arabidopsis* Germination Media [MS Salts (1×); sucrose (1%); myo-Inositol (100 mg/L); Thiamine-HCl (1 mg/L); Pyridoxine-HCl (50 mg/L); Nicotinic Acid (500 mg/L); MES pH 5.7 (0.05%) and Phytagar (0.7%) supplemented with 25 mg/L glufosinate ammonium (Sigma)].

Canola Transformation

Seeds of *Brassica napus* cv *Ebony* are planted in 2-inch pots containing Metro Mix 350 (The Scotts Company). The plants are grown in a growth chamber at 24° C., and a 16/8 hour photoperiod, with light intensity of 400 µEinstein/s/m$^2$ (HID lamps). After 2½ weeks, the plants are transplanted into 6-inch pots and grown in a growth chamber at 15/10° C. day/night temperature, 16/8 hour photoperiod, light intensity of 800 µEinstein/s/m$^2$ (HID lamps).

Four terminal internodes from plants just prior to bolting or in the process of bolting but before flowering are removed and surface sterilized in 70% v/v ethanol for 1 minute, 2% w/v sodium hypochlorite for 20 minutes and rinsing 3 times with sterile deionized water. Six to seven stem segments are cut into 5 mm discs, maintaining orientation of basal end.

The *Agrobacterium* culture is grown overnight on a rotator shaker at 24° C. in 2 mL of Luria Broth (10% bacto-tryptone, 5% yeast extract, and 10% NaCl) containing 50 mg/L kanamycin, 24 mg/L chloramphenicol and 100 mg/L spectinomycin. A 1:10 dilution is made in MS media (Murashige and Skoog, *Physiol. Plant*, 15:473-497 (1962)) giving approximately 9×10$^8$ cells per mL. The stem discs (explants) are inoculated with 1.0 mL of *Agrobacterium* and the excess is aspirated from the explants.

The explants are placed basal side down in petri plates containing media comprising 1/10 MS salts, B5 vitamins, 3% sucrose, 0.8% agar, pH 5.7, 1.0 mg/L 6-benzyladenine (BA). The plates are layered with 1.5 mL of media containing MS salts, B5 vitamins, 3% sucrose, pH 5.7, 4.0 mg/L p-chlorophenoxyacetic acid, 0.005 mg/L kinetin and covered with sterile filter paper.

Following a 2- to 3-day co-culture, the explants are transferred to deep dish petri plates containing MS salts, B5 vitamins, 3% sucrose, 0.8% agar, pH 5.7, 1 mg/L 6-benzyladenine, 500 mg/L carbenicillin, 50 mg/L cefotaxime, 200 mg/L kanamycin or 175 mg/L gentamycin for selection. Seven explants are placed on each plate. After 3 weeks they are transferred to fresh media, 5 explants per plate. The explants are cultured in a growth room at 25° C., continuous light (Cool White).

EXAMPLE 4

This example describes the analysis of transformed plants for oil and protein levels in the seed.

Oil levels in *Arabidopsis* seed tissues are established by near-infrared reflectance (NIR) spectroscopy (Williams and Norris (eds.), *Near-infrared Technology in the Agricultural and Food Industries*, American Association of Cereal Chemists, Inc., St. Paul (1987)), whereby NIR spectra of pooled seed samples harvested from individual plants are measured, and oil levels are calculated based on regression analysis using a standard curve generated from analysis of *Arabidopsis* seed with varying oil levels as determined gravimetrically following accelerated solvent extraction (*Better Solutions for Food and Beverage Analysis*, 2nd edition, Dionex Corporation, Sunnyvale, Calif. 1997).

Oil levels in canola seed are established by NIR as described above using a standard curve generated from analysis of canola seed with varying oil levels. Briefly, mature canola seeds previously dried to less than 10% moisture are equilibrated to ambient humidity in paper envelopes at room temperature. Single replicate sub-samples (2-3 g) are placed in NIR ring cups (aluminum/quartz; 2-inch diameter by 0.5-inch thick; purchased from Foss North America Inc., Silver Springs Md.), and sealed with a paperboard disk. The loaded ring cups are placed in an autoloader and scanned sequentially on a Foss Analytical model 6500 Spectrometer (Foss North America Inc, Silver Springs, Md.). Each sample is scanned 25 times from 400 to 2500 nm (resolution 2 nm) and the average spectrum is compiled. The averaged spectrum is reduced to second derivative spectra, smoothed and transformed to a series of principal component scores. The total oil and protein levels are predicted based on previously prepared calibration models. WinISI software (WinISI ver 1.00, Infrasoft International LLC, State College, Pa.) is used for calibration development and instrument operation.

Oil levels in soybean are established either by NIR as described above, using a standard curve generated from analysis of soybean seed with varying oil levels, or by near-infrared transmittance (NIT). When NIT is employed, the NIT spectra of pooled seed samples harvested from individual plants are measured, and oil levels are calculated based on regression analysis using a standard curve generated from analysis of soybean seed with varying oil levels as determined gravimetrically following accelerated solvent extraction.

Protein Analyses

For seed protein analysis, small bulk samples consisting of 50-100 seeds for each treatment are measured using near infrared reflectance spectroscopy (InfraTec model 1221, Teccator, Hogannas, Sweden). This procedure is based upon the observation that a linear relationship exists between the absorption of near infrared radiation and the quantity of chemical constituents comprised in a typical grain sample. Prior to analyzing unknown samples, spectral data is collected with calibration samples that are subsequently analyzed using a nitrogen combustion analysis technique (Murray and Williams, "Chemical Principles of Near-Infrared Technology", in *Near-Infrared Technology in the Agricultural and Food Industries*, Williams and Norris (eds.), 1987). A multivariate model is developed using the spectral data from the spectrometer and the primary data. In the present case, a PLS-1 (Partial Least Squares Regression Type I) multivariate model is constructed using 152 calibration samples. Each unknown sample is scanned on the spectrometer at least 5 times and its protein content predicted with each scan. Each time the sample is scanned, it is added back to the sample cuvette to minimize multiplicative scattering effects, which are not correlated to chemical property of interest. The predicted protein is averaged for the multiple scans and then reported for each sample.

EXAMPLE 5

This example sets forth the identification and sequencing of the mutant oil4 gene in an *Arabidopsis thaliana*, Landsberg *erecta* (Ler) mutant having high oil, high sum of oil plus protein, and altered seed color phenotype.

Mutagenized (M2) seeds of *Arabidopsis thaliana*, ecotype Landsberg are obtained both by purchase from Lehle Seeds (Round Rock, Tex., U.S.A.) and by standard EMS mutagenesis methodology. The M2 plants are grown from the M2 seeds in greenhouse conditions with one plant per 2.5 inch pot. The resulting M3 seeds are collected from individual M2 plants.

Seeds from approximately 5000 M3 lines of *Arabidopsis thaliana* are analyzed for total oil and protein levels as described above in Example 4, and compared to wild type control plants. A mutant (oil4) is identified that has increased levels of oil (39% vs. 32.9% for wild type) and higher oil plus protein (64.6% vs. 60.4% for wild type).

Using map-based cloning techniques (see, for example, Jander et al., *Plant Physiol.*, 129(2):440-450 (2002)), the mutant oil4 gene is mapped to a gene identified as F7H19.60. This gene possesses homology to known leucoanthocyanidin dioxygenases. Based on this homology, F7H19.60 is determined to contain the mutation responsible for the high oil, high sum of oil plus protein and seed color phenotypes in the oil4 mutant. The sequences of the F7H19.60 gene locus in the wild types and oil4 mutant are PCR amplified, and determined by standard sequencing methodology. The gene locus, in each case, is amplified using the following sequencing primers. Primer Pair F7H19.60_1 is Forward Primer (SEQ ID NO: 97) and Reverse Primer (SEQ ID NO: 98). Primer Pair F7H19.60_2 is Forward Primer (SEQ ID NO: 99) and Reverse Primer (SEQ ID NO: 100). Primer Pair F7H19.60_3 is Forward Primer (SEQ ID NO: 101) and Reverse Primer (SEQ ID NO: 102). Primer Pair F7H19.60_4 is Forward Primer (SEQ ID NO: 103) and Reverse Primer (SEQ ID NO: 104). Primer Pair F7H19.60_5 is Forward Primer (SEQ ID NO: 105) and Reverse Primer (SEQ ID NO: 106). Primer Pair F7H19.60_6 is Forward Primer (SEQ ID NO: 107) and Reverse Primer (SEQ ID NO: 108). Primer Pair F7H19.60_7 is Forward Primer (SEQ ID NO: 109) and Reverse Primer (SEQ ID NO: 110). Primer Pair F7H19.60_8 is Forward Primer (SEQ ID NO: 111) and Reverse Primer (SEQ ID NO: 112). Primer Pair F7H19.60_9 is Forward Primer (SEQ ID NO: 113) and Reverse Primer (SEQ ID NO: 114). Primer Pair F7H19.60_10 is Forward Primer (SEQ ID NO: 115) and Reverse Primer (SEQ ID NO: 116). Primer Pair F7H19.60_11 is Forward Primer (SEQ ID NO: 117) and Reverse Primer (SEQ ID NO: 118). Primer Pair F7H19.60_12 is Forward Primer (SEQ ID NO: 119) and Reverse Primer (SEQ ID NO: 120).

The following Polymerase Chain Reaction (PCR) mixture is prepared for each primer pair (10 μL 10× Opti-Prime™ Buffer 3 (Stratagene, La Jolla, Calif.); 2 μL 20 mM dNTPs; 5 μL Template DNA 30; 1.0 μL Taq Gold; 4 μL F/R Primers (at 20 μM/L); 84.0 μL dH$_2$O). The PCR amplification is carried out using the following Thermocycler program (1. 94° C. for 10 minutes; 2. 92° C. for 15 seconds; 3. 56° C. for 15 seconds; 4. 72° C. for 1 minute, 30 seconds; 5. Repeat Steps 2 through 4 an additional 44 times; 6. 72° C. for 10 minutes; Hold at 4° C.).

The resulting PCR products are purified using the QIAquick PCR Purification Kit (Qiagen, Valencia, Calif.). The purified PCR products are sequenced using the protocol set forth in the Applied Biosystems (ABI) (Foster City, Calif.) sequencing protocol and equipment (ABI PRISM BigDye Terminators (v 3.0) Ready Reaction Cycle Sequencing Kit and the ABI PRISM 377 Automated DNA Sequencer).

The LDOX gene (At4g22880; F7H19.60; gi:3292813) from the oil4 mutant has a nucleotide change that leads to a predicted amino acid substitution of serine for proline at position 148 (Pro 148Ser). FIG. 3 shows the alignment of the predicted protein sequences of the LDOX gene from the oil4 mutant (SEQ ID NO: 126) with that of wild type *Arabidopsis* Columbia(Col) (SEQ ID NO: 124) and Landsberg (Ler) (SEQ ID NO: 125) ecotypes. The nucleotide sequence of the LDOX gene for Landsberg and Columbia ecotypes as well as the oil4 mutant are shown in SEQ ID NOs: 121 through 123.

pMON65435 (p35S::AtLDOX (sense)::tml)

The vector pMON73273 contains a nopaline T-DNA right border sequence and an octopine T-DNA left border sequence. Between the two T-DNA border sequences are the e35S-CMV promoter, a polylinker to facilitate cloning, the 3' untranslated region of the tumor large locus (tml) from *Agrobacterium tumefaciens*, the 35S promoter from the Figwort Mosaic Virus, (FMV), driving expression of an CP4 EPSP synthase coding sequence consisting of the first exon of the *Arabidopsis* EPSP synthase gene (containing a chloroplast targeting sequence) linked to a synthetic EPSP synthase coding region and the 3' untranslated region from the pea rbcS E9 gene; and recognition sites for cre recombinase.

The EST clone LIB3177-088-P1-K1-D7 (SEQ ID NO: 145) is derived from 2-day whole seedlings/seed coats from *Arabidopsis thaliana* ecotype Columbia. This clone, encoding a full length cDNA from locus At4g22880, designated AtLDOX, is removed by digestion with SalI and NotI from a pSPORT1 vector. The resulting approximately 1.3 kb fragment is ligated between the e35S promoter and tml 3' UTR in SalI and NotI digested pMON73273. The resulting plasmid is named pMON65435.

pMON65436 (p35S::BnLDOX (sense)::tml)

The EST clone LIB4169-001-Q1-K1-E8 (SEQ ID NO: 144) is derived from the aleurone layer and seed coat of 25 to 28 days after pollination developing seed of *B. napus* (cv. *Quantum*). This clone, designated BnLDOX, which encodes a putative orthologue of AtLDOX, is removed by digestion with SalI and NotI. The resulting approximately 1.3 kb fragment is ligated between the e35S promoter and tml 3' UTR in SalI and NotI digested pMON73273. The resulting plasmid is named pMON65436.

pMON65437 (p35S::GmLDOX (sense)::tml)

The EST library SOYMON035 is constructed from seed coat tissue from soybean (*Glycine max*). Synthesis of cDNA is initiated using a NotI-oligo (dT) primer (SEQ ID NO: 146). Double-stranded cDNA is blunted, ligated to EcoRI adaptors, digested with NotI, size-selected, and cloned into the NotI and EcoRI sites of the pINCY vector (Incyte Genomics, Palo Alto, Calif.). The EST clone 701202688H1, designated GmLDOX, which encodes an orthologue of AtLDOX, is removed by digestion with EcoRI and NotI.

Prior to NotI digestion, the EcoRI site is blunt ended using Pfu polymerase according to the manufacturer's instructions (Stratagene, La Jolla, Calif.). The resulting approximately 1.2 kb fragment is ligated between the e35S promoter and tml 3' UTR in SalI and NotI digested pMON73273. The resulting plasmid is named pMON65437.

pMON65441 (pBAN::AtLDOX (sense)::nap)

The AtLDOX gene is modified by the addition of restriction sites to facilitate cloning using primers AtLDOXNco (SEQ ID NO: 169) and AtLDOXNotI (SEQ ID NO: 170). The reaction conditions for the PCR reaction follow a protocol recommended by the enzyme manufacturer (PE Applied Biosystems, Foster City, Calif.). AtLDOX is amplified using LIB3177-088-P1-K1-D7 DNA as the template, 30 nanomoles each of the primers AtLDOXNco and AtLDOX-NotI, 10 micromoles each of dATP, dCTP, dGTP and TTP, 2.5 units of AmpliTaq Gold (PE Applied Biosystems) in 1× Opti-Prime™ Buffer 3 (Stratagene, La Jolla, Calif.). After an initial incubation at 95° C. for 10 minutes, 28 cycles of PCR are performed with 94° C. for 15 seconds, 62° C. for 10 seconds, 52° C. for 10 seconds, and 72° C. for 3 minutes followed by 1 cycle of 72° C. for 7 minutes. The product of the PCR reaction is purified according to standard methodology well known in the art and cloned into pCR2.1 Topo (Invitrogen) according to manufacturer's instructions. The resulting plasmid is named pMON65439. The sequence of this clone is determined using standard sequencing methodologies as set forth by PE Applied Biosystems, (Foster City, Calif.).

A 1070-bp fragment, containing AtLDOX, is removed by digestion with NcoI and NotI from pMON65439. The fragment is ligated between the BANYULS promoter and napin 3' UTR in NcoI and NotI digested pMON70905. The resulting plasmid is named pMON65441. The nucleic acid sequence is determined using standard sequencing methodology and confirms the integrity of the cloning junctions.

pMON69840 (pWER::AtLDOX (sense)::tml)

A 1121-bp fragment, containing AtLDOX, is removed by digestion with NcoI and BamHI from pMON65439. The BamHI overhang is blunt ended using Pfu polymerase according to the manufacturer's instructions (Stratagene, La Jolla, Calif.). The fragment is ligated, in place of BnTTG1, between the WEREWOLF promoter and tml 3' UTR in NcoI and PstI digested pMON65442. The PstI overhang is blunt ended using Pfu polymerase according to the manufacturer's instructions (Stratagene, La Jolla, Calif.). The resulting plasmid is named pMON69840. The nucleic acid sequence is determined using standard sequencing methodology and confirms the integrity of the cloning junctions.

pMON69841 (pNapin::AtLDOX (sense)::napin)

The vector pMON73274 contains a nopaline T-DNA right border sequence and octopine T-DNA left border sequence. Between the two T-DNA border sequences are the FMV.35S promoter driving expression of an CP4 EPSP synthase coding sequence consisting of the first exon of the Arabidopsis EPSP synthase gene (containing a chloroplast targeting sequence) linked to a synthetic EPSP synthase coding region and the 3' UTR from the pea rbcS E9 gene; the napin promoter and 3' UTR and recognition signals for cre recombinase.

A 1342-bp fragment, containing AtLDOX, is removed by digestion with SalI and NotI from pMON65435. The result ing fragment is ligated between the napin promoter and napin 3' UTR in SalI and NotI digested pMON73274. The resulting plasmid is named pMON69841. The nucleic acid sequence is determined using standard sequencing methodology and confirms the integrity of the cloning junctions.

The resulting plasmids are introduced into Agrobacterium tumefaciens strain ABI using methodologies well known in the art. Arabidopsis plants homozygous for the oil4 mutation are transformed and grown as described in Example 3. The seed phenotype of the transgenic Arabidopsis plants is compared to both mutant and wild type seed.

Twelve independently derived oil4 plants transformed with pMON65435, pMON65436, pMON65437 or pMON65441 were grown in the same flat as six oil4 mutants and 6 wild type Ler control plants. Seed was harvested from each individual plant and analyzed for color and seed oil and protein levels using NIR methodologies as described in Example 4. Differences were determined by a means comparison using the Student's t-test (JMP Software, SAS Institute Inc.) with $p<0.05$.

Seed from plants transformed with pMON65435 did not have significantly different oil or protein levels than seeds from the untransformed oil4 mutant nor was the seed color of transformants significantly different from the oil4 mutant seed. Appropriate expression of AtLDOX in the transformed seed has not been confirmed.

Seed from plants transformed with pMON65436, pMON65437 and pMON65441 had significantly lower oil than seed from the untransformed oil4 mutant. Seed from plants transformed with pMON65436 had significantly higher oil than seed from the untransformed oil4 mutant. Although the color of seed in plants transformed with pMON65436 was indistinguishable from the mutant, seed from plants transformed with pMON65437 and pMON65441 was intermediate in color between seed from the untransformed oil4 mutant and wild type Ler plants.

The observation of transgenic seed that phenotypically resembles wild type seed indicates complementation of the mutant by the transformed gene, that LDOX is involved in the determination of oil and protein levels, and that GmL-DOX and BNLDOX encode functional homologues of the Arabidopsis thaliana LDOX gene.

EXAMPLE 6

This example provides the construction of plant transformation vectors for the suppression of LDOX expression in canola and soybean.

LDOX suppression vectors are prepared using a vector design based upon the intron-spliced hairpin RNAs (ih-pRNA) described in Smith et al. (Nature 407:319-320 (2000)). The suppression vector contains a nopaline T-DNA right border sequence and an octopine T-DNA left border sequence. Between the two T-DNA border sequences are the e35S-CMV promoter; a polylinker to facilitate cloning; the first intron from the Arabidopsis FAD2 gene (gi: 22655457) with flanking splice signal sequences; a second polylinker to facilitate cloning the 3' UTR of the tumor large locus (tml) from Agrobacterium tumefaciens; the 35S promoter from the Figwort Mosaic Virus, (35S-FMV), driving expression of an CP4 EPSP synthase coding sequence consisting of the first exon of the Arabidopsis EPSP synthase gene (contain ing a chloroplast targeting sequence) linked to a synthetic EPSP synthase coding region, and the 3' UTR from the pea rbcS E9 gene; and recognition sites for cre recombinase.

pMON69843 (e35S::BnLDOX (stabilized antisense)::tml)

The vector pMON65449 contains a nopaline T-DNA right border sequence and octopine T-DNA left border sequence, in between which are the enhanced CaMV35S promoter (P-CaMV.35S-enh-1), first intron of the *Arabidopsis* FAD2 gene, the tml 3' UTR, the P-FMV.35S-1 promoter and L-Ph.DnaK-1 leader sequence driving the expression of the CP4 EPSP synthase gene (CR-AGRtu.aroA-CP4.nno-1) containing a CTP linked to the 3' UTR from the pea rbsc E9 gene and the recognition sites for cre recombinase.

BnLDOX is removed from pMON65346 by digestion with SalI and NotI. The resulting approximately 1.4 kb fragment is ligated between the AtFAD2 intron and tml 3' UTR in SalI and PspOMI digested pMON65449. The resulting plasmid is named CLHEWI03.0045. The nucleic acid sequence was determined using standard sequencing methodology and confirmed the integrity of the cloning junctions. BnLDOX is removed from pMON65346 by digestion with SalI and NotI. The resulting approximately 1.4 kb fragment is ligated between the enhanced CaMV35S promoter and AtFAD2 intron in XhoI and NotI digested CLHEWI03.0045. The resulting plasmid is named pMON69843. The nucleic acid sequence was determined using standard sequencing methodology and confirmed the integrity of the cloning junctions pMON69842 (Napin::BnLDOX (ihp RNA)::tml)

The vector pMON82351 contains a nopaline T-DNA right border sequence and an octopine T-DNA left border sequence, in between which are the napin promoter, first intron of the *Arabidopsis* FAD2 gene, the tml 3' UTR, the P-FMV.35S-1 promoter and L-Ph.DnaK-1 leader sequence driving the expression of the CP4 EPSP synthase gene (CR-AGRtu.aroA-CP4.nno-1) containing a CTP linked to the 3' UTR from the pea rbsc E9 gene and the recognition sites for cre recombinase.

BNLDOX is removed from pMON65346 by digestion with SalI and NotI. The resulting approximately 1.4 kb fragment is ligated between the AtFAD2 intron and tml 3' UTR in SalI and PspOMI digested pMON82351. The resulting plasmid is named CLHEWI03.0046. The nucleic acid sequence was determined using standard sequencing methodology and confirmed the integrity of the cloning junctions. BnLDOX is removed from pMON65346 by digestion with SalI and NotI. The resulting approximately 1.4 kb fragment is ligated between the napin promoter and AtFAD2 intron in XhoI and NotI digested CLHEWI03.0046. The resulting plasmid is named pMON69842. The nucleic acid sequence was determined using standard sequencing methodology and confirmed the integrity of the cloning junctions pMON65446 (BAN::BnLDOX (ihp RNA)::tml)

The vector pMON65443 contains a nopaline T-DNA right border sequence and an octopine T-DNA left border sequence, in between which are the Banyuls promoter, first intron of the *Arabidopsis* FAD2 gene, the tml 3' UTR, the P-FMV.35S-1 promoter and L-Ph.DnaK-1 leader sequence driving the expression of the CP4 EPSP synthase gene (CR-AGRtu.aroA-CP4.nno-1) containing a CTP linked to the 3' UTR from the pea rbsc E9 gene and the recognition sites for cre recombinase.

Figure 4:
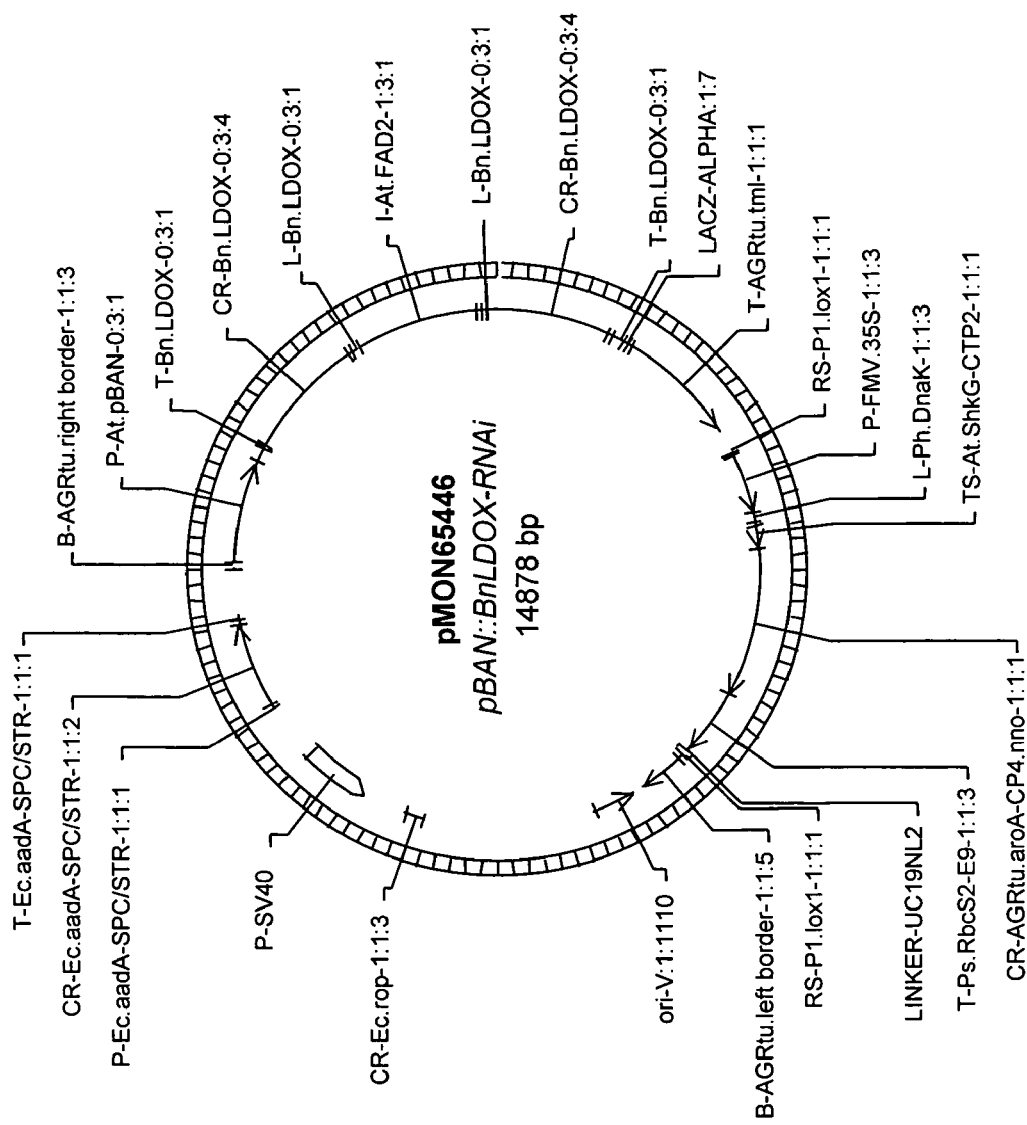
FIG. 4 shows a schematic representation of pMON65446.

BnLDOX is removed from EST clone LIB4169-001-Q1-K1-E8 (SEQ ID NO: 144) by digestion with SalI and NotI. The resulting approximately 1.4 kb fragment is ligated between the AtFAD2 intron and trnl 3' UTR in SalI and PspOMI digested pMON65443. The resulting plasmid is named DMRUEZ03.0053. The nucleic acid sequence was determined using standard sequencing methodology and confirmed the integrity of the cloning junctions. BnLDOX is removed from EST clone LIB4169-001-Q1-K1-E8 (SEQ ID NO: 144) by digestion with SalI and NotI. The resulting approximately 1.4 kb fragment is ligated between the banyuls promoter and AtFAD2 intron in XhoI and NotI digested DMRUEZ03.0053. The resulting plasmid is named pMON65446 (FIG. 4). The nucleic acid sequence was determined using standard sequencing methodology and confirmed the integrity of the cloning junctions pMON65447 (WER::BnLDOX (ihp RNA)::tml)

The vector pMON65444 contains a nopaline T-DNA right border sequence and octopine T-DNA left border sequence, in between which are the WEREWOLF promoter, first intron of the *Arabidopsis* FAD2 gene, the tml 3' UTR, the P-FMV.35S-1 promoter and L-Ph.DnaK-1 leader sequence driving the expression of the CP4 EPSP synthase gene (CR-AGRtu.aroA-CP4.nno-1) containing a CTP linked to the 3' UTR from the pea rbsc E9 gene and the recognition sites for cre recombinase.

BnLDOX is removed from EST clone LIB4169-001-Q1-K1-E8 (SEQ ID NO: 144) by digestion with SalI and NotI. The resulting approximately 1.4 kb fragment is ligated between the AtFAD2 intron and tml 3' UTR in SalI and PspOMI digested pMON65444. The resulting plasmid is named DMRUEZ03.0054. The nucleic acid sequence was determined using standard sequencing methodology and confirmed the integrity of the cloning junctions. BnLDOX is removed from EST clone LIB4169-001-Q1-K1-E8 (SEQ ID NO: 144) by digestion with SalI and NotI. The resulting approximately 1.4 kb fragment is ligated between the banyuls promoter and AtFAD2 intron in XhoI and NotI digested DMRUEZ03.0054. The resulting plasmid is named pMON65447. The nucleic acid sequence was determined using standard sequencing methodology and confirmed the integrity of the cloning junctions pMON69847 (e35S::GmLDOX (ihp RNA)::tml)

Figure 5:
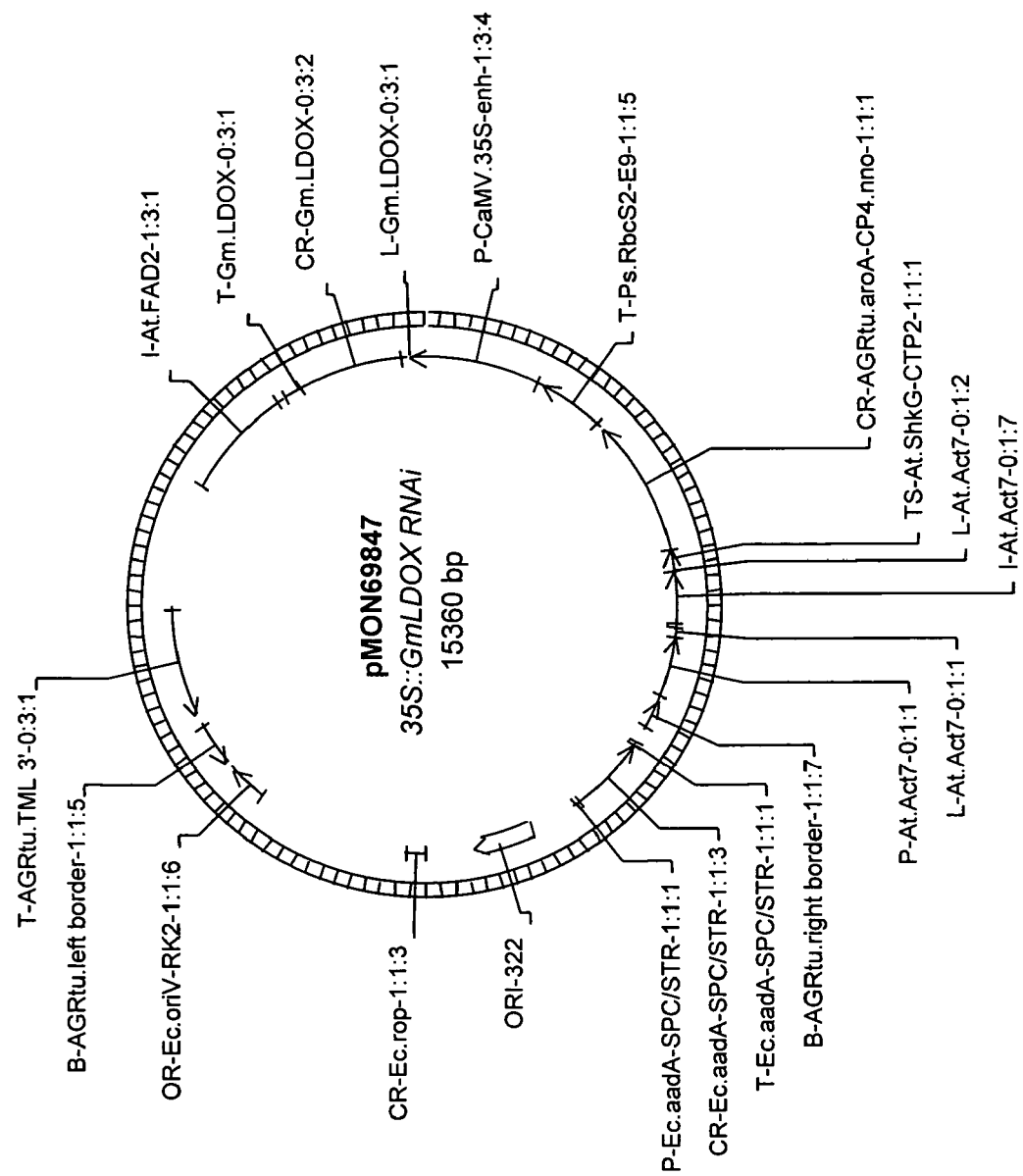
FIG. 5 shows a schematic representation of pMON69847.

The vector pMON82359 contains a nopaline T-DNA right border sequence and octopine T-DNA left border sequence, in between which are the promoter, leader sequence and intron from the *Arabidopsis* actin-7 gene, driving the expression of the *Agrobacterium tumefaciens* CP4 EPSP synthase gene, containing a CTP, and the 3' UTR from the pea rbsc E9 gene. A 3810-bp fragment containing the enhanced CaMV 35S promoter, GmLDOX and tml 3' UTR is removed by digestion with PacI and AscI from pMON65437. The resulting fragment is ligated between the 3' UTR from the pea rbsc E9 gene and the octopine T-DNA left border sequence in PacI and AscI digested pMON82359. The resulting plasmid is named CLHEWI03.0055. The nucleic acid sequence was determined using standard sequencing methodology and confirmed the integrity of the cloning junctions. An 1156-bp fragment containing part of the GmLDOX gene is removed by digestion with StuI and NotI from pMON65437. The NotI overhang was blunt ended using Pfu polymerase according to the manufacturer's instructions (Stratagene, La Jolla, Calif.). The resulting fragment was ligated between the AtFAD2 intron and tml 3' UTR in SmaI digested pMON65449. The resulting plasmid is named CLHEWI03.0059. The nucleic acid sequence was determined using standard sequencing methodology and confirmed the integrity of the cloning junctions. A 2410 bp fragment containing the AtFAD2 intron and GmLDOX is removed by SacI and NotI digestion of CLHEWI03.0059. The SacI overhang is blunt ended using Pfu polymerase according to the manufacturer's instructions (Stratagene, La Jolla, Calif.). The resulting fragment is ligated between GmLDOX and the tml3' UTR in SwaI and NotI digested CLHEWI03.0055. The resulting plasmid is named pMON69847 (FIG. 5). The nucleic acid sequence was determined using standard sequencing methodology and confirmed the integrity of the cloning junctions.

Additional suppression vectors are constructed by substituting tissue specific promoters such as pBANYULs or pWEREWOLF for the e35S promoter. These constructs allow for tissue specific suppression of the LDOX orthologues. Table 2 summarizes the vectors constructed. Canola plants are transformed with the vectors as described in Example 3.

TABLE 2

Vectors constructed (ihpRNA = intron-hairpin RNA).

| Construct ID | Promoter | Gene of Interest | Vector Type | Intron | 3' UTR |
| --- | --- | --- | --- | --- | --- |
| pMON69843 | e35S | BnLDOX | ihpRNA | AtFAD2 | tml |
| pMON69841 | Napin | BnLDOX | ihpRNA | AtFAD2 | tml |
| pMON65446 | Banyuls | BnLDOX | ihpRNA | AtFAD2 | tml |
| pMON65447 | WEREWOLF | BnLDOX | ihpRNA | AtFAD2 | tml |
| pMON69847 | e35S | GmLDOX | ihpRNA | AtFAD2 | tml |
| pMONXXXXX | Banyuls | GmLDOX | ihpRNA | AtFAD2 | tml |
| pMONXXXXX | WEREWOLF | GmLDOX | ihpRNA | AtFAD2 | tml |

EXAMPLE 7

This example describes the identification of orthologues to the *Arabidopsis* CHS, LDOX and TTG1 genes.

The sequence for the *Arabidopsis* TTG1 protein (gi: 5123716, SEQ ID NO: 1) was used to BLAST search against 6 frame translations of proprietary soybean and corn cDNA libraries using the tBLASTn protocol. The cDNA sequence of the top 2-4 hits were then used to BLAST search against a proprietary *Arabidopsis thaliana* sequence database. Both the soybean cDNA (700727328_FL1, SEQ ID NO: 2) and the corn cDNA (ZEAMA-22JAN02-CLUSTER6987_1, SEQ ID NO: 3) had TTG1 as their top hit in *Arabidopsis*, thus confirming the soybean and corn sequences as orthologs of TTG1.

The sequence for the *Arabidopsis* CHS (gi: 23308391, SEQ ID NO: 168) was used to BLAST search against six frame translations of proprietary soybean and corn cDNA libraries. Five corn and three soy ESTs had an expectation value of 0.0. These eight ESTs (SEQ ID NOs: 4-11) were used to BLAST search against a proprietary *Arabidopsis* sequence database. The top hit for each of the sequences was the *Arabidopsis* chalcone synthase gene, thus confirming the soybean and corn sequences as orthologs for *Arabidopsis* CHS.

The sequence of corn cDNA (ZEAMA-22JAN02-CLUSTER6987_1, SEQ ID NO: 3) was used as a BLAST query against proprietary and public *Zea mays* sequence databases. Two sequences were identified as having high homology in proprietary databases (SEQ ID NOs: 12 and 13). There were no sequences in public databases that were identified as having high homology.

The sequence of soybean cDNA (700727328_FL1, SEQ ID NO: 2) was used as a BLAST query against proprietary and public *Glycine max* sequence databases. Four sequences were identified as having high homology in proprietary databases (SEQ ID NOs: 14-17). Eleven sequences were identified as having high homology in public databases (SEQ ID NOs: 18-28). Table 3 shows the NCBI annotations for the public orthologs.

TABLE 3

Annotations for public orthologs.

| SEQ ID NO | NCBI Description | Genbank sequence ID |
| --- | --- | --- |
| 18 | similar to TR: Q9XGN1 Q9XGN1 TTG1 PROTEIN. | 19936077 |
| 19 | similar to TR: O24514 O24514 AN11. | 4303493 |
| 20 | similar to TR: Q9XGN1 Q9XGN1 TTG1 PROTEIN. | 18848414 |
| 21 | similar to TR: O24514 O24514 AN11. | 15000120 |

TABLE 3-continued

Annotations for public orthologs.

| SEQ ID NO | NCBI Description | Genbank sequence ID |
| --- | --- | --- |
| 22 | similar to TR: Q9XGN1 Q9XGN1 TTG1 PROTEIN. | 14991581 |
| 23 | similar to TR: O24514 O24514 AN11. | 18040199 |
| 24 | similar to TR: Q9XGN1 Q9XGN1 TTG1 PROTEIN. | 10843406 |
| 25 | similar to TR: Q9XGN1 Q9XGN1 TTG1 PROTEIN. | 14011464 |
| 26 | similar to TR: O24514 O24514 AN11. | 4307857 |
| 27 | similar to TR: O24514 O24514 AN11. | 15203321 |
| 28 | similar to TR: O24514 O24514 AN11. | 10844218 |

The sequence of *Brassica napus* cDNA (LIB3169-025-P1-K2-B5, SEQ ID NO: 30) was used as a BLAST query against proprietary and public *Brassica napus* databases. One sequence was identified as having high homology in proprietary databases (SEQ ID NO: 29). There were no sequences identified in the public databases searched as having high homology. The predicted amino acid sequence for the *Arabidopsis* LDOX protein (SEQ ID NO: 124) was used as a query in a BLAST search, using the tBLASTn protocol, against both public (non-redundant) and proprietary databases. Fourteen sequences were identified as having high homology in the proprietary databases (SEQ ID NOs: 127-140). Table 4 shows the results of the searches.

TABLE 4

*Brassica napus sequences.*

| SEQ ID NO: | DESCRIPTION | ANNOTATION |
|---|---|---|
| 127 | ARATH-01JUL02-CLUSTER5762_1 | leucoanthocyanidin dioxygenase (EC 1.14.11.—) |
| 128 | HORVU-20MAR02-CLUSTER23174_1 | AB073919) anthocyanidin synthase [*Ipomoea nil*] |
| 129 | BRANA-18JUN02-CLUSTER39879_1 | leucoanthocyanidin dioxygenase (EC 1.14.11.—) |
| 130 | LIB80-012-Q1-E1-C7 | leucoanthocyanidin dioxygenase (EC 1.14.11.—) |
| 131 | ZEAMA-06JUN02-CLUSTER2276_1 | leucoanthocyanidin dioxygenase (LDOX) |
| 132 | GOSHI-09MAY01-CLUSTER11019_1 | |
| 133 | LIB3135-036-Q1-K1-E8 | leucoanthocyanidin dioxygenase (EC 1.—.—.—) (LDOX) |
| 134 | LIB3146-009-Q1-K1-A4 | leucoanthocyanidin dioxygenase (LDOX) |
| 135 | ALLPO-19APR01-CLUSTER7272_2 | (AB011796) flavonol synthase [*Citrus unshiu*] |
| 136 | ALLPO-19APR01-CLUSTER7272_1 | (AB011796) flavonol synthase [*Citrus unshiu*] |
| 137 | ORYSA-27FEB02-CLUSTER915_1 | leucoanthocyanidin dioxygenase (EC 1.14.11.—) |
| 138 | ORYSA-27FEB02-CLUSTER84577_1 | (AB026295) Similar to leucoanthocyanidin dioxygenase |
| 139 | SORBI-27FEB02-CLUSTER59710_1 | (AC069300) putative dioxygenase [*Oryza sativa*] |
| 140 | GLYMA-06JUN02-CLUSTER7806_1 | leucoanthocyanidin dioxygenase (EC 1.14.11.—) |

EXAMPLE 8

This example sets forth the identification and sequence analysis of PAL orthologs from corn, soybean and *Brassica*.

Sequences for the three forms of phenylalanine ammonia lyase from *Arabidopsis* were retrieved from the NCBI database by entering a search using the keywords PAL1, PAL2 and PAL3. The nucleic acid sequences for these three enzymes are given in SEQ ID NO: 151-153, respectively. These three sequences were then used to BLAST search against proprietary databases for *Arabidopsis*, soybean, and *Brassica*. Only one hit was identified when using the BLASTN 2.0.12 protocol. This sequence, LIB4315-024-R1-N1-B9, from the corn database, is shown in SEQ ID NO: 154. Six frame translations were then BLAST searched against six fram translations of the corn, soybean and *Brassica* databases using the TBLASTX 2.0.12 protocol. The top five hits from the corn and rice databases are shown in Table 5.

TABLE 5

PAL orthologs.

| Query | Database | SEQ ID NO: | Identification |
|---|---|---|---|
| AtPAL1 | CornUnigeneDNA | 155 | ZEAMA-06JUN02-CLUSTER1962_14 |
| AtPAL1 | CornUnigeneDNA | 156 | ZEAMA-06JUN02-CLUSTER1962_42 |
| AtPAL1 | CornUnigeneDNA | 157 | ZEAMA-06JUN02-CLUSTER1962_26 |
| AtPAL1 | CornUnigeneDNA | 158 | ZEAMA-06JUN02-CLUSTER1962_30 |
| AtPAL1 | CornUnigeneDNA | 159 | ZEAMA-06JUN02-CLUSTER1962_27 |
| AtPAL2 | CornUnigeneDNA | 155 | ZEAMA-06JUN02-CLUSTER1962_14 |
| AtPAL2 | CornUnigeneDNA | 156 | ZEAMA-06JUN02-CLUSTER1962_42 |
| AtPAL2 | CornUnigeneDNA | 159 | ZEAMA-06JUN02-CLUSTER1962_27 |
| AtPAL2 | CornUnigeneDNA | 157 | ZEAMA-06JUN02-CLUSTER1962_26 |
| AtPAL2 | CornUnigeneDNA | 158 | ZEAMA-06JUN02-CLUSTER1962_30 |
| AtPAL3 | CornUnigeneDNA | 158 | ZEAMA-06JUN02-CLUSTER1962_30 |
| AtPAL3 | CornUnigeneDNA | 157 | ZEAMA-06JUN02-CLUSTER1962_26 |
| AtPAL3 | CornUnigeneDNA | 159 | ZEAMA-06JUN02-CLUSTER1962_27 |
| AtPAL3 | CornUnigeneDNA | 160 | ZEAMA-06JUN02-CLUSTER1962_36 |
| AtPAL3 | CornUnigeneDNA | 155 | ZEAMA-06JUN02-CLUSTER1962_14 |
| AtPAL1 | RiceUnigeneDNA | 161 | ORYSA-27FEB02-CLUSTER243_23 |
| AtPAL1 | RiceUnigeneDNA | 162 | ORYSA-27FEB02-CLUSTER243_24 |
| AtPAL1 | RiceUnigeneDNA | 163 | ORYSA-27FEB02-CLUSTER243_13 |
| AtPAL1 | RiceUnigeneDNA | 164 | ORYSA-27FEB02-CLUSTER243_9 |
| AtPAL1 | RiceUnigeneDNA | 165 | ORYSA-27FEB02-CLUSTER243_19 |
| AtPAL2 | RiceUnigeneDNA | 161 | ORYSA-27FEB02-CLUSTER243_23 |
| AtPAL2 | RiceUnigeneDNA | 162 | ORYSA-27FEB02-CLUSTER243_24 |
| AtPAL2 | RiceUnigeneDNA | 163 | ORYSA-27FEB02-CLUSTER243_13 |
| AtPAL2 | RiceUnigeneDNA | 164 | ORYSA-27FEB02-CLUSTER243_9 |
| AtPAL2 | RiceUnigeneDNA | 165 | ORYSA-27FEB02-CLUSTER243_19 |
| AtPAL3 | RiceUnigeneDNA | 162 | ORYSA-27FEB02-CLUSTER243_24 |
| AtPAL3 | RiceUnigeneDNA | 161 | ORYSA-27FEB02-CLUSTER243_23 |
| AtPAL3 | RiceUnigeneDNA | 163 | ORYSA-27FEB02-CLUSTER243_13 |
| AtPAL3 | RiceUnigeneDNA | 164 | ORYSA-27FEB02-CLUSTER243_9 |
| AtPAL3 | RiceUnigeneDNA | 165 | ORYSA-27FEB02-CLUSTER243_19 |

EXAMPLE 9

This example describes the construction of plant transformation vectors containing PAL orthologs.

PAL suppression vectors are prepared using a vector design based upon the intron-spliced hairpin RNAs described in Smith et al. (*Nature* 407:319-320 (2000)). The suppression vector contains a nopaline T-DNA right border sequence and an octopine T-DNA left border sequence. Between the two T-DNA border sequences are the e35S-CMV promoter; a polylinker to facilitate cloning; the first intron from the *Arabidopsis* FAD2 gene (gi: 22655457) with flanking splice signal sequences; a second polylinker to facilitate cloning the 3' UTR of the tumor large locus (tml) from *Agrobacterium tumefaciens*; the 35S promoter from the Figwort Mosaic Virus (35S-FMV) driving expression of an CP4 EPSP synthase coding sequence consisting of the first exon of the *Arabidopsis* EPSP synthase gene (containing a chloroplast targeting sequence) linked to a synthetic EPSP synthase coding region, and the 3' UTR from the pea rbcS E9 gene; and recognition sites for cre recombinase.

Gene segments containing at least 100 base pairs of one or more *Brassica* PAL orthologs are cloned in the opposite (antisense) orientation on either side of the AtFAD2 intron in the vector described above. Additional suppression vectors are constructed by substituting tissue-specific promoters such as pBANYULs or pWEREWOLF for the e35S promoter. These constructs allow for tissue-specific suppression of the PAL orthologs. Similar suppression vectors containing sequences suitable for soybean transformation and soybean PAL orthologs are prepared for suppression of PAL orthologs in soybean.

pMON82708 (pBAN::PAL1-PAL2-PAL3 (ihp RNA)::tml)

Gene fragments from *Brassica napus* PAL genes are isolated by PCR using primers: PAL_A_FWD_19617 (SEQ ID NO: 171); PAL_A_REV_19618 (SEQ ID NO: 172); PAL_B_FWD_19619 (SEQ ID NO: 173); PAL_B_REV_19620 (SEQ ID NO: 174); PAL_C_FWD_19621 (SEQ ID NO: 175); and PAL_C_Rev_19622 (SEQ ID NO: 176).

The reaction conditions for the PCR reaction follow a protocol recommended by the enzyme manufacturer (PE Applied Biosystems, Foster City, Calif.). BnPAL1 is amplified using LIB3032-008-Q1-E1-H7 as a template with 30 nanomoles each of the primers PAL_B_FWD_19619 (SEQ ID NO: 173) and PAL_B_REV_19620 (SEQ ID NO: 174), using 10 micromoles each of dATP, dCTP, dGTP and TTP, 2.5 units of AmpliTaq Gold (PE Applied Biosystems) in 1× Opti-Prime™ Buffer 3 (Stratagene). After an initial incubation at 95° C. for 10 minutes, 28 cycles of PCR are performed with 94° C. for 15 seconds, 62° C. for 10 seconds, 52° C. for 10 seconds, and 72° C. for 3 minutes followed by 1 cycle of 72° C. for 7 minutes. The product of the PCR reaction is purified according to standard methodology well known in the art and cloned into pCR2.1 Topo (Invitrogen) according to manufacturer's instructions. The resulting plasmid is designated pBnPAL1. The sequence of this clone was determined using standard sequencing methodologies as set forth by PE Applied Biosystems, (Foster City, Calif.). BnPAL2 is amplified using LIB4169-009-Q1-K1-B3 as a template with 30 nanomoles each of the primers PAL_C_FWD_19621 (SEQ ID NO: 175) and PAL_C_Rev_19622 (SEQ ID NO: 176), 10 micromoles each of dATP, dCTP, dGTP and TTP, 2.5 units of AmpliTaq Gold (PE Applied Biosystems) in 1× Opti-Prime™ Buffer 3 (Stratagene). After an initial incubation at 95° C. for 10 minutes, 28 cycles of PCR are performed with 94° C. for 15 seconds, 62° C. for 10 seconds, 52° C. for 10 seconds, and 72° C. for 3 minutes followed by 1 cycle of 72° C. for 7 minutes. The product of the PCR reaction is purified according to standard methodology well known in the art and cloned into pCR2.1 Topo (Invitrogen) according to manufacturer's instructions.

The resulting plasmid is designated pBnPAL2. The sequence of this clone was determined using standard sequencing methodologies as set forth by PE Applied Biosystems, (Foster City, Calif.).

BnPAL3 is amplified using LIB4153-016-R1-K1-D2 as a template with 30 nanomoles each of the primers PAL_A_FWD_19617 (SEQ ID NO: 171) and PAL_A_REV_19618 (SEQ ID NO: 172), 10 micromoles each of dATP, dCTP, dGTP and TTP, 2.5 units of AmpliTaq Gold (PE Applied Biosystems) in 1× Opti-Prime™ Buffer 3 (Stratagene). After an initial incubation at 95° C. for 10 minutes, 28 cycles of PCR were performed with 94° C. for 15 seconds, 62° C. for 10 seconds, 52° C. for 10 seconds, and 72° C. for 3 minutes followed by 1 cycle of 72° C. for 7 minutes. The product of the PCR reaction is purified according to standard methodology well known in the art and cloned into pCR2.1 Topo (Invitrogen) according to manufacturer's instructions. The resulting plasmid is designated pBnPAL3. The sequence of this clone was determined using standard sequencing methodologies as set forth by PE Applied Biosystems (Foster City, Calif.).

BnPAL2 is removed from pBnPAL2 by digestion with AatII and KpnI. The resulting fragment is ligated next to BnPAL1 in AatII and KpnI digested pBnPAL1 to create pBNPal12. BnPAL3 is removed from pBnPAL3 by digestion with EagI. The resulting fragment is ligated next to BnPAL1 in NotI digested pBnPAL12 to create PDROBER03.0020.

The nucleic acid sequence was determined using standard sequencing methodology and confirmed the integrity of the cloning junctions.

Figure 6:
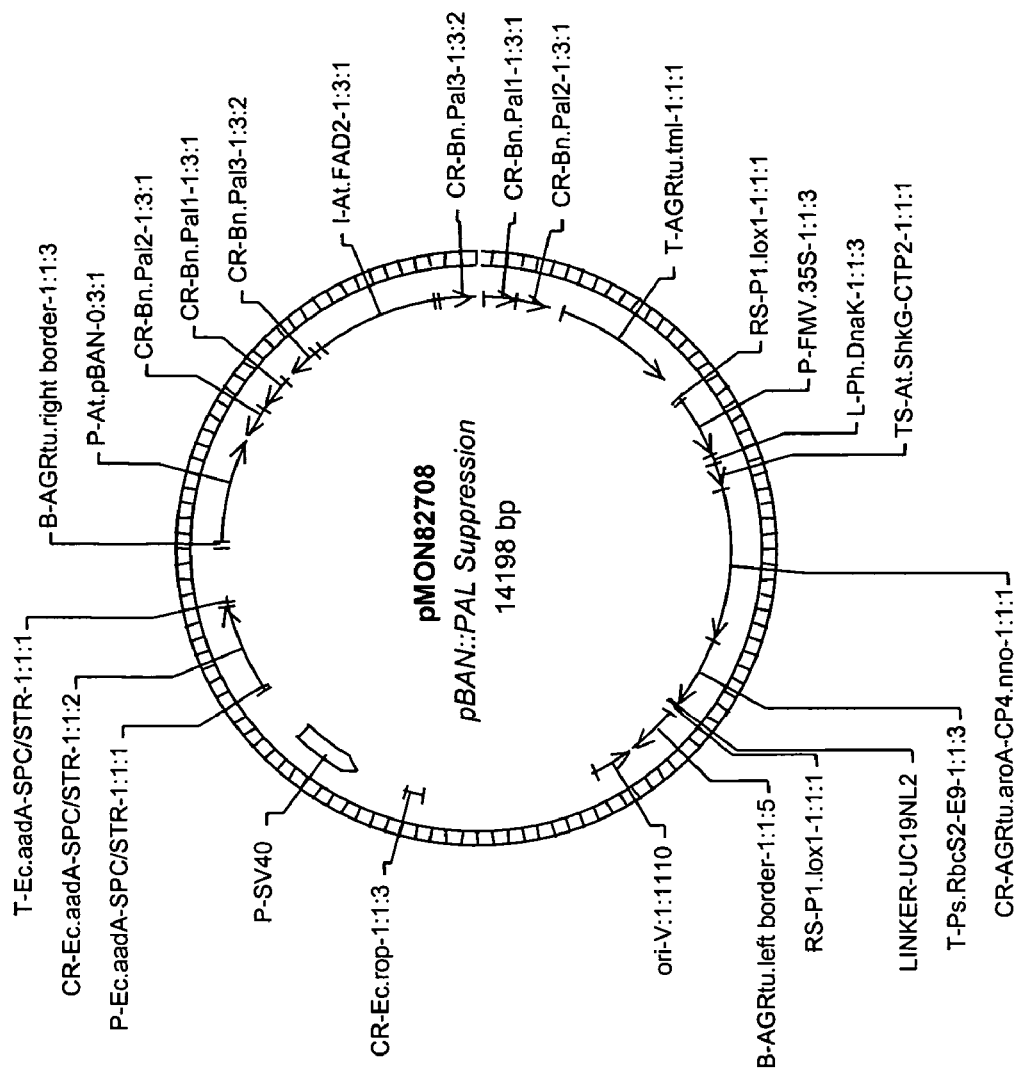
FIG. 6 shows a schematic representation of pMON82708.

A 1053 bp fragment containing BnPAL1, BnPAL2 and BnPAL3 is removed from PDROBER03.0020 by digestion with BamHI and XhoI. The BamHI overhang is blunt ended using standard methodology. The resulting fragment is ligated in between the AtFAD2 intron and tml 3' UTR in SalI and SmaI digested pMON65443. The resulting plasmid is named PDROBER03.0023. The nucleic acid sequence was determined using standard sequencing methodology and confirmed the integrity of the cloning junctions. A 1053 bp fragment containing BnPAL1, BnPAL2 and BnPAL3 is removed from PDROBER03.0020 by digestion with BamHI and XhoI. The BamHI overhang is blunt ended using standard methodology. The resulting fragment is ligated in between the banyuls promoter and AtFAD2 intron in XhoI and NotI digested PDROBER03.0023. The NotI overhang is blunt ended using standard methodology. The resulting plasmid is named pMON82708 (FIG. 6). The nucleic acid sequence was determined using standard sequencing methodology and confirmed the integrity of the cloning junctions.

pMON82709 e35S::PAL1-PAL2-PAL3 (ihp RNA)::tml)

A 1053 bp fragment containing BnPAL1, BnPAL2 and BnPAL3 is removed from PDROBER03.0020 by digestion with BamHI and XhoI. The BamHI overhang is blunt ended using standard methodology. The resulting fragment is ligated in between the AtFAD2 intron and tml 3' UTR in SalI and SmaI digested pMON65449. The resulting plasmid is named PDROBER03.0025. The nucleic acid sequence is determined using standard sequencing methodology and confirmed the integrity of the cloning junctions. A 1053 bp fragment containing BnPAL1, BnPAL2 and BnPAL3 is removed from PDROBER03.0020 by digestion with BamHI and XhoI. The BamHI overhang is blunt ended using standard methodology. The resulting fragment is ligated in between the enhanced 35S promoter and AtFAD2 intron in XhoI and NotI digested PDROBER03.0025. The NotI overhang is blunt ended using standard methodology. The resulting plasmid is named pMON82709. The nucleic acid sequence was determined using standard sequencing methodology and confirmed the integrity of the cloning junctions. Table 6 summarizes several of the vectors described above. Canola plants are transformed with the vectors as described in Example 3.

TABLE 6

Vector constructs (ihpRNA = intron-hairpin RNA).

| Construct ID | Promoter | Gene of Interest | Vector Type | Intron | 3' UTR |
|---|---|---|---|---|---|
| pMONXXXXX | e35S | BnPAL1 | ihpRNA | AtFAD2 | tml |
| pMONXXXXX | Banyuls | BnPAL1 | ihpRNA | AtFAD2 | tml |
| pMONXXXXX | WEREWOLF | BnPAL1 | ihpRNA | AtFAD2 | tml |
| pMONXXXXX | e35S | GmPAL1 | ihpRNA | AtFAD2 | tml |
| pMONXXXXX | Banyuls | GmPAL1 | ihpRNA | AtFAD2 | tml |
| pMONXXXXX | WEREWOLF | GmPAL1 | ihpRNA | AtFAD2 | tml |
| pMONXXXXX | e35S | BnPAL2 | ihpRNA | AtFAD2 | tml |
| pMONXXXXX | Banyuls | BnPAL2 | ihpRNA | AtFAD2 | tml |
| pMONXXXXX | WEREWOLF | BnPAL2 | ihpRNA | AtFAD2 | tml |
| pMONXXXXX | e35S | GmPAL2 | ihpRNA | AtFAD2 | tml |
| pMONXXXXX | Banyuls | GmPAL2 | ihpRNA | AtFAD2 | tml |
| pMONXXXXX | WEREWOLF | GmPAL2 | ihpRNA | AtFAD2 | tml |
| pMONXXXXX | e35S | BnPAL3 | ihpRNA | AtFAD2 | tml |
| pMONXXXXX | Banyuls | BnPAL3 | ihpRNA | AtFAD2 | tml |
| pMONXXXXX | WEREWOLF | BnPAL3 | ihpRNA | AtFAD2 | tml |
| pMONXXXXX | e35S | GmPAL3 | ihpRNA | AtFAD2 | tml |
| pMONXXXXX | Banyuls | GmPAL3 | ihpRNA | AtFAD2 | tml |
| pMONXXXXX | WEREWOLF | GmPAL3 | ihpRNA | AtFAD2 | tml |
| pMON82709 | e35S | BnPAL1-PAL2-PAL3 | ihpRNA | AtFAD2 | tml |
| pMON82708 | Banyuls | BnPAL1-PAL2-PAL3 | ihpRNA | AtFAD2 | tml |
| pMONXXXXX | WEREWOLF | BnPAL1-PAL2-PAL3 | ihpRNA | AtFAD2 | tml |
| pMONXXXXX | e35S | GmPAL1-PAL2-PAL3 | ihpRNA | AtFAD2 | tml |
| pMONXXXXX | Banyuls | GmPAL1-PAL2-PAL3 | ihpRNA | AtFAD2 | tml |
| pMONXXXXX | WEREWOLF | GmPAL1-PAL2-PAL3 | ihpRNA | AtFAD2 | tml |

EXAMPLE 10

This example describes complementation of *Arabidopsis* mutants transformed with pMON65442 or pMON65440 as described in Example 3.

One proof of successful identification and cloning involves complementation of the mutant phenotype with the wild type allele (Lui et al., *Proc. Natl. Acad. Sci.* (U.S.A.,) 96:6535-6540 (1999)). Furthermore, Dong et al. established that complementation of *Arabidopsis* transparent testa mutants should be a useful system for establishing the function of genes with homology to flavonoid biosynthetic enzymes (Dong et al., *Plant Physiology*, 127:46-57 (2001)), and Nesi et al. used genetic complementation to confirm the identification of the gene encoded by TT16, a transcription factor that regulates genes in the flavonoid biosynthetic pathway (Nesi et al., *Plant Cell*, 14:2463-2479 (2002)).

By expressing a functional TTG1 gene in a tissue-specific manner, cells or organs where expression of TTG1 influences seed composition can be identified. Twelve independently derived ttg1-1 plants transformed with pMON65442 or pMON65440 were grown in the same flat as six ttg1-1 mutants and 6 wild type Ler control plants. Seed was harvested from each individual plant and analyzed for color and seed oil and protein levels using NIR methodologies as described in Example 4. Seed from plants transformed with pMON65442 had significantly lower oil levels than seeds from the untransformed ttg1-1 mutant (38.7% vs. 44.2%). Wild type Ler plants produced seed with an average oil level of 41.4%. pMON65442 did not complement the high protein or seed color phenotypes of the ttg1-1 mutant. This shows that expression of TTG1 in the root atrichoblast is involved in determining the oil and protein levels in seeds.

Seedlings were also scored for the presence of trichomes on true leaves. From 80 transformants tested, all had trichomes. The transformants have brown seeds and significantly lower protein levels than untransformed ttg-1 plants, and equivalent levels to the wild type, as determined by a means comparison using the Student's t-test (JMP Software, SAS Institute Inc.). For wild type, the average protein level was 21.5%. For untransformed ttg-1 plants, the average protein level was 25%. For transformants, the average protein level was 23%. These results show that the BnTTG1 constructs complemented the mutant ttg-1 plants and restored oil and protein to wild type levels. This shows that TTG1 is involved in determining the levels of oil and protein in seeds and that BnTTG1 is a functional homologue of the *Arabidopsis* TTG1 gene.

For pMON65440, successful complementation could not be determined because no significant difference in oil was detected between the control wild type and mutant plants due to a high level of variation. Complementation tests for pMON65440 are being repeated.

EXAMPLE 11

This example describes results in canola transformed by methods in Example 3 with constructs from Example 2.

Analysis of Canola plants transformed with pMON75051

For each event tested, seventeen gene of interest positive (transgenic) and seventeen null segregants (control) R1 plants derived from the same initial transformant were grown. Seed was harvested from each individual plant and analyzed for oil and protein levels using NIR methodologies as described in Example 4 (Table 7). Differences between transgenic and control plants for each event were determined by a means comparison using the Student's t-test (JMP Software, SAS Institute Inc.) with p<0.05. No significant differences in oil level were found between transgenic and control seed. Transgenic seed for plants for one event, BN_G942, had a significantly higher level of protein.

TABLE 7

Average R2 seed oil and protein levels of plants transformed with pMON75051

| | % OIL | | % PROTEIN | |
|---|---|---|---|---|
| EVENT | Control | Transgenic | Control | Transgenic |
| BN_G895 | 39.4 | 40.0 | 25.2 | 24.9 |
| BN_G910 | 39.4 | 39.6 | 28.2 | 27.8 |
| BN_G913 | 39.5 | 39.5 | 26.8 | 26.8 |
| BN_G918 | 38.8 | 39.6 | 27.8 | 27.7 |
| BN_G942 | 39.6 | 39.1 | 27.0 | 27.4 |

Analysis of Canola Plants Transformed with pMON75052

For each of five individual events tested, seventeen gene of interest positive (transgenic) and seventeen null segregants (control) R1 plants derived from the same initial transformant were grown. Seed was harvested from each individual plant and analyzed for oil and protein levels using NIR methodologies as described in Example 4 (Table 8). Differences between transgenic and control plants for each event were determined by a means comparison using the Student's t-test (JMP Software, SAS Institute Inc.) with $p<0.05$. No significant differences in oil or protein level were found between transgenic and control seed.

TABLE 8

Average R2 seed oil and protein levels of plants transformed with pMON75052

| | % OIL | | % PROTEIN | |
|---|---|---|---|---|
| EVENT | Control | Transgenic | Control | Transgenic |
| BN_G950 | 40.6 | 40.6 | 26.1 | 26.0 |
| BN_G965 | 42.7 | 42.6 | 26.1 | 26.1 |
| BN_G966 | 40.2 | 41.3 | 27.8 | 27.5 |
| BN_G975 | 41.2 | 40.3 | 24.6 | 24.8 |
| BN_G979 | 40.3 | 40.0 | 26.8 | 27.0 |

Analysis of Canola Plants Transformed with pMON75702

For each of six individual events tested, seventeen gene of interest positive (transgenic) and seventeen null segregants (control) R1 plants derived from the same initial transformant, were grown. Seed was harvested from each individual plant and analyzed for oil and protein levels using NIR methodologies as described in Example 4 (Table 9). Differences between transgenic and control plants for each event were determined by a means comparison using the Student's t-test (JMP Software, SAS Institute Inc.) with $p<0.05$. No significant differences in oil or protein level were found between transgenic and control seed.

TABLE 9

Average R2 seed oil and protein levels of plants transformed with pMON75702

| | Leaf | % OIL | | % PROTEIN | |
|---|---|---|---|---|---|
| EVENT | Trichomes | Control | Transgenic | Control | Transgenic |
| BN_G1439 | Absent | 44.9 | 44.5 | 23.1 | 23.1 |
| BN_G1441 | Absent | 42.6 | 43.0 | 21.7 | 22.0 |
| BN_G1524 | Absent | 43.3 | 43.1 | 21.6 | 21.9 |
| BN_G1550 | Absent | 43.7 | 43.3 | 23.5 | 24.2 |
| BN_G1602 | Absent | 42.5 | 43.3 | 24.2 | 23.6 |
| BN_G1604 | Absent | 42.0 | 42.1 | 24.5 | 24.0 |

Herbicide-resistant seedlings from all six events had no detectable leaf trichomes, whereas herbicide-sensitive segregants of the same event had normal leaf trichomes. This indicates that TTG1 activity is suppressed in leaf trichome forming cells. There were no visually detectable differences in color between seed harvested from herbicide resistant and non resistant segregants.

To determine whether TTG1 was suppressed in transgenic plants, RNA isolated from developing seed and leaf was analyzed for expression levels of BnTTG1 by real time RT-PCR. Plants with a significant decrease in TTG1 transcript when compared to wild type could not be identified. Developing seed from pMON75702 transformants was screened for expression of BnLDOX, a potential target of TTG1. Plants with a significant decrease in LDOX transcript when compared to wild type could not be identified.

Analysis of Canola Plants Transformed with pMON70906

For each of five individual events tested, seventeen gene of interest positive (transgenic) and seventeen null segregants (control) R1 plants derived from the same initial transformant, were grown. Seed was harvested from each individual plant and analyzed for oil and protein levels using NIR methodologies as described in Example 4 (Table 10). Differences between transgenic and control plants for each event were determined by a means comparison using the Student's t-test (JMP Software, SAS Institute Inc.) with $p<0.05$. No significant differences in oil level were found between transgenic and control seed. Transgenic seed for plants for one event, BN_G1303, had a significantly lower level of protein.

TABLE 10

Average R2 seed oil and protein levels of plants transformed with pMON70906.

| | % OIL | | % PROTEIN | |
|---|---|---|---|---|
| EVENT | Control | Transgenic | Control | Transgenic |
| BN_G1234 | 44.3 | 44.3 | 23.8 | 23.7 |
| BN_G1235 | 42.6 | 42.6 | 23.6 | 23.5 |
| BN_G1243 | 44.1 | 44.0 | 22.9 | 23.0 |
| BN_G1264 | 43.6 | 43.9 | 22.9 | 23.0 |
| BN_G1303 | 40.3 | 40.8 | 26.4 | 26.0 |

To determine whether TTG1 was suppressed in transgenic plants, RNA isolated from developing seed was analyzed for expression levels of BnTTG1 by real time RT-PCR. Plants with a significant decrease in TTG1 transcript when compared to wild type could not be identified. RNA isolated from developing whole seed, embryos and seed coats of pMON70906 transformants was screened for expression of BnLDOX, a potential target of TTG1. Plants with a significant decrease in LDOX transcript when compared to wild type could not be identified.

Extracts from transgenic and control seed, seed coat, root or vegetative tissue will be analyzed by HPLC, TLC, histochemical staining or spectrophotometric assay for phenylpropanoids using methods known to those skilled in the art. Morphological analysis to determine whether epidermal cell development has been altered, particularly in the seed coat and root, is also performed. Plants with reduced levels of phenylpropanoids are positively correlated to seed with increased levels of oil or protein.

To facilitate down regulation of the phenylpropanoid pathway, additional suppression constructs are introduced into transgenic plants. Preferred polynucleotide sequences used in the context of down regulating the phenylpropanoid pathway include those that encode a phenylpropanoid pathway gene, including, for example, TTG1, CHS, PAL, and LDOX. More preferably such polynucleotides include SEQ ID NOs: 2-17, 29, 30, 32-96, 121-123, 127-141, 144, 145, 147-165, and 168. A construct capable of forming a ds RNA containing coding or noncoding sequences from the aforementioned TTG1, CHS, PAL, and/or LDOX genes under control of a constitutive (such as CaMV 35S or FMV) or tissue specific (such as a root atrichoblast, seed coat, or seed) promoter is introduced into canola, soy, or corn by methods known to one skilled in the art, such as those described in Example 3.

We claim:

1. An isolated polynucleotide comprising a DNA sequence selected from the group consisting of: a) a polynucleotide comprising the sequence set forth in SEQ ID NO: 147; b) a polynucleotide encoding a polypeptide with transcriptional activity, which polynucleotide has a sequence that is at least 90% identical to the sequence set forth in SEQ ID NO: 147; and c) a polynucleotide encoding a polypeptide with transcriptional activity and hybridizing under stringent conditions to any one of a) or b), wherein said stringent conditions comprise 50% formamide, 5×SSC at 42° C., and washing in 0.1×SSC, 0.1% SDS at 65° C.

2. A vector comprising at least one polynucleotide of claim 1.

3. An expression cassette comprising the isolated polynucleotide of claim 1, wherein the isolated polynucleotide is operably linked to a promoter, and wherein the polynucleotide is in sense or antisense orientation.

4. A plant comprising the expression cassette of claim 3.

5. The plant of claim 4, wherein the promoter is a seed coat-specific promoter, a tissue-specific promoter, a monocot promoter, the napin promoter, the WEREWOLF promoter, the 35S promoter, the CaMV 19S, the nos promoter, the Adh promoter, the sucrose synthase promoter, the tubulin promoter, the actin promoter, the PEPCase promoter, the 7S-alpha'-conglycinin promoter or those promoters associated with the R gene complex, the tomato E8 promoter, the patatin promoter, the ubiquitin promoter, the mannopine synthase (mas) promoter, the glycinin promoter, the soybean vegetative storage protein (vsp) promoter, or a pBAN promoter.

6. The plant of claim 5, wherein the plant is soybean, corn or canola.

7. A method of increasing oil content in a plant comprising disrupting the function of a protein in the phenylpropanoid pathway of the plant by expressing in the plant the polynucleotide of claim 1 in sense or anti-sense orientation.

8. The method of claim 7, wherein the function of the protein in the phenylpropanoid pathway is disrupted by suppressing the expression of the gene for said protein.

9. A method of generating a plant having increased oil or protein content, as compared to a substantially similar plant not subjected to this method, comprising:
 a) preparing a chimeric gene comprising a polynucleotide sufficient to suppress the endogenous expression of TTG1, wherein said polynucleotide comprises at least a portion of the polynucleotide of claim 1, operably linked in sense or antisense orientation on the upstream side to a promoter that directs gene expression, and operably linked on the downstream side to a regulatory sequence for transcriptional termination; and
 b) transforming the plant with the chimeric gene of step (a).

10. A plant generated by the method of claim 9, which expresses the polynucleotide of claim 1.

11. A seed produced by the plant of claim 10, wherein the seed is from canola or soybean and comprises the polynucleotide of claim 1.

12. A food product prepared from the seed of claim 11, wherein the food product comprises the polynucleotide of claim 1.

13. A meal produced from the seed of claim 11, wherein the meal comprises the polynucleotide of claim 1.

14. A feed produced from the seed of claim 11, wherein the feed comprises the polynucleotide of claim 1.

15. The plant of claim 10, wherein the plant is a monocot or a dicot.

16. The plant of claim 15, wherein the monocot is selected from the group consisting of corn, rice, wheat, barley, and palm.

17. The plant of claim 15, wherein the dicot is selected from the group consisting of *Arabidopsis*, soybean, oilseed *Brassica*, peanut, sunflower, safflower, cotton, tobacco, tomato, potato, and cocoa.

18. A method for producing a plant with altered protein content comprising disrupting or reducing the activity of a protein in the phenylpropanoid pathway of the plant by expressing in the plant the polynucleotide of claim 1 in sense or anti-sense orientation.

19. The method of claim 18, wherein the activity of the protein in the phenylpropanoid pathway is disrupted or reduced by suppressing the expression of the gene for said protein.

20. A transgenic plant comprising the polynucleotide of claim 1.

21. A cell of the plant of claim 20.

22. A seed of the plant of claim 20, wherein the seed comprises the polynucleotide of claim 1.

* * * * *